(12) United States Patent
Walsh et al.

(10) Patent No.: US 9,351,900 B2
(45) Date of Patent: May 31, 2016

(54) SOFT EXOSUIT FOR ASSISTANCE WITH HUMAN MOTION

(71) Applicant: President and Fellows of Harvard College, Cambridge, MA (US)

(72) Inventors: Conor Walsh, Cambridge, MA (US); Alan Thomas Asbeck, Waltham, MA (US); Ignacio Galiana Bujanda, Cambridge, MA (US); Ye Ding, Cambridge, MA (US); Robert Joseph Dyer, Concord, MA (US); Arnar Freyr Larusson, Hanover, NH (US); Brendan Thomas Quinlivan, Rutland, MA (US); Kai Schmidt, Berlin (DE); Diana Wagner, Charlotte, NC (US); Michael Wehner, Berkeley, CA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 14/371,675

(22) PCT Filed: Sep. 17, 2013

(86) PCT No.: PCT/US2013/060225
§ 371 (c)(1),
(2) Date: Jul. 10, 2014

(87) PCT Pub. No.: WO2014/109799
PCT Pub. Date: Jul. 17, 2014

(65) Prior Publication Data
US 2015/0173993 A1    Jun. 25, 2015

Related U.S. Application Data

(60) Provisional application No. 61/873,433, filed on Sep. 4, 2013, provisional application No. 61/829,686, filed on May 31, 2013, provisional application No. 61/701,970, filed on Sep. 17, 2012.

(51) Int. Cl.
*A61H 3/00* (2006.01)
*A61H 1/02* (2006.01)
*F03G 7/08* (2006.01)

(52) U.S. Cl.
CPC .............. *A61H 3/00* (2013.01); *A61H 1/024* (2013.01); *A61H 1/0244* (2013.01);
(Continued)

(58) Field of Classification Search
CPC . A61H 3/00; A61H 2201/1261; A25J 9/0015; A25J 9/0006
USPC .............. 602/23, 26–28, 60–62, 65; 128/882
See application file for complete search history.

(56) References Cited

U.S. PATENT DOCUMENTS 3,411,511 A * 11/1968 Marino ..................... 450/155
4,023,215 A    5/1977 Moore
(Continued)

FOREIGN PATENT DOCUMENTS

CN    202342034    7/2012
CN    101175456    3/2013
(Continued)

OTHER PUBLICATIONS

A. Dollar and H. Herr, "Lower extremity exoskeletons and active orthoses: Challenges and state-of-the-art," Robotics, IEEE Transactions on, vol. 24, No. 1, pp. 144-158, Feb. 2008.
(Continued)

*Primary Examiner* — Justine Yu
*Assistant Examiner* — Timothy Stanis
(74) *Attorney, Agent, or Firm* — Greenberg Traurig, LLP; David J. Dykeman; Todd C. Basile

(57) ABSTRACT

In at least one aspect, there is provided a system for generating force about one or more joints including a soft exosuit having a plurality of anchor elements and at least one connection element disposed between the plurality of anchor elements. The system also includes at least one sensor to determine a force the at least one connection element or at least one of the plurality of anchor elements and to output signals relating to the force, at least one actuator configured to change a tension in the soft exosuit and at least one controller configured to receive the signals output from the at least one sensor and actuate the at least one actuator responsive to the received signals.

44 Claims, 104 Drawing Sheets

(52) U.S. Cl.
CPC .............. *A61H 1/0266* (2013.01); *F03G 7/08* (2013.01); *A61H 2201/1215* (2013.01); *A61H 2201/1238* (2013.01); *A61H 2201/1246* (2013.01); *A61H 2201/1261* (2013.01); *A61H 2201/1481* (2013.01); *A61H 2201/164* (2013.01); *A61H 2201/165* (2013.01); *A61H 2201/1628* (2013.01); *A61H 2201/1652* (2013.01); *A61H 2201/1664* (2013.01); *A61H 2201/501* (2013.01); *A61H 2201/5007* (2013.01); *A61H 2201/5061* (2013.01); *A61H 2201/5064* (2013.01); *A61H 2201/5069* (2013.01); *A61H 2201/5084* (2013.01); *A61H 2201/5097* (2013.01); *A61H 2230/60* (2013.01)

(56) References Cited

U.S. PATENT DOCUMENTS

| | | | |
|---|---|---|---|
| 4,252,112 A * | 2/1981 | Joyce | A61F 5/0104 601/34 |
| 4,370,977 A | 2/1983 | Mauldin et al. | |
| 4,697,808 A | 10/1987 | Larson et al. | |
| 4,760,850 A | 8/1988 | Phillips et al. | |
| 5,020,790 A | 6/1991 | Beard et al. | |
| 5,282,460 A | 2/1994 | Boldt | |
| 5,865,770 A * | 2/1999 | Schectman | 601/23 |
| 6,129,691 A * | 10/2000 | Ruppert | A61F 5/026 128/845 |
| 6,168,634 B1 | 1/2001 | Schmitz | |
| 6,500,138 B1 | 12/2002 | Irby et al. | |
| 6,517,503 B1 | 2/2003 | Naft et al. | |
| 6,633,783 B1 | 10/2003 | Dariush et al. | |
| 6,635,024 B2 | 10/2003 | Hatton et al. | |
| 6,689,075 B2 | 2/2004 | West | |
| 6,783,555 B2 | 8/2004 | Kuhn et al. | |
| 6,955,692 B2 | 10/2005 | Grundei | |
| 6,989,669 B2 | 1/2006 | Low et al. | |
| 7,034,432 B1 | 4/2006 | Pelrine et al. | |
| 7,034,527 B2 | 4/2006 | Low et al. | |
| 7,049,732 B2 | 5/2006 | Pei et al. | |
| 7,090,650 B2 | 8/2006 | Ou et al. | |
| 7,153,242 B2 | 12/2006 | Goffer | |
| 7,166,953 B2 | 1/2007 | Heim et al. | |
| 7,190,141 B1 | 3/2007 | Ashrafiuon et al. | |
| 7,199,501 B2 | 4/2007 | Pei et al. | |
| 7,211,937 B2 | 5/2007 | Kornbluh et al. | |
| 7,224,106 B2 | 5/2007 | Pei et al. | |
| 7,252,644 B2 | 8/2007 | Dewald et al. | |
| 7,259,503 B2 | 8/2007 | Pei et al. | |
| 7,307,418 B2 | 12/2007 | Low et al. | |
| 7,341,295 B1 | 3/2008 | Veatch et al. | |
| 7,368,862 B2 | 5/2008 | Pelrine et al. | |
| 7,378,878 B2 | 5/2008 | Pelrine et al. | |
| 7,390,309 B2 | 6/2008 | Dariush | |
| 7,410,471 B1 | 8/2008 | Campbell et al. | |
| 7,411,332 B2 | 8/2008 | Kornbluh et al. | |
| 7,429,253 B2 | 9/2008 | Shimada et al. | |
| 7,436,099 B2 | 10/2008 | Pei et al. | |
| 7,456,549 B2 | 11/2008 | Heim et al. | |
| 7,521,840 B2 | 4/2009 | Heim | |
| 7,521,847 B2 | 4/2009 | Heim | |
| 7,537,573 B2 | 5/2009 | Horst | |
| 7,549,969 B2 | 6/2009 | van den Bogert | |
| 7,567,681 B2 | 7/2009 | Pelrine et al. | |
| 7,578,799 B2 | 8/2009 | Thorsteinsson et al. | |
| 7,595,580 B2 | 9/2009 | Heim | |
| 7,598,651 B2 | 10/2009 | Kornbluh et al. | |
| 7,598,652 B2 | 10/2009 | Kornbluh et al. | |
| 7,626,319 B2 | 12/2009 | Heim | |
| 7,650,204 B2 | 1/2010 | Dariush | |
| 7,652,386 B2 | 1/2010 | Donelan et al. | |
| 7,654,973 B2 | 2/2010 | Firsov | |
| 7,679,267 B2 | 3/2010 | Heim | |
| 7,684,896 B2 | 3/2010 | Dariush | |
| 7,705,521 B2 | 4/2010 | Pelrine et al. | |
| 7,737,685 B2 | 6/2010 | Low et al. | |
| 7,750,532 B2 | 7/2010 | Heim | |
| 7,758,481 B2 * | 7/2010 | Drennan | 482/124 |
| 7,774,177 B2 | 8/2010 | Dariush | |
| 7,775,999 B2 * | 8/2010 | Brown | 602/24 |
| 7,785,656 B2 | 8/2010 | Pei et al. | |
| 7,787,646 B2 | 8/2010 | Pelrine et al. | |
| 7,804,227 B2 | 9/2010 | Pelrine et al. | |
| 7,857,774 B2 | 12/2010 | Sankai | |
| 7,860,562 B2 | 12/2010 | Endo et al. | |
| 7,883,546 B2 | 2/2011 | Kazerooni et al. | |
| 7,911,761 B2 | 3/2011 | Biggs et al. | |
| 7,915,790 B2 | 3/2011 | Heim et al. | |
| 7,921,541 B2 | 4/2011 | Pei et al. | |
| 7,923,064 B2 | 4/2011 | Pelrien et al. | |
| 7,923,902 B2 | 4/2011 | Heim | |
| 7,947,004 B2 | 5/2011 | Kazerooni et al. | |
| 7,952,261 B2 | 5/2011 | Lipton et al. | |
| 7,977,923 B2 | 7/2011 | Pelrine et al. | |
| 7,985,193 B2 | 7/2011 | Thorsteinsson et al. | |
| 7,990,022 B2 | 8/2011 | Heim | |
| 8,048,007 B2 | 11/2011 | Roy | |
| 8,057,410 B2 | 11/2011 | Angold et al. | |
| 8,058,861 B2 | 11/2011 | Pelrine et al. | |
| 8,075,633 B2 | 12/2011 | Herr et al. | |
| 8,096,965 B2 | 1/2012 | Goffer et al. | |
| 8,125,755 B2 | 2/2012 | Garcia et al. | |
| 8,127,437 B2 | 3/2012 | Lipton et al. | |
| 8,147,436 B2 | 4/2012 | Agrawal et al. | |
| 8,164,232 B2 | 4/2012 | Kornbluh et al. | |
| 8,183,739 B2 | 5/2012 | Heim | |
| 8,222,799 B2 | 7/2012 | Polyakov et al. | |
| 8,231,687 B2 | 7/2012 | Bedard et al. | |
| 8,235,869 B2 | 8/2012 | Rastegar et al. | |
| 8,246,559 B2 | 8/2012 | Hoffman et al. | |
| 8,248,750 B2 | 8/2012 | Biggs et al. | |
| 8,283,839 B2 | 10/2012 | Heim | |
| 8,287,477 B1 | 10/2012 | Herr et al. | |
| 8,299,634 B2 | 10/2012 | Donelan et al. | |
| 8,311,623 B2 | 11/2012 | Sanger | |
| 8,316,526 B2 | 11/2012 | Pei et al. | |
| 8,316,719 B2 | 11/2012 | Majidi et al. | |
| 8,323,355 B2 | 12/2012 | Latour | |
| 8,325,458 B2 | 12/2012 | Prahlad et al. | |
| 8,348,875 B2 | 1/2013 | Goffer et al. | |
| 8,376,971 B1 | 2/2013 | Herr et al. | |
| 8,409,117 B2 | 4/2013 | Cheng et al. | |
| 8,436,508 B2 | 5/2013 | Kornbluh et al. | |
| 8,467,904 B2 | 6/2013 | Dariush | |
| 8,488,295 B2 | 7/2013 | Garcia et al. | |
| 8,508,109 B2 | 8/2013 | Pelrine et al. | |
| 8,551,029 B1 | 10/2013 | Herr et al. | |
| 8,564,926 B2 | 10/2013 | Prahlad et al. | |
| 8,585,620 B2 | 11/2013 | McBean et al. | |
| 8,608,674 B2 | 12/2013 | Krebs et al. | |
| 8,622,938 B2 | 1/2014 | Sankai | |
| 2001/0007845 A1 | 7/2001 | Afanasenko et al. | |
| 2003/0009120 A1 * | 1/2003 | MacAllister | 602/23 |
| 2003/0030397 A1 | 2/2003 | Simmons | |
| 2003/0092545 A1 | 5/2003 | Koscielny et al. | |
| 2003/0120183 A1 | 6/2003 | Simmons | |
| 2003/0125781 A1 | 7/2003 | Dohno et al. | |
| 2004/0043879 A1 | 3/2004 | Huang | |
| 2004/0064195 A1 | 4/2004 | Herr | |
| 2004/0106881 A1 | 6/2004 | McBean et al. | |
| 2004/0116260 A1 | 6/2004 | Drennan | |
| 2004/0147378 A1 | 7/2004 | Conklin et al. | |
| 2005/0010150 A1 | 1/2005 | Firsov | |
| 2005/0070834 A1 | 3/2005 | Herr et al. | |
| 2005/0157893 A1 | 7/2005 | Pelrine et al. | |
| 2006/0079817 A1 | 4/2006 | Dewald et al. | |
| 2006/0108755 A1 | 5/2006 | Smyler et al. | |
| 2006/0192465 A1 | 8/2006 | Kornbluh et al. | |
| 2006/0249315 A1 | 11/2006 | Herr et al. | |
| 2007/0004570 A1 * | 1/2007 | Afanasenko et al. | 482/124 |
| 2007/0004571 A1 | 1/2007 | Gonzalez | |
| 2007/0066918 A1 | 3/2007 | Dewald et al. | |
| 2007/0111868 A1 | 5/2007 | Fujii et al. | |
| 2007/0123997 A1 | 5/2007 | Herr et al. | |

(56) References Cited

U.S. PATENT DOCUMENTS

| | | | |
|---|---|---|---|
| 2007/0135279 A1* | 6/2007 | Purdy et al. ................ | 482/124 |
| 2008/0039756 A1 | 2/2008 | Thorsteinsson et al. | |
| 2008/0062589 A1 | 3/2008 | Drabing | |
| 2008/0071386 A1 | 3/2008 | McBean et al. | |
| 2008/0075930 A1 | 3/2008 | Kornbluh et al. | |
| 2008/0097269 A1 | 4/2008 | Weinberg et al. | |
| 2008/0156363 A1 | 7/2008 | Ikeuchi et al. | |
| 2008/0218132 A1 | 9/2008 | Pelrine et al. | |
| 2008/0224564 A1 | 9/2008 | Pelrine et al. | |
| 2008/0289952 A1 | 11/2008 | Pelrine et al. | |
| 2009/0042702 A1 | 2/2009 | Toronto et al. | |
| 2009/0221928 A1 | 9/2009 | Einav et al. | |
| 2009/0255531 A1 | 10/2009 | Johnson et al. | |
| 2009/0256817 A1 | 10/2009 | Perlin et al. | |
| 2009/0319054 A1 | 12/2009 | Sankai | |
| 2010/0000547 A1 | 1/2010 | Johnson et al. | |
| 2010/0007240 A1 | 1/2010 | Kornbluh et al. | |
| 2010/0024180 A1 | 2/2010 | Pei et al. | |
| 2010/0026143 A1 | 2/2010 | Pelrine et al. | |
| 2010/0030343 A1 | 2/2010 | Hansen et al. | |
| 2010/0152630 A1 | 6/2010 | Matsuoka et al. | |
| 2010/0185259 A1 | 7/2010 | Shiba et al. | |
| 2010/0185301 A1 | 7/2010 | Hansen et al. | |
| 2010/0271051 A1 | 10/2010 | Sankai et al. | |
| 2010/0280628 A1 | 11/2010 | Sankai | |
| 2010/0286796 A1 | 11/2010 | Clausen | |
| 2010/0298834 A1 | 11/2010 | Hildebrandt | |
| 2010/0319215 A1 | 12/2010 | Roser | |
| 2010/0324698 A1 | 12/2010 | Sverrisson et al. | |
| 2011/0004322 A1 | 1/2011 | Sankai | |
| 2011/0025170 A1 | 2/2011 | Rosenthal et al. | |
| 2011/0033835 A1 | 2/2011 | Endo et al. | |
| 2011/0040216 A1 | 2/2011 | Herr et al. | |
| 2011/0062948 A1 | 3/2011 | Arns, Jr. et al. | |
| 2011/0105966 A1 | 5/2011 | Kazerooni et al. | |
| 2011/0154641 A1 | 6/2011 | Pelrine et al. | |
| 2011/0155307 A1 | 6/2011 | Pelrine et al. | |
| 2011/0174524 A1 | 7/2011 | Sharm et al. | |
| 2011/0193362 A1 | 8/2011 | Prahlad et al. | |
| 2011/0201978 A1 | 8/2011 | Jeon et al. | |
| 2011/0209337 A1 | 9/2011 | Pei et al. | |
| 2011/0245738 A1 | 10/2011 | Agrawal et al. | |
| 2011/0295384 A1 | 12/2011 | Herr et al. | |
| 2011/0295385 A1 | 12/2011 | Herr et al. | |
| 2012/0019223 A1 | 1/2012 | Pelrine et al. | |
| 2012/0056903 A1 | 3/2012 | Shinohara et al. | |
| 2012/0071797 A1 | 3/2012 | Aoki et al. | |
| 2012/0100286 A1 | 4/2012 | Sharma et al. | |
| 2012/0120544 A1 | 5/2012 | Pelrine et al. | |
| 2012/0128960 A1 | 5/2012 | Busgen et al. | |
| 2012/0165709 A1 | 6/2012 | Goffer et al. | |
| 2012/0169184 A1 | 7/2012 | Pelrine et al. | |
| 2012/0177934 A1 | 7/2012 | Vogel et al. | |
| 2012/0179075 A1 | 7/2012 | Perry et al. | |
| 2012/0181896 A1 | 7/2012 | Kornbluh et al. | |
| 2012/0185052 A1 | 7/2012 | Lefeber | |
| 2012/0209152 A1 | 8/2012 | Cordo | |
| 2012/0238914 A1 | 9/2012 | Goldfield et al. | |
| 2012/0248942 A1 | 10/2012 | Biggs et al. | |
| 2012/0271207 A1 | 10/2012 | Schoen et al. | |
| 2012/0279175 A1 | 11/2012 | Biggs et al. | |
| 2012/0289870 A1 | 11/2012 | Hsiao-Wecksler et al. | |
| 2012/0330198 A1 | 12/2012 | Patoglu | |
| 2013/0013085 A1 | 1/2013 | Smith et al. | |
| 2013/0040783 A1 | 2/2013 | Duda et al. | |
| 2013/0058001 A1 | 3/2013 | Prahlad et al. | |
| 2013/0079686 A1 | 3/2013 | Sessions | |
| 2013/0093439 A1 | 4/2013 | Ulmen et al. | |
| 2013/0102935 A1 | 4/2013 | Kazerooni et al. | |
| 2013/0123672 A1 | 5/2013 | Goffer et al. | |
| 2013/0165817 A1 | 6/2013 | Horst et al. | |
| 2013/0186699 A1 | 7/2013 | Prahlad et al. | |
| 2013/0211295 A1 | 8/2013 | Johnson et al. | |
| 2013/0226048 A1 | 8/2013 | Unluhisarcikli et al. | |
| 2013/0230667 A1 | 9/2013 | Sharma et al. | |
| 2013/0237884 A1 | 9/2013 | Kazerooni et al. | |
| 2013/0245512 A1 | 9/2013 | Goffer et al. | |
| 2013/0253385 A1 | 9/2013 | Goffer et al. | |
| 2013/0261513 A1 | 10/2013 | Goffer et al. | |
| 2013/0261766 A1 | 10/2013 | Langlois et al. | |
| 2013/0268256 A1 | 10/2013 | Dariush | |
| 2013/0274640 A1 | 10/2013 | Butters et al. | |
| 2013/0288863 A1 | 10/2013 | Yamamoto et al. | |
| 2013/0296746 A1 | 11/2013 | Herr et al. | |
| 2013/0307370 A1 | 11/2013 | Jenninger et al. | |
| 2013/0312541 A1 | 11/2013 | Majidi et al. | |
| 2013/0328440 A1 | 12/2013 | Kornbluh et al. | |
| 2014/0046455 A1 | 2/2014 | Herr et al. | |

FOREIGN PATENT DOCUMENTS

| | | |
|---|---|---|
| CN | 102327173 | 5/2013 |
| DE | 19944139 | 4/2001 |
| EP | 0016268 | 10/1980 |
| EP | 0141640 | 10/1984 |
| EP | 0302148 | 2/1989 |
| EP | 1306792 | 5/2003 |
| EP | 1324403 | 7/2003 |
| EP | 1260201 | 12/2008 |
| EP | 2226053 | 9/2010 |
| EP | 1842518 | 9/2011 |
| EP | 1589059 | 6/2012 |
| EP | 2497610 | 9/2012 |
| EP | 2548543 | 1/2013 |
| EP | 1550689 | 4/2013 |
| EP | 2649976 | 10/2013 |
| JP | 4345025 | 10/2009 |
| JP | 4424269 | 3/2010 |
| JP | 4582523 | 11/2010 |
| JP | 2011036375 | 2/2011 |
| JP | 4848260 | 12/2011 |
| JP | 2012192013 | 10/2012 |
| WO | WO2004/017890 | 3/2004 |
| WO | WO2004/039292 | 5/2004 |
| WO | WO2004/047928 | 6/2004 |
| WO | WO2005/102208 | 11/2005 |
| WO | WO2011008934 | 1/2011 |
| WO | WO2011/026086 | 3/2011 |
| WO | WO2011/030641 | 3/2011 |
| WO | WO2012050938 | 4/2012 |
| WO | WO2012/103073 | 8/2012 |
| WO | WO2012/124328 | 9/2012 |
| WO | 2012178171 | 12/2012 |
| WO | 2013019749 | 2/2013 |
| WO | WO2013/033669 | 3/2013 |
| WO | WO2013/044226 | 3/2013 |

OTHER PUBLICATIONS

A. F. da Silva, A. F. Goncalves, P. M. Mendes, and J. H. Correia, "FBG Sensing Glove for Monitoring Hand Posture," Sensors Journal, . . . , vol. 11, No. 10, pp. 2442-2448, 2011. [Online]. Available: http://ieeexplore.ieee.org/xpls/abs all.jsp?arnumber=5742669.

A. Schiele, "Ergonomics of Exoskeletons: Objective Performance Metrics" in Euro Haptics conference on Haptic Interfaces, Salt Lake City, UT, USA, Mar. 2009.

C. Majidi, R. K. Kramer, and R. J. Wood, "A non-differential elastomer curvature sensor for softer-than-skin electronics," Smart Materials and Structures, vol. 20, No. 10, p. 105017, Oct. 2011. [Online]. Available: http://stacks.iop.org/0964-1726/20/i=10/a=105017?key=crossref.0cca7e97d6ad7110bcdcaf45f30f3b60.

Chu, H. Kazerooni and A. Zoss, On the biomimetic design of the Berkeley lower extremity exoskeleton (BLEEX), in IEEE Int. Conf. Robotics and Automation (ICRA) (IEEE Press, Barcelona, Spain, 2006), pp. 4356-4363.

Collins, S., et al., Efficient Bipedal Robots Based on Passive-Dynamic Walkers. Science, 2005. 307(5712): p. 1082-1085.

Cool JC. Biomechanics of orthoses for the subluxed shoulder. Prosthetics & Orthotics International 1989;13:90-6.

D. De Rossi and P. Veltink, "Wearable technology for biomechanics: e-textile or micromechanical sensors?" IEEE engineering in medicine and biology magazine, vol. 29, No. 3, pp. 37-43, 2010. [Online].

(56) References Cited

OTHER PUBLICATIONS

Available: http://www.ncbi.nlm.nih.gov/pubmed/20659856.
D. Ferris and C. Lewis, "Robotic lower limb exoskeletons using proportional myoelectric control," in EMBC 2009, Annual International Conference of the IEEE Engineering in Medicine and Biology Society, 2009.
D. J. Lipomi, M. Vosgueritchian, B. C.-K. Tee, S. L. Hellstrom, J. A. Lee, C. H. Fox, and Z. Bao, "Skin-like pressure and strain sensors based on transparent elastic films of carbon nanotubes." Nature nanotechnology, vol. 6, No. 12, pp. 788-792, Jan. 2011. [Online]. Available: http://www.ncbi.nlm.nih.gov/pubmed/22020121.
D. Vogt, Y.-L. Park, and R. J. Wood, Design and Characterization of a Soft Multi-Axis Force Sensor Using Embedded Microfluidic Channels, IEE Sensors Journal, vol. 13. No. 10, Oct. 2013, 9 pages.
D.-H. Kim, N. Lu, R. Ma, Y.-S. Kim, R.-H. Kim, S. Wang, J. Wu, S. M. Won, H. Tao, A. Islam, K. J. Yu, T.-i. Kim, R. Chowdhury, M. Ying, L. Xu, M. Li, H.-J. Chung, H. Keum, M. McCormick, P. Liu, Y.-W. Zhang, F. G. Omenetto, Y. Huang, T. Coleman, and J. A. Rogers, "Epidermal electronics." Science, vol. 333, No. 6044, pp. 838-843, Aug. 2011. [Online]. Available: http://www.sciencemag.org/cgi/doi/10.1126/science.1206157.
D. Newman, K. Bethke, C. Carr, J. Hoffman, and G. Trotti. Astronauth Bio-Suit System to enable planetary exploration. In International Astronautical Conference, Vancouver, Canada, Oct. 2004.
E. Scilingo, F. Lorussi, A. Mazzoldi, and D. De Rossi, "Strain-sensing fabrics for wearable kinaesthetic-like systems," IEEE Sensors Journal, vol. 3, No. 4, pp. 460-467, Aug. 2003. [Online]. Available: http://ieeexplore.ieee.org/lpdocs/epic03/wrapper.htm?arnumber=1226639.
Farris DJ, Sawicki GS. Human medial gastrocnemius force-velocity behavior shifts with locomotion speed and gait. Proc Natl Acad Sci U S A. 2012;109:977-982.
Ferris, D.P., G.S. Sawicki, and M.A. Daley, A Physiologist's Perspective on Robotic Exoskeletons for Human Locomotion. Int J HR, 2007. 4(3): p. 507-528.
H. Quintero, R. Farris, and M. Goldfarb, "Control and Implementation of a Powered Lower Limb Orthosis to Aid Walking in Paraplegic Individuals," in IEEE International Conference on Rehabilitation Robotics, Jul. 2011, pp. 1-6.
Hallemans A, De Clercq D, Otten B, Aerts P: 3D joint dynamics of walking in toddlers. A cross-sectional study spanning the first rapid development phase of walking. Gait & Posture 2005, 22:107-118.
J. Pratt, B. Krupp, C. Morse and S. Collins, The RoboKnee: An exoskeleton for enhancing strength and endurance during walking, in IEEE Int. Conf. Robotics and Automation (ICRA), New Orleans, USA (IEEE Press, 2006), pp. 2430-2435.
K. a. Erk, K. J. Henderson, and K. R. Shull, "Strain stiffening in synthetic and biopolymer networks," Biomacromolecules, vol. 11, No. 5, pp. 1358-1363, May 2010.
K. N. Gregorczyk, J. P. Obusek, L. Hasselquist, J. M. Schiffman, C. K. Bensel, D. Gutekunst and P. Frykman, The effects of a lower body exoskeleton load carriage assistive device on oxygen consumption and kinematics during walking with loads, in 25th Army Sci. Conf., Florida, USA (2006).
Kawamoto, H., et al. Power assist method for HAL-3 using EMG-based feedback controller. in Systems, Man and Cybernetics, 2003. IEEE International Conference on. 2003.
M. I. Tiwana, S. J. Redmond, and N. H. Lovell, "A review of tactile sensing technologies with applications in biomedical engineering," Sensors and Actuators A: Physical, vol. 179, pp. 17-31, Jun. 2012. [Online]. Available: http://linkinghub.elsevier.com/retrieve/pii/S0924424712001641.
M. P. Kadaba, H. K. Ramakrishnan, and M. E. Wootten, "Measurement of lower extremity kinematics during level walking." Journal of orthopaedic research : official publication of the Orthopaedic Research Society, vol. 8, No. 3, pp. 383-392, May 1990. [Online]. Available: http://www.ncbi.nlm.nih.gov/pubmed/2324857.
M. Ramuz, B. C.-K. Tee, J. B.-H. Tok, and Z. Bao, "Transparent, Optical, Pressure-Sensitive Artificial Skin for Large-Area Stretchable Electronics," Advanced Materials, pp. n/a-n/a, May 2012. [Online] Available: http://doi.wiley.com/10.1002/adma.201200523.
M. Tesconi, A. Tognetti, E. P. Scilingo, G. Zupone, N. Carbonaro, D. De Rossi, E. Castellini, and M. Marella, "Wearable sensorized system for analyzing the lower limb movement during rowing activity," 2007 IEEE International Symposium on Industrial Electronics, pp. 2793-2796, Jun. 2007. [Online]. Available: http://ieeexplore.ieee.org/lpdocs/epic03/wrapper.htm?arnumber=4375052.
M. Wehner, 2012 "Man to Machine, Applications in Electromyography," EMG Methods for Evaluation Muscle and Nerve Functions. Intech Publishing, Sep. 13, 2012 http://www.intechopen.com/articles/show/title/man-to-machine-applications-in-electromyography.
M. Wehner, D. Rempel and H. Kazerooni, "Lower Extremity Exoskeleton Reduces Back Forces in Lifting" ASME Dynamic Systems and Control Conference Oct. 12-14, 2009, Hollywood, California, USA pp. 49-56.
M. Wehner, Y.-L. Park, C. Walsh, R. Nagpal, R. J. Wood, T. Moore, and E. Goldfield, "Experimental characterization of components for active soft orthotics," in Submitted in Proc. IEEE Int. Conf. Biomed. Rob. Biomechatron., Roma, Italy, Jun. 2012.
McGeer, T., Passive Bipedal Running. Proceedings of the Royal Society of London. Series B, Biological Sciences, 1990. 240(1297): p. 107-134.
O. J. Woodman, "An introduction to inertial navigation," Technical Report UCAM-CL-TR-696, 2007.
R. K. Kramer, C. Majidi, and R. J. Wood, "Wearable tactile keypad with stretchable artificial skin," 2011 IEEE International Conference on Robotics and Automation, pp. 1103-1107, May 2011. [Online]. Available: http://ieeexplore.ieee.org/lpdocs/epic03/wrapper.htm?arnumber=5980082.
R. K. Kramer, C. Majidi, R. Sahai, and R. J. Wood, "Soft curvature sensors for joint angle proprioception," in 2011 IEEE/RSJ International Conference on Intelligent Robots and Systems. IEEE, Sep. 2011, pp. 1919-1926. [Online]. Available: http://ieeexplore.ieee.org/lpdocs/epic03/wrapper.htm?arnumber=6094701.
R. Zhang, H. Deng, R. Valenca, J. Jin, Q. Fu, E. Bilotti, and T. Peijs, "Carbon nanotube polymer coatings for textile yarns with good strain sensing capability," Sensors and Actuators A: Physical, vol. 179, pp. 83-91, Jun. 2012. [Online]. Available: http://linkinghub.elsevier.com/retrieve/pii/S0924424712001938.
R.C. Browning, J.R. Modica, R. Kram, and A. Goswami, "The effects of adding mass to the legs on the energetics and biomechanics of waling," Medicine and science in sports and exercise, col. 39, p. 515, 2007.
Reid, S. A. and Whiteside, R. A. 2001a, Biomechanical assessment of rucksack shoulder strap attachment locations and effect on load distribution to the torso, Soldier Mobility: Innovations in Load Carriage System Design and Evaluation, NATO-RTO Meeting Proceedings: MP-056 (Neuilly-sur-Seine: NATO) 20, 1-6.
Royer, T.D. and Martin, P.E (2005) 'Manipulations of Leg Mass and Moment of Inertia: Walking', Medicine & Science in Sports & Exercise, pp. 37(4): 649-656.
S. K. Banala, S. K. Agrawal, and J. P. Scholz, "Active leg exoskeleton (alex) for gait rehabilitation of motor-impaired patients," in Proc. 2007 IEEE 10th Int. Conf. Rehabil. Robotics, 2007, pp. 401-407.
S. L. Delp, F. C. Anderson, A. S. Arnold, P. Loan, A. Habib, C. T. John, E. Guendelman, and D. G. Thelen, "OpenSim: open-source software to create and analyze dynamic simulations of movement." IEEE transactions on bio-medical engineering, vol. 54, No. 11, pp. 1940-1950, Nov. 2007. [Online]. Available: http://www.ncbi.nlm.nih.gov/pubmed/18018689.
Strauser, K, Kazerooni, H. "The development and testing of a human machine interface for a mobile medical exoskeleton" in IEEE Int Conf, Intelligent Robots and Systems, San Francisco, CA. USA, Sep. 2011.
T. Yamada, Y. Hayamizu, Y. Yamamoto, Y. Yomogida, A. Izadi-Najafabadi, D. N. Futaba, and K. Hata, "A stretchable carbon nanotube strain sensor for human-motion detection." Nature nanotechnology, vol. 6, No. 5, pp. 296-301, May 2011. [Online] Available: http://www.ncbi.nlm.nih.gov/pubmed/21441912.

(56) References Cited

OTHER PUBLICATIONS

Walsh, C., Endo, K., Herr, H.A. Quasi-Passive Leg Exoskeleton for Load Carrying Augmentation. International Journal of Humanoid Robotics, Special Issue: Active Exoskeletons, 4(3): 487-506, 2007.

Y.L. Park, Active Modular Elastomer Sleeve for Soft Wearable Assistance Robots, Oct. 7-12, 2012, 8 pages.

Y.-L. Park, B.-r. Chen, and R. J. Wood, "Design and Fabrication of Soft Artificial Skin Using Embedded Microchannels and Liquid Conductors," IEEE Sensors Journal, vol. 12, No. 8, pp. 2711-2718, Aug. 2012. [Online]. Available: http://ieeexplore.ieee.org/lpdocs/epic03/wrapper.htm?arnumber=6203551.

Y.-L. Park, C. Majidi, R. K. Kramer, P. Bérard, and R. J. Wood, "Hyperelastic pressure sensing with a liquid-embedded elastomer," Journal of Micromechanics and Microengineering, vol. 20, No. 12, p. 125029, Dec. 2010. [Online]. Available: http://stacks.iop.org/0960-1317/20/i=12/a=125029?key=crossref. 84cffc44789ba7bde0bdfd169e25af91.

Zoss, A.B., Kazerooni and A. Chu, Biomechanical deign of the Berkeley lower extremity exoskeleton (BLEEX),. Mechatronics, IEE/ASME Transactions on, Apr. 2006. 11(2): p. 128-138.

Christina Isabelle Goodvin: Development of a Real-time Spinal Motion Inertial Measurement System for Vestibular Disorder Application, University of Victoria, date 2003, 155 pages.

Clevertex,: Development of a strategic Master Plan for the transformation of the traditional textile and clothing into a knowledge driven industrial sector by, date 2015, dated prior to Jul. 2014, 160 pages.

Gavriel Salvendy: Smart Clothing Technology and Applications, Human Factors and Ergonomics, © 2010 by Taylor and Francis Group, LLC, 290 pages.

H. R. Mattila, Intelligent textiles and clothing © 2006, Woodhead Publishing Limited, 525 pages.

H. R. Silva, J. A. Afonso, P. C. Morim, P. M. Oliveira, J. H. Correia: Wireless Hydrotherapy Smart-Suit Network for Posture Monitoring, Dated 2007, 5 pages.

International Search Report, PCT/EP03/12123, date of mailing Jun. 22, 2004; 8 pages.

Pedro Filipe Pereira da Fonseca: Validation of two types of textile electrodes for electrocardiography and electromyography measurement applications, dated Jul. 2012, 126 pages.

Peter T. Gibbs and H. Harry Asada: Wearable Conductive Fiber Sensors for Multi-Axis Human Joint Angle Measurements. Journal of NeuroEngineering and Rehabilitation, Mar. 2, 2005.

Sang Wook Lee and Hyung-Soon Park: Biomimetic Approach Enables Functional Movements of Hand Post Stroke: A Pilot Study, dated 2012, 2 pages.

Vladimir A. Kulyukin,: Advances in Human-Robot Interaction, Dec. 2009, 56 pages.

Yong-Lae Park, Bor-rong Chen, Diana Young, Leia Stirling, Robert J. Wood, Eugene Goldfield, and Radhika Nagpal: Bio-inspired Active Soft Orthotic Device for Ankle Foot Pathologies, 2011 IEEE/RSJ International Conference on Intelligent Robots and Systems, Sep. 25-30, 2011. San Francisco, CA, USA, 8 pages.

International Search Report, PCT/US2013/060225, date of mailing May 27, 2004, 2 pages.

International Written Opinion, PCT/US2013/060225, date of mailing May 27, 2004, 8 pages.

\* cited by examiner

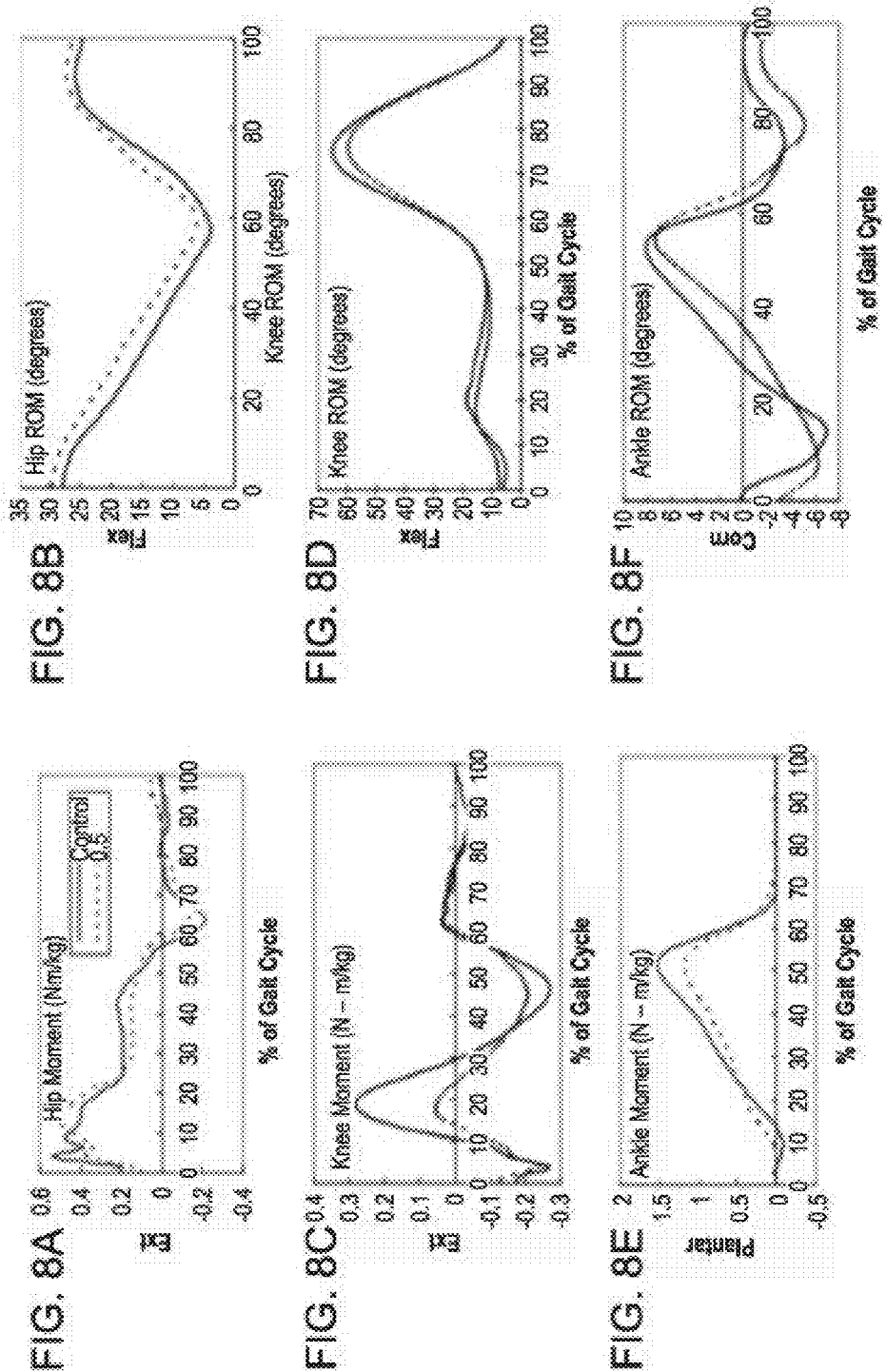

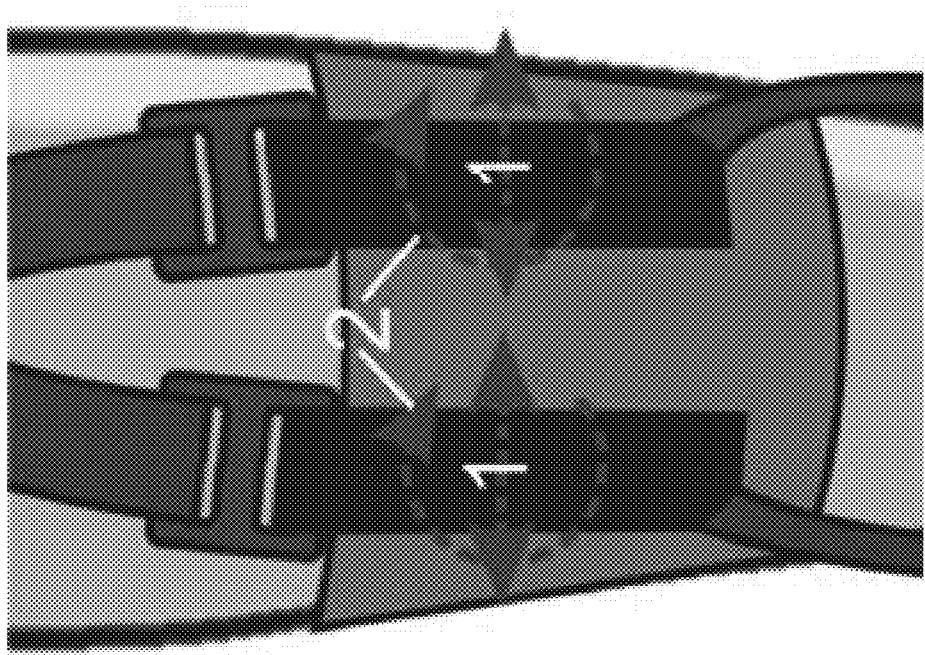
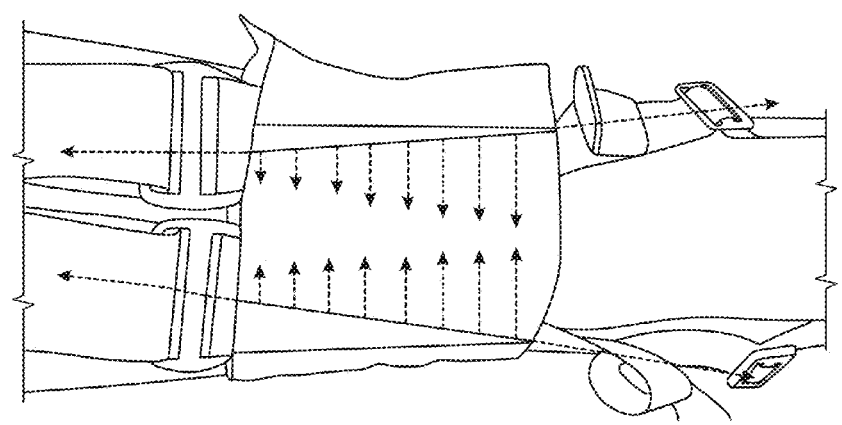
FIG. 20B
FIG. 20A

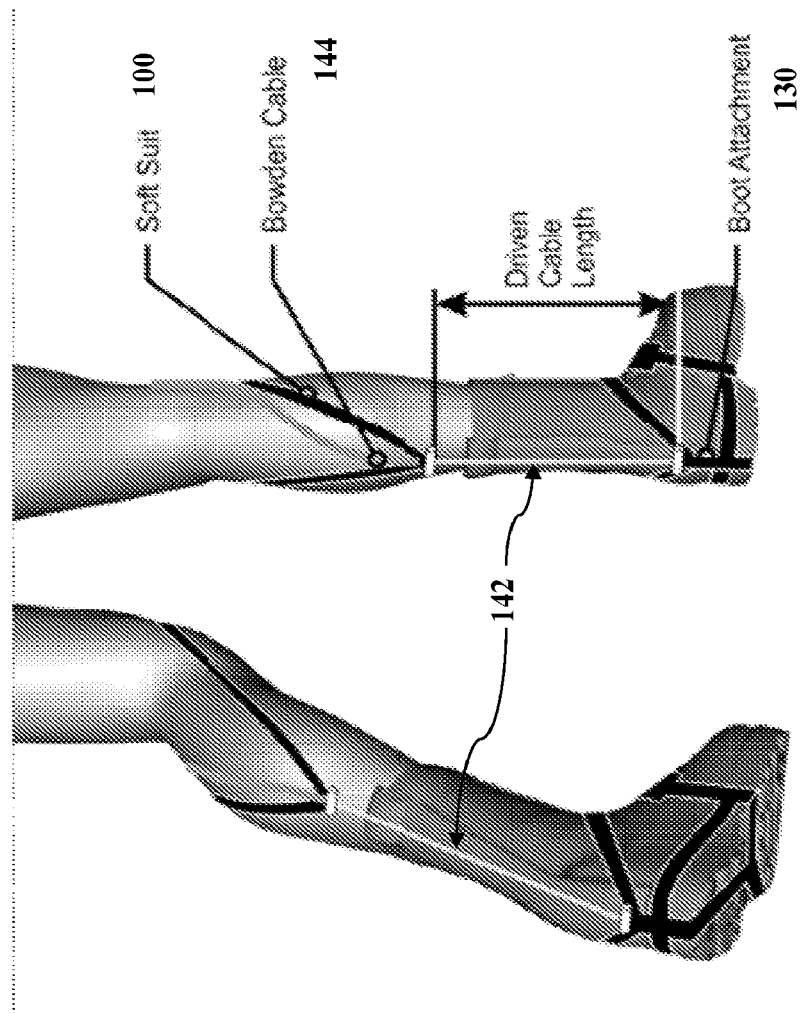
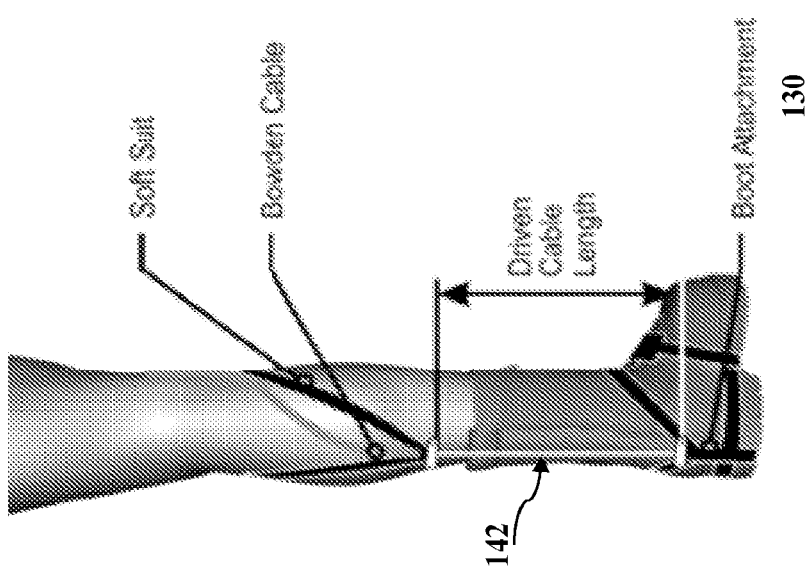
FIG. 22
FIG. 21

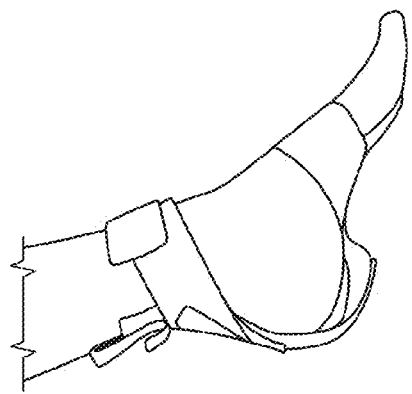
FIG. 26 D₃
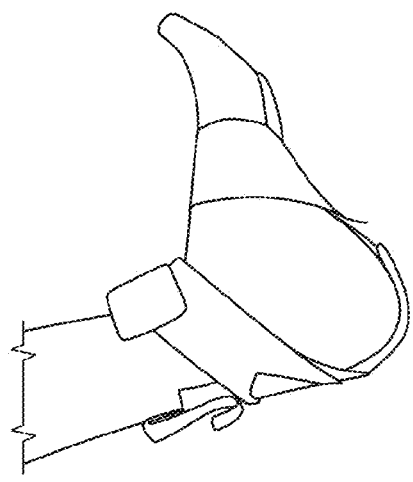
FIG. 26 D₂
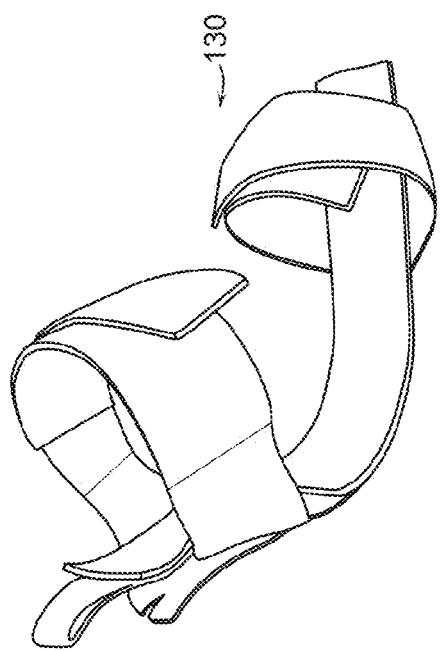
FIG. 26 D₅
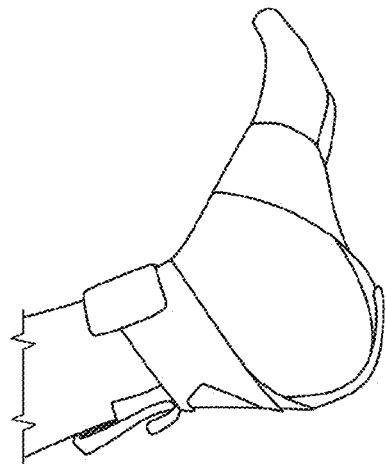
FIG. 26 D₁
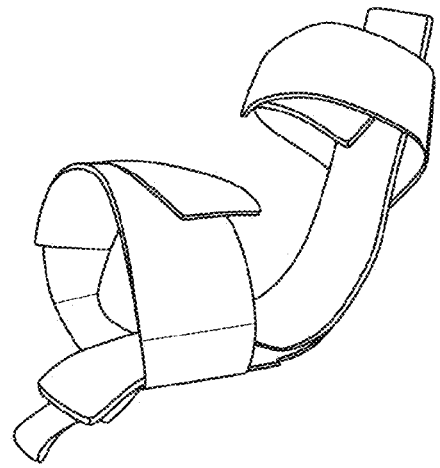
FIG. 26 D₄

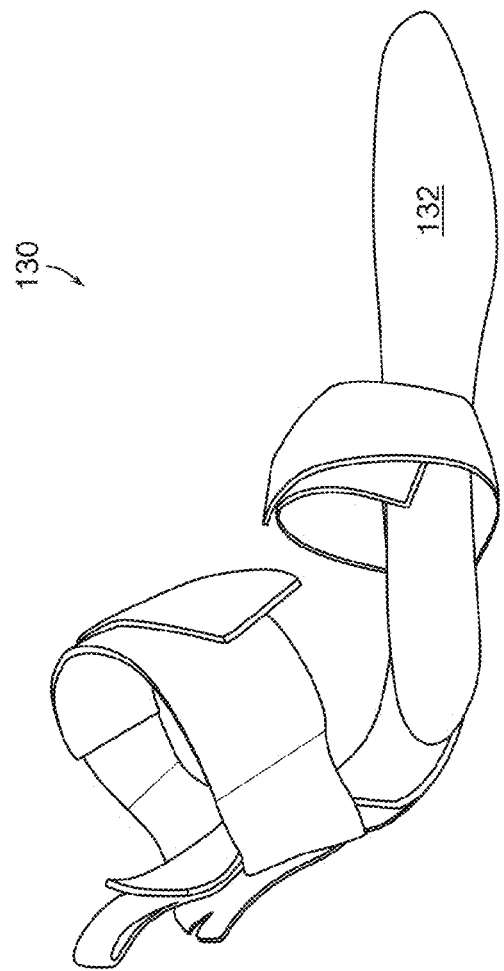
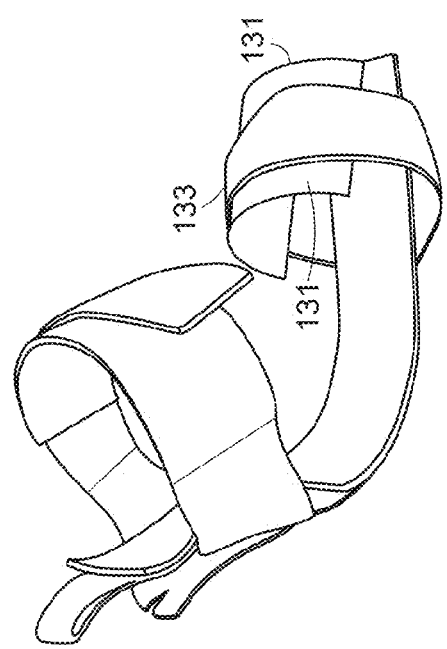

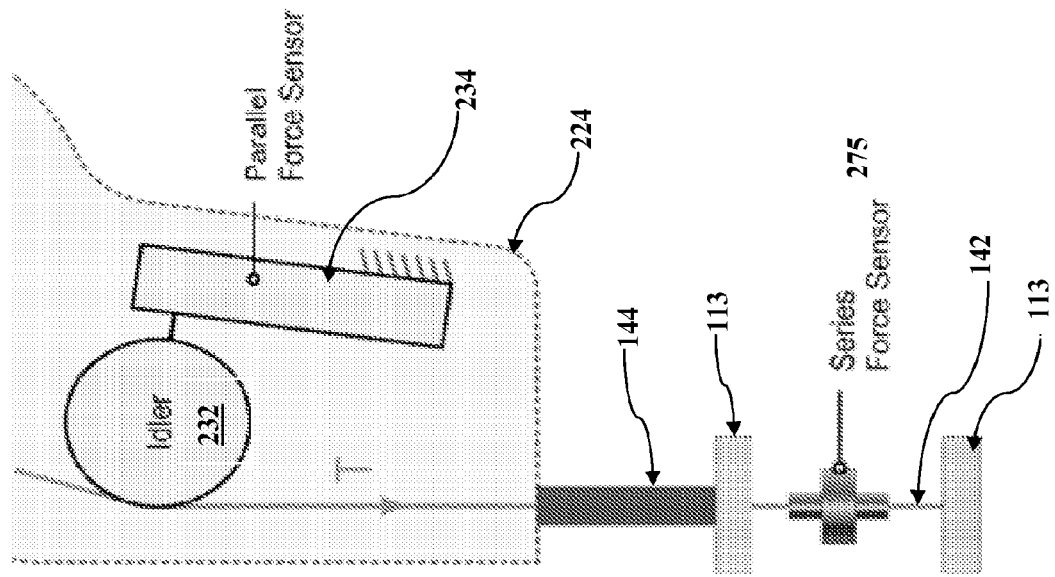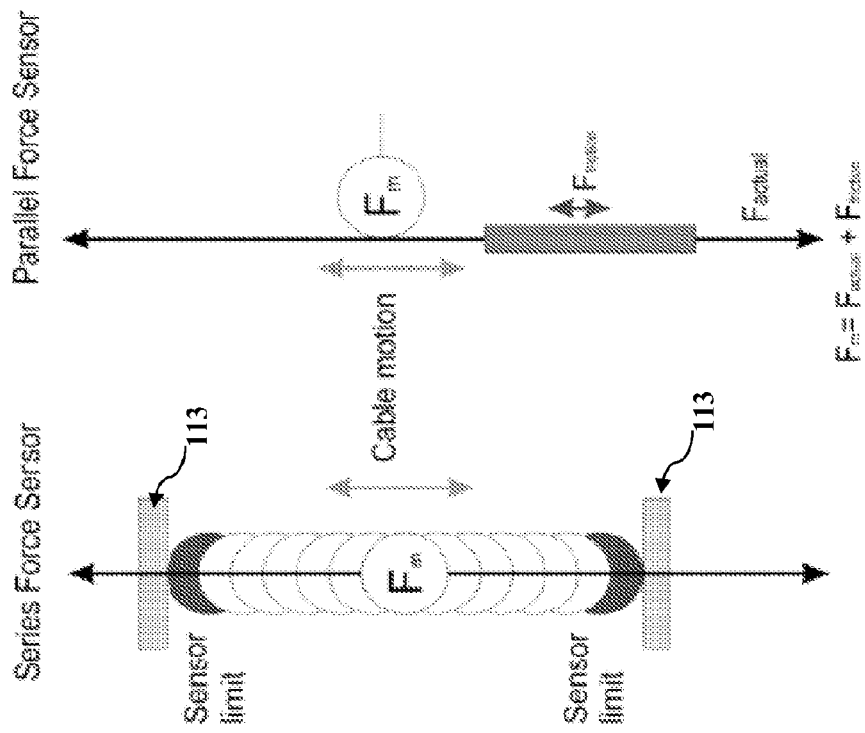
FIG. 39

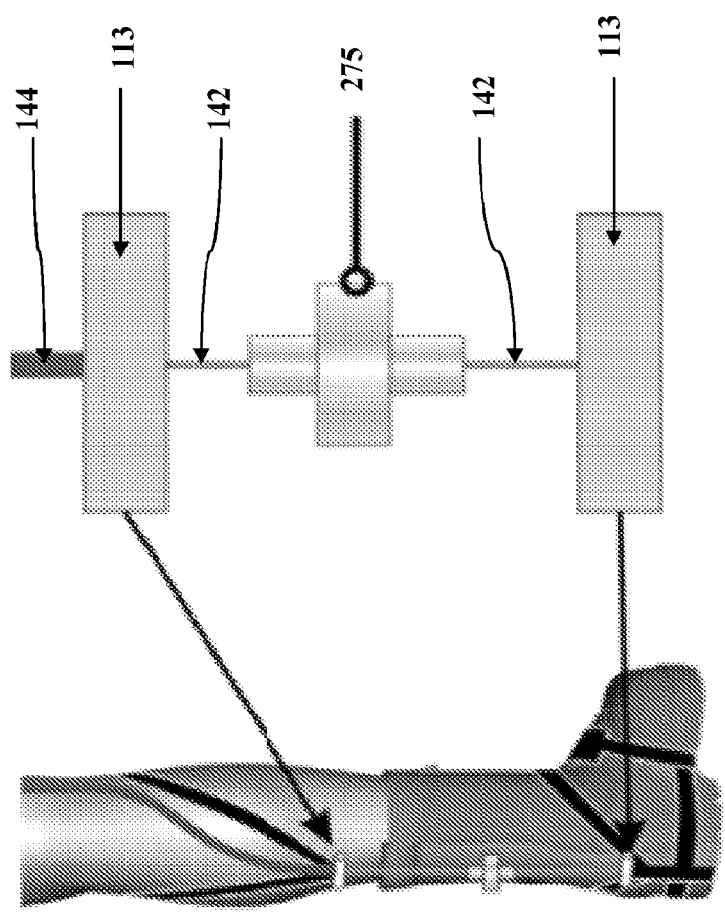

System efficiency: ~63%
Pulling force: 300N

- Ribbon speed: 0.35 m/s
- Cable travel: ~200mm
- $F_r$: ~110N
- $F_p$: 300Nm

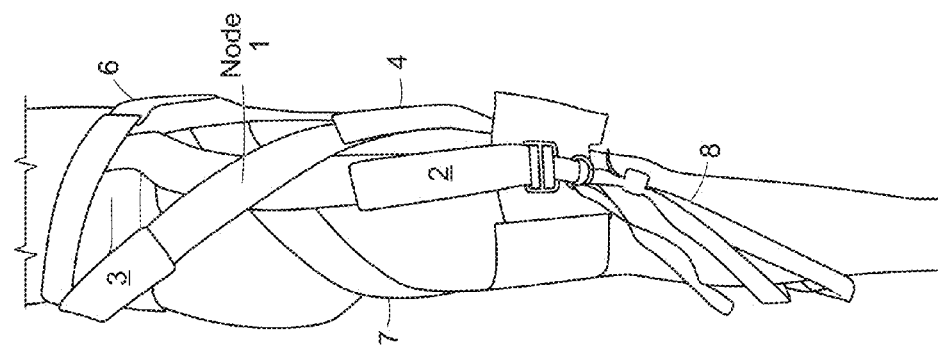
FIG. 44C (V3)
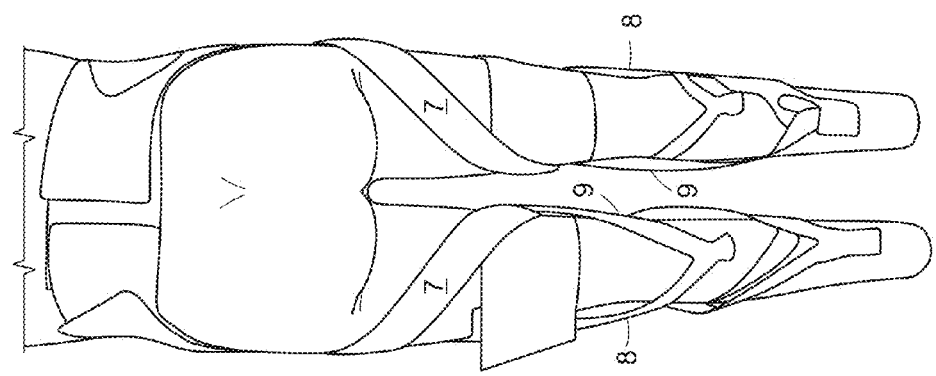
FIG. 44B (V3)
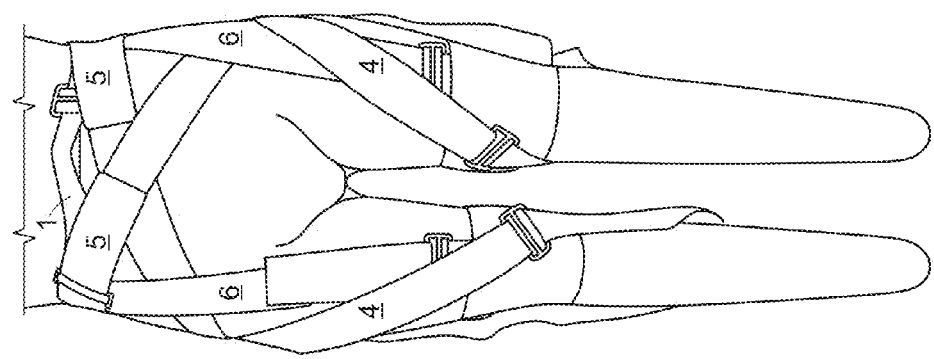
FIG. 44A (V3)

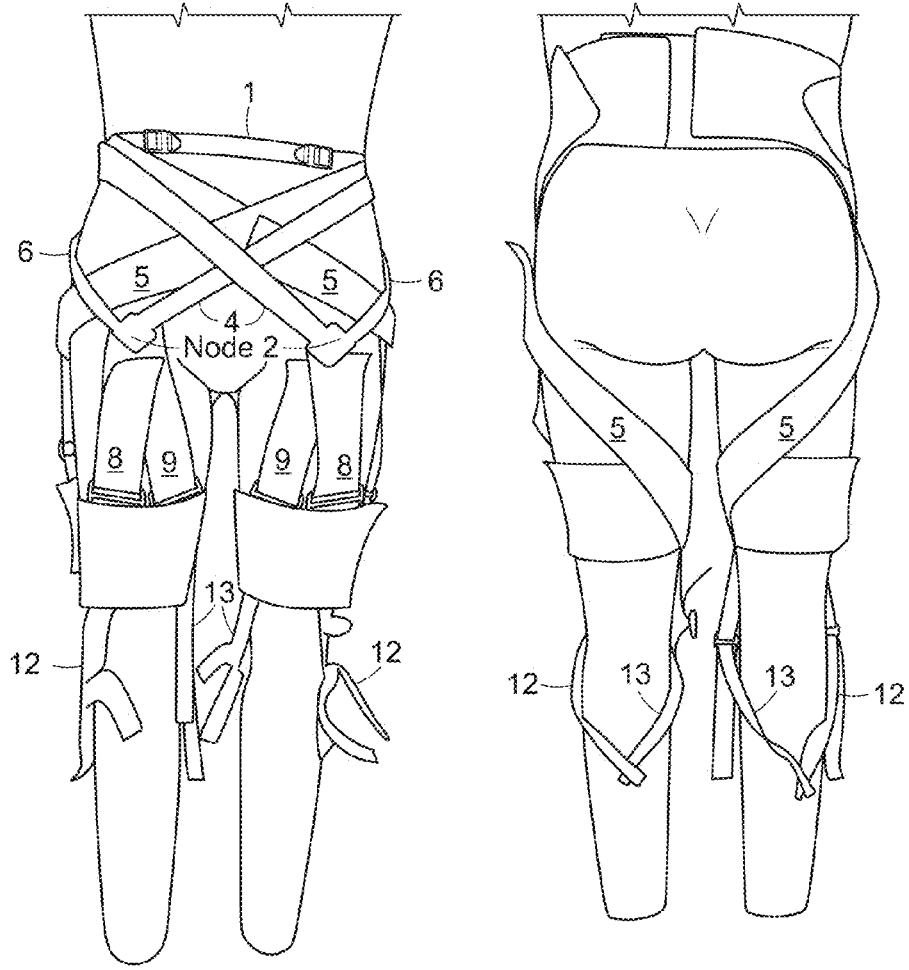
FIG. 45A (V4)    FIG. 45B (V4)

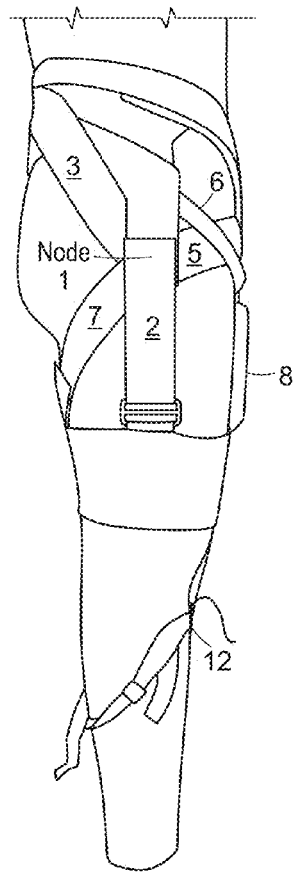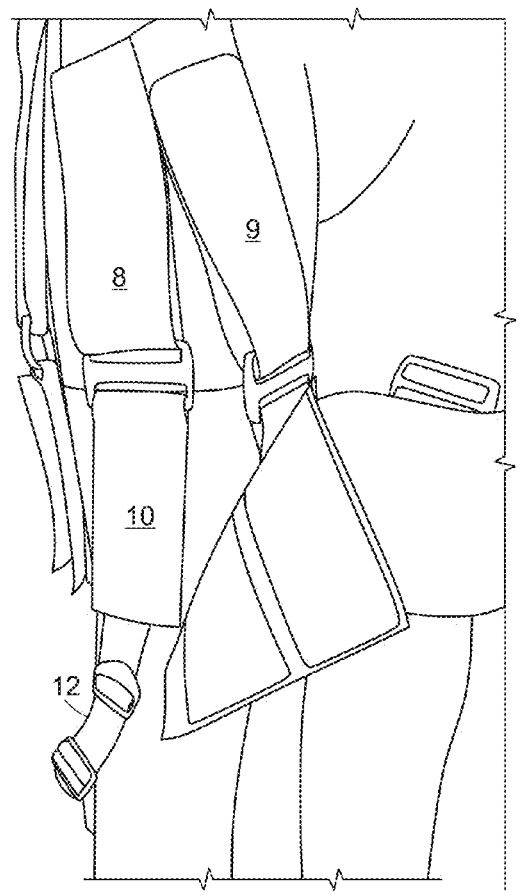
FIG. 45C (V4)    FIG. 45D (V4)

System Vital Stats

| Variable | V1 System | V2 System | V3 System |
|---|---|---|---|
| Maximum walking speed | 1.25 m/s = 2.8 mph | 1.5 m/s = 3.4 mph | 2 m/s = 4.5 mph |
| Total power draw | 59.2W | 59.2W | 50W |
| Duration with 2.5kg of batteries | 4.1 hours | 4.1 hours | 5.5 hours |
| Maximum force able to be delivered | 150N | 200N | 270N |
| Stiffness at 100N | 3500 N/m | 4000 N/m | 5000 N/m |

FIG. 47

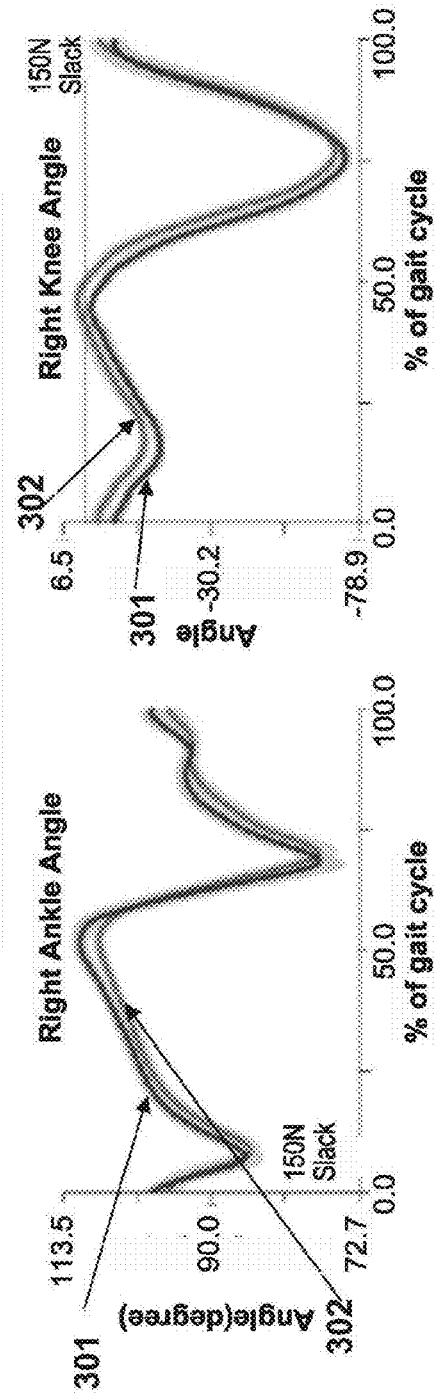
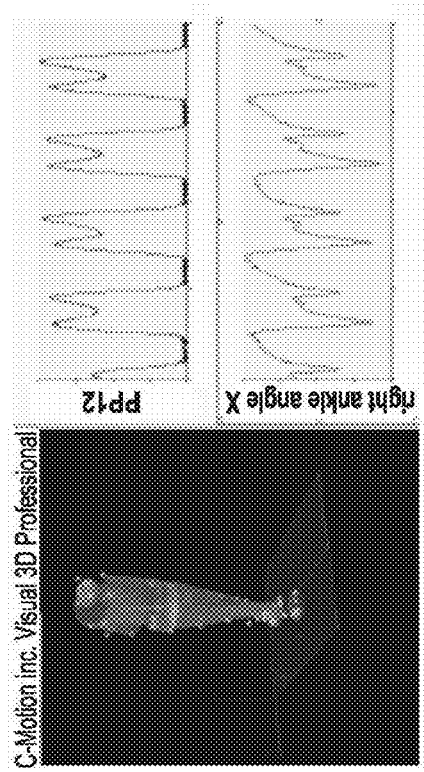
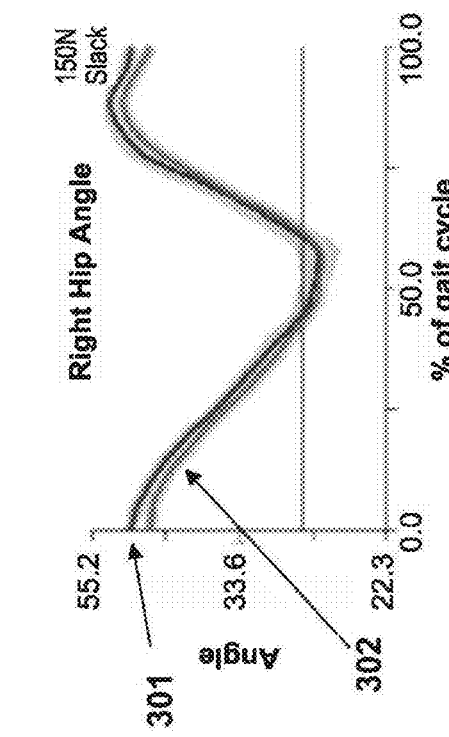
FIG. 49A, FIG. 49B, FIG. 49C, FIG. 49D, FIG. 49E

| Subject | Shock | Best Active | Reduction [W] | Reduction [%] |
|---|---|---|---|---|
| 1 | 710 W | 611 W | - 99 W | - 14 % |
| 2 | 530 W | 460 W | - 70 W | - 13 % |
| 3 | 600 W | 555 W | - 45 W | - 7.5 % |
| 4 | 550 W | 525 W | - 25 W | - 4.5 % |
| 5 | 580 W | 555 W | - 25 W | - 4 % |
| Average | | | - 53 W | - 9 % |

Metabolic Power (joint)
Joint Active Power @1.25 m/s
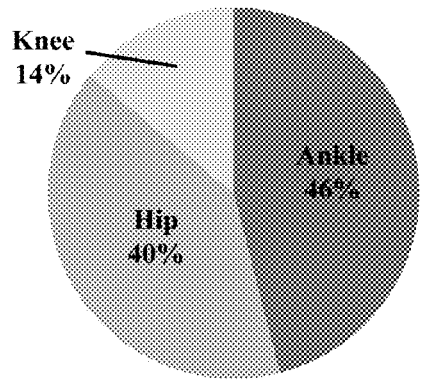
Suit Metabolic Benefit @1.25 m/s
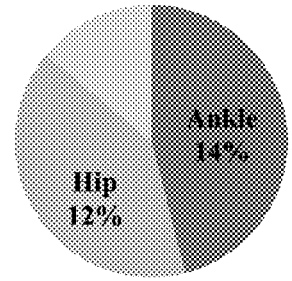
FIG. 52A
FIG. 52B
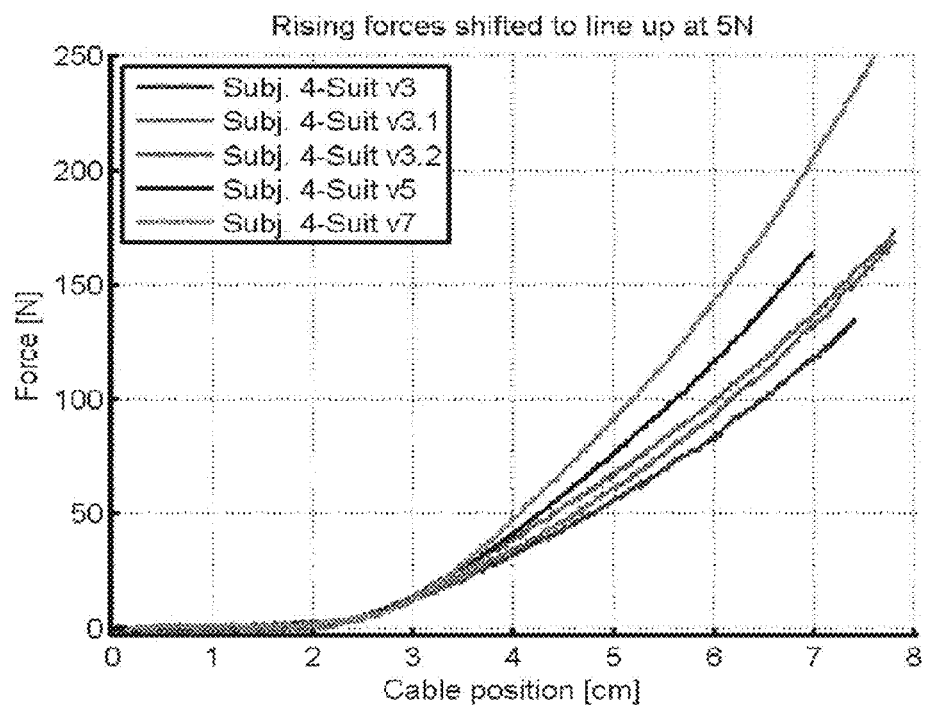
FIG. 53

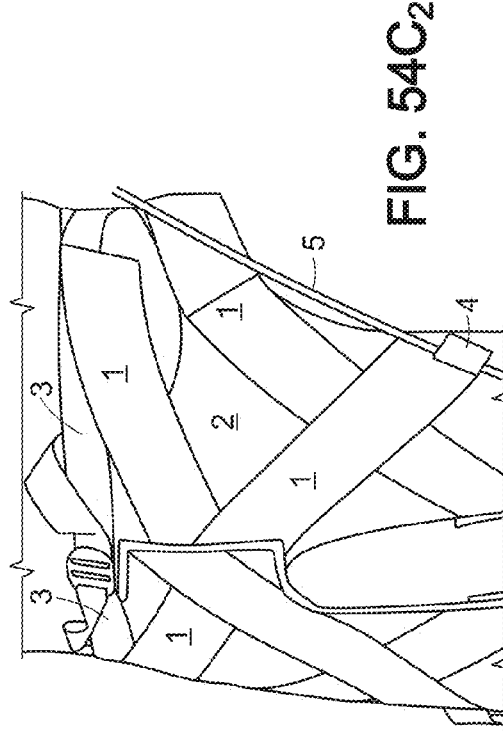
FIG. 54C₁
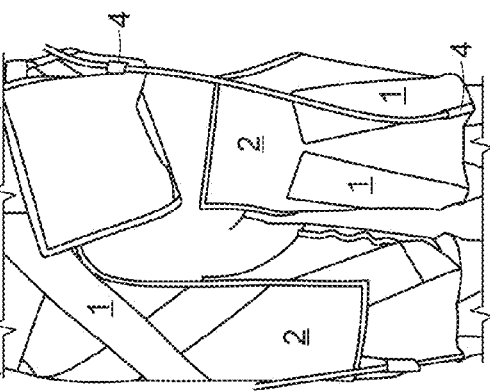
FIG. 54C₂
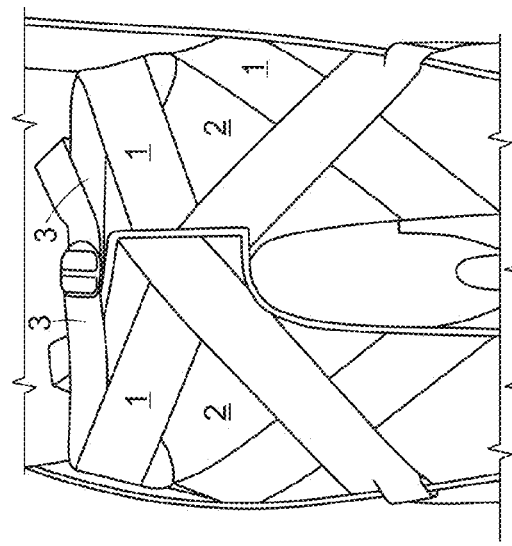
FIG. 54C₃
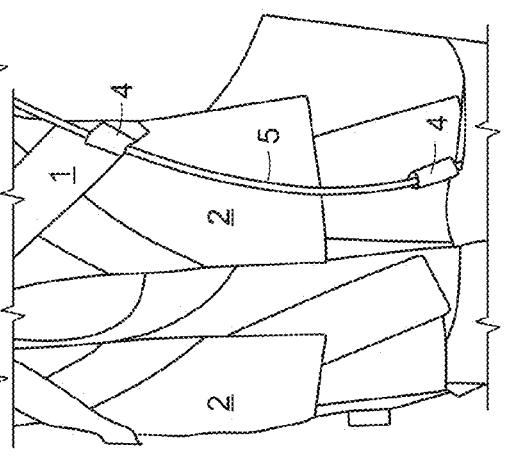
FIG. 54C₄

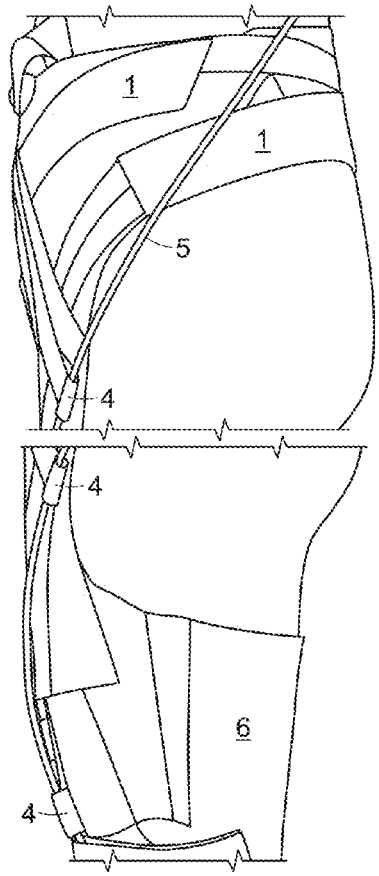
FIG. 54D₁
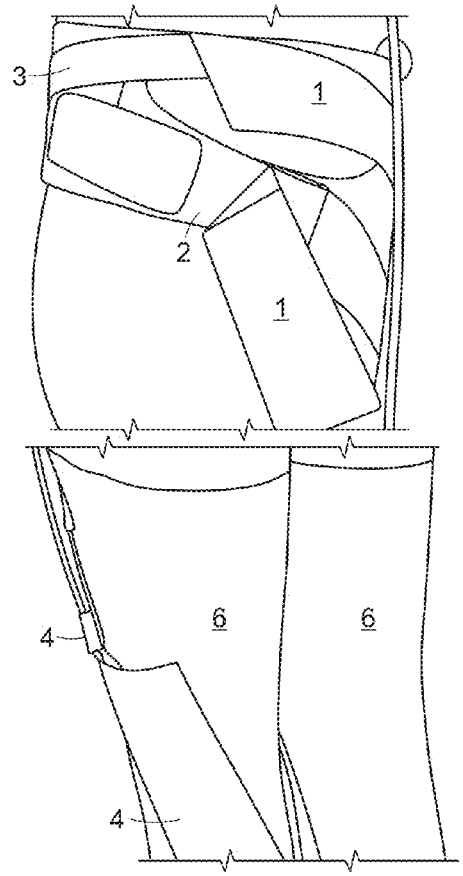
FIG. 54D₂
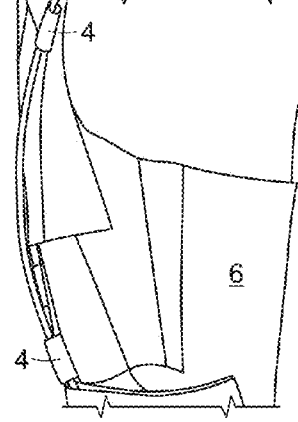
FIG. 54D₃
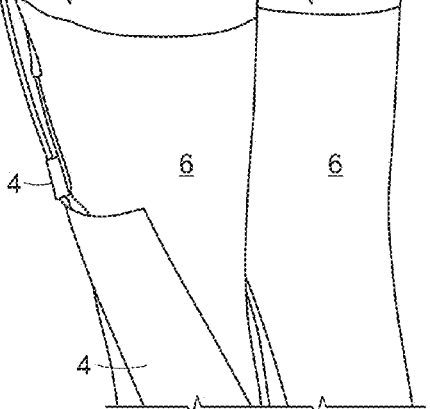
FIG. 54D₄

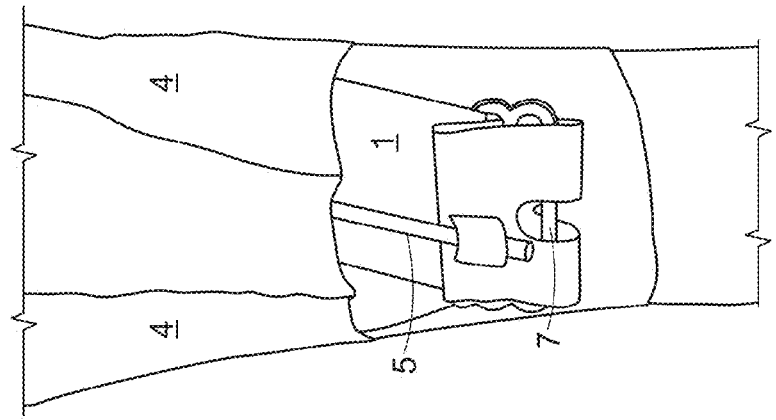
FIG. 54E₃
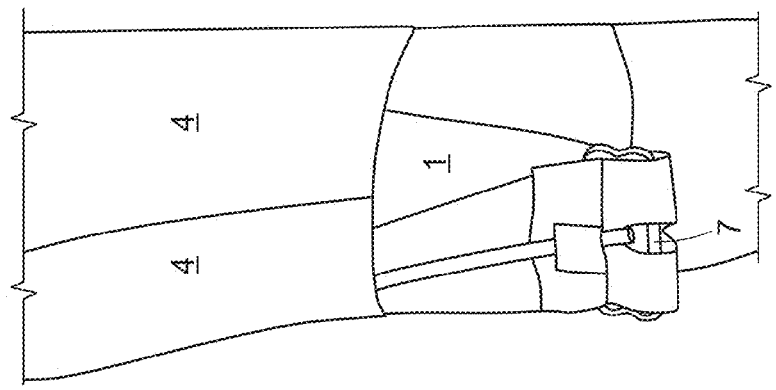
FIG. 54E₂
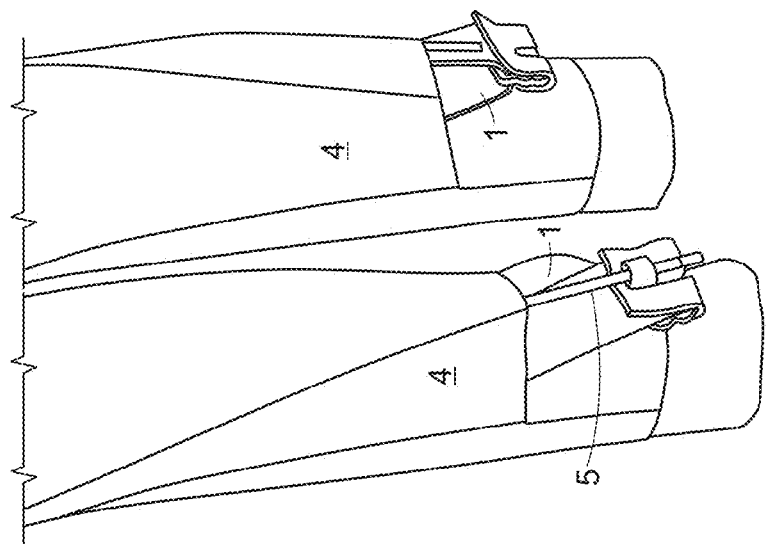
FIG. 54E₁

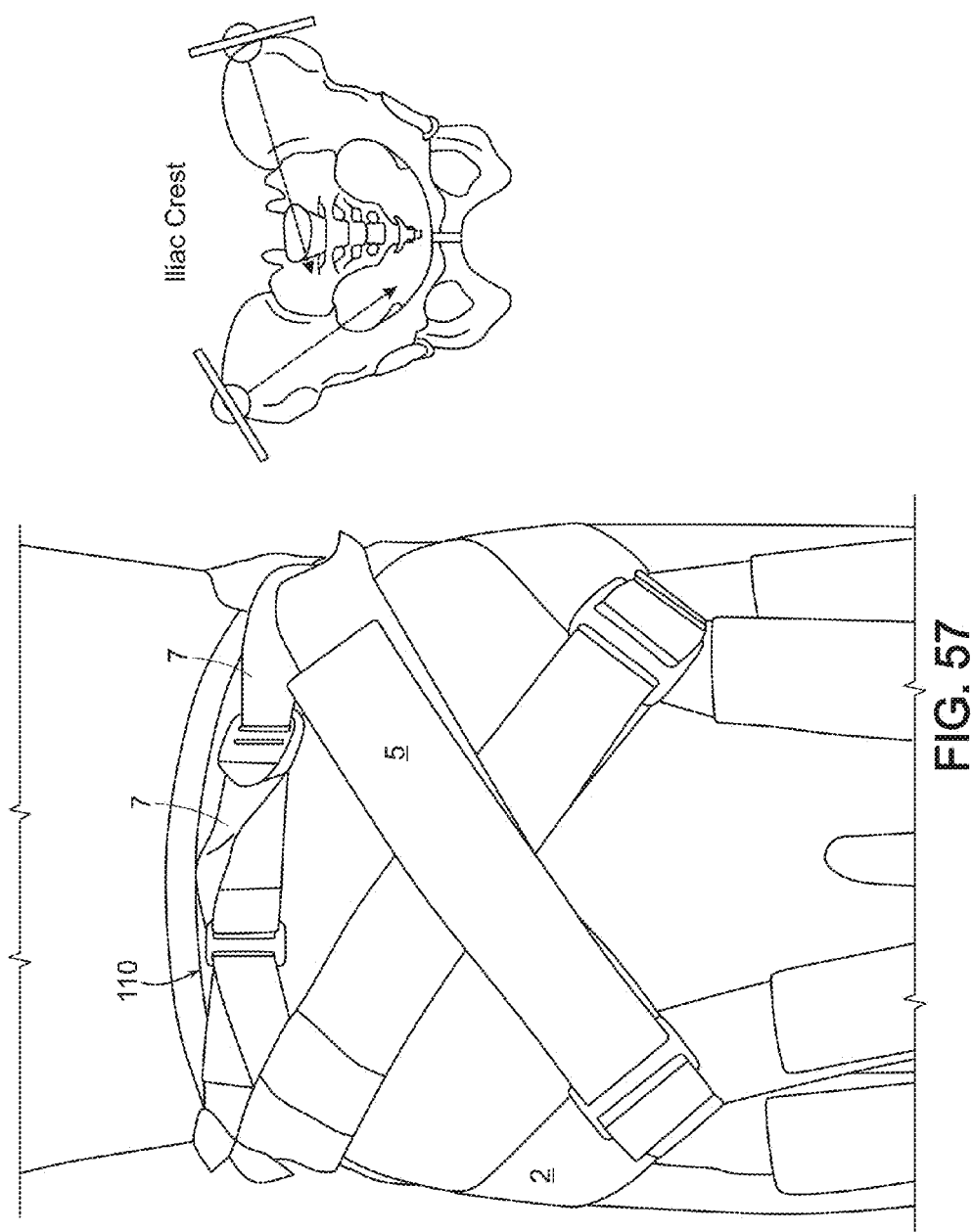

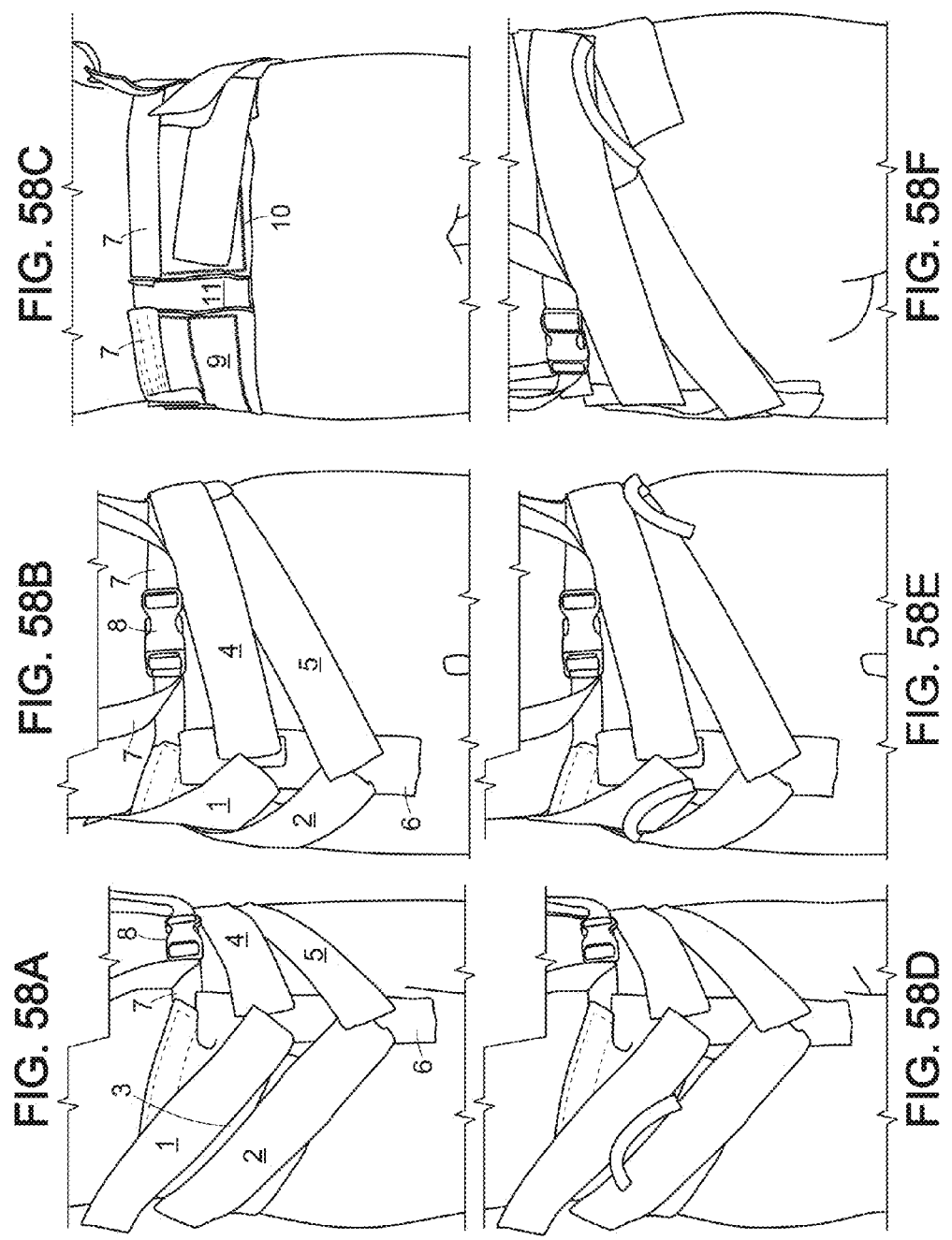

Front    Back

Front    Back

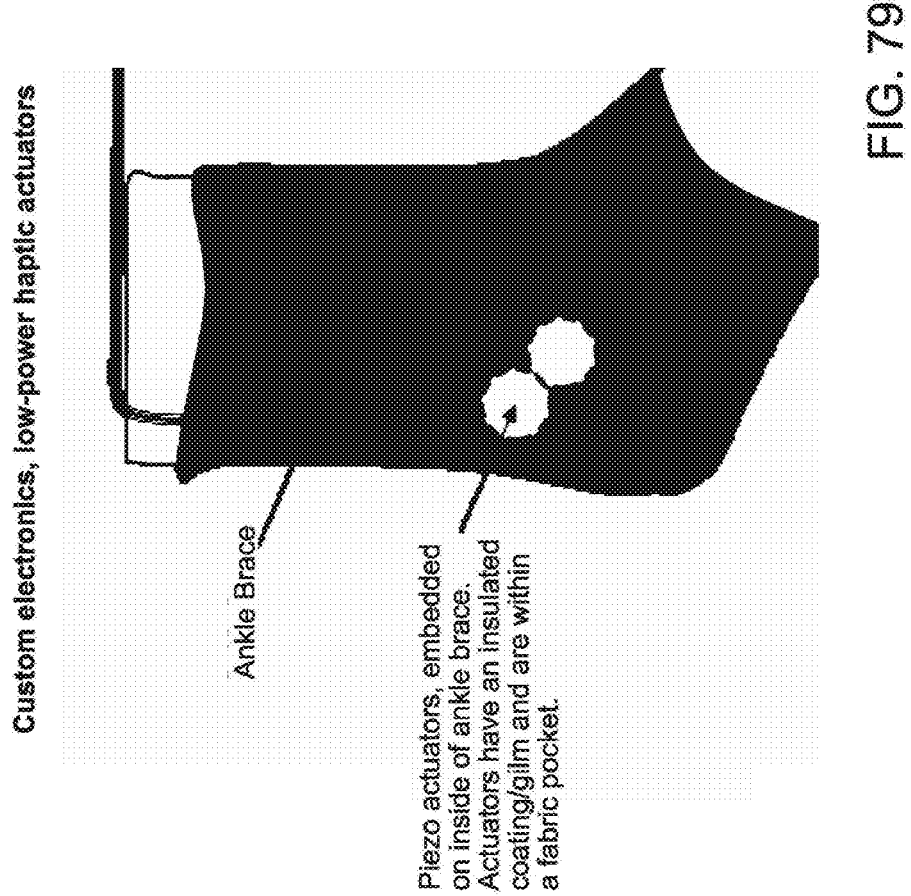

SOFT EXOSUIT FOR ASSISTANCE WITH HUMAN MOTION

CROSS-REFERENCE TO RELATED APPLICATIONS

The present application is a U.S. national stage under 35 U.S.C. §371 of International Patent Application No. PCT/US2013/060225, filed on Sep. 17, 2013 which claims priority to, and incorporates by reference in its entirety, U.S. Provisional Patent Application Ser. No. 61/701,970, titled "Soft Wearable Motion Sensing Suit for Lower Limb Biomechanics Measurements," filed on Sep. 17, 2012, U.S. Provisional Patent Application Ser. No. 61/829,686, titled "Method and System for Assisted Motion," filed on May 31, 2013, and U.S. Provisional Patent Application Ser. No. 61/873,433, titled "Soft Exosuit for Assistance with Human Motion," filed on Sep. 4, 2013.

STATEMENT REGARDING FEDERALLY SPONSORED RESEARCH

Some aspects of the present disclosure were made with government support, under Grant No. W911QX-12-C-0084 awarded by the U.S. Army, and the government shares rights to such aspects of the present disclosure.

Some aspects of this present disclosure were made with government support, under NSF Grant No. CNS-0932015 awarded by the National Science Foundation, and the government shares rights to such aspects of the present disclosure.

TECHNICAL FIELD OF THE INVENTION

The present concepts are generally directed to methods and systems for assisted motion in humans and, more particularly, to methods and systems for providing assistance with motion and reducing the energy expending during motion (e.g., walking) by passively and/or actively adding assistive energy to one or more movements.

BACKGROUND OF THE INVENTION

Prior art systems for assisted motion utilize exoskeletons, comprising rigid components (e.g., linkages) and joints (e.g., pin joint), attached to the user's body with the exoskeleton joint(s) being disposed to have an axis of rotation ideally collinear with a natural axis of rotation for adjacent joint(s). Exemplary prior art exoskeletons are shown in US Published Patent Application Nos. 2007/0123997 and 2011/0040216, both to Herr et al., and both of which are incorporated by reference herein in their entirety. Such rigid exoskeletons provide the ability to replace human movements that have been lost or severely compromised and are accordingly designed to enhance the user's stability, balance and safety. Other rigid exoskeletons serve as a platform to provide physical therapy sessions in a clinical environment, such as in a physical therapy clinic, or serve to assist able-bodied users to perform tasks more easily or for longer duration.

However, these rigid exoskeletons rely on rigid frameworks of linkages, coupled to the body at select locations via pads, straps, or other interface techniques. As the user flexes or extends their limbs, these rigid links move in parallel with the limb, adding considerable inertia to movement which must be overcome by motors or by the user. Though great effort has been made to reduce the weight and profile of these devices, they still cause considerable restriction to the user's motion and, in particular, add considerable impedance to the natural dynamics and kinematics of gait. This change to the normal kinematics of walking is one reason why these exoskeleton systems do not reduce the metabolic power required for locomotion. The rigid links also cause difficulty, particularly at the extremes of motion, because the pin-joints of the exoskeleton do not precisely match with the axes of the human joints, which move through intricate three dimensional paths. This causes misalignment of up to 10 cm during normal movement, causing pain and even injury to users. One solution has been to include redundant, passive degrees of freedom to allow the exoskeleton to travel and deform in key areas for wearer motion, however, this adds further weight to the systems.

SUMMARY OF THE INVENTION

The present concepts are directed to methods, systems, and devices configured to assist movements of a user, and more particularly to methods, systems, and devices relating to a soft exosuit comprising a plurality of non-extensible or semi-extensible elements flexible connection elements (e.g., webbing, straps, cords, functional textile, wires, cables, composites or combinations thereof, etc.), disposed between a plurality of anchor points or anchor areas (e.g., iliac crests, shoulders, thigh, ankle, calf, etc.), and one or more actuators adapted to selectively create tension in selected flexible members at times at which the transmitted forces to specific limbs or body parts would be beneficial to movement of the specific limbs or body parts. The soft exosuit, as described herein, generally refers to and includes a wearable device utilizing flexible connection elements to provide assistive forces to at least one limb (e.g., a leg) or portion of a limb (e.g., a foot). In some aspects, the soft exosuit utilizes flexible connection elements to provide assistive forces to a plurality of limbs (e.g., two legs) or a plurality of portions of one or more limbs (e.g., two feet). It at least some aspects, apart from actuating one or more joints in opposite legs or opposite arms to facilitate motions wherein the limbs move in different directions at different times (e.g., walking), the present concepts also include actuating more than one limb at one time and includes, for example, coupling legs to each other, coupling leg and arm movement (same side or opposite side), coupling arm movement, or coupling other body movements to exploit potentially synergetic movements.

As compared to the prior art rigid exoskeletons, the soft exosuit is lighter, more comfortable to wear and permits a more complete, and more natural, range of joint(s) motion(s), while still being able to transfer forces or torques able to beneficially assist motion. In accord with the present concepts, the flexible connection elements can optionally be used in combination with rigid or semi-rigid connection elements and it is not necessary that all connection elements be flexible.

In at least some aspects of the present concepts, a wearable soft exosuit includes a first anchor element configured for positioning at or near a first body part of a person wearing the wearable soft exosuit and a second anchor element configured for positioning at or near a second body part of a person wearing the wearable soft exosuit. The soft exosuit also includes a plurality of connection elements extending between the first anchor element and the second anchor element, and at least one of the plurality of connection elements spanning at least one joint disposed between the first anchor element and the second anchor element, at least one actuator and at least one controller configured to actuate the at least one actuator at a predetermined time during movement of the at least one joint to generate a beneficial moment about the at least one joint.

In at least some other aspects of the present concepts, a system for generating force about one or more joints includes a soft exosuit comprising a plurality of anchor elements and a plurality of connection elements disposed between the plurality of anchor elements, at least one sensor to determine a force in at least one of the plurality of connection elements or at least one of the plurality of anchor elements and to output signals relating to the force, at least one actuator configured to change a tension in the soft exosuit and at least one controller configured to receive the signals output from the at least one sensor and actuate the at least one actuator responsive to the received signals.

In at least some aspects, the soft exosuit connection elements are disposed in a wearable matrix defining a plurality of nodes, points or regions at which a plurality of connection elements are interconnected, and are connected directly or indirectly to a plurality of anchor points. The forces on a node are controlled in part by the configuration of connection elements (e.g., number of connection elements interconnected at the node, the relative angles of each of the connection elements interconnected at the node, etc.) and the applied forces along each of those constituent connection elements. During motion, soft exosuit actuator(s) selectively apply tensile forces along the connection elements to selected node(s) and/or anchor point(s). As a result of the applied tension, moment forces are created in one or more joints. When these moments are in the same direction as the natural moments created by the musculature, these moments are considered beneficial moments and assist with motion (and/or absorb power), requiring less energy from the user and reducing the metabolic cost of the motion.

The magnitude and direction of the moment applied by the actuator(s) and associated connection elements at each joint are determined based on the location of the connection elements relative to an axis of rotation of the joint. The magnitude of the moment can be determined based on the offset of the tension forces relative to the axis of rotation of the joint, such offset being affected by the user's natural body structures (e.g., muscle, fat, etc.), clothing (e.g., boots), and intermediary elements (e.g., anchor elements connecting the anchor point to a connecting element). The soft exosuit is configured, in at least some aspects, to advantageously reduce moments that are not beneficial by disposing connecting elements to symmetrically pass on both sides of a joint, thereby applying substantially balanced forces to each side of the joint. The soft exosuit can still further reduce undesirable moments by configuring the soft exosuit flexible elements pass as close as possible to, if not overlying, the joint's axis of rotation. Elements in the soft exosuit that resist extension can prevent a point (e.g., a node or another point) on the soft exosuit from moving in the direction which would cause the element to extend. Placing several such elements around a point (e.g., node) on the soft exosuit can restrain that point (e.g., node) from moving despite a number of different force vectors acting thereupon, thereby limiting movement of that point with respect to the body.

In at least some aspects, the soft exosuit comprises a control system configured to monitor one or more parameters (e.g., a resultant stiffness of the soft exosuit, joint angles, heel strikes, etc.), and preferably a plurality of parameters, to guide the application of forces from one or more actuators to selected flexible connection elements. The applied forces can be applied intermittently as appropriate to the movement to be assisted, the level of force required, comfort and/or performance.

In at least some aspects, the stiffness of the soft exosuit, and therefore the ability of the soft exosuit to produce resulting tension changes, is a variable that is influenced by many different factors such as, but not limited to, degree of adaptation of the soft exosuit to a user's anatomy (e.g., placement of nodes relative to joints, etc.), the soft exosuit material(s), the soft exosuit element configuration stiffness (e.g., disposition of nodes and anchor points), and the user's body stiffness (e.g., a user's body stiffness is higher if the user's muscles are tensed, rather than relaxed). By way of example, a stiffness of the soft exosuit can be selectively enhanced through the use of non-extensible or semi-extensible element(s) across a joint. As a further example, in at least one aspect, such enhancement of stiffness through the use of non-extensible or semi-extensible element(s) across a joint is preferentially on only one side of the joint rather than both sides of the joint so that, when the joint is at its point of maximum flexion or extension, as a result, the soft exosuit becomes tenser as a result of the body's configuration but slack during other configurations, when the joint is not at its position of maximum flexion or extension. In yet other aspects, the soft exosuit is tensioned using a multi-articular system configured to create tension across multiple joints due to the combined motion of those joints. Suit pre-tension can be used to increase the resulting tension force in the overall system and may be achieved by, for example, tensioning (e.g., passively or actively changing the length of prior to use and/or during use) soft exosuit connection elements between nodes and/or anchor points (e.g., between the hip/ground and the thigh conical section) or by reducing the overall length of the connection elements between nodes and/or anchor points.

In accord with at least some aspects of the present concepts, the actuator(s) can provide a position or force profile which, in conjunction with the soft exosuit and body position at a time of actuation(s), provides a desired tension, stiffness and moment about a selected joint or joints. The control system is configured to use the actuator(s) to selectively tension the constituent parts of the soft exosuit, such as nodes and connection members. In one aspect, this tensioning is used to dynamically and instantly change a tension of the system across one or more joints. In one aspect, this tensioning may be applied (e.g., an auto tension function) to adjust the soft exosuit performance, comfort and fit by measuring the force and displacement of the actuator unit(s) to identify the most effective exosuit stiffness at a particular moment and/or at a particular point in gait (e.g., while walking or running) or stance (e.g., standing).

In general, the disclosed soft exosuit is configured to provide assistance to motion of a user. This motion-based assistance is not limited to walking or running, as are featured predominantly in the embodiments described herein. Rather, the motion-based assistance disclosed herein broadly relates to any movement-based assistance, which may include, for example, assistance with motion of any one or more body parts relative to another body part including, for example, movement of only one limb (e.g., one arm relative to the torso, one leg relative to the hip, or one foot relative to the corresponding leg), a plurality of limbs (e.g., two arms relative to the torso, two legs relative to the hip, one arm relative to the torso and one leg relative to the hip, etc.), the head and/or the torso. By way of example, an upper-body embodiment of the soft exosuit can be advantageously utilized by a wheel-chair bound individual to assist with locomotion.

In one implementation, the soft exosuit can be used to assist the motion of a person walking with or without a load, with such assistance providing a beneficial reduction in the metabolic consumption of energy by the user and reducing the loading on the soft tissue across the joints (e.g., ligaments, muscles and tendons), thus also reducing the risk of injury and/or exacerbation of existing injuries or preexisting conditions. This can be particularly advantageous to a soldier walking with a load. In yet other implementations, the soft exosuit disclosed herein can be used by injured, disabled and elderly people to increase mobility and/or reduce fatigue (e.g., walking, upper body mobility, rotational movements, pivoting movements, etc.).

In at least some aspects of the present concepts, the soft exosuit is passive and is configured to generate forces about one or more joints (e.g., the hip, etc.) without the use of an actuator. In such a passive soft exosuit, the soft exosuit includes an upper anchor element and a plurality of lower anchor elements and a plurality of at least substantially inextensible connection elements disposed between the upper anchor element and the plurality of lower anchor elements and disposed along paths that transmit force, wherein the connection elements are configured to provide a restorative torque to the hip to bias the thighs toward a neutral position. The suit acts in parallel with the muscles to reduce the extension torques required by the body.

In addition to motion-based assistance, the soft exosuit may be further utilized for motion assessment, rehabilitation or gait assistance activities, and movement training such as by providing resistance instead of assistance (e.g., to strengthen muscles, to provide negative feedback for improper movement, etc.) or by providing corrective assistance where needed to assist with training (e.g. golf-swing training, tennis training, etc.).

Yet further, the soft exosuit can be used by healthy people engaged in activities for which motion-based assistance is desired, inclusive of personal activities (e.g., hiking, climbing, biking, walking, kayaking, canoeing, skiing, etc.) or work activities (e.g., construction work, refuse collection, freight handling, lawn care, first responders, etc.). Moreover, depending on the activity, the weight of and positioning of the actuators and/or power supply, and type of power supply, may also be varied in accord with the changing design envelope.

These and other capabilities of the soft exosuit are more fully described below.

BRIEF DESCRIPTION OF THE FIGURES

FIGS. 8A-8F shows plots (left side) showing hip, knee and ankle moments generated as a percent of gait cycle and (right side) showing hip, knee and ankle range of motion generated with respect to percent of gait cycle.

FIGS. 20A-20B show, respectively, a representation of forces along the thigh brace of a soft exosuit and adjustments that may be made to (1) the location and (2) the angle at which connecting elements exit the thigh brace according to at least some aspects of the present concepts.

FIG. 21 shows a view of a T-connection in the lower portion of a soft exosuit according to at least some aspects of the present concepts.

FIG. 22 shows a rear view diagram of attachment members (T-connectors) connecting the boots to calf strap of a soft exosuit according to at least some aspects of the present concepts.

FIGS. $26D_1$-$26D_5$ show views of one embodiment of soft exosuit footwear attachment according to at least some aspects of the present concepts.

Figure 26A:
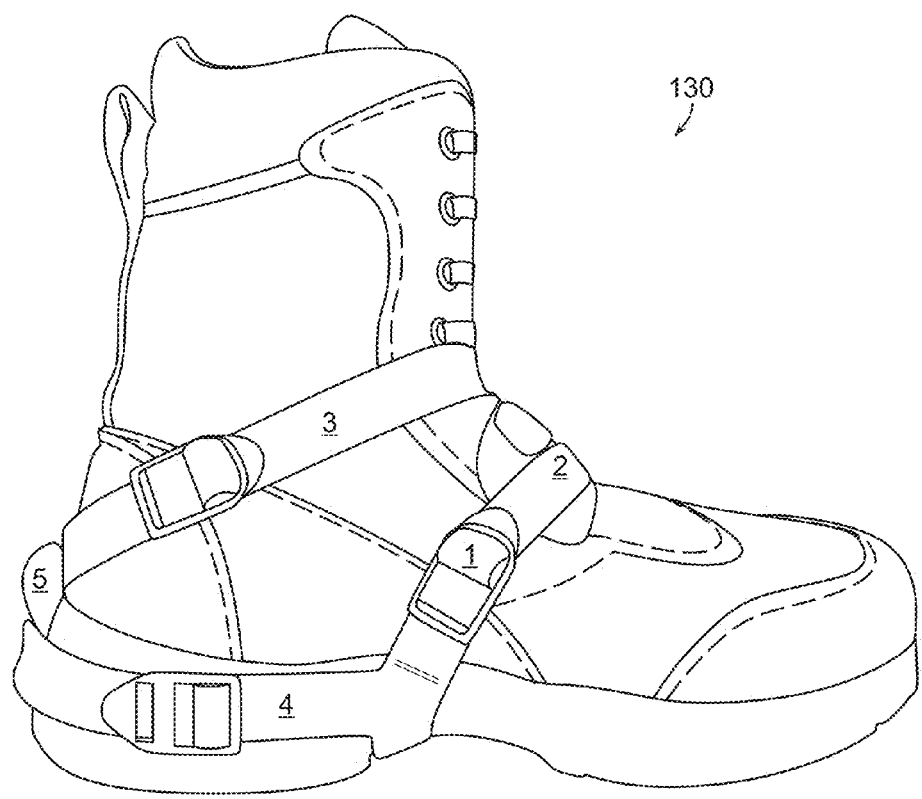
FIGS. 26A-26C show one embodiment of soft exosuit footwear attachment according to at least some aspects of the present concepts.
Figure 26C:
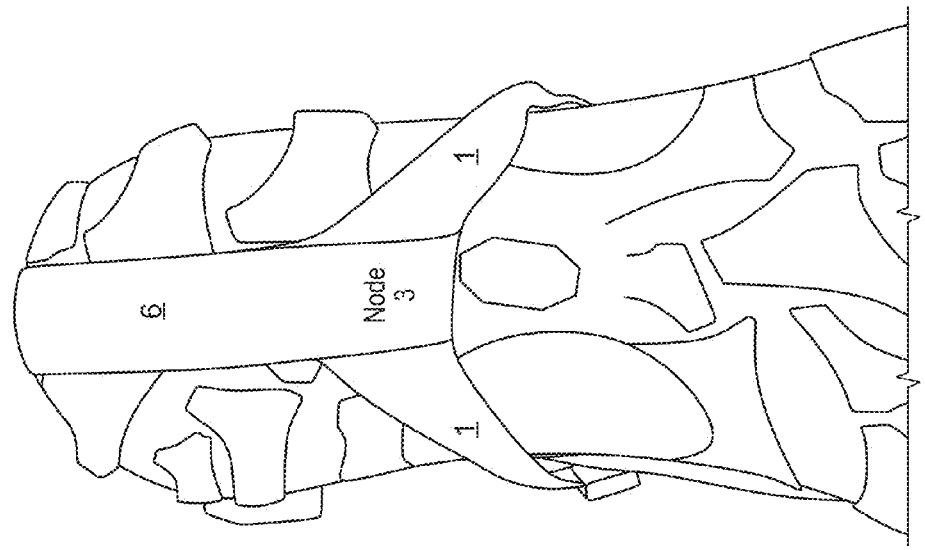
Figure 26B:
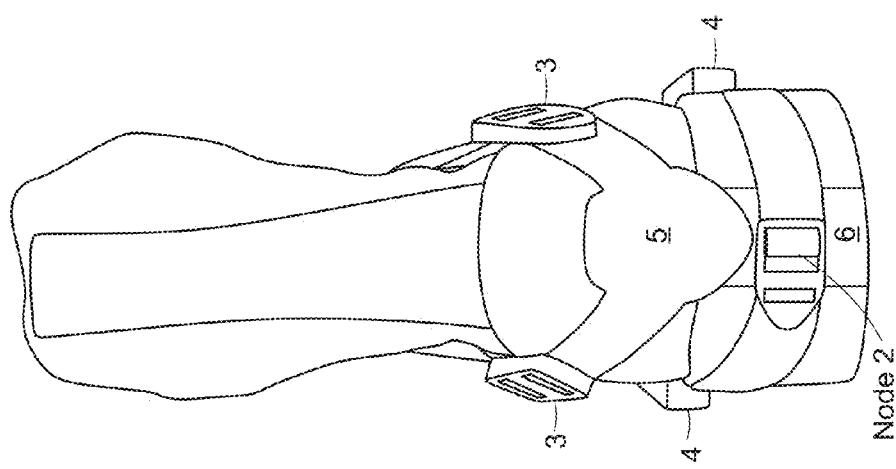
Figure 26E:
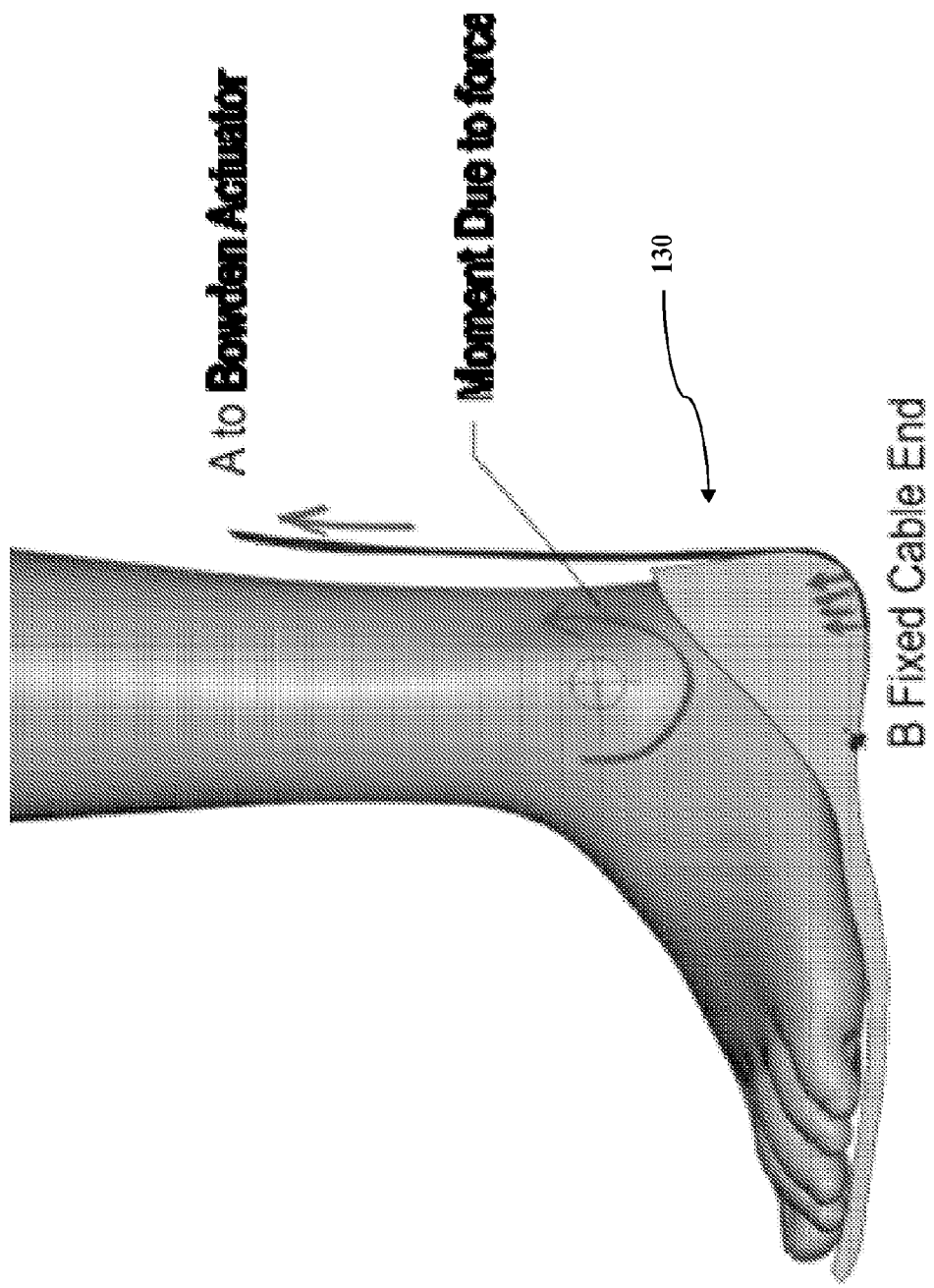

FIGS. 26E-$26G_2$ show aspects of other embodiments of soft exosuit footwear attachments according to at least some aspects of the present concepts.

Figure 27:
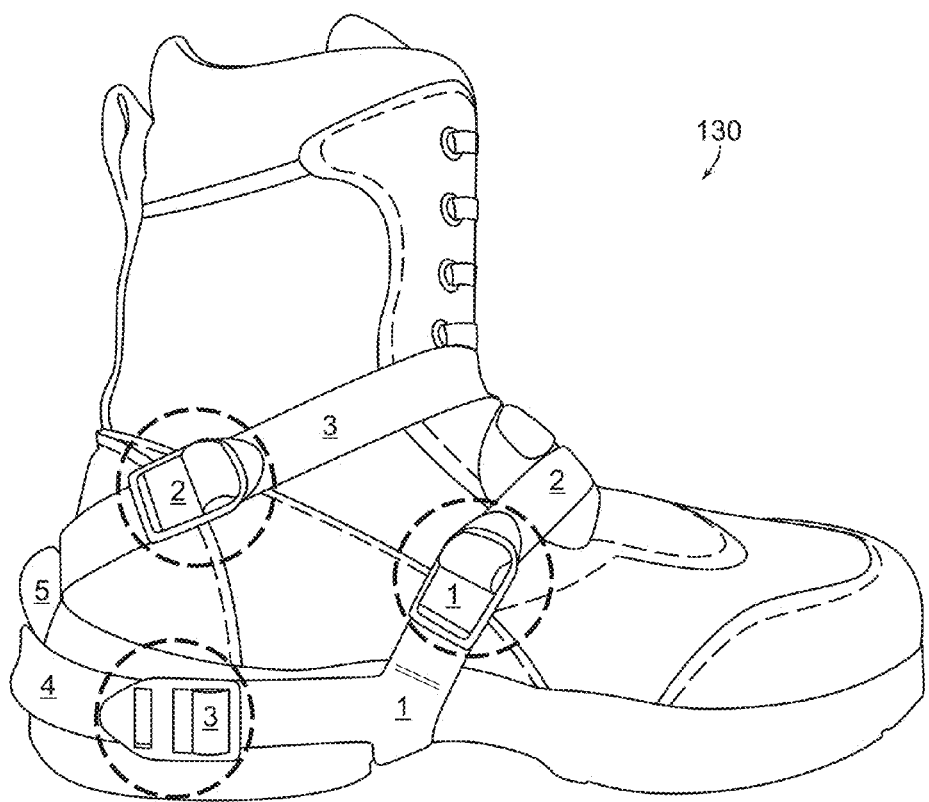

FIG. 27 shows a detailed view of one embodiment of soft exosuit footwear attachment according to at least some aspects of the present concepts.

Figure 28B:
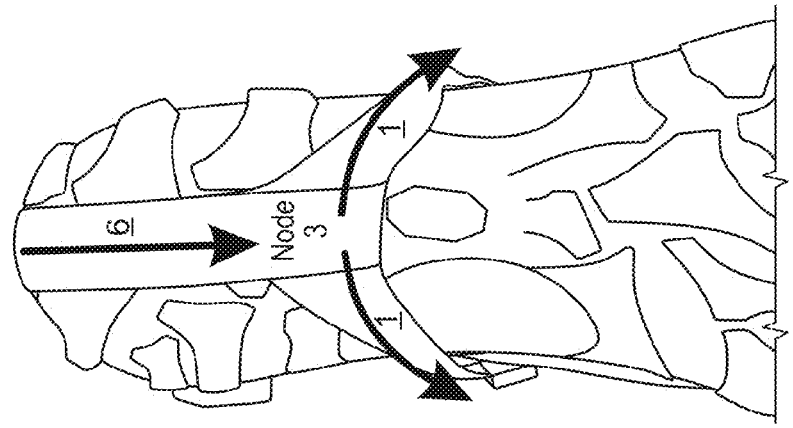
Figure 28A:
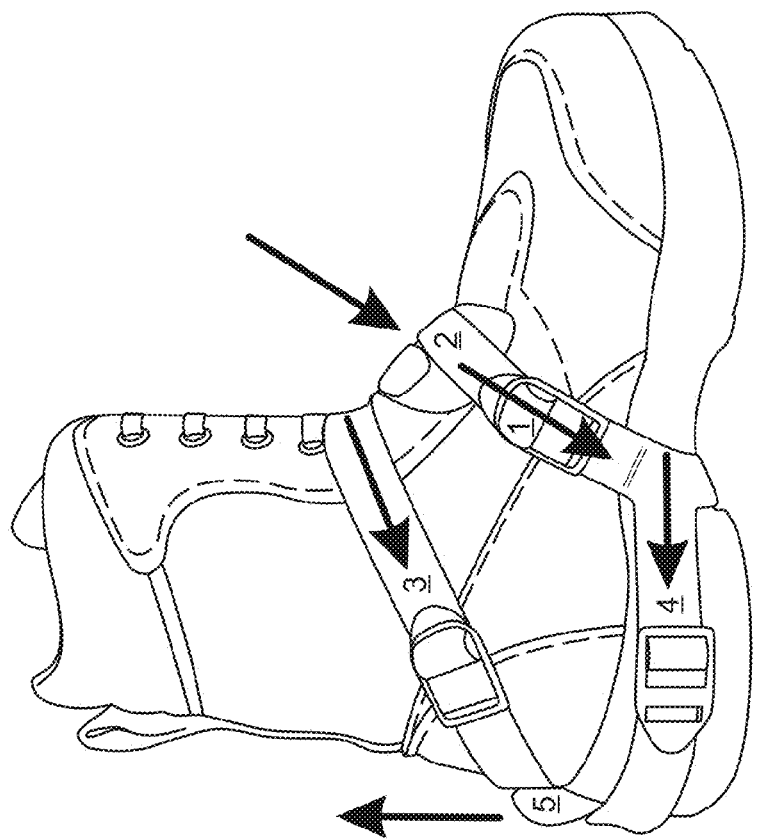

FIGS. 28A-28B shows a detailed view of one embodiment of soft exosuit footwear attachment, according to at least some aspects of the present concepts, showing force paths on the boot from the side and bottom, respectively.

Figure 29:
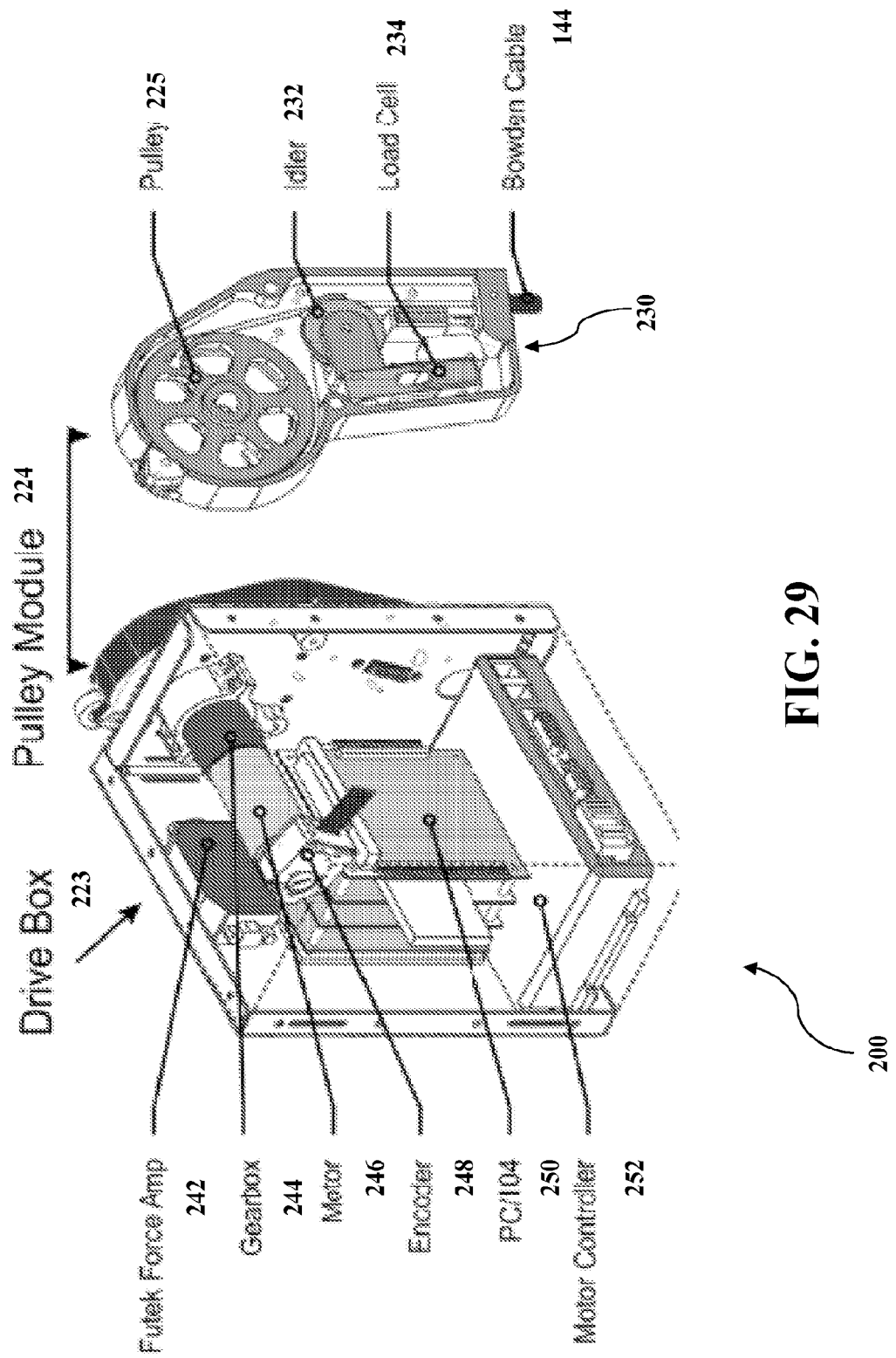

FIG. 29 shows an example of one embodiment of an actuation system, showing a drive box and pulley module, for a soft exosuit according to at least some aspects of the present concepts.

Figure 30:
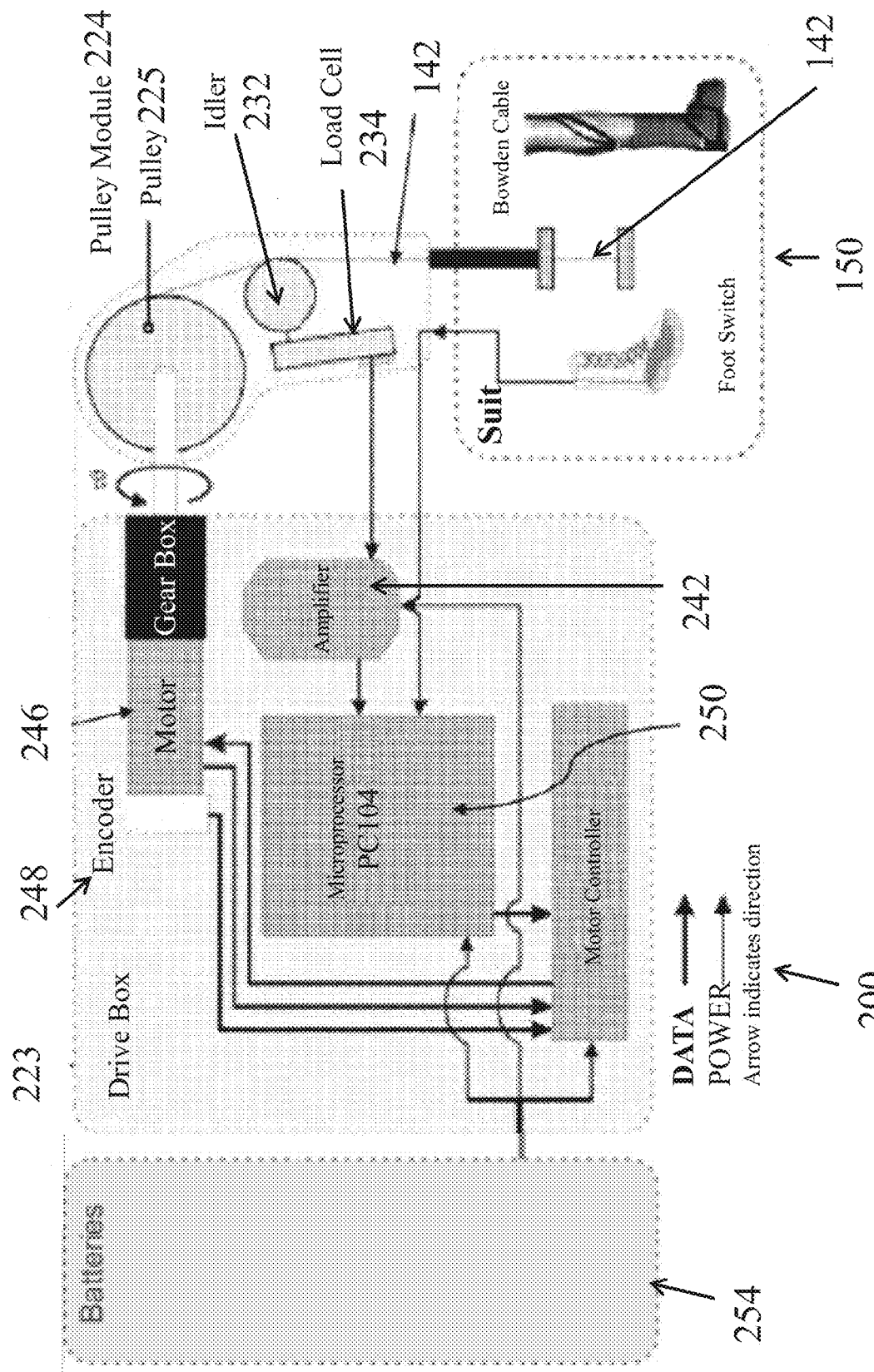

FIG. 30 shows a block diagram of an example of one embodiment of an actuation system for a soft exosuit according to at least some aspects of the present concepts.

Figure 31:
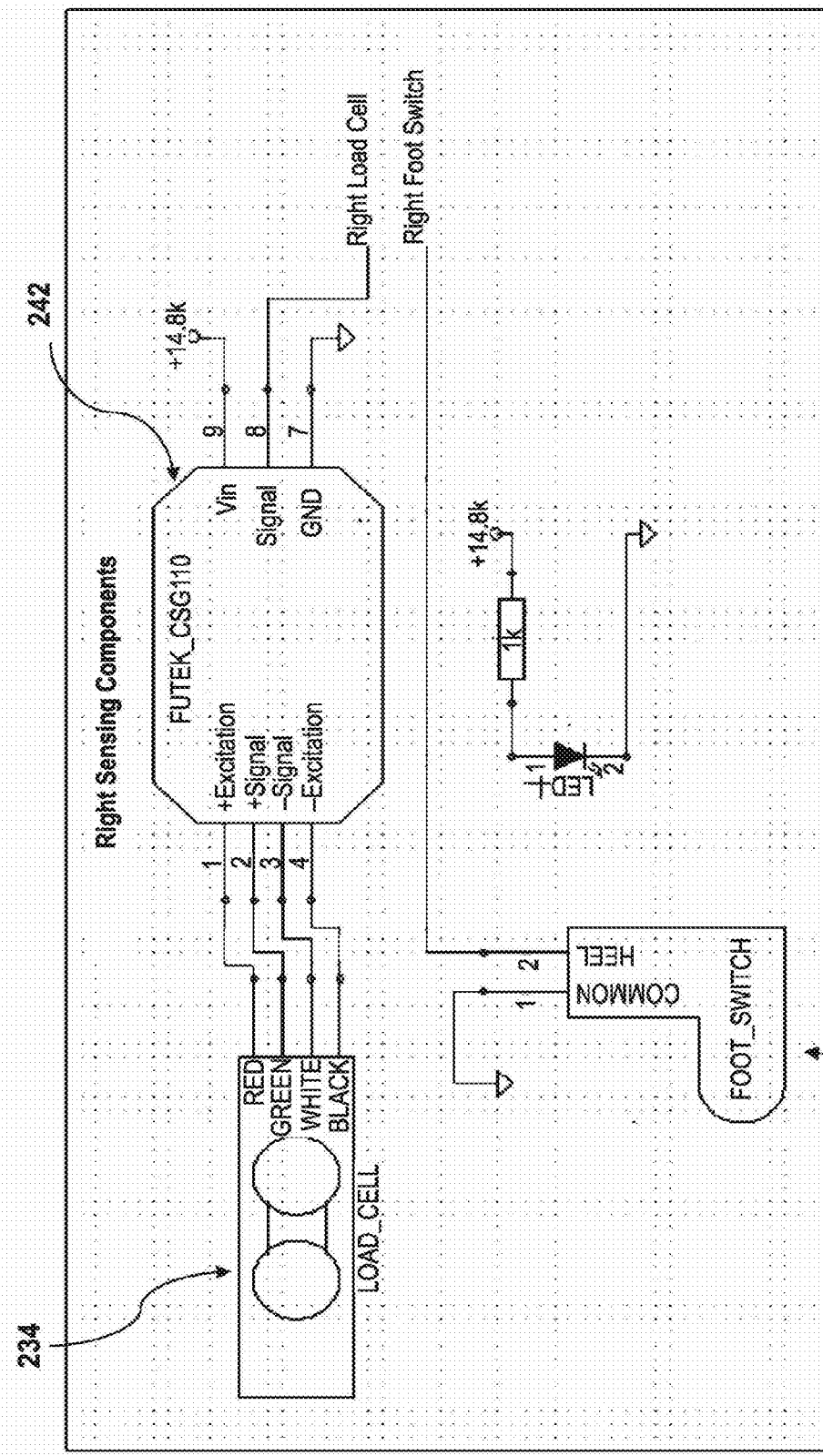

FIG. 31 shows a diagram of connections for sensing components for a soft exosuit according to at least some aspects of the present concepts.

Figure 32:
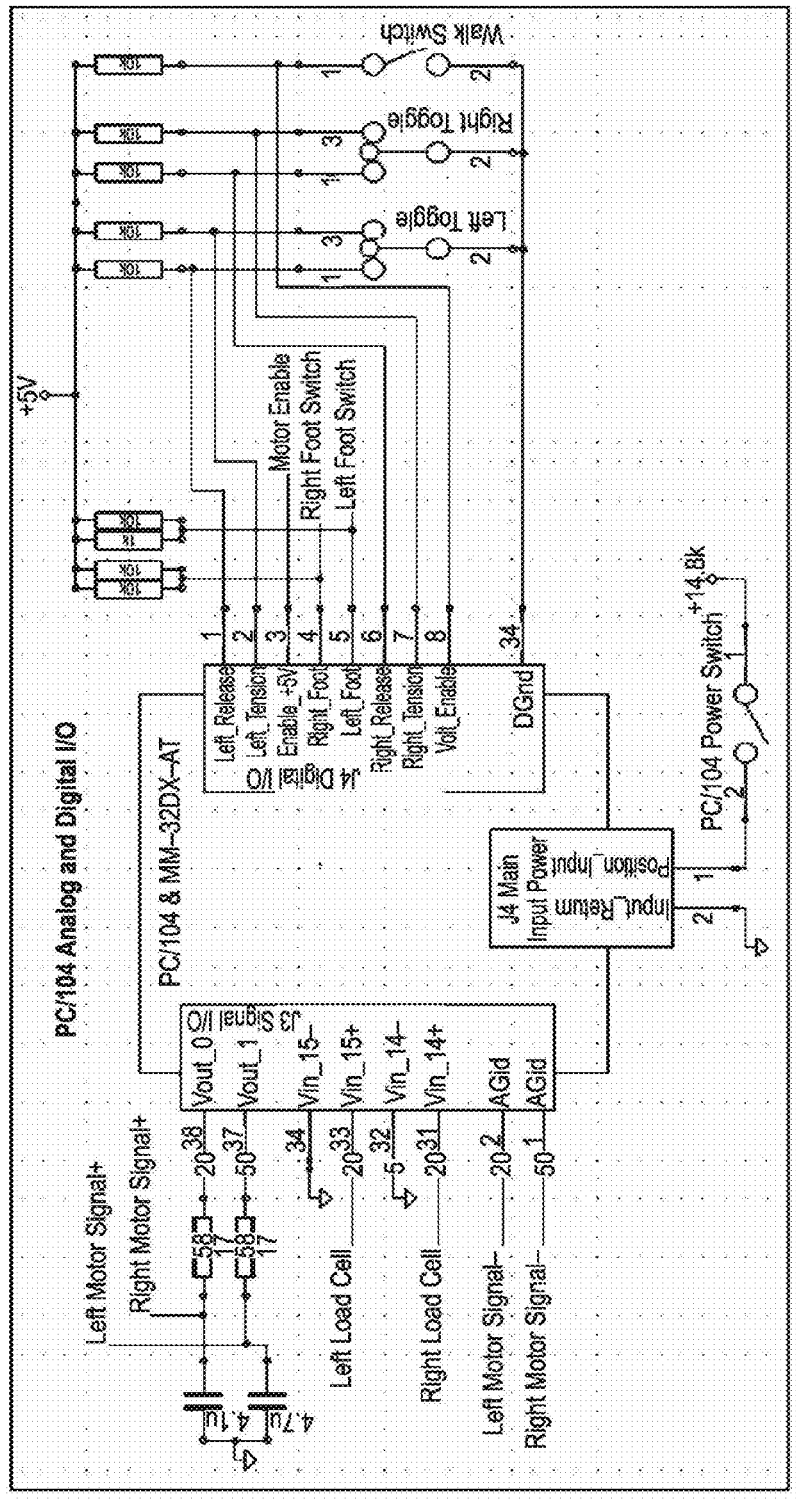

FIG. 32 shows a diagram of an analog and digital I/O for a soft exosuit according to at least some aspects of the present concepts.

Figure 33:
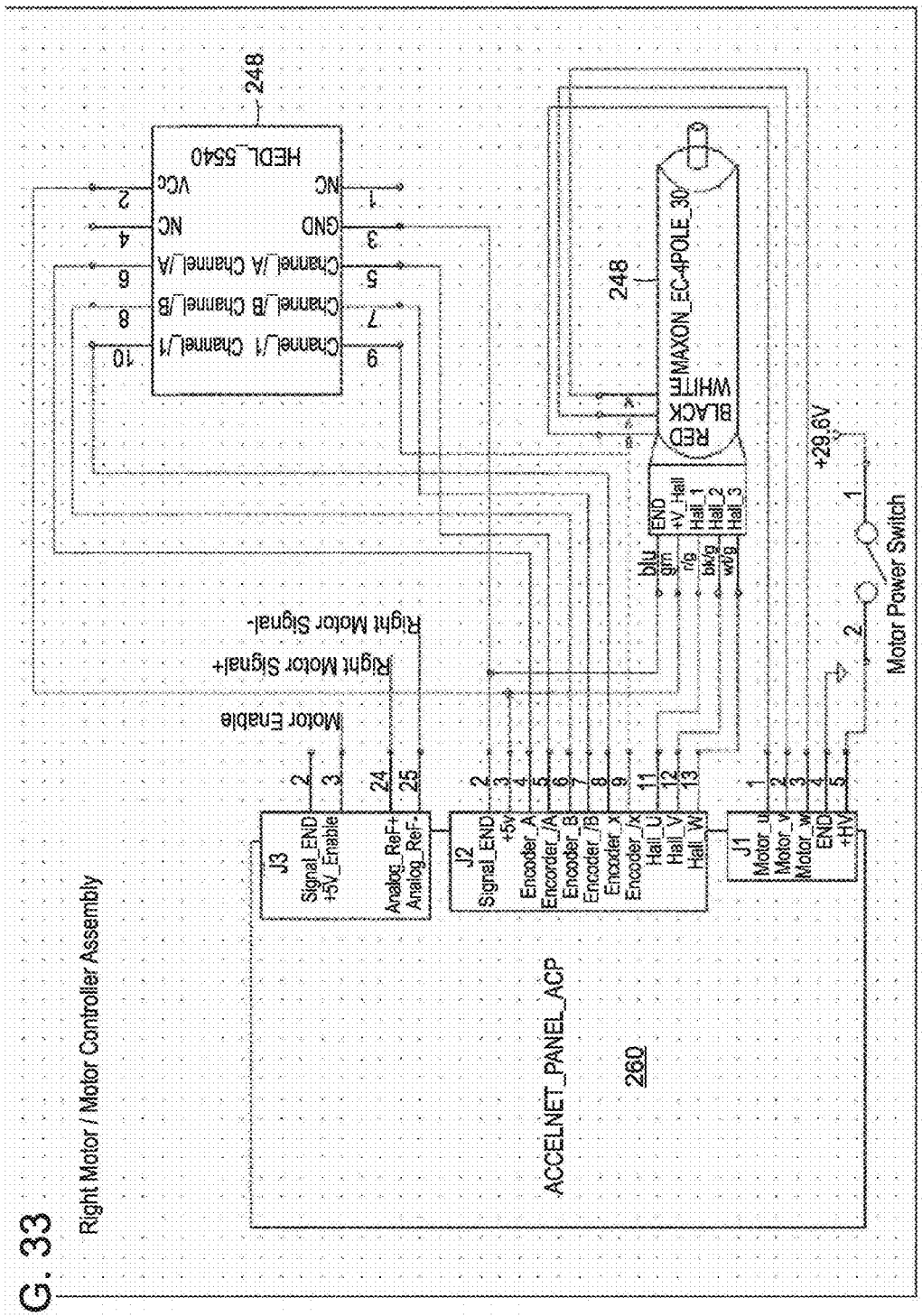

FIG. 33 shows a diagram of a motor controller assembly for an actuating system for a soft exosuit according to at least some aspects of the present concepts.

Figure 34:
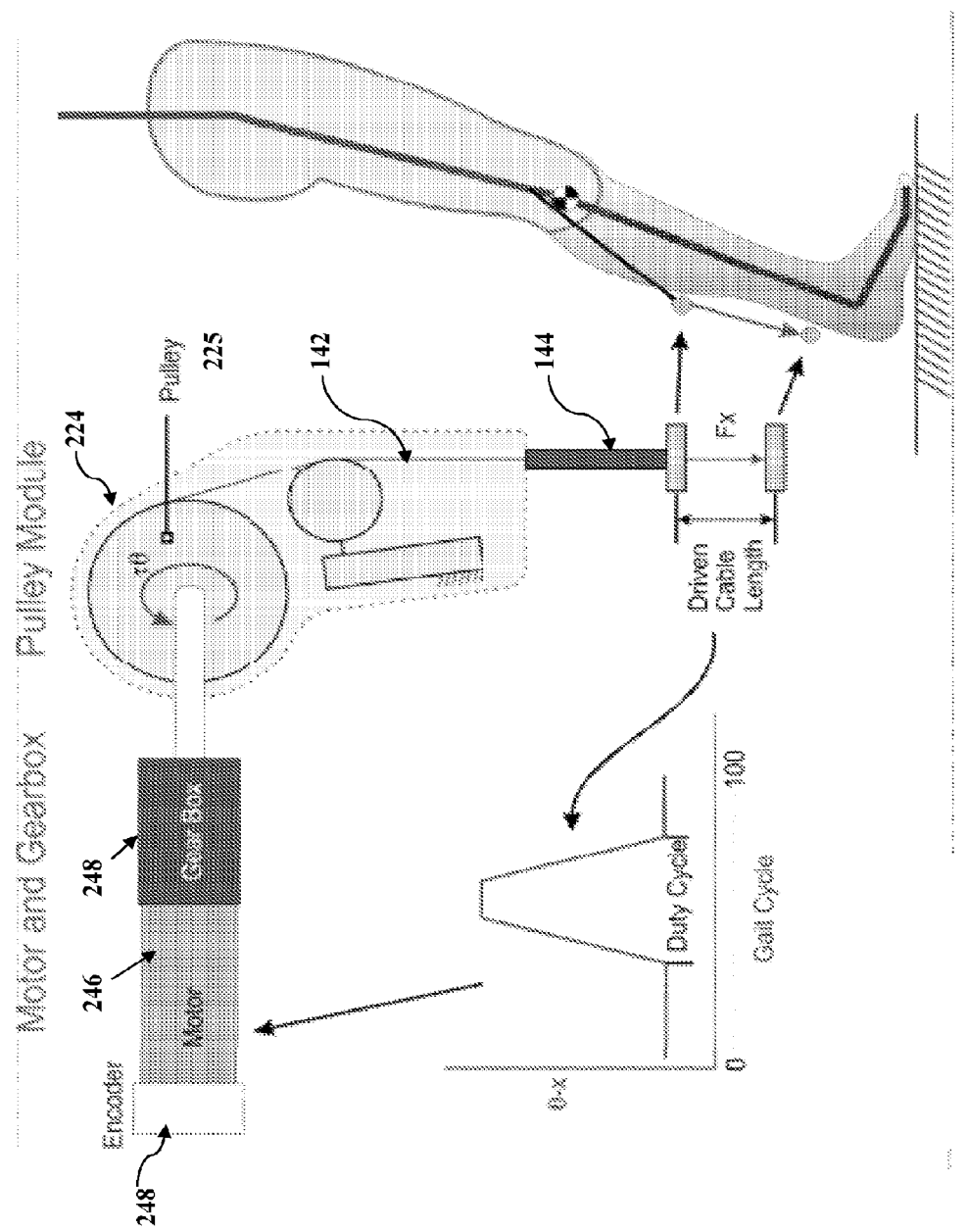

FIG. 34 shows a representation of the controlled actuation of the soft exosuit during a portion of a gait cycle in a soft exosuit according to at least some aspects of the present concepts.

Figure 35:
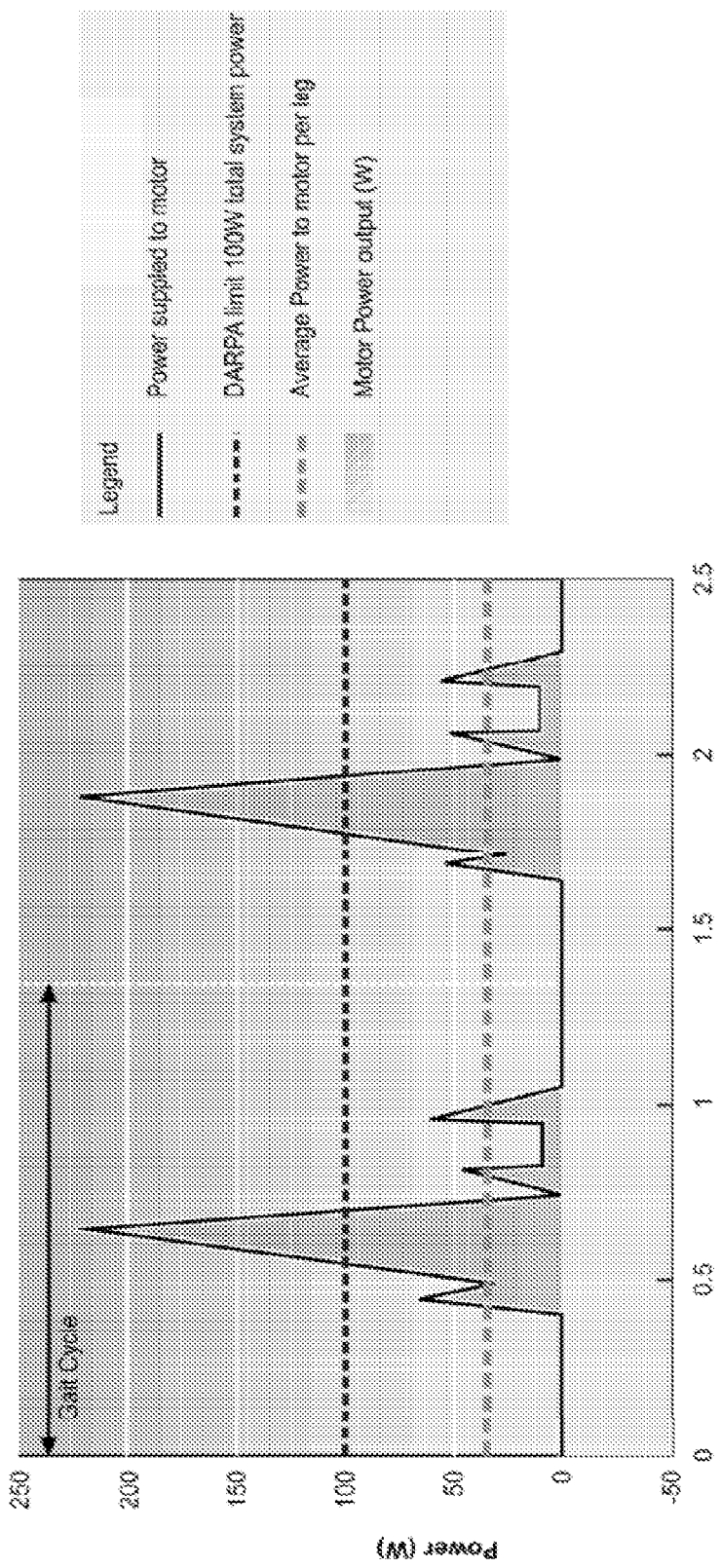

FIG. 35 shows an approximation of power input to a motor over a gait cycle in a soft exosuit according to at least some aspects of the present concepts.

Figure 36:
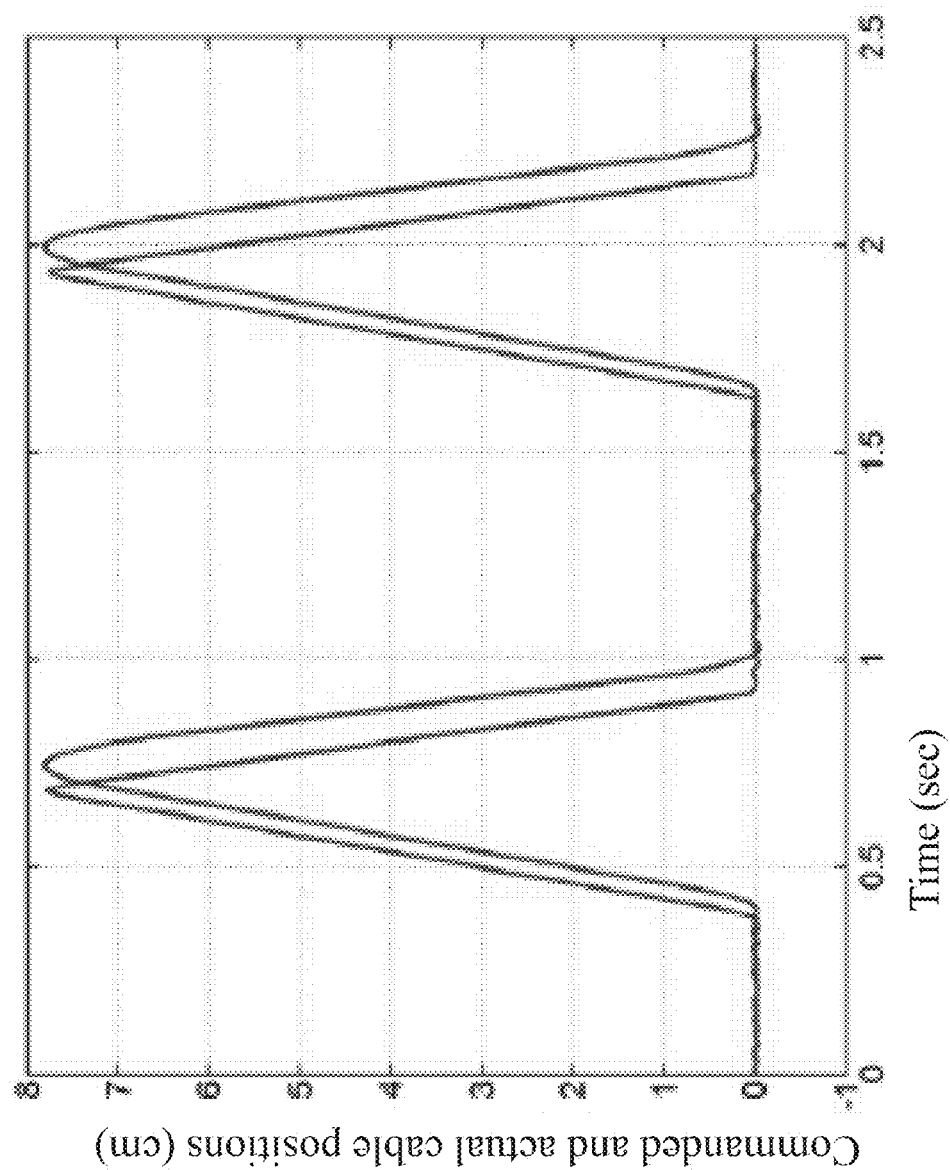

FIG. 36 shows an example of a plot of cable displacements as a function of time in a soft exosuit according to at least some aspects of the present concepts.

Figure 37:
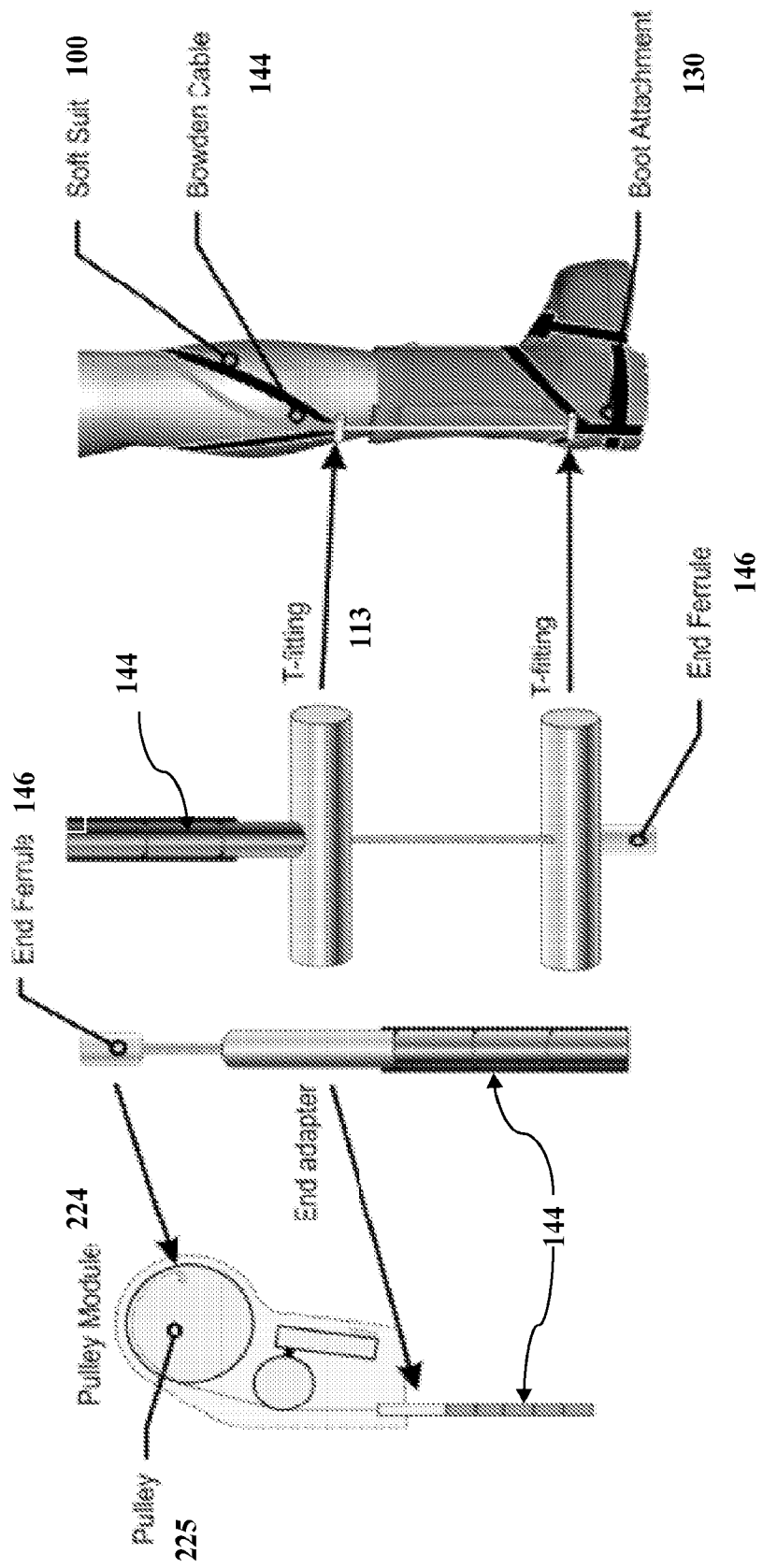

FIG. 37 shows a Bowden cable end fittings for a soft exosuit actuator attachment according to at least some aspects of the present concepts.

Figure 38:
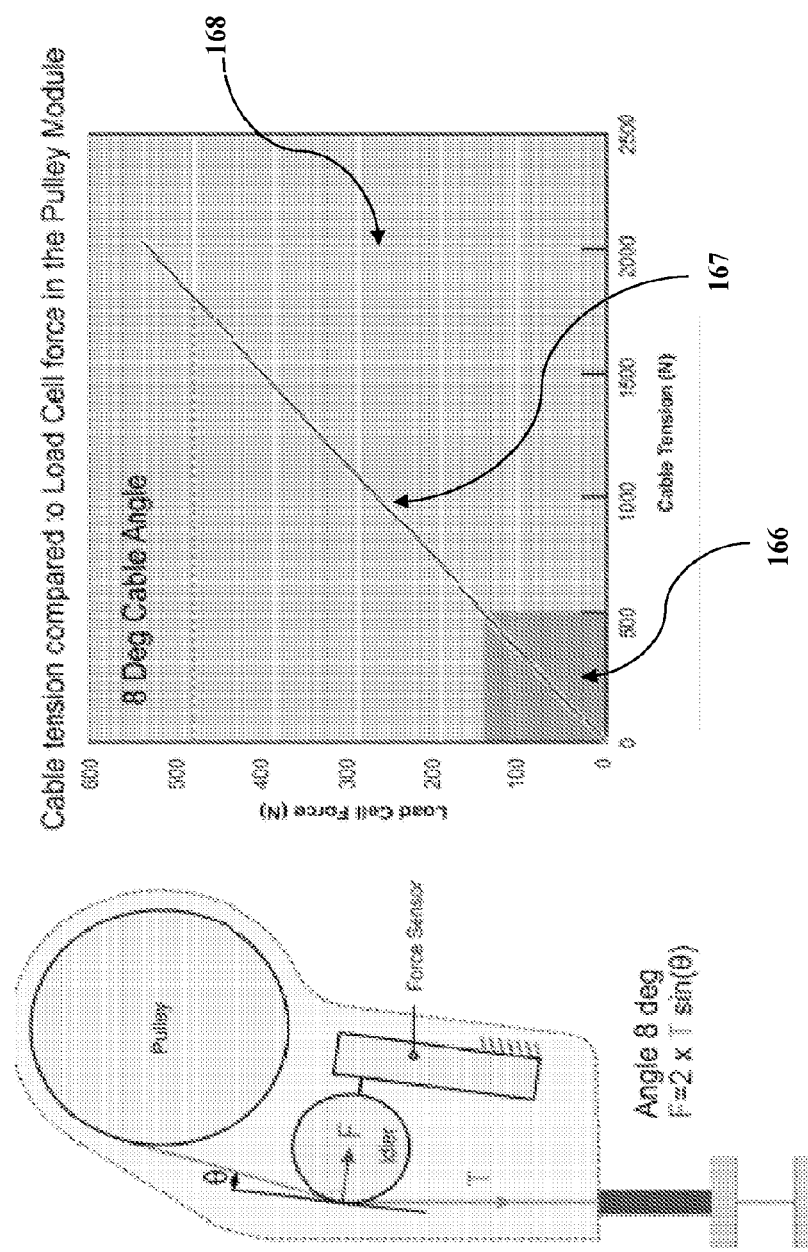

FIG. 38 shows a load cell arrangement is a pulley model and graph of theoretical input to output force in a soft exosuit according to at least some aspects of the present concepts.

FIG. 39 shows examples of parallel and series arrangements for cable tensioning in a soft exosuit according to at least some aspects of the present concepts and a diagram of deflecting idler pulley for measuring cable tension in a soft exosuit according to at least some aspects of the present concepts.

FIG. 40 shows a series load cell location at an ankle of a user's footwear in a soft exosuit according to at least some aspects of the present concepts.

Figure 41A:
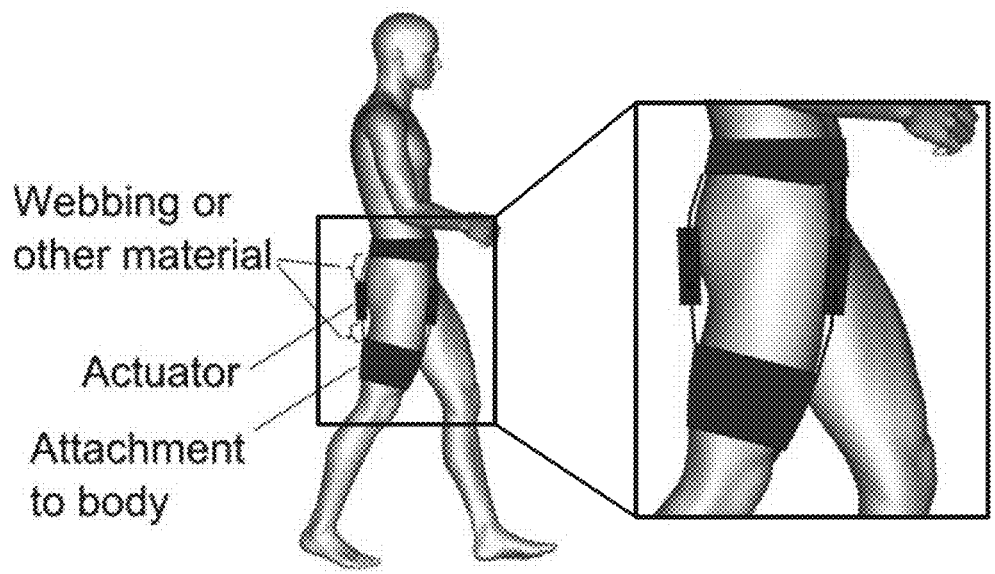
Figure 41B:
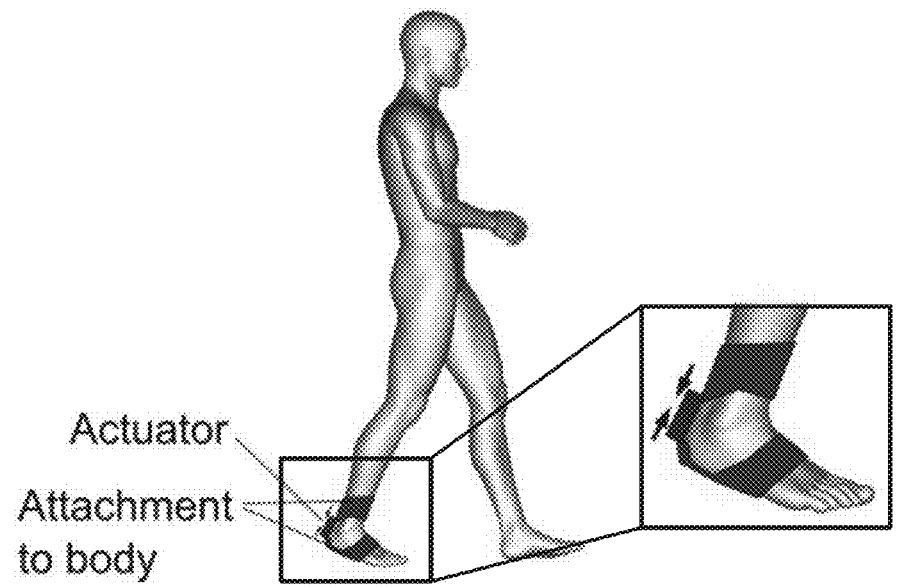

FIG. 41A-41B show, respectively, examples of soft exosuits according to at least some aspects of the present concepts wherein forces may be selectively applied to both sides of the hip joint (anterior/posterior) or to the ankle.

FIGS. 42A-42G show, respectively, example of components and systems of one example of an actuator in accord with at least some aspects of the present concepts.

Figure 43A:
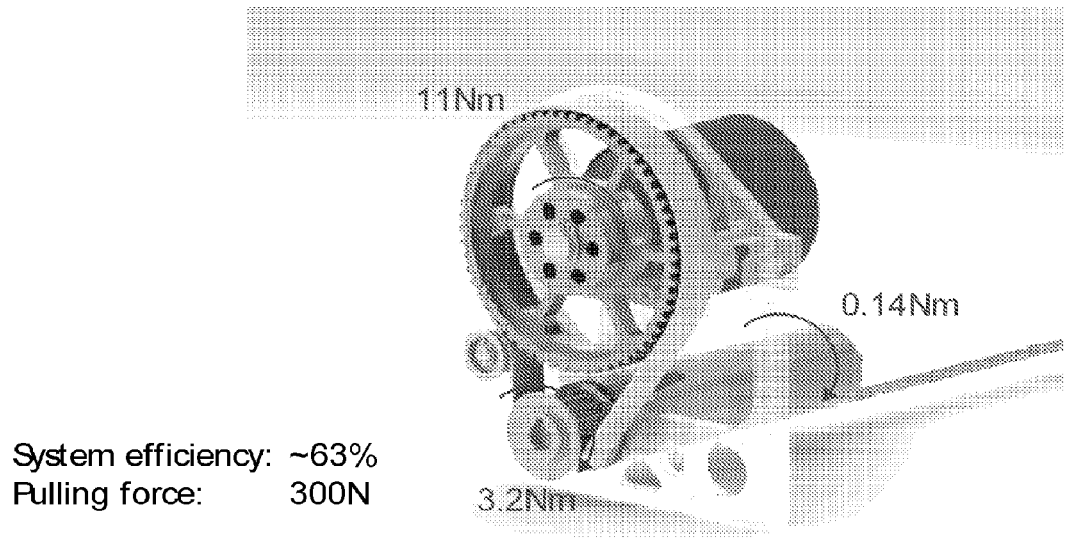
Figure 43B:
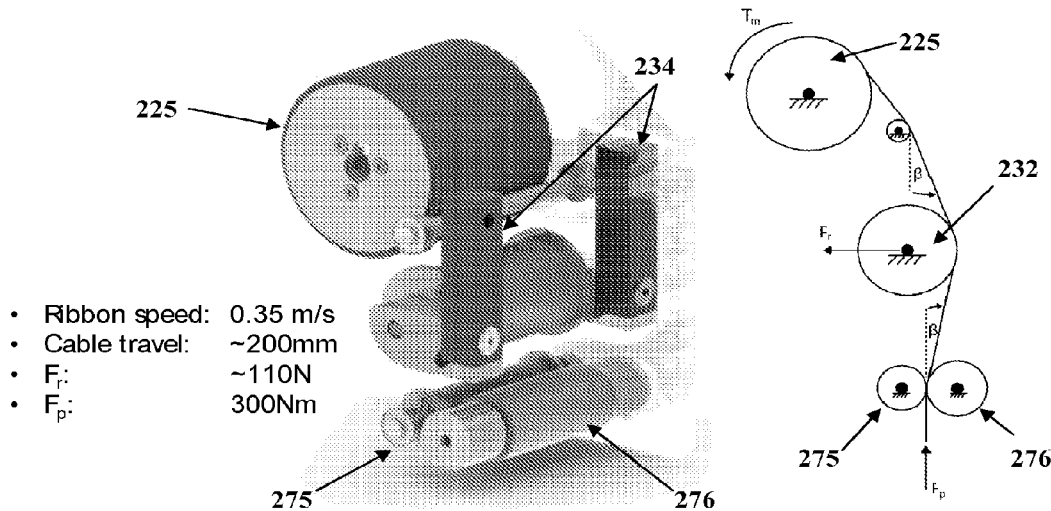

FIGS. 43A-43B show, respectively, an example of a timing pulley configuration for a soft exosuit according to at least some aspects of the present concepts and an example of an idler configuration for webbing utilized in a soft exosuit according to at least some aspects of the present concepts.

FIGS. 44A-44C show, respectively, front, back and side views of a soft exosuit (V3.2) in accord with at least some aspects of the present concepts.

FIGS. 45A-45D show, respectively, front, back and side views of a soft exosuit (V4) in accord with at least some aspects of the present concepts.

Figure 46A:
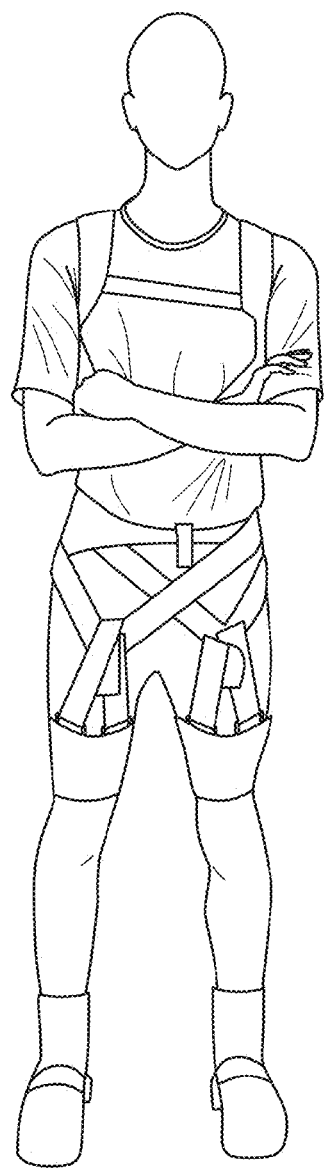
Figure 46B:
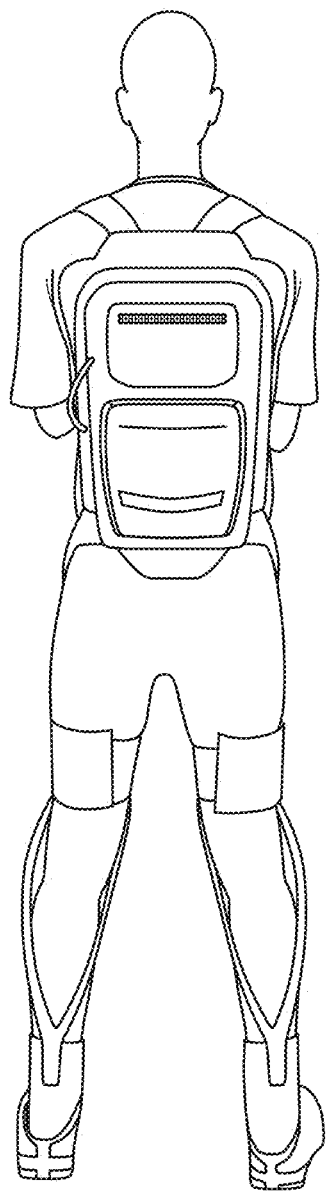

FIGS. 46A-46B shows front view and rear view pictures, respectively, of an example of a soft exosuit worn by a user in accord with at least some aspects of the present concepts.

FIG. 47 presents a comparison of statistics showing evolution of initial embodiments of soft exosuits in accord with at least some aspects of the present concepts.

Figures 48A, 48B:
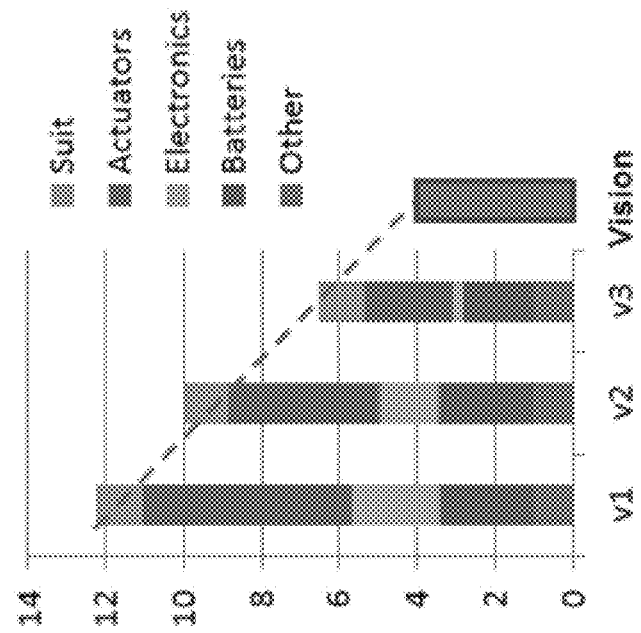

FIGS. 48A-48B show a bar chart depicting a decrease in weight of soft exosuits in accord with at least some aspects of the present concepts as the inventors developed and improved the technology from soft exosuit (V1) to soft exosuit (V3).

FIGS. 49A-49E show kinematic results for the soft exosuit shown in FIGS. 46A-46B in accord with at least some aspects of the present concepts.

Figures 50, 51:
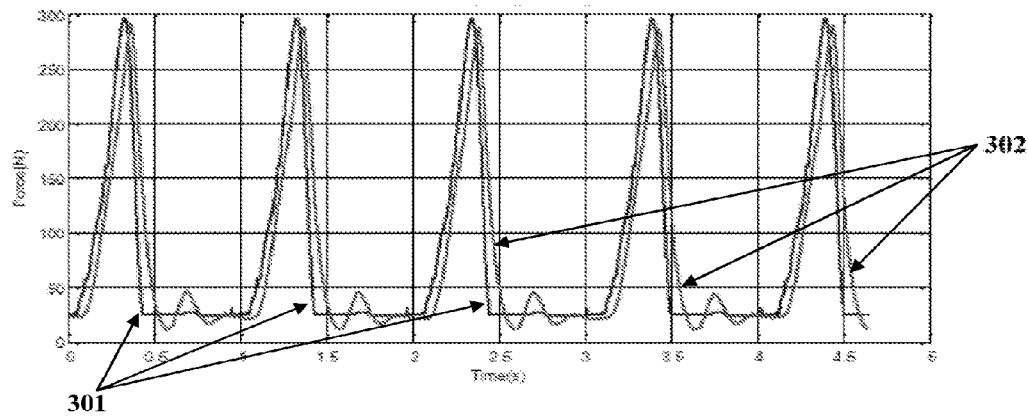

FIG. 50 shows a force versus time curve for ankle actuation performance for the soft exosuit shown in FIGS. 46A-46B in accord with at least some aspects of the present concepts.

FIG. 51 shows metabolic results for different subjects utilizing the soft exosuit shown in FIGS. 46A-46B in accord with at least some aspects of the present concepts.

FIGS. 52A-52B show, respectively, a biological metabolic power pie chart and a suit metabolic benefit pie chart.

FIG. 53 shows evolution of soft exosuit stiffness between different versions of soft exosuits (V3-V7) in accord with at least some aspects of the present concepts.

Figure 54A:
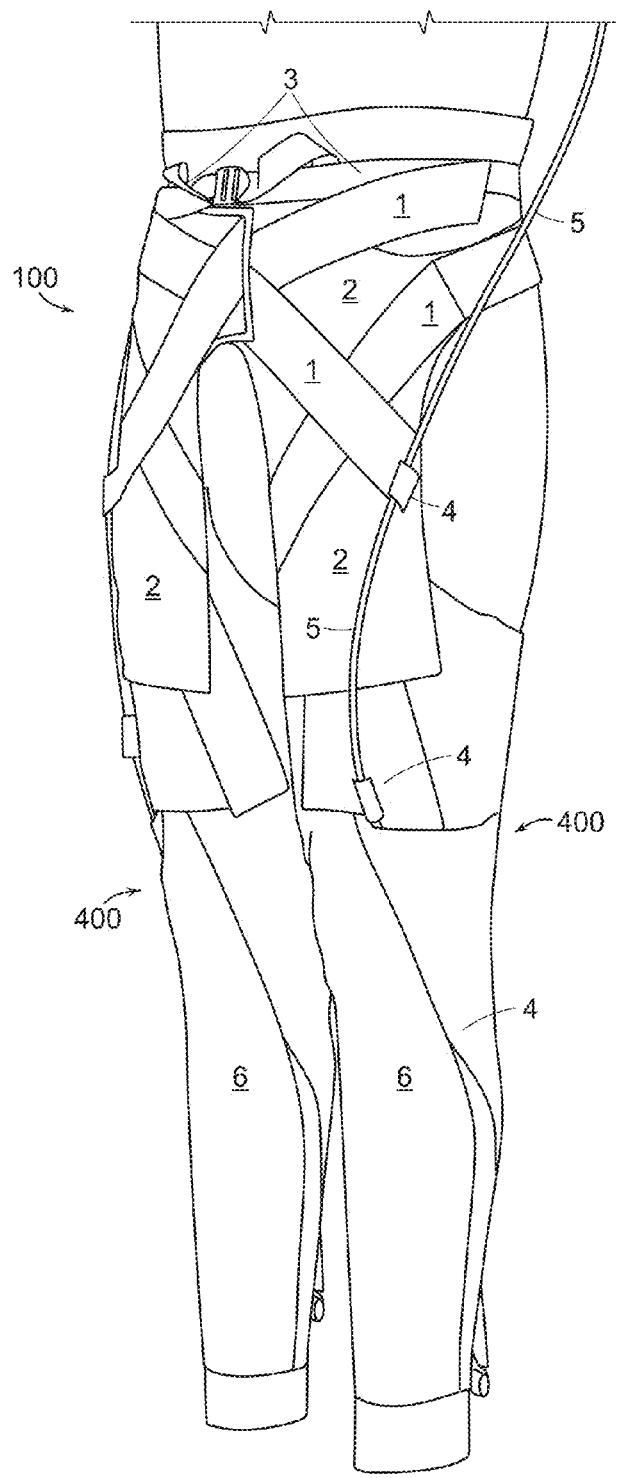
Figure 54B:
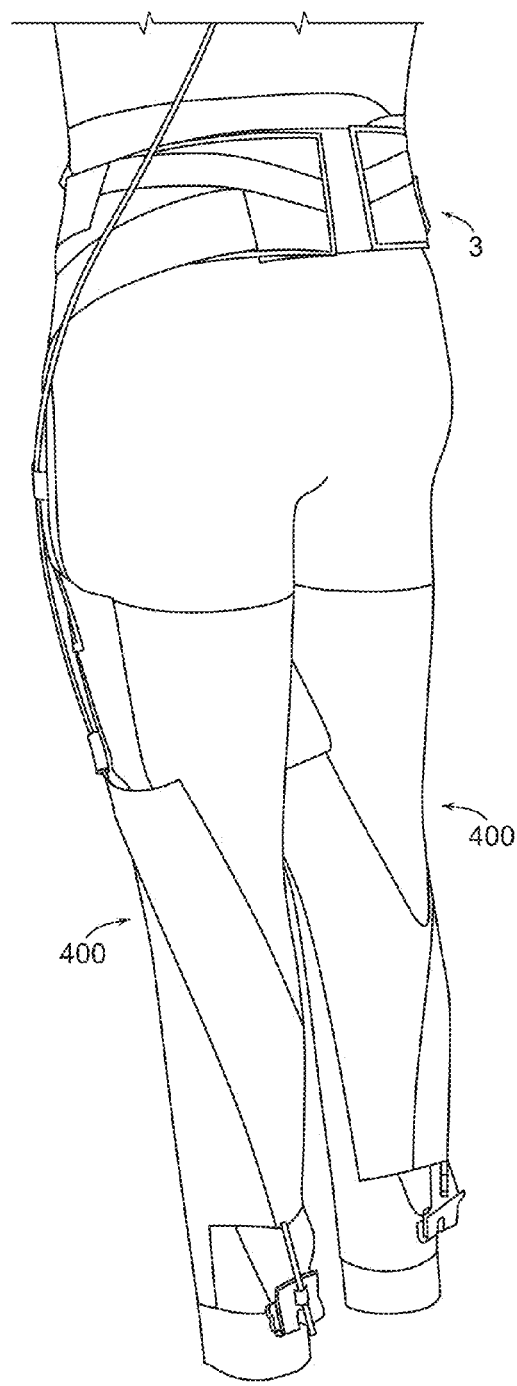

FIG. 54A-$54E_3$ shows aspects of a soft exosuit (V7) in accord with at least some aspects of the present concepts.

Figures 55A, 55B:
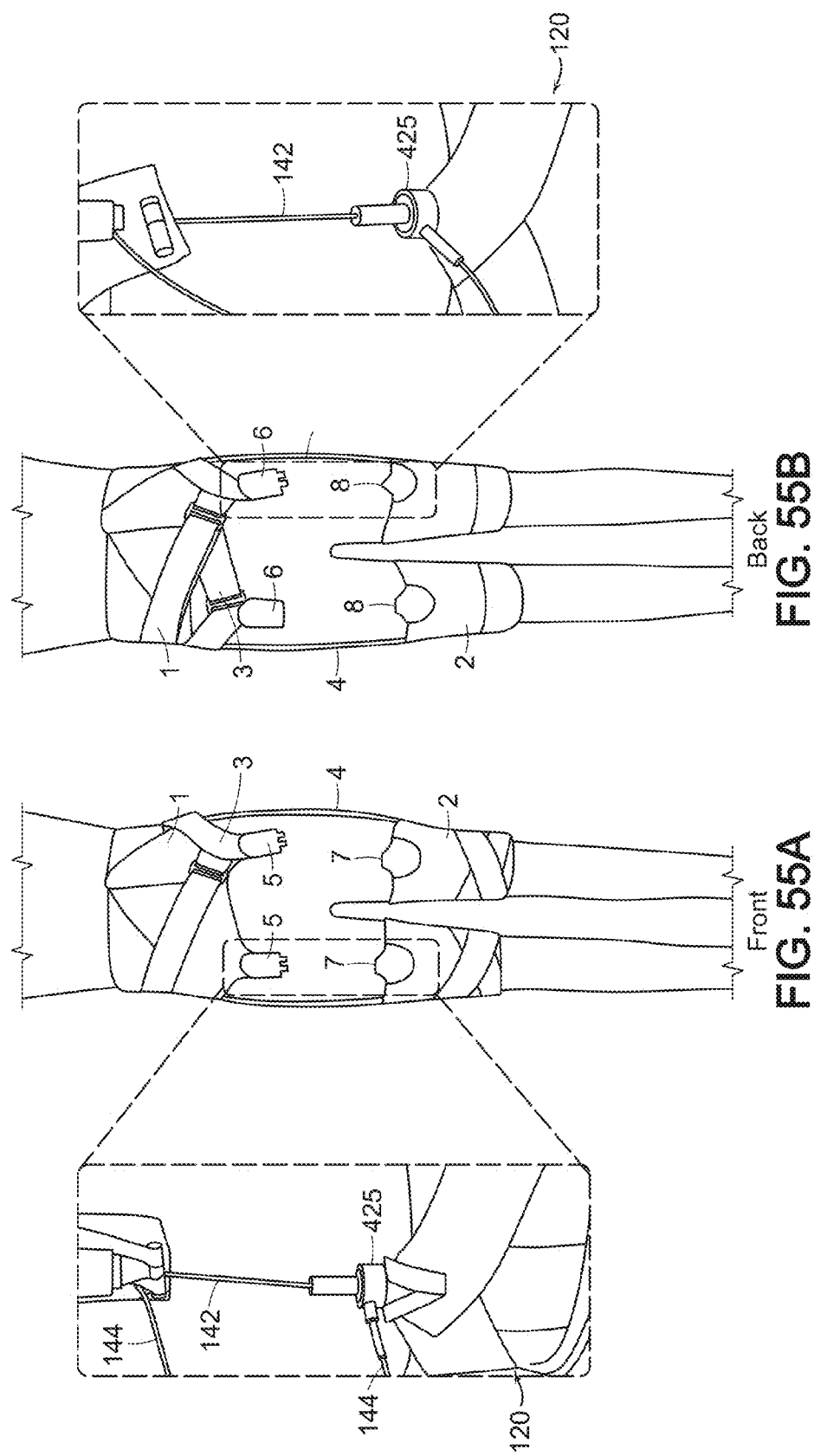

FIGS. 55A-55B show aspects of a soft exosuit in accord with at least some aspects of the present concepts.

Figure 56A:
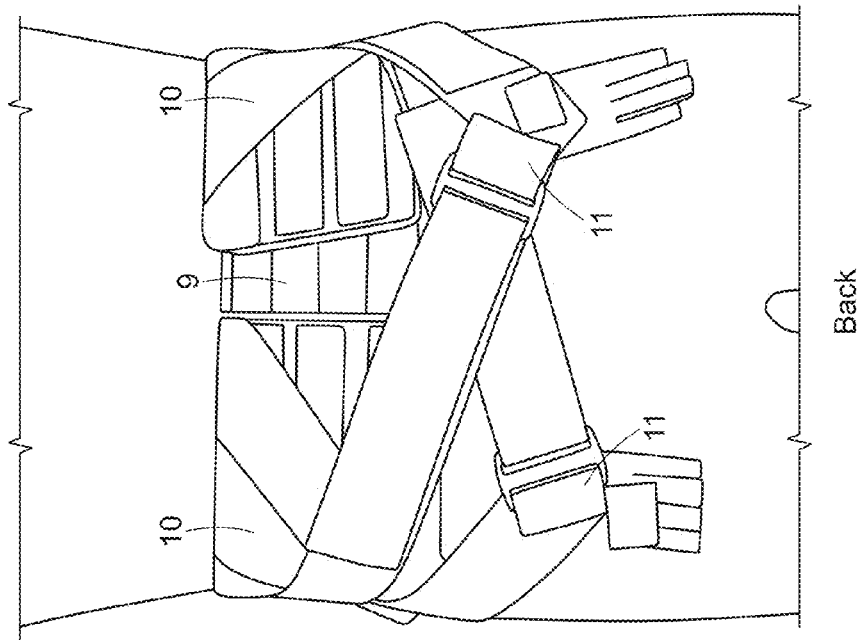
Figure 56B:
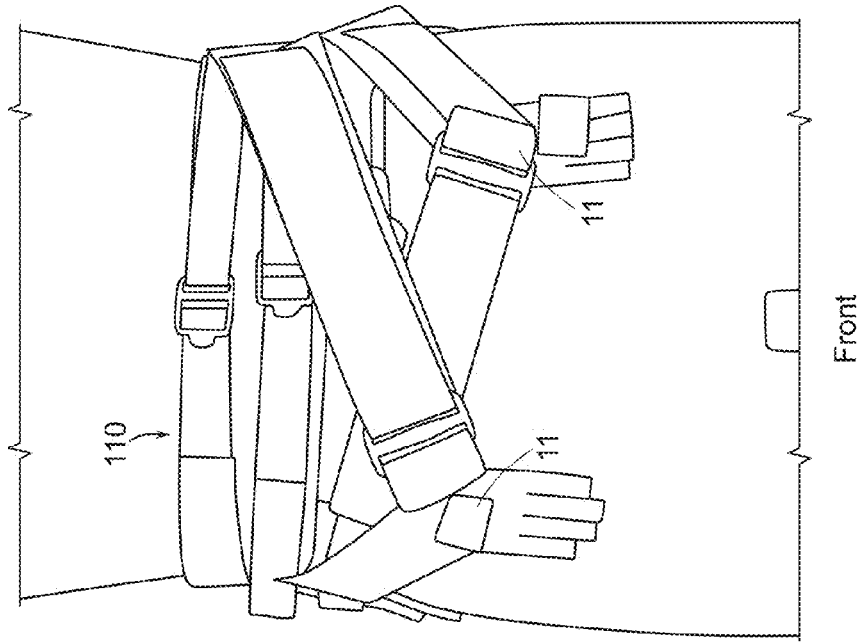

FIGS. 56A-56B show aspects of a waist belt for a soft exosuit in accord with at least some aspects of the present concepts.

FIG. 57 shows aspects of another waist belt (V5) for a soft exosuit in accord with at least some aspects of the present concepts.

FIGS. 58A-58F show aspects of yet another waist belt (V5) for a soft exosuit in accord with at least some aspects of the present concepts.

FIGS. 59A-59D show aspects of yet another waist belt (V7.1) for a soft exosuit in accord with at least some aspects of the present concepts.

Figure 59A:
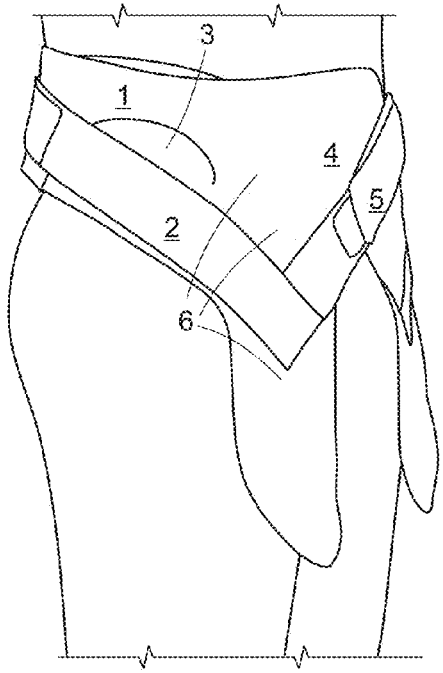
Figure 59B:
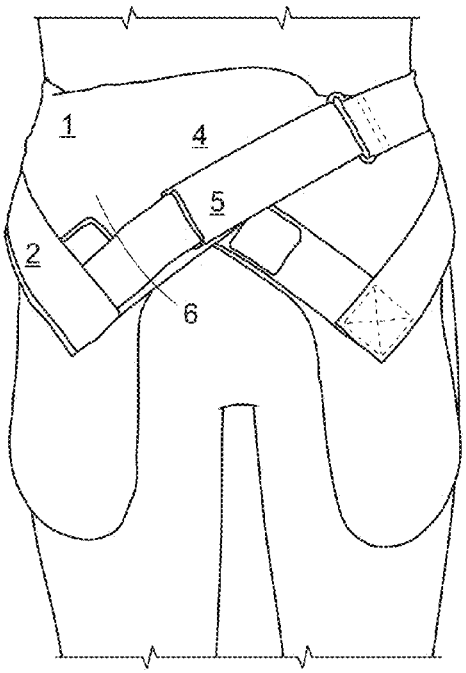
Figure 59C:
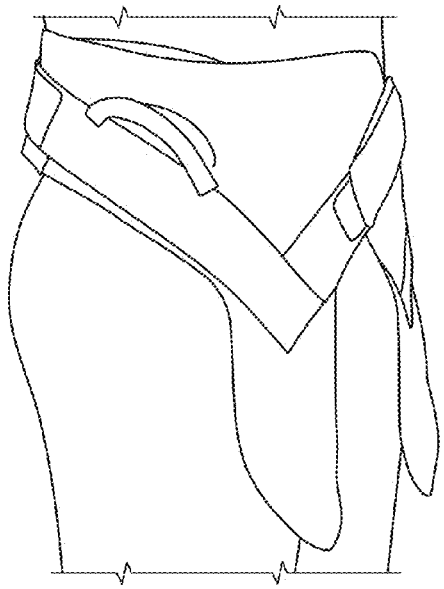
Figure 59D:
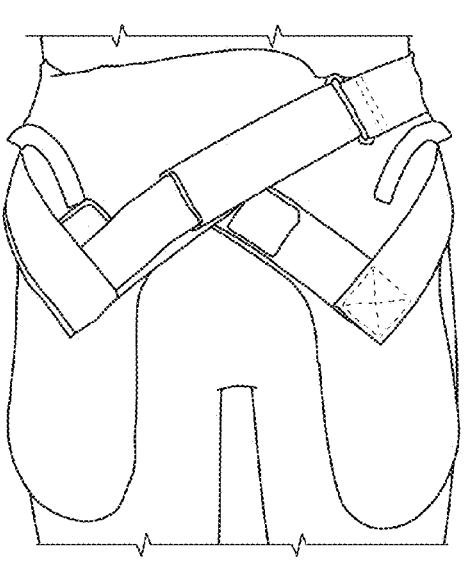
Figure 60:
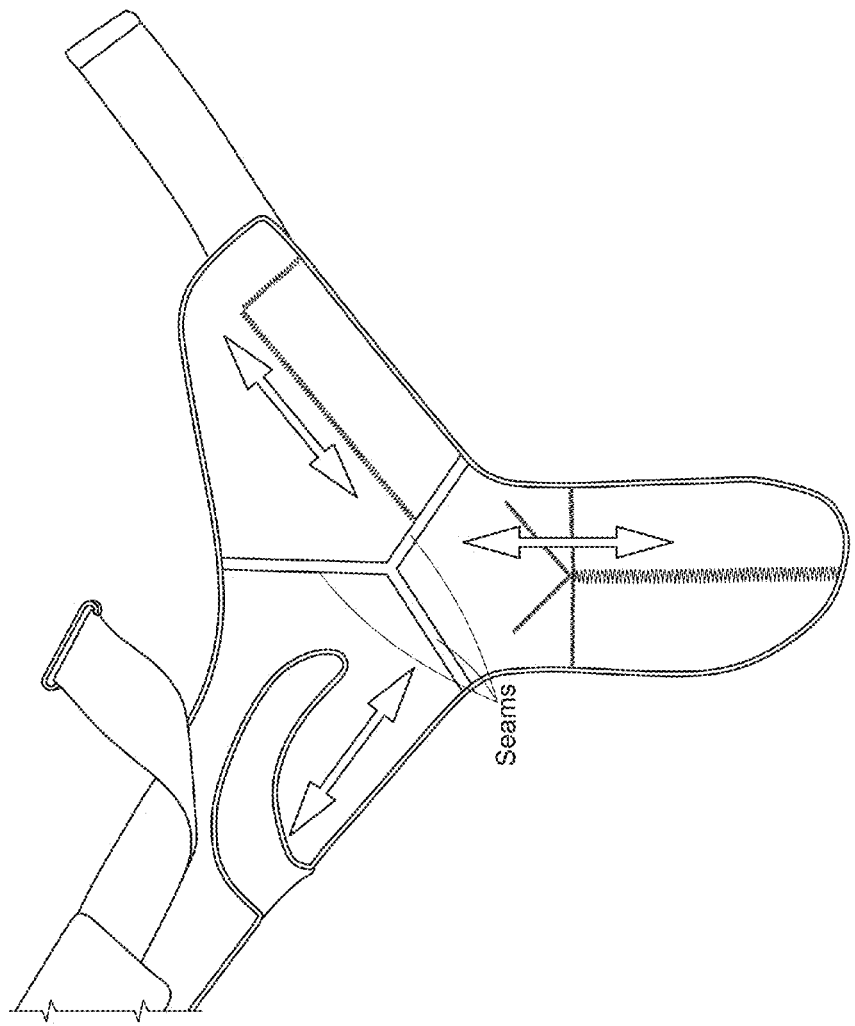
Figure 61A:
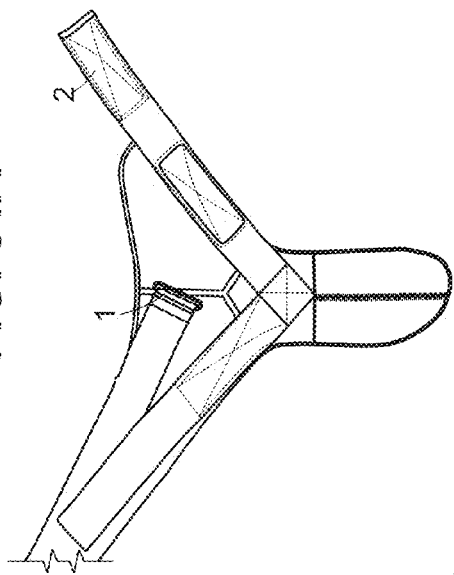
Figure 61C:
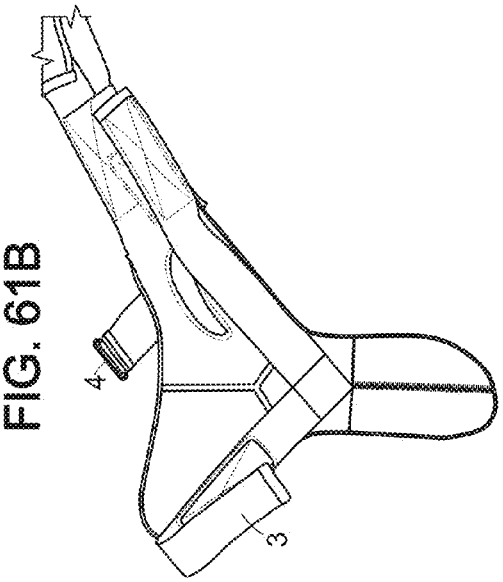
Figure 61B:
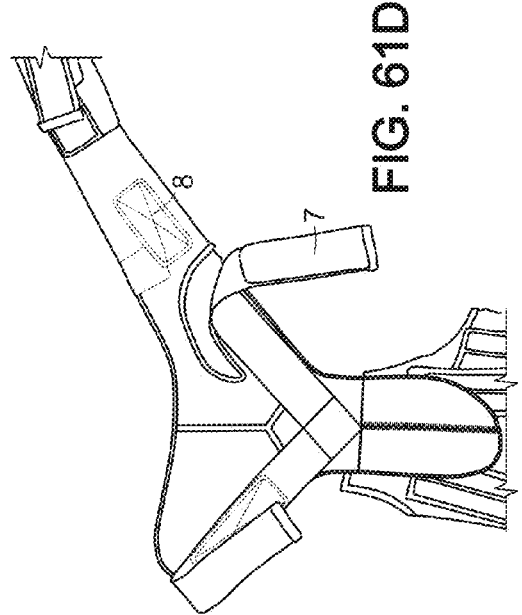
Figure 61D:
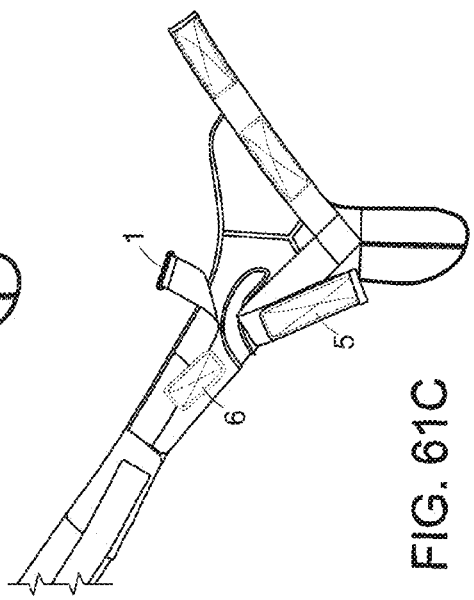

FIG. 60 shows aspects of the waist belt (V7.1) of FIGS. 59A-59D.

FIGS. 61A-61D show additional aspects of the waist belt (V7.1) of FIGS. 59A-59D.

Figure 62:
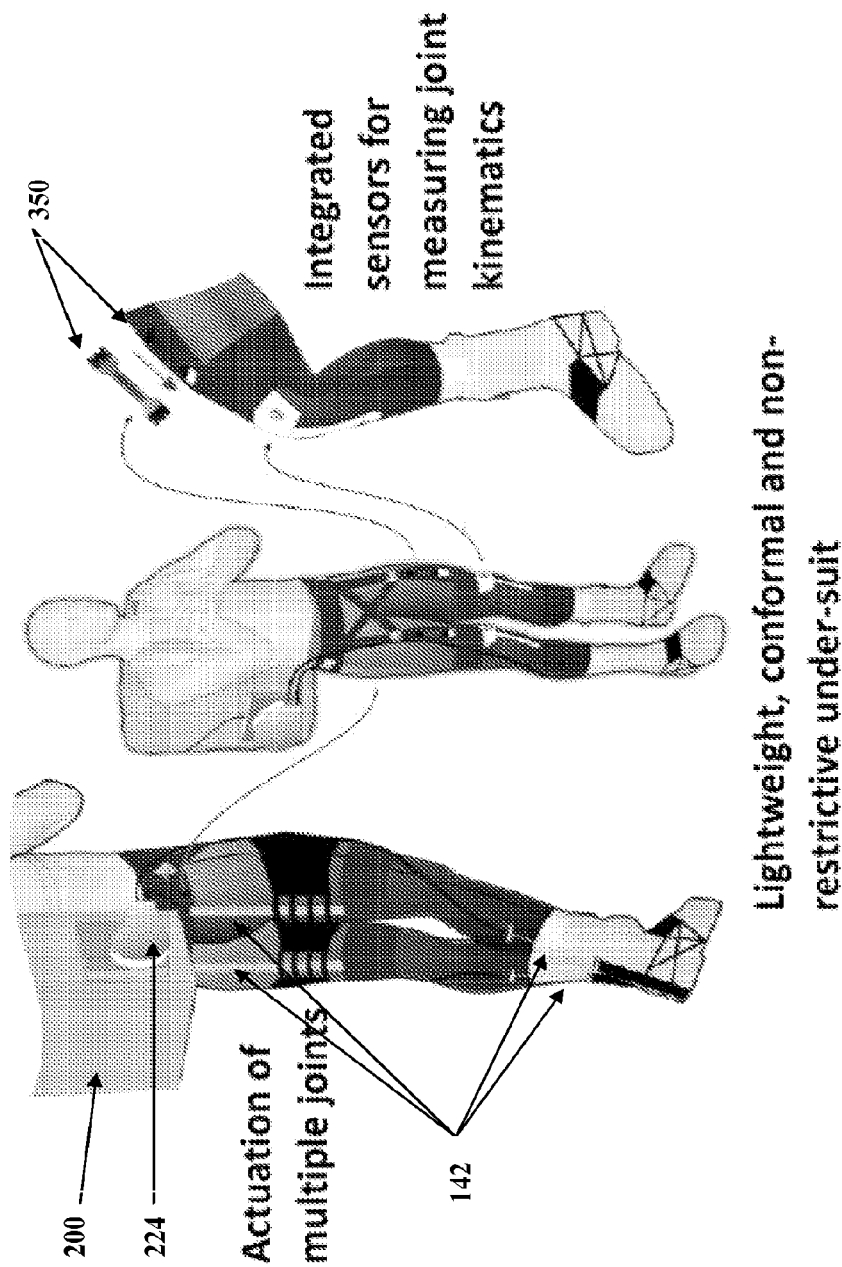

FIG. 62 depicts a soft exosuit in accord with at least some aspects of the present concepts configured for actuation of multiple joints.

Figures 63A, 63B:
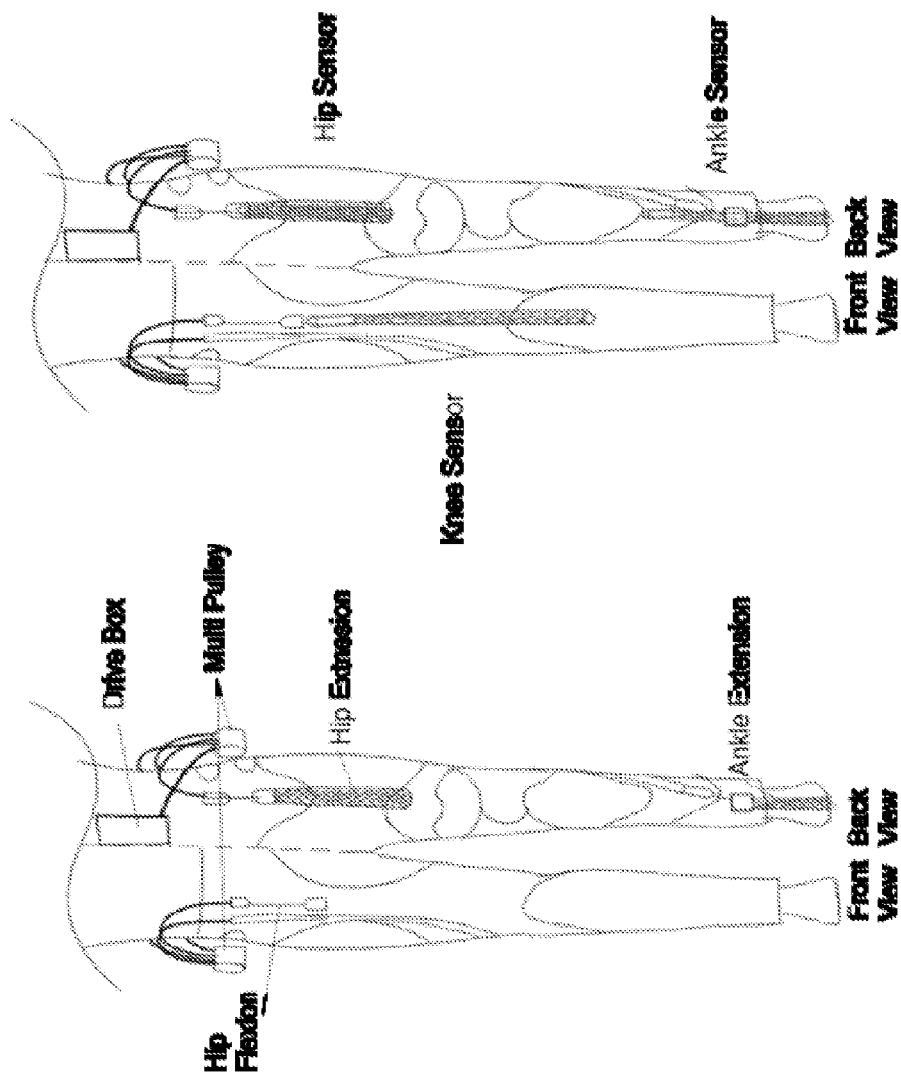

FIGS. 63A-63B show examples of a soft exosuit in accord with at least some aspects of the present concepts configured for actuation of multiple joints.

Figure 64A:
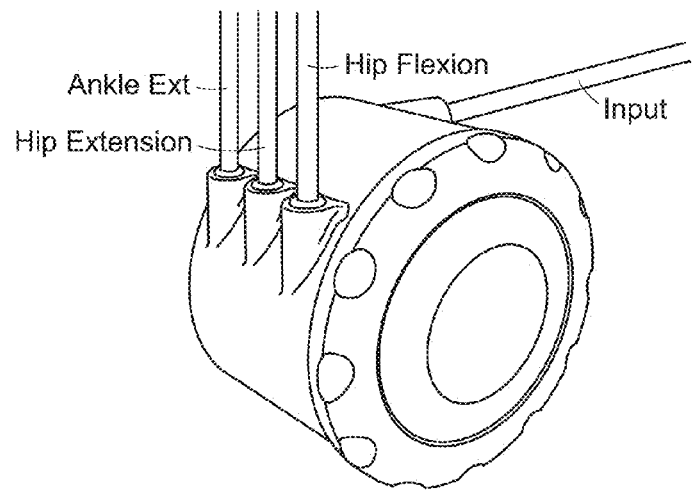
Figure 64B:
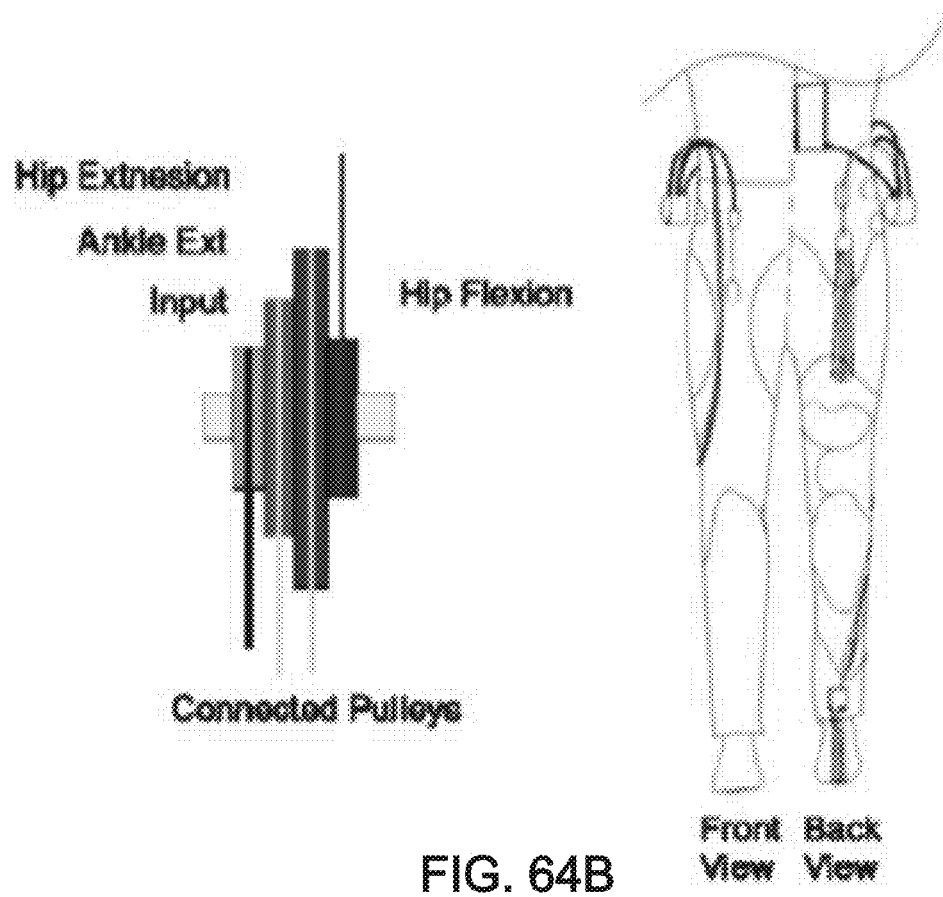

FIG. 64A-64B show a multi-pulley for a soft exosuit configured for actuation of multiple joints in accord with at least some aspects of the present concepts.

Figure 65:
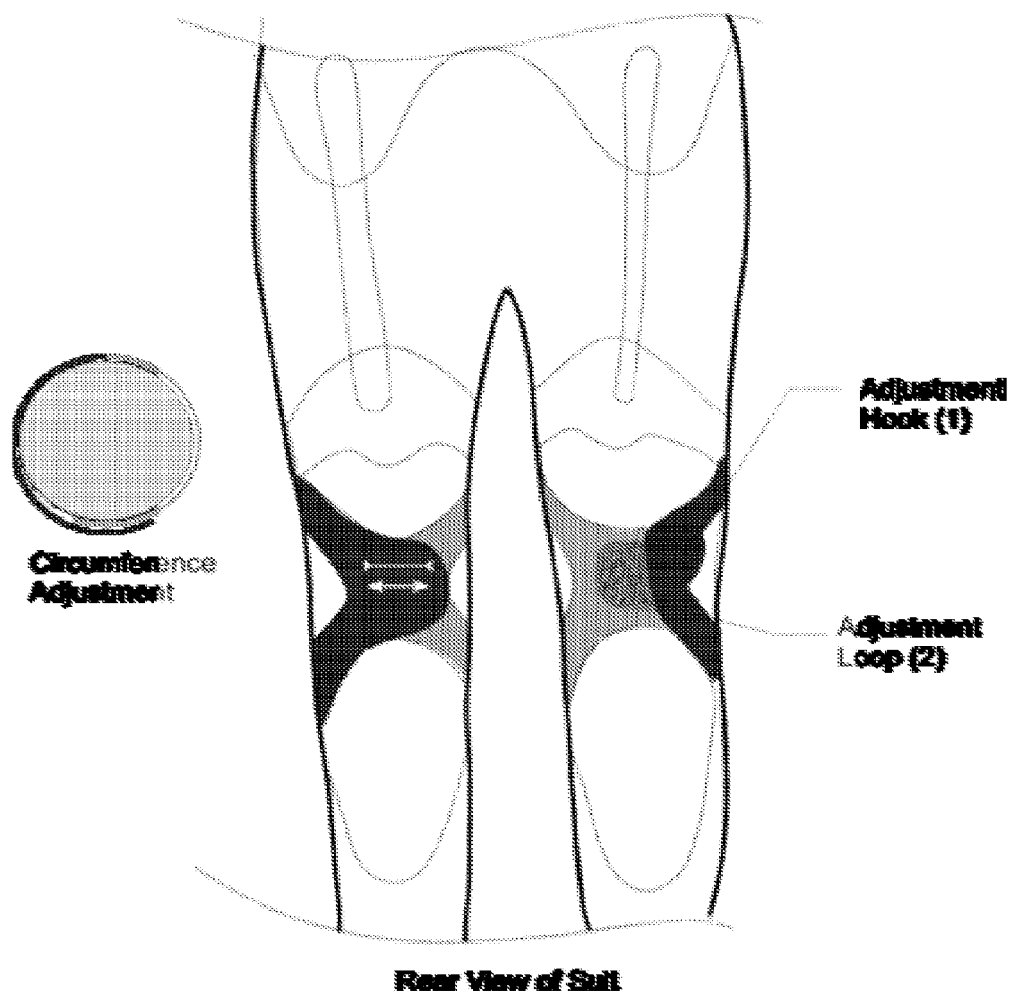

FIG. 65 shows a rear view of a thigh brace for a soft exosuit in accord with at least some aspects of the present concepts.

Figure 66:
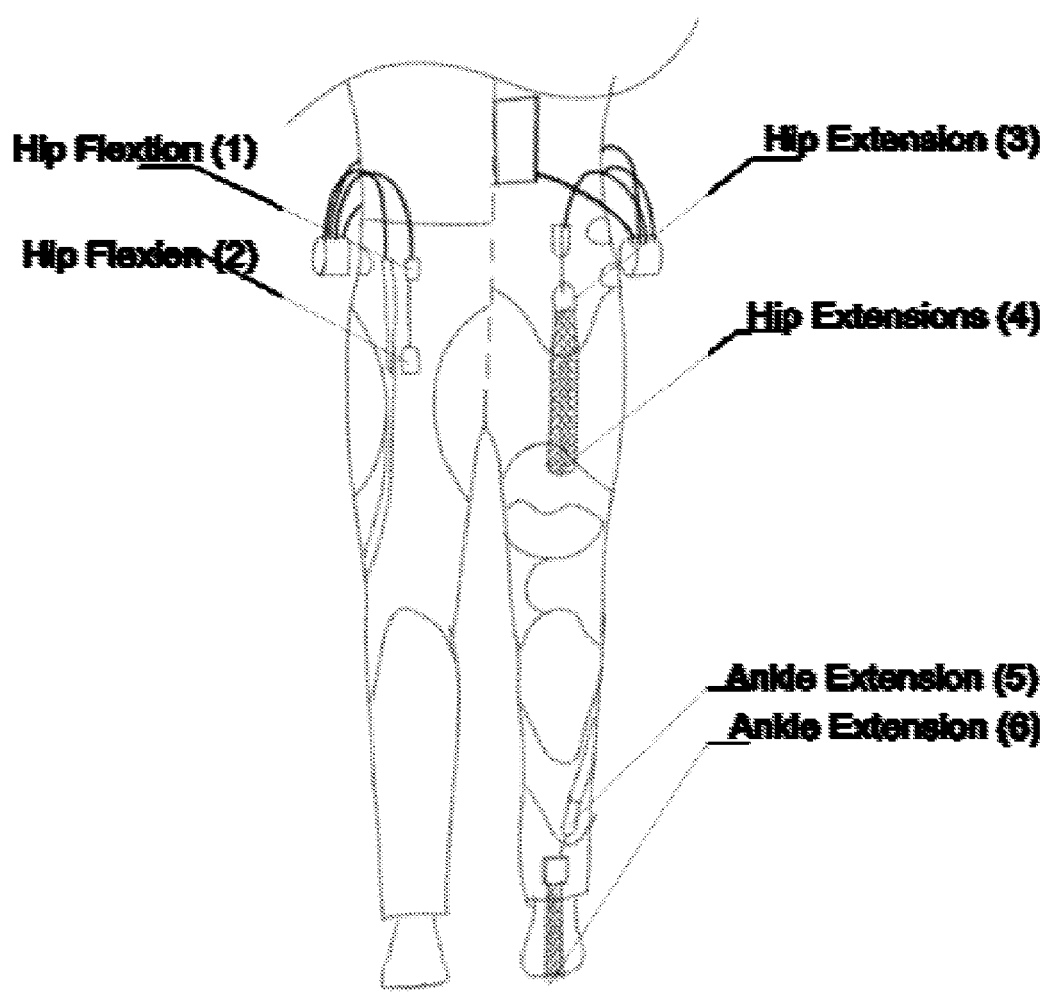

FIG. 66 shows Bowden cable termination points for a soft exosuit in accord with at least some aspects of the present concepts.

FIGS. 67A-67D show aspects of an actuator for a soft exosuit in accord with at least some aspects of the present concepts.

Figure 68:
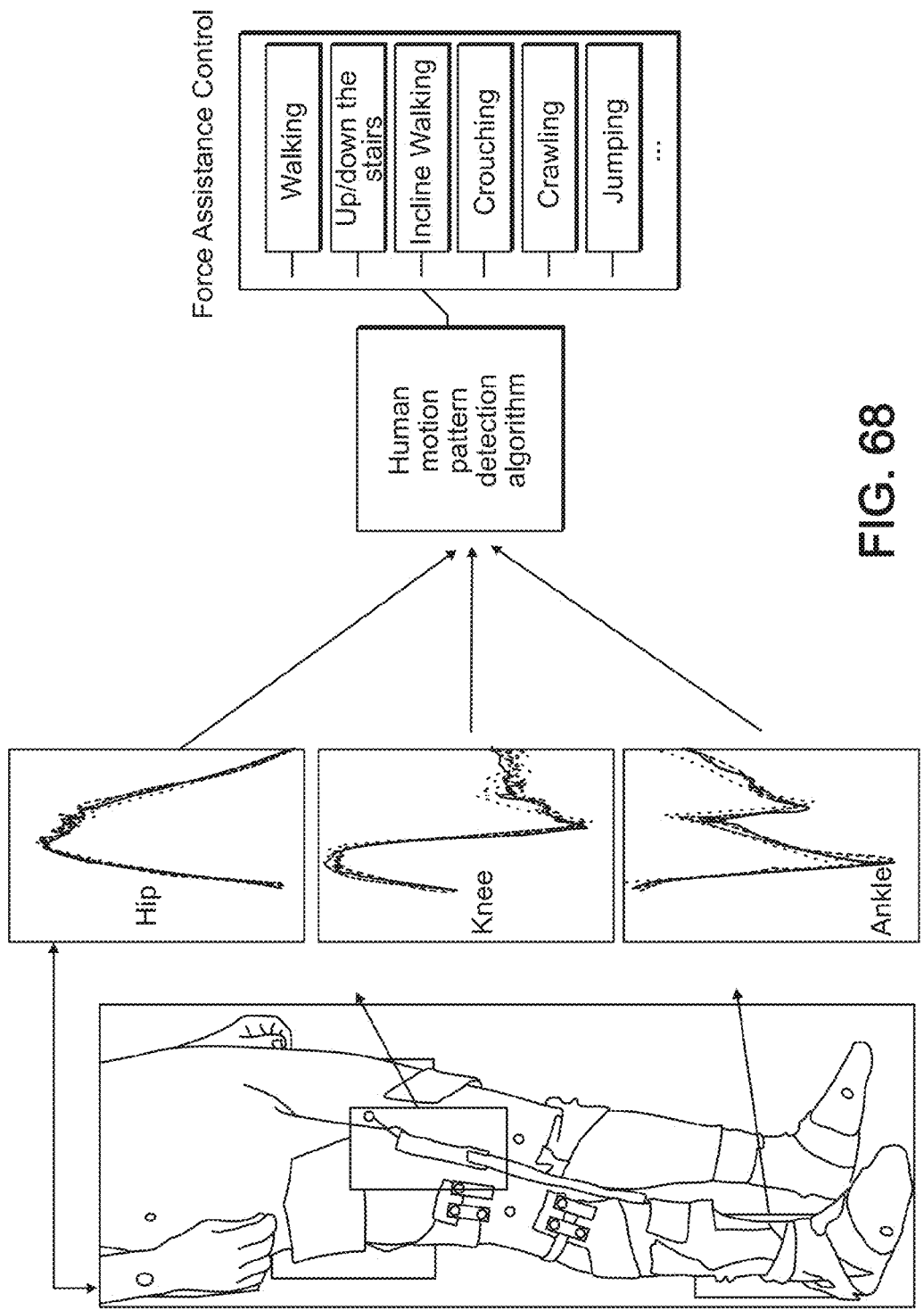

FIG. 68 shows aspects of a control scheme for a soft exosuit in accord with at least some aspects of the present concepts.

Figure 69:
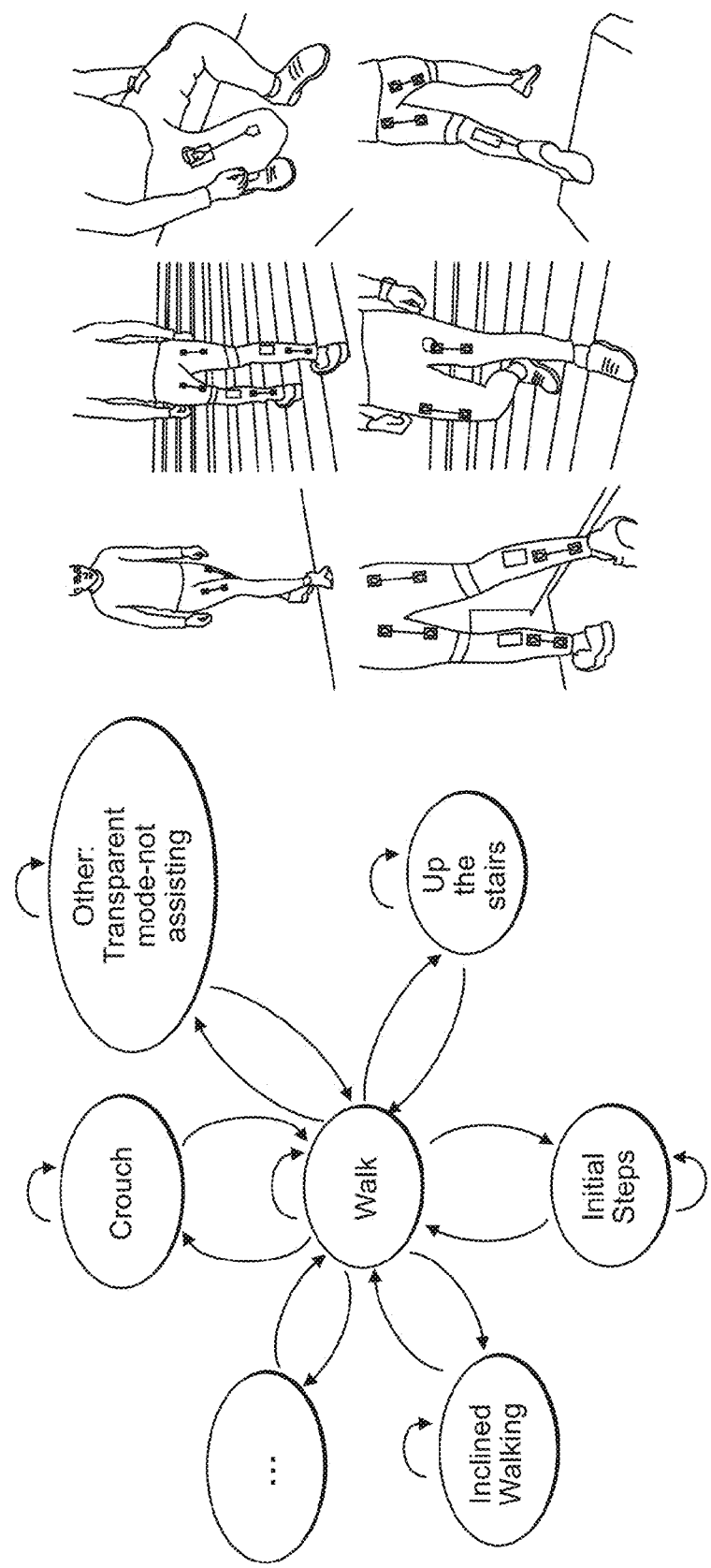

FIG. 69 shows aspects of a control scheme for a soft exosuit in accord with at least some aspects of the present concepts.

Figure 70:
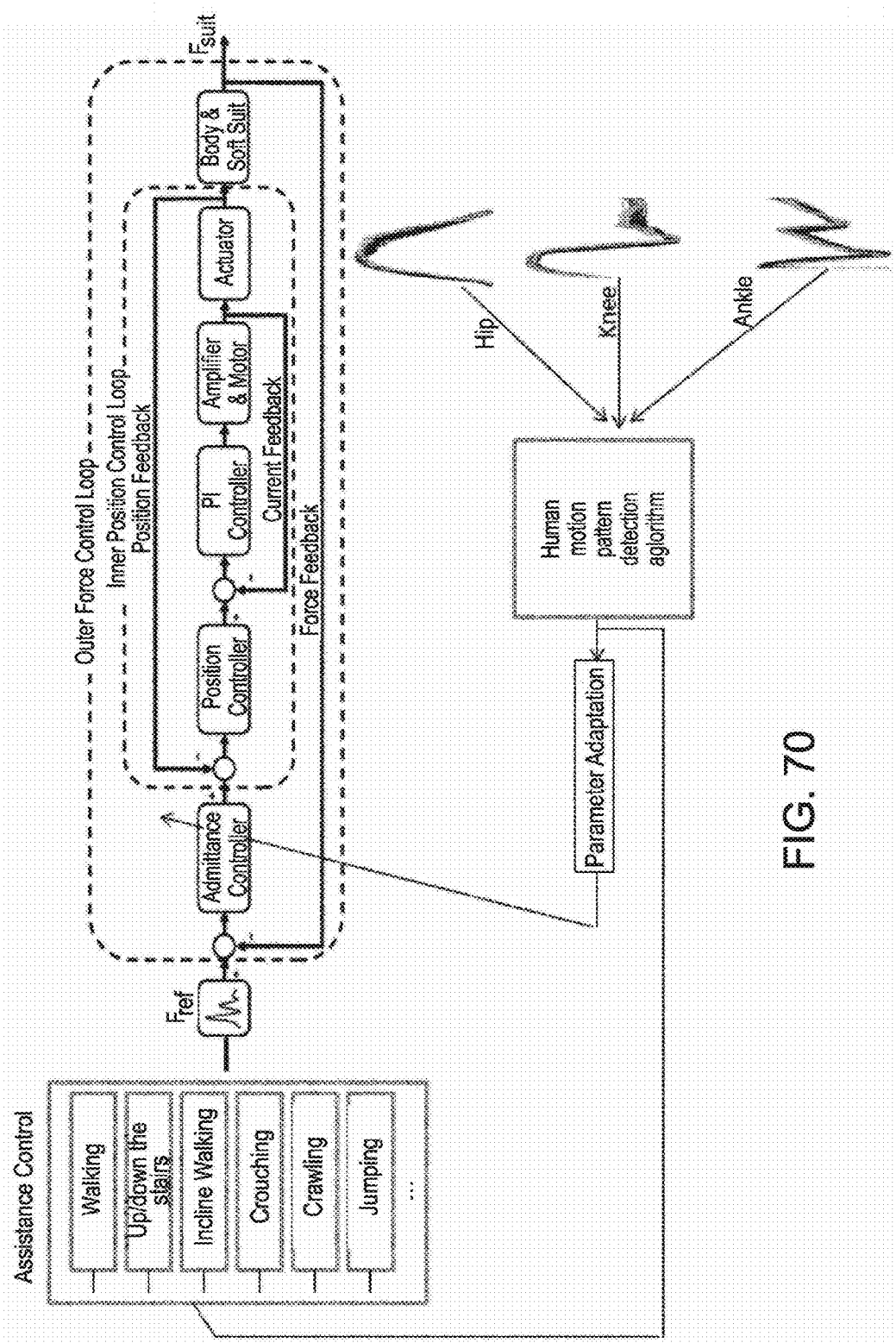

FIG. 70 shows aspects a control scheme for a soft exosuit in accord with at least some aspects of the present concepts.

FIG. 71A-71H show aspects of an embodiment of a soft exosuit in accord with at least some aspects of the present concepts.

Figure 72A:
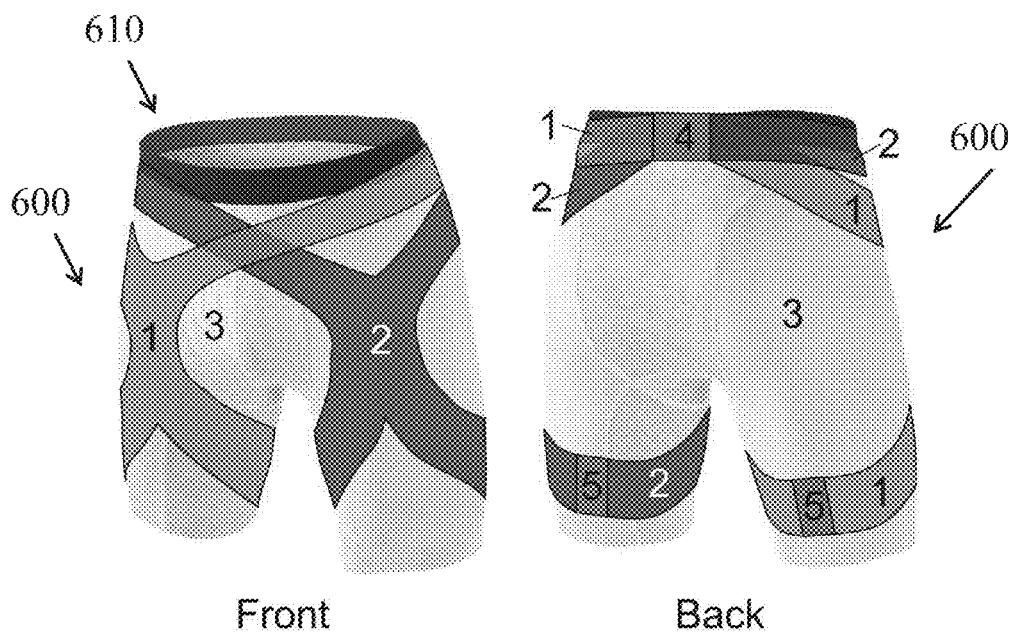
Figure 72B:
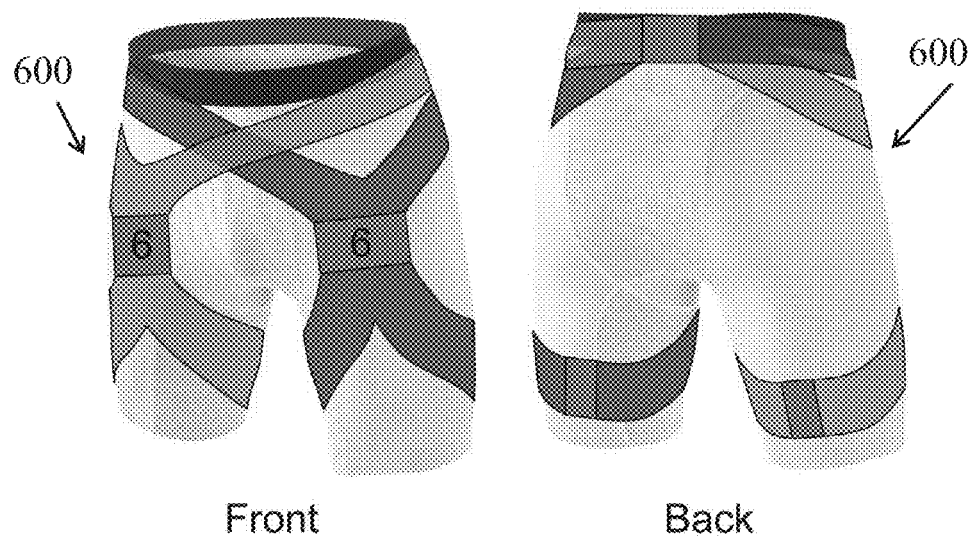

FIGS. 72A-72B show (a), front and back views of a passive hip system aiding hip flexion and (b) front and back views of the same system with added elastic material in the front in accord with at least some aspects of the present concepts.

Figure 73A:
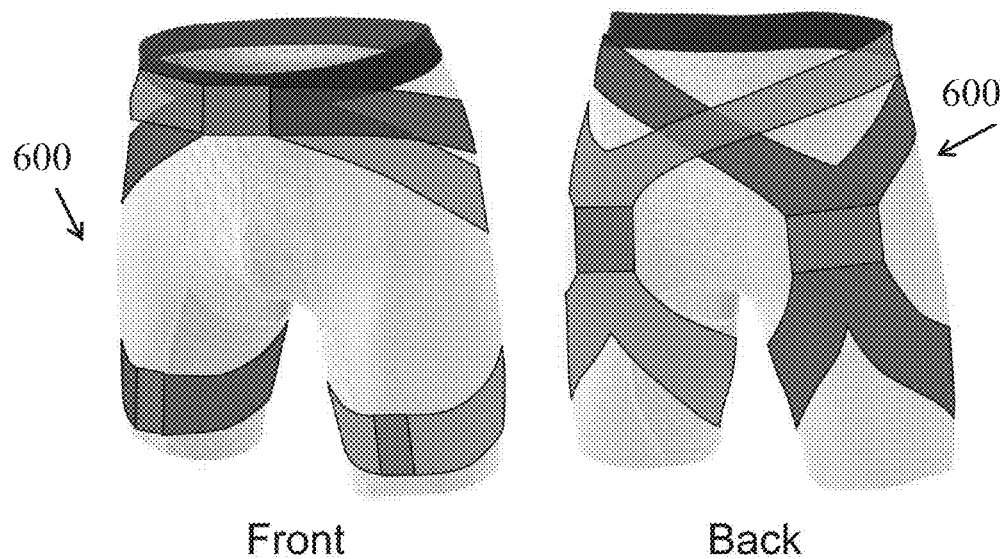
Figure 73B:
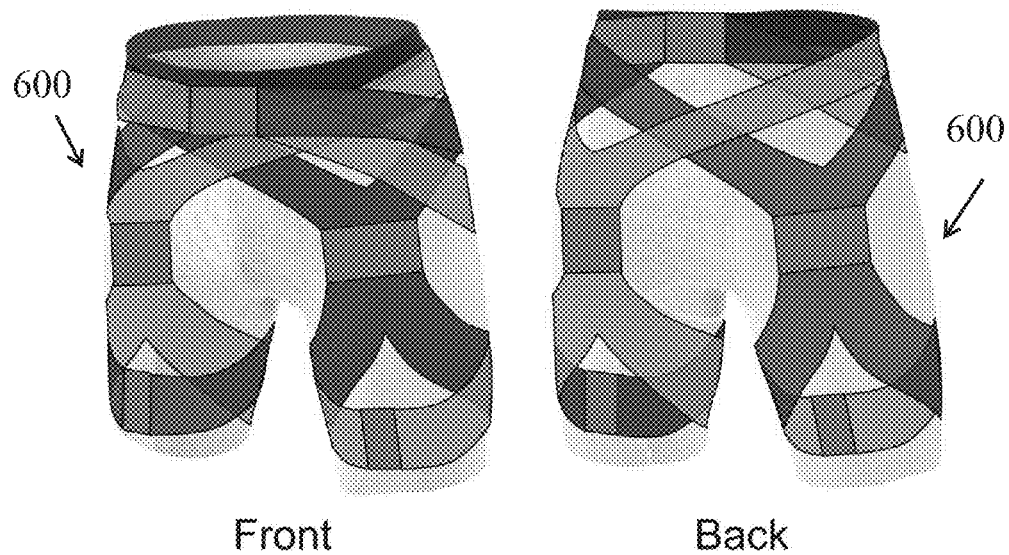

FIGS. 73A-73B show (a) front and back views of a passive hip system supporting hip extension and (b) front and back views of a garment supporting both hip flexion and hip extension in accord with at least some aspects of the present concepts.

Figure 74:
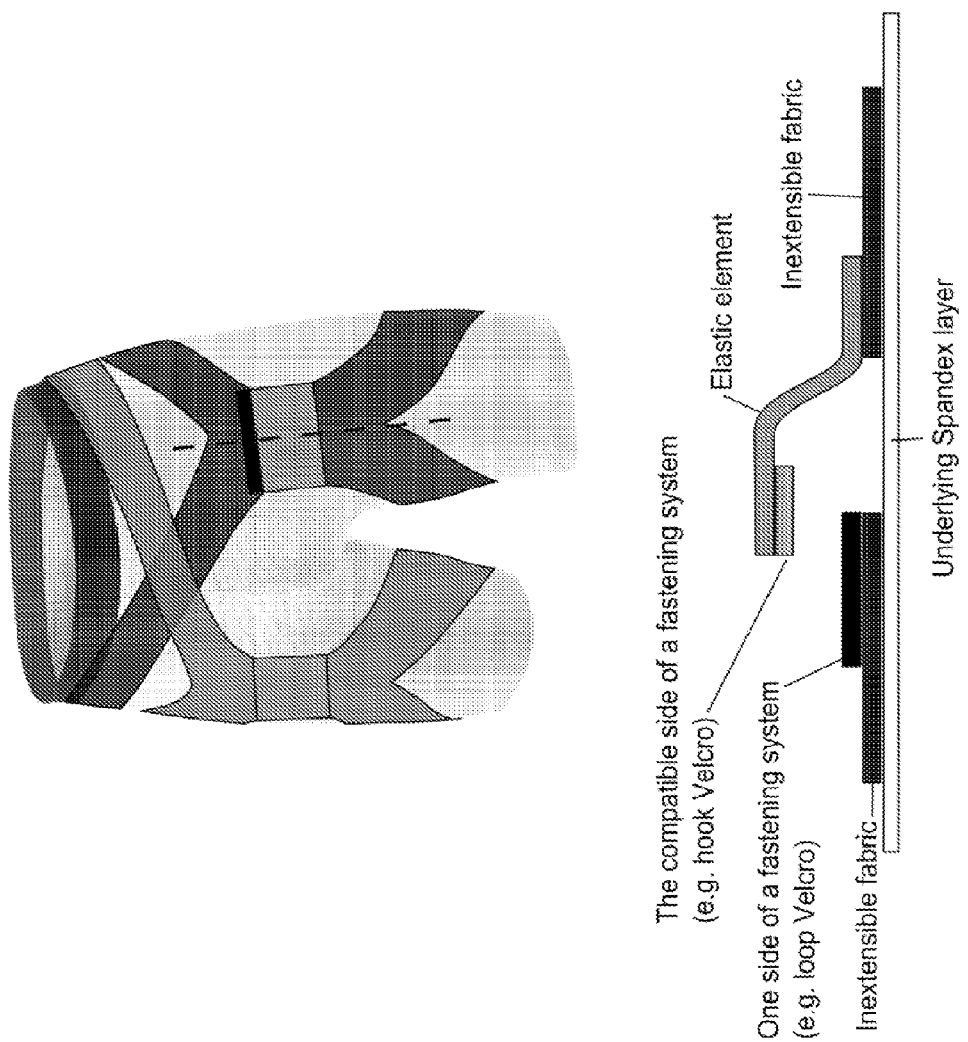

FIG. 74 shows a fastening system with an elastic element at the front of the suit in accord with at least some aspects of the present concepts wherein the bottom diagram is a cross-section of the suit along the dashed line in the top drawing.

Figure 75:
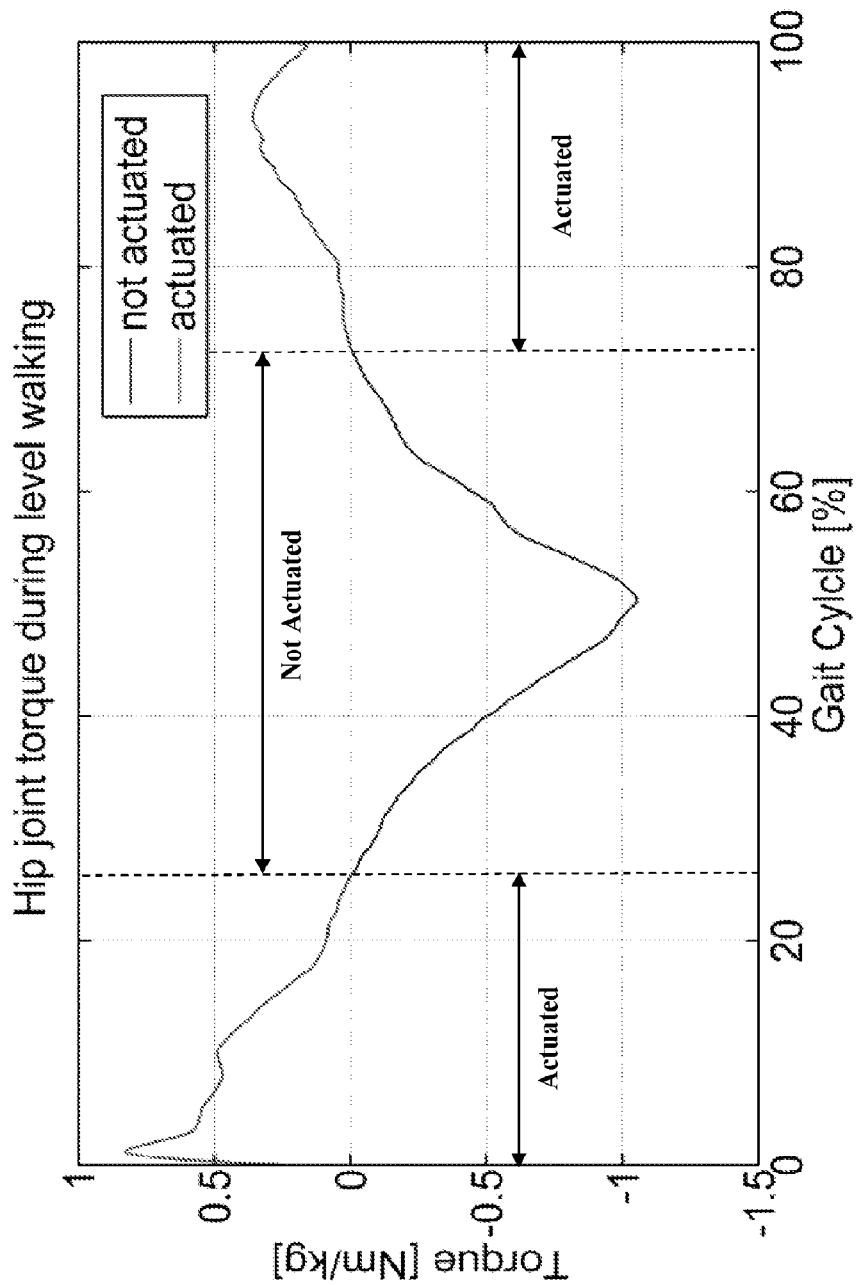

FIG. 75 shows hip joint torque during level walking.

Figure 76:
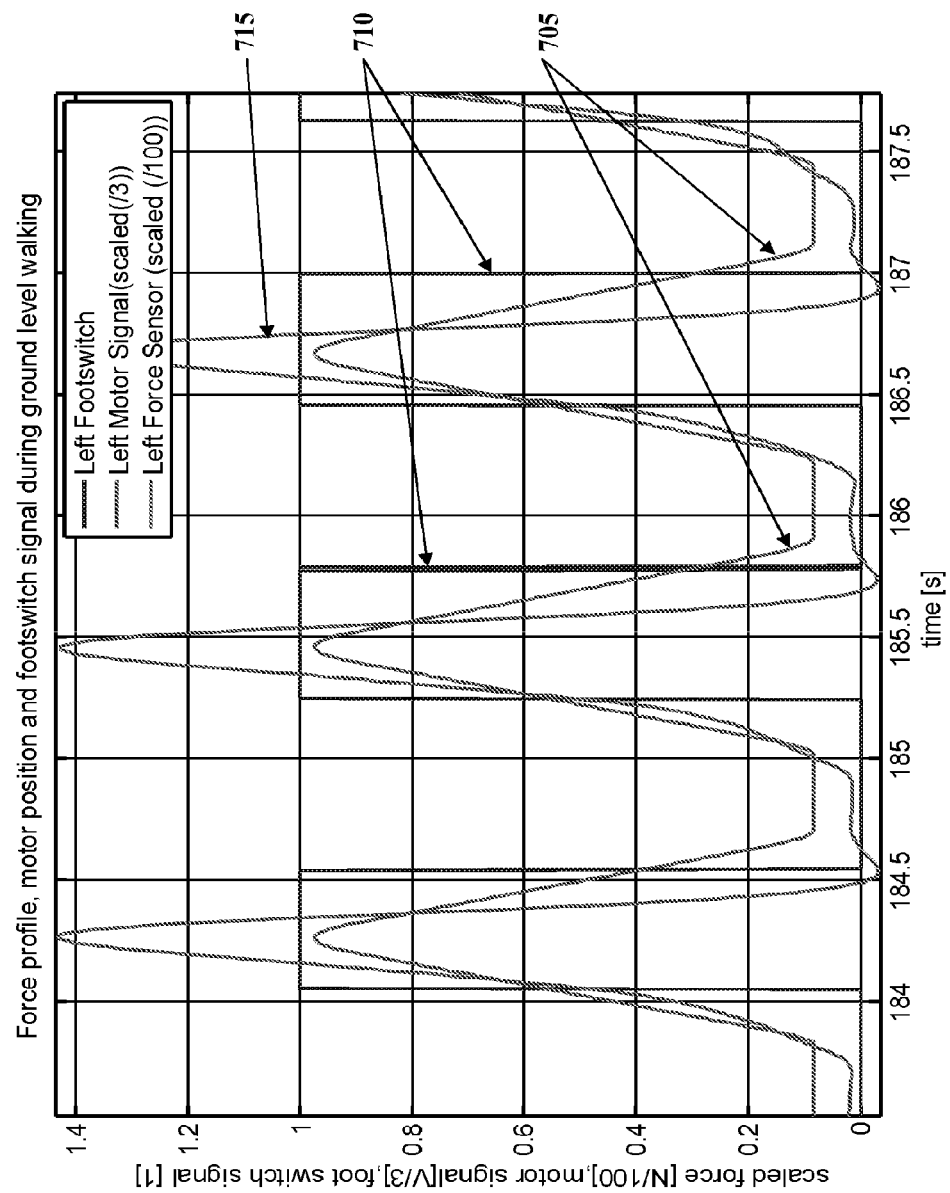

FIG. 76 shows profile, motor position and footswitch signal during ground level walking.

Figure 77:
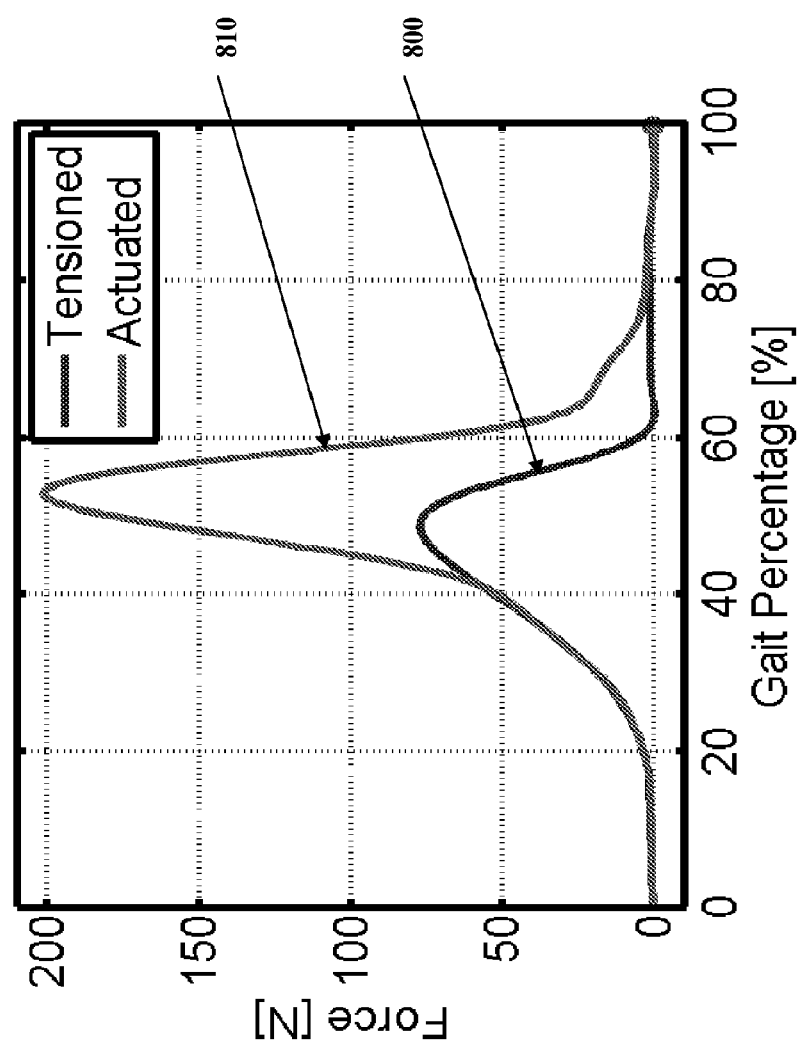

FIG. 77 shows a graph depicting the timing of actuation of the soft exosuit during a gait cycle and the corresponding suit force in relation to cable position.

Figure 78:
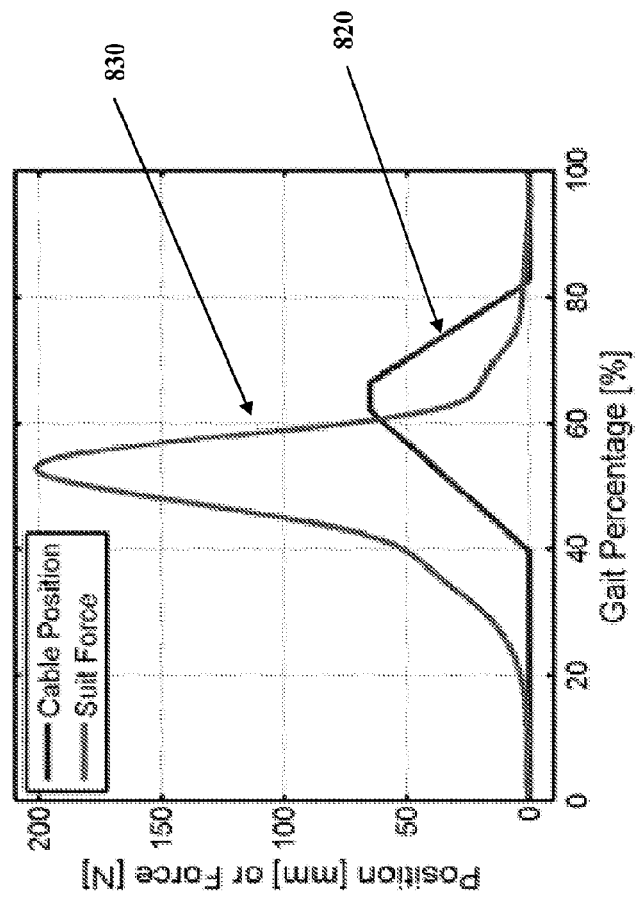

FIG. 78 shows another graph depicting the timing of actuation of the soft exosuit during a gait cycle and the corresponding suit force in relation to cable position.

FIG. 79 shows an example of a soft exosuit component (here a footwear attachment element) comprising a haptic actuator to provide user feedback according to at least some aspects of the present concepts.

Figure 80A:
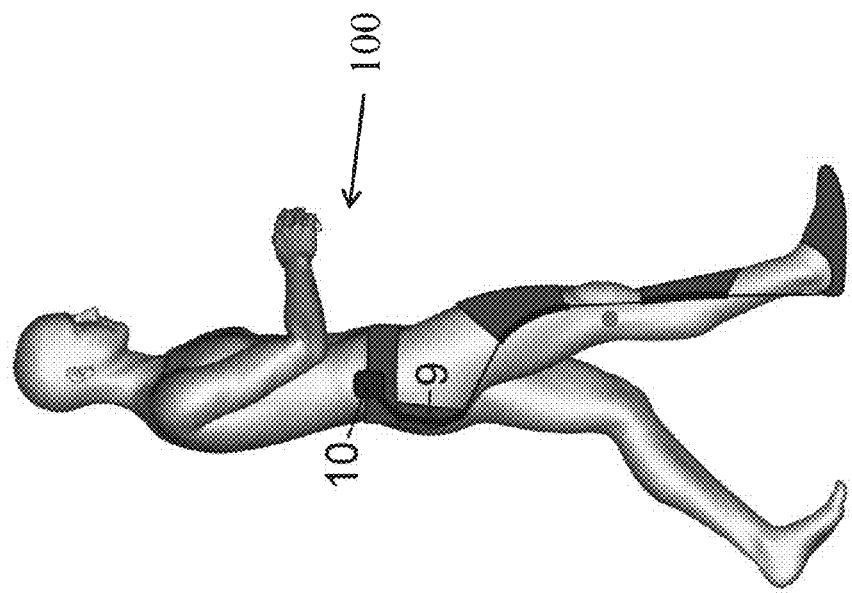
Figure 80B:
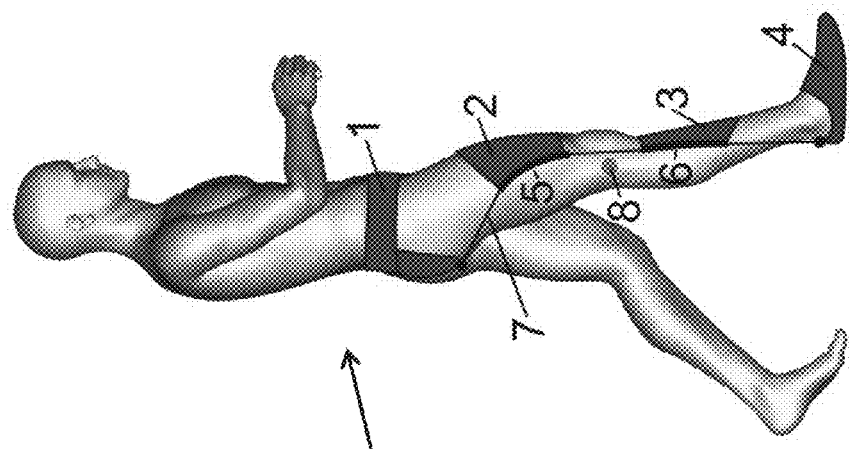

FIGS. 80A-80B show an example of soft exosuit components according to at least some aspects of the present concepts.

DETAILED DESCRIPTION OF PREFERRED EMBODIMENTS

The present invention is directed to a soft exosuit system that can be used in combination with an actuator system to provide active assistance with natural motions, such as walking, running, stepping up, stepping down, etcetera.

In contrast with prior art rigid exoskeletons, the soft exosuit in accord with the present concepts utilizes flexible materials and actuators to specifically address the human factors challenges associated with exoskeleton devices and does not have a load bearing exoskeleton, but rather relies on the user's biological skeleton to assist with the application of forces and transfer of load.

The soft exosuit greatly reduces the mechanical impedance and kinematic restrictions compared to traditional exoskeletons with rigid components and does not significantly constrain or restrict the user's degrees of freedom. With such a system, it is possible to add controlled impulses of energy (e.g., during key portions of the gait cycle), rather than direct control of limb position(s), to provide assistance to locomotion and reduce the metabolic cost of movement (e.g., walking/load carrying) without significantly constraint of movement.

Initial design parameters utilized data for a $50^{th}$ percentile male, with the specification that the soft exosuit must be capable of emulating the forces and ranges of motion of normal walking. To translate torques and rotational motion into linear values for McKibben pneumatic actuators 15 (known to contract 25% during actuation) used in the soft exosuit 10 depicted in FIGS. 1-6B, anthropometric values were found for each joint to estimate moment arm and total required travel. By estimating a position relative to joint center, moment arms were estimated and, knowing the ranges of motion, the required force and displacement were determined. On these initial parameters, device specifications were developed and are shown in Table I, below, which shows range, moment, and power during normal walking of 50% male, 79 kg mass, 1.75 m height.

TABLE 1

| Degree of Freedom | Range of motion (deg) | Moment (Nm) | Moment Arm (m) | Max Force (N) |
|---|---|---|---|---|
| Ankle Plantarflexion | 25 | 100 | 0.06 | 1867 |
| Ankle Dorsiflexion | 10 | 5 | 0.06 | 67 |
| Knee Flexion | 60 | 25 | 0.07 | 457 |
| Knee Extension | −5* | 25 | 0.07 | 457 |
| Hip Flexion | 35 | 80 | 0.12 | 750 |
| Hip Extension | 10 | 50 | 0.12 | 367 |

*Maximum knee extension is less than zero (straight leg) during walking

Figure 3A:
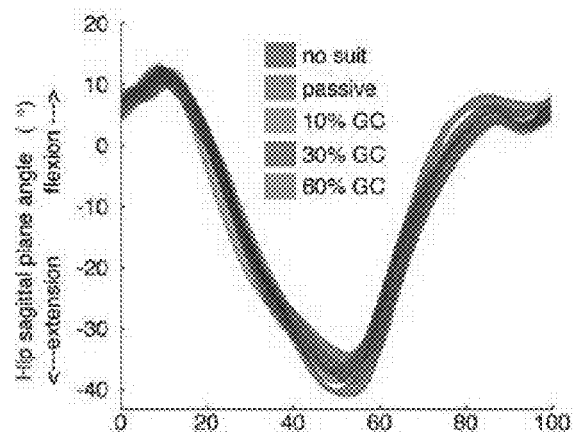
FIGS. 3A-3C show kinematic test data with respect to the gait cycle for the soft exosuit of FIG. 1 depicted mean plus or minus one standard deviation, with actuation at different points of the gait cycle.
Figure 3B:
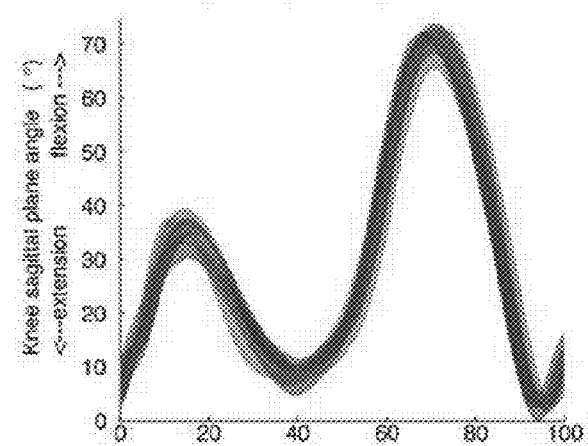
Figure 3C:
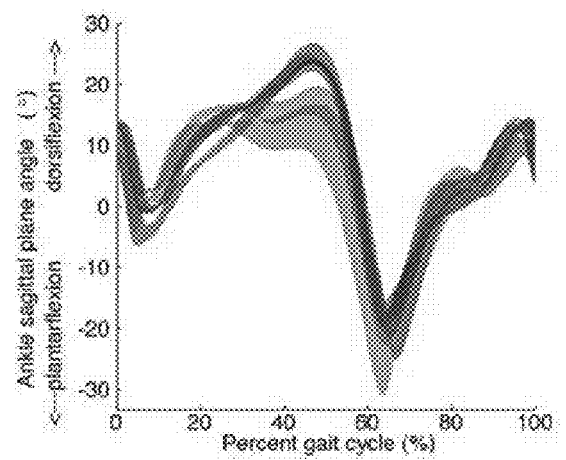
Figure 4:
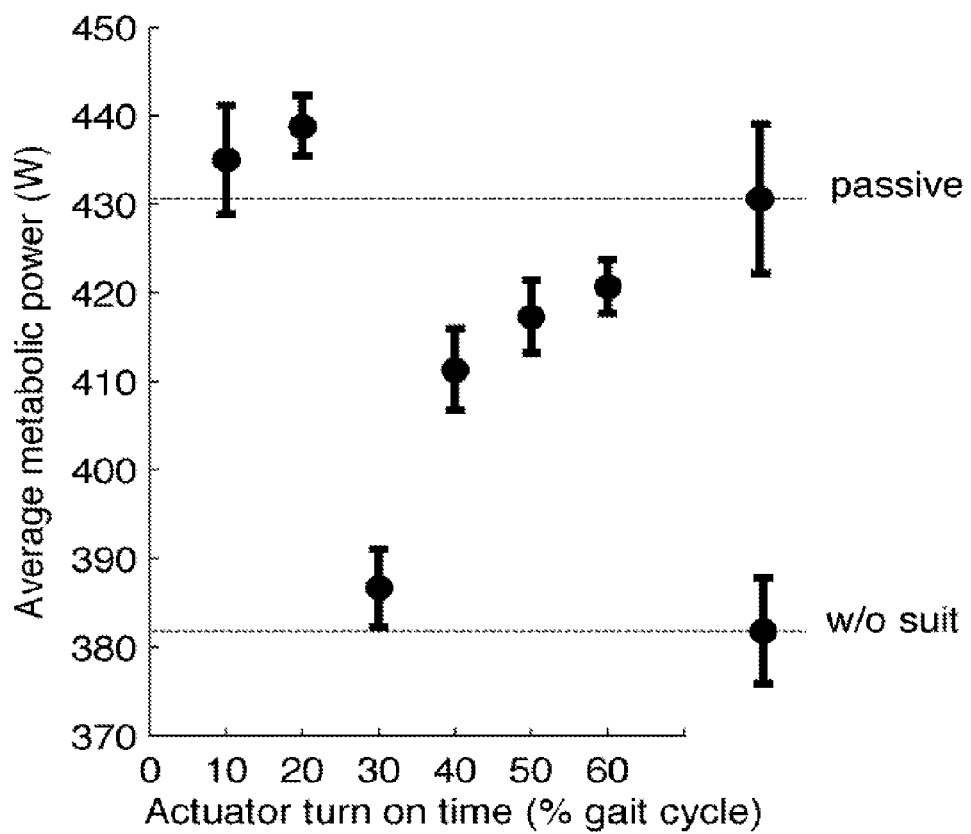
FIG. 4 shows, for the soft exosuit of FIG. 1(a), average metabolic power for six different actuator turn-on times during the gait cycle.
Figure 5:
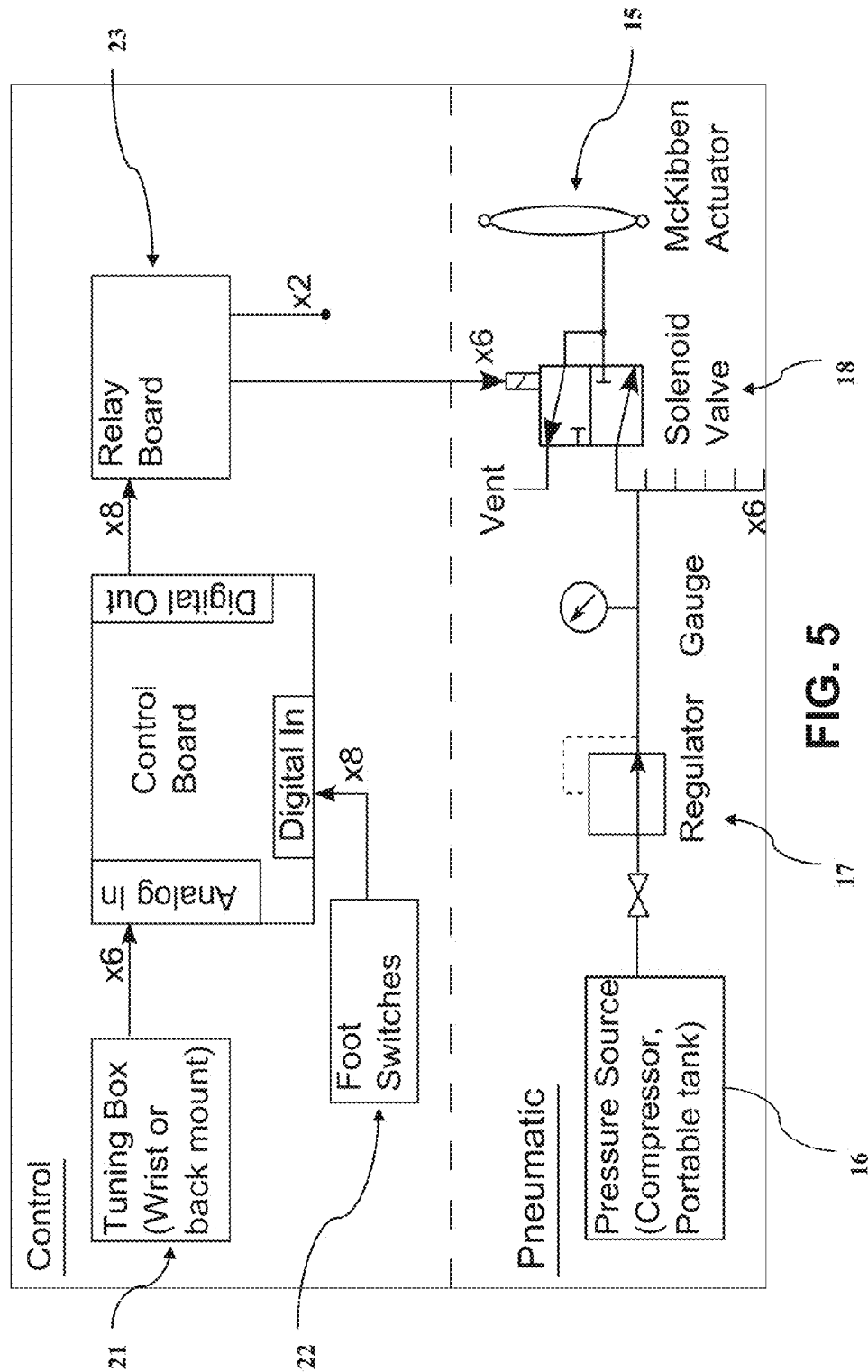
FIG. 5 shows an example of a soft exosuit control and power system for a pneumatic system utilizing McKibben actuators in accord with at least some aspects of the present concepts.

In the embodiment of the soft exosuit 10 described in FIGS. 1-6B, the actuators selected to assist motion were McKibben pneumatic actuators 15. As compressed air is pumped into the pneumatic actuators 15, they expand radially and shorten in length, thereby providing actuation. The applied force can be modified by changing input pressure. Stroke length is determined based on the actuator length. A pneumatic actuator 15 with an active length (excluding end hardware such as fittings and steel loops) of 200 mm was prototyped and force versus displacement data were recorded on an Instron 5544 load frame system for 1 to 5 bar (14.7 to 73.5 psi) input pressures. For this prototype, 4 bar (58.8 psi) was chosen as an operating pressure to provide substantial actuating force, yet provide an additional safety measure, providing forces 40% lower than the design pressure of 5 bar. As shown in FIG. 5, air flow from the pressure source 16, via a regulator 17, to the pneumatic actuators 15 was controlled by inline solenoid valves 18, and air was supplied from the compressor to the system with ⅜ inch OD (¼ TD) tubing, and distributed from the valves to the actuators with individual ¼ inch OD (⅛ TD) tubes to each actuator.

To adequate assist with dynamic motions, such as assisting with gait, inflation and deflation times of each pneumatic actuator 15 must be considered, as the actuators do not inflate and deflate instantaneously. Thus, the precise point of application of force during the movement (e.g., at what percentage of the gait cycle) must be understood and defined to ensure that forces are appropriately applied to the joint during inflation and to ensure that deflation occurs rapidly enough so as not to restrict joint motion. As one example, in evaluating the dynamic performance of the McKibben pneumatic actuators 15 utilized in the soft exosuit 10 of FIG. 1, the force versus time was recorded at 4 bar during inflation and deflation and it was determined that force versus time curve was generally sigmoidal wherein, for inflation, 90% of max force (235N)

was obtained after 0.316 seconds from when pressure was applied and wherein, for deflation, force dropped from maximum force to 10% of maximum force in 0.098 seconds. Using this pneumatic actuator 15, the force and power requirements listed in Table 1, above, could be met by selecting the appropriate number of actuators for each degree of freedom. For example, four actuators could be configured in parallel at each ankle joint to assist with ankle plantarflexion.

Air consumption for the test pneumatic actuator 15 at 4.0 bar, gauge pressure, was determined to consume 0.60 gram (0.021 mol) of air per actuation.

In order to develop a soft exosuit (e.g., 10, FIG. 1) of primarily soft components, the present inventors set about to develop a method of applying loads to the user using tension, augmenting selected muscles at selected time which relying upon the user's skeletal structure to generate any compressive, bending, or shear loads required in the system. Initial human factors design specifications were to provide a soft exosuit that was (1) lightweight, with minimal inertia added that could potentially disrupt normal gait dynamics; (2) non-restrictive so as not to disrupt natural joint kinematics in all body planes and (3) comfortable.

In order to apply a torque to a first location (e.g., at a joint), the actuator(s) (e.g., pneumatic actuators 15 in the example of FIGS. 1-6B) must apply a reaction force to one or more other parts of the user's body. As seen above in Table 1, the forces applied to joints during movement can be quite high (e.g., 1867 N for ankle plantar flexion of 25°). Accordingly, although tight straps or skin-adhesives could be used to maintain the position of wearable devices, tight straps or skin-adhesives are not desirable means by which to maintain the position of wearable devices used to apply forces required for actuating the limbs. Instead, it is presently preferred that tight straps or skin-adhesives be used only to support small loads, such as the weight of the components, and not to apply limb-actuation forces. Further, forces parallel to the skin cause slippage, chafing, discomfort, and present a high likelihood of deforming and/or slipping, which would render actuation ineffective.

In the context of a soft exosuit 10 (e.g., FIG. 1), it was determined that the reaction forces could be advantageously directed to anchor points 12 known to readily support load such as, but not limited to, the shoulders, iliac crest of hips, and plantar aspect of the feet. These anchor points are characterized by large bony landmarks near the surface of the skin and are able to withstand large applied normal or nearly normal reaction forces (e.g., at the hips, downwardly directed loads borne on the top of the iliac crest region are preferable to forces in shear borne along the side of the hip). The inventors further observed that, during joint motion, some paths on the skin surface change in length substantially relative to one another (high strain paths), while other paths on the skin surface exhibit little relative motion (low strain paths or lines of non-extension).

Figure 1:
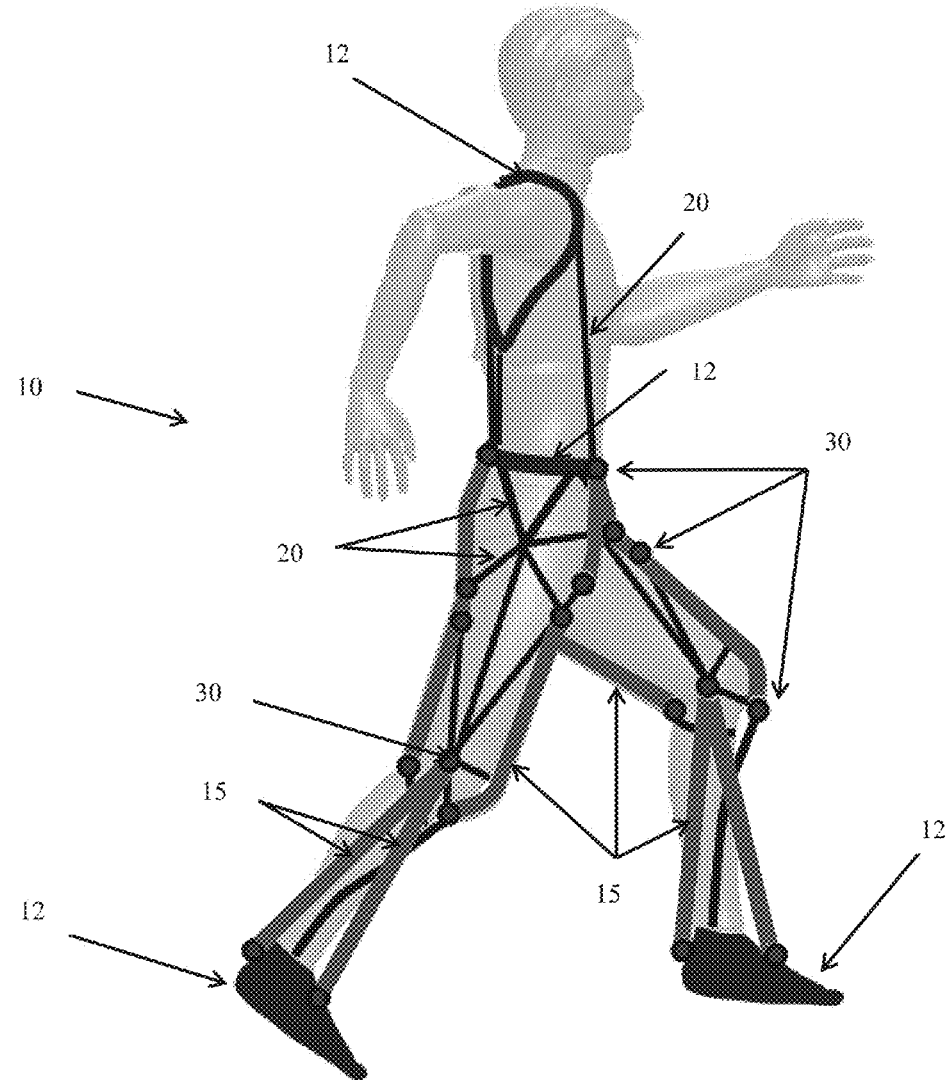
FIG. 1 is a figure depicting a first example of a soft exosuit in accord with at least some aspects of the present concepts.

Turning again to one design goal of applying moments about one or more of the hip, knee and/or ankle joints, during motion via a soft exosuit, the inventors determined that the reaction forces from a desired actuation should be redirected to one or more of the anchor points along the lines of non-extension via a matrix of connectors from the desired actuation point, triangulating with other connectors to maintain stability during normal range of motion while redirecting the forces to terminate at one or more of the anchor points (see, e.g., FIG. 1). This configuration of the soft exosuit robustly constrains the desired actuation point, minimizes distortion and effect on range of motion, and transmits reaction forces to portions of the user's body better adapted to receive such forces. Consistent with these concepts, the soft exosuit (e.g., 10 of FIG. 1) advantageously utilizes connection elements 20 forming triangulation paths selected along lines of non-extension for hip flexion and extension, knee flexion, and ankle dorsi flexion and plantar flexion. In the example of FIG. 1, soft exosuit 10 connects the distal end of the pneumatic actuators 15 to the ankles and the proximal ends of the pneumatic actuators are connected to the hips and/or shoulders, via intermediary nodes 30 and connection elements 20, to distribute forces as broadly as possible and to maintain forces at least substantially normal to the skin.

Figure 2A:
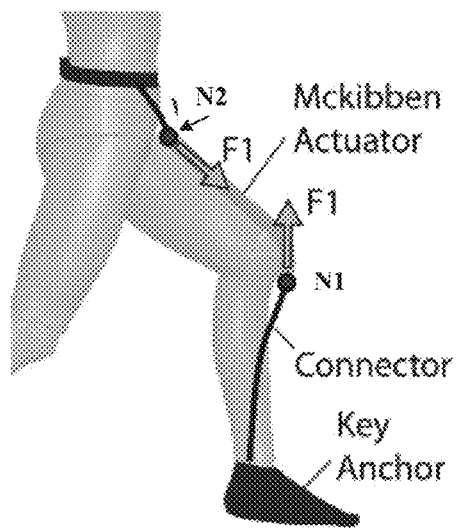
FIGS. 2A-2D are figures depicting exemplary force vectors for a portion of the soft exosuit of FIG. 1.
Figure 2B:
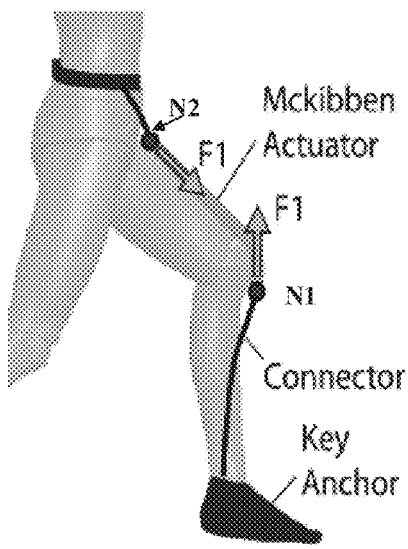
Figure 2C:
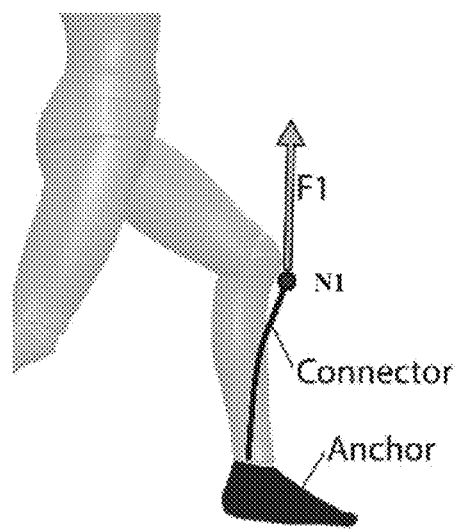
Figure 2D:
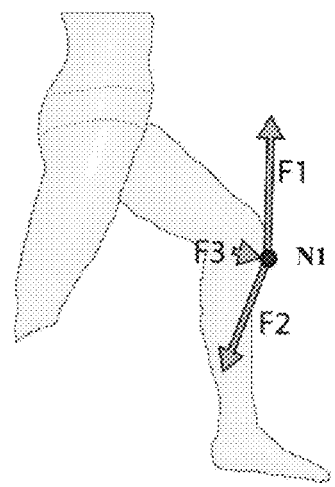

To illustrate the above concepts, FIGS. 2A-2D show an example of the forces involved in actuation of the knee joint. FIG. 2A shows a first node N1 and a second node N2 on opposite sides of the left knee joint. Tension applied between these two nodes are able to actuate (or assist actuation of) the knee in extension. In accord with the present concepts, nodes N1 and N2 are desired not to move relative to the underlying limb and are accordingly rigidly constrained or anchored with sufficient stiffness to resist significant forces (e.g., see Table 1, above). Viewing node N1 from the frontal view in FIG. 2B, it can be seen that an additional connection is required along a contralateral path to the anchor point at the ankle, for stabilization. In order to maintain equilibrium and avoid anchor dislocation, F1 must remain within the angle between F2-1 and F2-2 connectors. Similar analyses apply to the anchor point at the proximal end of the pneumatic actuator transmitting reaction forces to the waist belt and/or shoulder harness (if provided), distributing forces along the iliac crest of the hip (and/or to the shoulders).

Figure 6B:
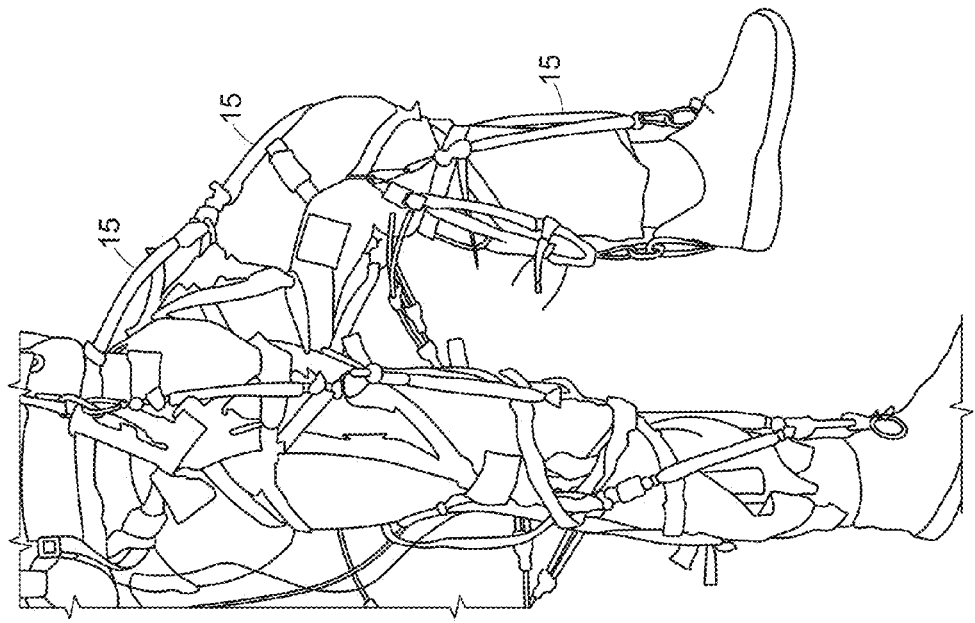
FIGS. 6A-6B show an example of the soft exosuit of FIG. 1 showing the soft exosuit connector matrix without actuators and the soft exosuit connector matrix with actuators, respectively.
Figure 6A:
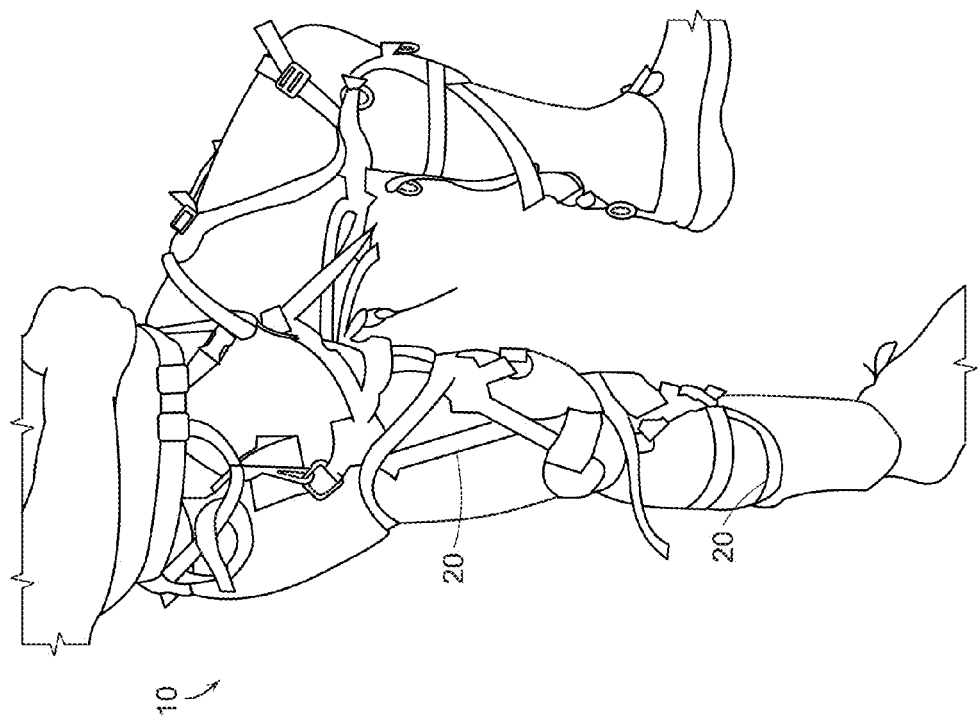

The soft exosuit 10 of FIG. 1 is shown in FIGS. 6A-6B. In construction, nodes 30 comprising triangular threaded links (Quik-Links) were sewn into a matrix of connection elements 20, formed from nylon strapping material, attaching the nodes to one or more anchor points 12 and/or other node(s). Carabiners, squeeze-release buckles, and oval Quick-Links were used as necessary between portions of connector straps to facilitate donning and doffing of the soft exosuit. The quantity and length of actuators are selected to achieve the desired force and ranges required for the associated degree of freedom for a soft exosuit with hip, knee and ankle joint actuation designed for gait assistance. To this end, the soft exosuit 10 of FIG. 6B has twelve McKibben pneumatic actuators 15 attached to nodes 30 and anchor points 12 through a network of non-rigid connection elements 20, comprising webbing, to leverage lines of non-extension.

In the prototype soft exosuit 10 represented in FIGS. 3A-6B, the pneumatic valves 18 and controller 20 were housed in a back-mounted assembly. Signals from the controller 20 were output to relay board 23 which, in turn, controlled the solenoid valves 18 operating the pneumatic actuators 18. Inputs to the controller 20 included tuning box 21 and foot switches 22. The tuning box 21 was wrist mounted and enabled the user to perform real-time, on-the-fly adjustment of onset delays and actuation durations. Heel strikes were sensed via footswitch-instrumented insoles (B&L Engineering), sending a signal to an Arduino Mega 2560 microcontroller (http://arduino.cc/en/). Upon sensing a heel strike, the controller 20 was configured to initiate a timing sequence for actuating three degrees of freedom on that limb. Each degree of freedom had a programmable turn on time (actuator turn on time after heel strike) and actuation duration. Heel-strike was sensed for both feet and was used to initiate delays and actuations independently. Timing sequences were identical for both legs to maintain symmetry, but could be adjusted independently if desired to account for any user asymmetry in gait. Although during testing, compressed air could be supplied via central compressed air (shop air) or a local compressor for stationary/treadmill testing, the soft exosuit 10 could alternatively utilize compressed air supplied by a one or more back-mounted compressed air tank(s) at 306 bar (4500 psi).

The soft exosuit 10 of FIG. 6B has a total mass of 7144 grams when tethered to a compressor and 9121 grams when using a single user-borne compressed air tank. The soft exosuit 10 itself has a mass of only 3500 grams (suit, pants, shoes, actuators, support straps), minimizing distal mass, known to have greater effect on metabolic cost. The mass of the valve box and batteries was 3280 grams and the control module, including the tuning box 21 was 364 grams. The soft exosuit 10 consumed 0.166 mol (4.8 gram) of air per gait cycle and, assuming a stride frequency of 1 Hz, would consumes 9.94 mol per minute. Under these assumptions, a 64 $in^3$, 4500 psi compressed air tank contains 41.3 mol (415 gram) of air, and would last for 4.15 minutes of constant walking.

A pilot study using the soft exosuit 10 of FIG. 6B examined the performance of the soft exosuit 10 in assisting gait by using the pneumatic actuators 15 to enhance ankle joint torque during push off. All other actuators in the soft exosuit 10 of FIG. 6B had their actuation duration adjusted to zero milliseconds so that they generated no force. Kinematic and metabolic data were collected at the Wyss Institute's Motion Capture Laboratory in order to quantify soft exosuit efficacy and the effect of the exo-gastrocnemius actuator's engagement timing on joint kinematics and metabolic power was investigated by varying the actuator turn on time within the gait cycle. Six actuator turn on times were investigated, ranging from 10% of the gait cycle to 60% of the gait cycle, in 10% increments. As controls, joint kinematics and metabolic power were also investigated with the soft exosuit 10 in a completely passive unpowered mode and with the subject not wearing the soft exosuit. Heel strike of the ipsilateral leg was defined as 0% of the gait cycle.

A Vicon® motion analysis system with 8 infrared cameras (Oxford Metrics, Oxford, UK) was used to obtain the kinematics of one healthy male subject aged 42, 65 kg and 1.73 m tall. The participant walked at 1.5 m/s along a 10 meter flat ground walk-way. Trials with a walking speed greater than ±5% of 1.5 m/s were excluded until three acceptable gait trials were attained. Motion capture data was collected at a sampling rate of 120 Hz. A total of 44 markers were attached to the participant based on a modified Cleveland Clinic marker set. Lower body markers were placed on the following anatomical landmarks: bilateral anterior superior iliac spines, bilateral apex of the iliac crests, dorsal aspect at the L5-sacral interface, lateral and medial femoral condyles, lateral and medial malleoli, calcaneal tuberosities and the superior aspect of the first and fifth metatarsophalangeal joints. Triad marker clusters were placed on the femora and tibae. Upper body markers where placed at the forehead, left and right temple, seventh cervical vertebra, sternum, tip of the tip of the acromia processes, humeral lateral epicondyles and the midpoint between the radial and ulna styloid processes.

Opensim 3.0 was used to perform the inverse kinematic analysis. An OpenSim 23 degrees of freedom head, torso and lower limb model was scaled to the subject based on 14 anthropomorphic measurements. After scaling the generic model, anatomical joint angles were calculated based on the three dimensional marker trajectories. Means and standard deviations of the ankle, knee and hip joint angles with respect to the gait cycle were computed. As shown in FIGS. 3A-3B, the sagittal plane hip and knee joint angles remained similar between the no soft exosuit 10, passive soft exosuit (no actuation), and actuated soft exosuit conditions. For all test conditions, the hip joint had typical sagittal plane behavior with initial flexion at heel strike, extension throughout the stance phase and then flexion during the swing phase (FIG. 3A). The sagittal plane knee angle for both the passive and actuated test cases also had a typical pattern with the knee initially flexing from heel strike through the loading response, extending from midstance to heel rise, flexing from heel rise to toe off and finally extending during swing (FIG. 3B). However, sagittal plane ankle joint kinematics were affected by the actuated soft exosuit 10 (FIG. 3C). Providing additional joint torque at the ankle joint via the Mckibben pneumatic actuators 15 during the stance phase caused the ankle to become more dorsiflexed during the loading response and more plantarflexed from the end of terminal stance to the beginning of pre-swing. The conditions which had the actuator turned on at 10% and 60% of the gait cycle caused the greatest change in ankle joint kinematics with up to approximately 15° of deviation from baseline walking without wearing the soft exosuit 10. In contrast, when the exo-gastrocnemius actuator turned on at 30% of the gait cycle the sagittal plane ankle joint kinematics remained similar to baseline walking without wearing the soft exosuit and was similar to the sagittal plane ankle joint kinematics when wearing the passive suit with no actuation (FIG. 3C).

In accord with the above testing, the subject's metabolic power was measured for the following eight test conditions: 1) standing at rest; 2) walking while not wearing the soft exosuit 10; 3) walking with the soft exosuit unpowered (passive); and 4-8) walking while wearing the soft exosuit with actuator turn on times of 10% through 60%, adjusted in 10% increments. For each test case, the same subject walked on a level treadmill at 1.5 m/s for 8 to 10 min. A Cosmed K4b2 cardio pulmonary exercise testing device (COSMED USA, Concord, Calif.) was used to measure the pulmonary gas exchange ($VO_2$, $VCO_2$) during the test. The average metabolic power (W) over a 4 min steady state interval was calculated and the standard deviation of the metabolic power was calculated according to inter-breath variability.

As shown in FIG. 4, the average metabolic power for the powered soft exosuit 10 conditions was minimized when the exo-gastrocnemius actuator turned on at 30% of the gait cycle. With this actuator timing the average metabolic power (± one standard deviation) while walking was 386.7±4.4 W, almost identical to the average power when wearing no soft exosuit at all (381.8±6.0 W), and substantially less than walking with the passive unpowered soft exosuit (430.6±8.6 W). There was a 43.9 W or 10.2% reduction in average metabolic power when comparing the powered and optimally tuned soft exosuit to the passive unpowered soft exosuit. The highest average metabolic power (438.8±3.4 W) occurred when the pneumatic actuators were activated at 20% of the gait cycle.

It was determined that, through proper turning of actuator turn on times, the soft exosuit 10 synergistically (and comfortably) enhance the user's kinematics while minimizing the metabolic power. It was further determined that improperly provided powered joint torque assistance adversely alters gait kinematics and adversely increases metabolic power. The soft, compliant exosuit system disclosed herein is able utilize the user's underlying bone structure as structural support while facilitating passive assistance of motion through tension and active assistance of motion using an actuator system that can provide additional force generation above that generated using passive motion.

The soft exosuits according to the present concepts, disclosed above and disclosed herein, provide numerous advantages over traditional, rigid robotic exoskeletons. The presently disclosed soft exosuits can be readily constructed from flexible materials such as, but not limited to, fabrics, cords, wires, cables, webs, functional textiles, and straps. In accord with at least some embodiments of the invention, the flexible materials are used to form connection elements that are substantially inelastic in tension (e.g., to provide stiffness under tension), elastic (e.g., to absorb energy and return energy to the user), and/or a combination of inelastic and elastic flexible materials. Connection elements formed from flexible materials are substantially lighter than conventional exoskeleton rigid elements and require less energy to carry and to move (e.g., low inertial impact). Moreover, these flexible connection elements are sufficiently conformable to accommodate the user's natural motion and kinematics and to avoid problems associated with joint misalignment typically found in rigid exoskeleton based systems.

The anchor points 12 or support features include, but are not limited to, bony and projecting parts of the body that are covered by a relatively thin layer of skin which can provide low displacement and minimal compliance when the soft exosuit is pressed against the skin (e.g., iliac crest of the hip bone, shoulders, etc.). As noted above, the connection elements 20 (e.g., flexible straps or webbing) are used to transfer forces to selected nodes 30 and/or anchor points 12 (e.g., via associated anchor elements). Higher levels of soft exosuit stiffness can be achieved by aligning the connection elements 20 in direct paths and/or indirect paths to the anchor points 12 to the point (e.g., node 30) where tension can be applied (e.g., by actuator(s)). For example, in accord with some embodiments of the invention, the connection elements can be aligned with the force vectors created as a result of the tension created in the soft exosuit. Alternatively, the connection elements 20 and/or nodes 30 can be arranged at angles and positions to permit force vectors created as a result of the tension introduced in the soft exosuit 10 to be applied to joints that are not aligned with the tension.

Figure 7:
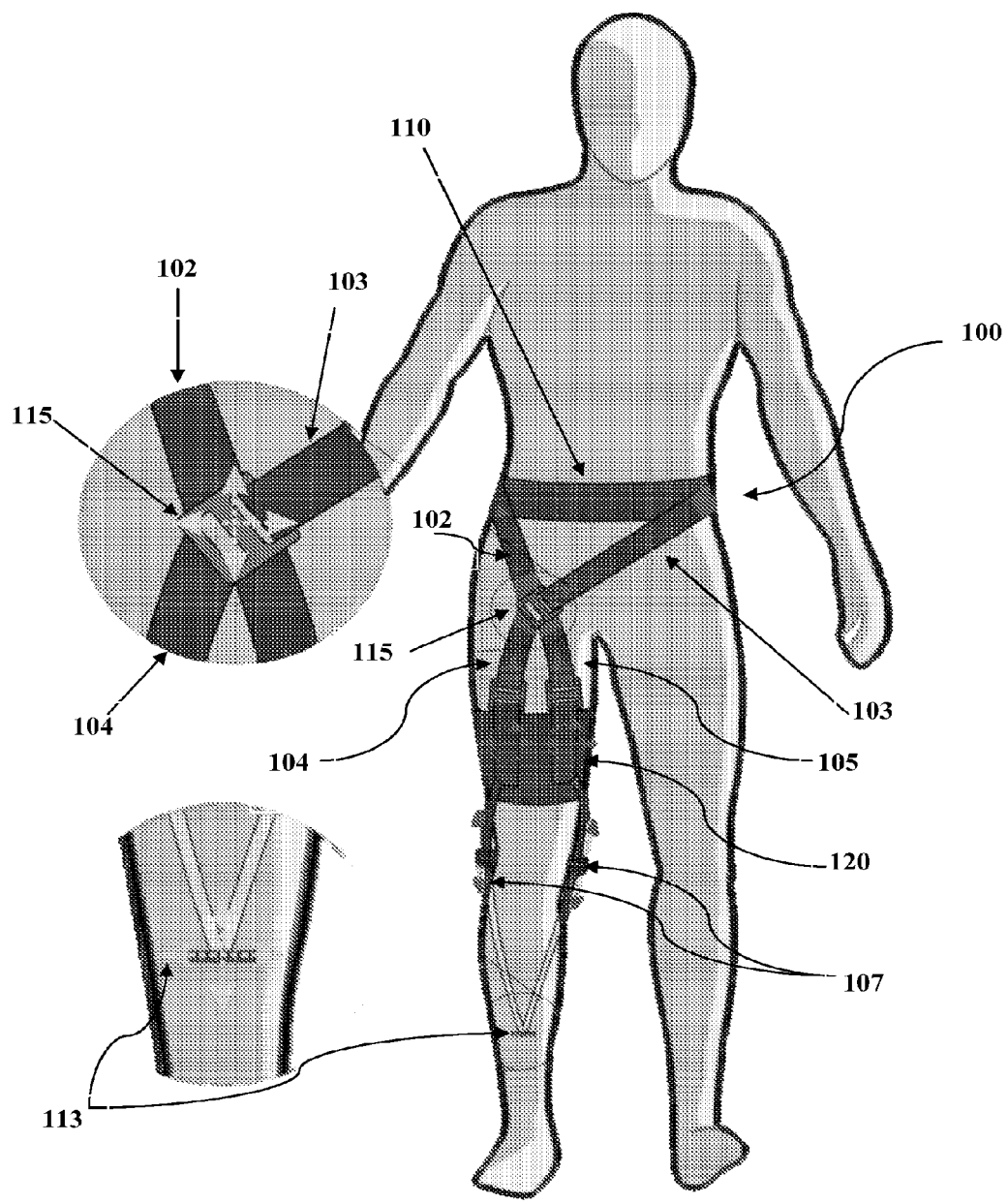
FIG. 7 is a diagram showing a front view of a second example of a soft exosuit in accord with at least some aspects of the present concepts.

FIG. 7 shows an embodiment of a soft exosuit 100 in accord with at least some aspects of the present concepts. As discussed above, the soft exosuit 100 is configured to apply a moment to one or more joints (e.g., a hip joint and ankle joint as shown in FIG. 7) using one or more connection elements (e.g., 102-105, 107). These connection elements can be pre-tensioned across the joint, such that the tension imposes an assistive moment on the joint. In accord with at least some embodiments, the user can selectively increase or decrease a pre-tension in the soft exosuit. This feature of user-selective pre-tensioning modification can comprise one or more independent channels (e.g., whole suit and/or independent controls for left/right and/or front/back), controlled by a mechanical or an electro-mechanical tensioning device configured to adjust a tension along the channel (e.g., by adjusting a functional length of one or more connection elements). Pre-tensioning may also optionally be adjusted by and/or optimized by the soft exosuit controller, with or without user-inputs providing feedback to the controller as to acceptable pre-tension comfort. In yet other aspects, the user may advantageously adjust tension in one or more connection elements or anchor elements by adjusting lengths of one or more connection elements or anchor elements (e.g., by looping webbing through buckle and using a VELCRO® region for attachment).

FIG. 7 shows a soft exosuit 100 comprising a waist belt 110, a node 115, a thigh brace 120 and connection elements 102, 103 connecting the waist belt and the thigh brace. The waist belt 110 encircles the waist and engages the iliac crest as a support member. One or more additional support elements (e.g., shoulder straps (not shown)) could also be utilized in addition to, or alternatively to, the waist belt 110. By allowing the waist belt 110 to tightly conform to the body at a narrow portion of the waist, the natural body features help to maintain the waist belt in position. The thigh brace 120 provides a support point or node on the thigh to guide and align the connection elements 102, 103 over the hip joint and along the thigh and, owing to the tapered shape of the thigh, the thigh can be used as a support point that resists upward tension applied to the thigh brace. Tensioning between the waist belt 110 and thigh brace 120 enables creation of an initial tension higher than would be achieved with the waist belt 110 alone.

FIGS. 8A-8F show plots (left side) showing hip (FIG. 8A), knee (FIG. 8C) and ankle (FIG. 8E) moments generated as a percent of gait cycle and (right side) showing hip (FIG. 8B), knee (FIG. 8D) and ankle (FIG. 8F) range of motion generated with respect to percent of gait cycle. The connection elements 102, 103 can be tensioned such that, during walking, the tension in connection elements 102, 103 applies a moment that encourages flexion of the hip joint at the time when the hip is extended. During the portion of the gait cycle just before pushoff (30-50%), the hip absorbs power. The soft exosuit could aid the absorption of energy during this time by resisting hip extension. Immediately after this, from 50-70% of the gait cycle, the hip provides positive power. The soft exosuit can aid this power generation as well by applying a complementary moment to the hip. Further, the connection elements 102, 103 can be connected (e.g., directly or indirectly via thigh brace 120) to calf connection elements 107 that extend down around the knee and meet at the back of the leg below the calf.

Figure 10A:
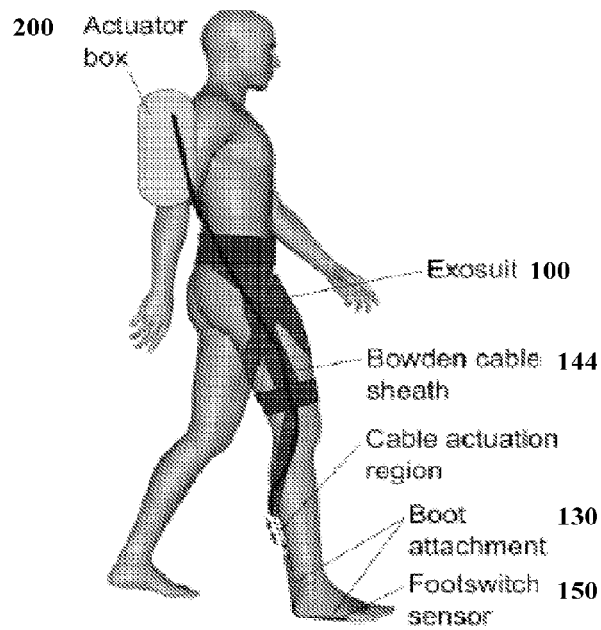
FIGS. 10A-10B are diagrams showing, respectively a representation of a side view of a soft exosuit according to at least some aspects of the present concepts, and representations of perspective views of a soft exosuit according to at least some aspects of the present concepts.

As shown in FIG. 10A, for example, in the back of the leg, the calf connection elements 107 are connected, in at least some embodiments, to a heel attachment or anchor element that directly (e.g., inside footwear of the user, between a sock or liner and inner surfaces of a user's footwear) or indirectly (through footwear) engages the foot (e.g., an anchor point that resists upward tension). The connection element 107 can also be attached, or alternatively be attached, directly or indirectly (e.g., via an intermediary anchor element) to a point located on the outside of footwear (e.g., a boot). Thus, in some aspects of the present concepts, the soft exosuit terminates at the user's foot (or feet) where the inferior (lower) anchor points comprise anchor members engaging the user's foot (or feet) or the user's footwear.

In each of the above configurations of anchoring the soft exosuit at or near the foot or feet of a user, the connection elements are secured and tensioned to promote stiffness of the soft exosuit as well as to effectively apply forces at the heel to generate the moments needed for plantar flexion (or to assist plantar flexion, which may vary on a case-to-case basis).

In an embodiment wherein forces from the connection elements 107 are applied to a user's foot or footwear, the force may be applied at the calcaneus (heel) via, for example, fabric which encompasses the heel, via an insole insert secured under or to the user's foot, or via a sock-like webbing structure. The forces may be applied to the heel itself (or to a heel portion of footwear), to assist with dorsiflexion, or may be redirected from the heel to the superior surfaces of the foot (or to superior portions of footwear) via connecting elements, fabric, webbing, or the like (e.g., wires, cables, gears, gear trains, levers, etc. appropriate to the application) to apply a downward force thereon to assist with plantar flexion.

An insole insert may, for example, comprise a rigid or semi-rigid element enabling forces to be applied at the back of the rigid or semi-rigid element via a heel connection element. Tension from connection elements 102-105 can then be applied to the calf connection elements 107 to a heel connection element attached to the insole insert (or alternatively to a heel or rear portion of footwear or to heel or rear portion of a sock-like structure or webbing structure disposed over the foot). The heel connection element can extend under the heel along the bottom of the foot and couple to one or more connection element(s) that encircle the superior surfaces of the foot, such that a tension applied to the heel connection element causes plantar flexion of ankle joint (e.g., a foot pushing off motion).

Figure 9A:
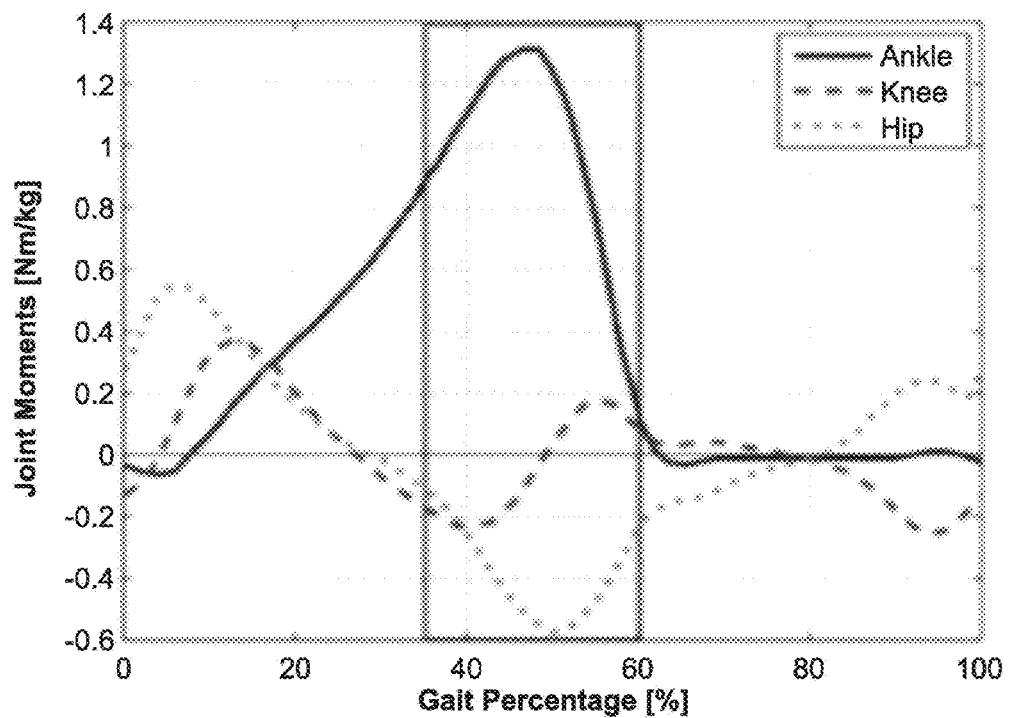
FIG. 9A shows graphs of the joint moments for the ankle, knee and hip over a single step or one gait cycle.

In accord with some embodiments of the invention, the soft exosuit is constructed, designed and optimized for a specific biomechanical activity (e.g., walking, etc.). When the body executes a normal, unassisted motion such as walking, the musculature expends metabolic energy to move the bones of the body and transfer the weight from one foot to another and provide energy for forward propulsion and resisting gravity. The muscles apply moments to a specific set of joints causing them to extend and flex in a timed and coordinated manner to take each step, such as is represented in FIG. 9A by the joint moments (Nm/kg) expressed as a function of gait percentage for the ankle, knee and hip joints. In accord with some embodiments of the invention, the soft exosuit can be configured to apply a moment or torque at a joint to assist or inhibit the bodily movement with respect to that joint. Whether the moment is beneficial, and assists the motion, or is harmful, and opposes, the motion can be a function of timing of applied motion and the configuration of the connection elements of the exosuit. Motion usually involves reciprocating movement of the body parts around the joint and the application of an external moment, in a specific direction, at the proper time can supplement the forces exerted by the muscles to assist the motion. The same moment applied at a time when the joint is articulating in the opposite direction can oppose the forces exerted by the muscles and present resistance to the motion.

Figure 9B:
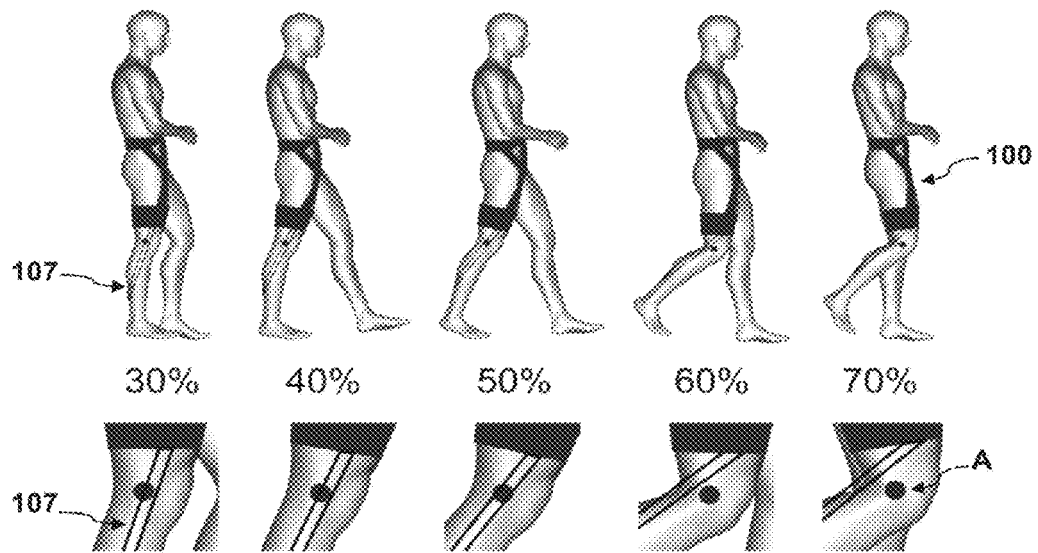
FIG. 9B shows a representation of a movement of a strap extending between the thigh and the heel during the gait cycle.

The connection members of the soft exosuit are naturally offset from the center of rotation of the joints by natural body structures (e.g., larger diameter legs displace the soft exosuit farther from center of rotation). In at least some aspects of the present concepts, this distance could be increased through the use of passive elements, such as spacers (e.g., fabric, foam elements, pads, etc.), or active elements, such as actuators, to increase a distance between the soft exosuit and the body of the wearer or to dynamically increase a distance between the soft exosuit and the body of the wearer in the case of such active elements. Further, as the joints move with respect to one other, the line of action of one or more soft exosuit connection members can change with respect to the joint, thus changing the moment were a force to be applied along that connection member. Yet further, the nodes and/or anchor elements may be caused to move during operation of the soft exosuit, responsive to applied forces, which can also change the line of action of one or more soft exosuit connection members. An example of the changing line of action of a soft exosuit connection member during movement of the joint is represented in FIG. 9B, which shows the connection member 107 (see also FIGS. 7-8) extending between the thigh brace 120 and a footwear connection element 130 can change position relative to the knee axis of rotation "A" as the leg moves through 30-70% of the gait cycle. The relative change in position of the connection member 107 changes the moment that the soft exosuit can apply to or across the knee joint during those phases of movement. Thus, were tension to be applied to the connection member 107 between 30-70% of the gait cycle, the connection member 107 provides a small moment extending the knee at 30-40% of the gait cycle, provides almost no moment at the knee at 50% of the gait cycle, and provides a larger moment at 60-70% of the gait cycle.

In at least some aspects of the present concepts, the calf connection elements 107 are disposed to be slightly asymmetrically disposed relative to one another, with the lateral (outer) calf connection element 107 (see e.g., FIG. 9B) being disposed slightly behind the knee axis of rotation A and the medial calf connection element 107 being placed slightly forward of the lateral (outer) calf connection element or slightly forward of the knee axis of rotation. This configuration facilitates directing of tensile forces exactly through the knee center of rotation at all times. Dynamically, in the early stages of the gait, the medial calf connection element 107 is slightly in front of the knee center of rotation, and the later calf connection element 107 is through it or slightly behind it and, in the later stages of the gait, this reduces the effective moment arm (and moment) around the knee.

Figure 9C:
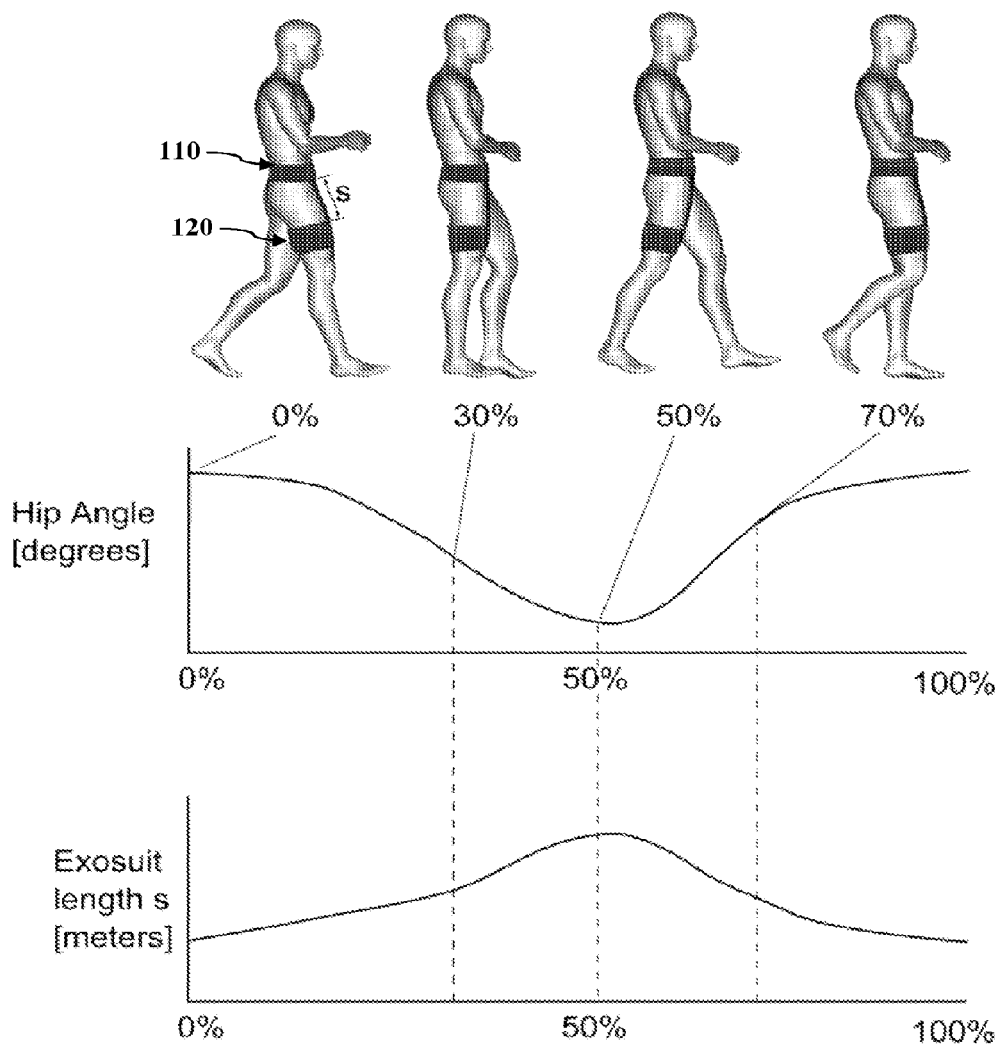
FIG. 9C shows a representation of a change in path length along the body of the soft exosuit of FIG. 7 during the gait cycle responsive to changes in hip angle.

FIG. 9C shows a person moving through different parts of the walking cycle. A graph of the hip angle over the walking cycle is also shown. As can be seen in this example, the hip angle is largest at 0% and 100% of the walking cycle, and is smallest at 50% in the walking cycle. Due to the angle change of the hip and the structure of the body, the path length S between the waist belt 110 and the top of the thigh brace 120 changes as the body moves through the walking cycle. Accordingly, the soft exosuit will be tensioned to different degrees during movement. If a connection element is provided corresponding to path length S, such connection element will draw taut at some points of movement (e.g., 50% of gait cycle) and will grow slack at another point of movement (e.g., 0% of gait cycle). The degree of this natural (non-actuated) state of the connection element is influenced, of course, by pre-tensioning and material selection, for example.

Figure 9D:
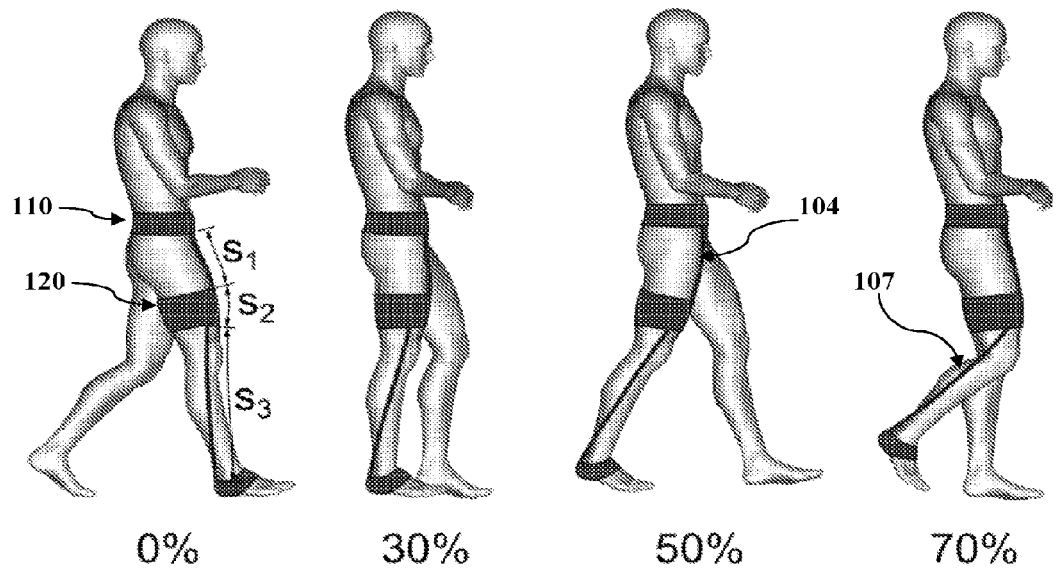
FIG. 9D shows a representation of a path length between two anchor points (the hip and the heel in the example shown) as a combination of lengths s1, s2 and s3.
Figure 9E:
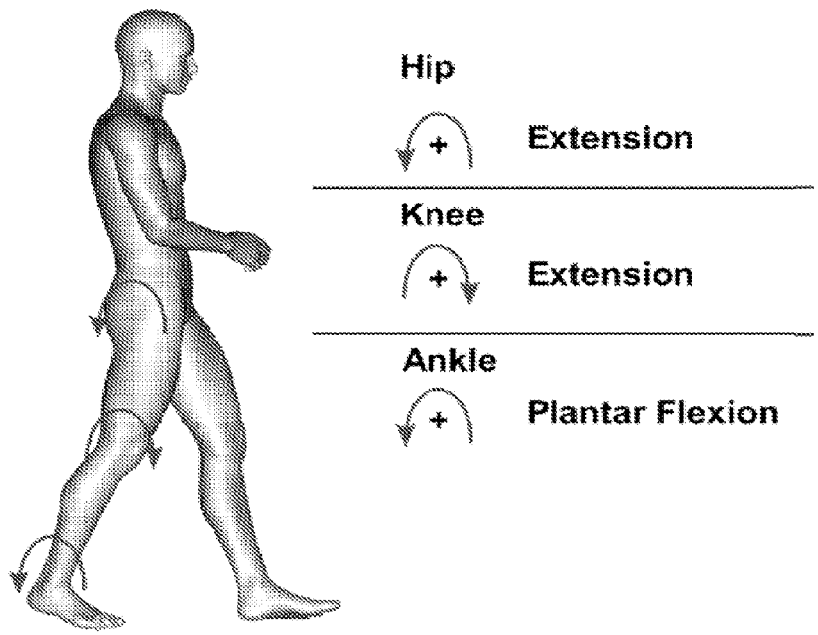
FIG. 9E shows the convention used to represent the moments at the hip, knee, and ankle.

FIG. 9D likewise shows an example of a soft exosuit extending across multiple joints and being anchored at the hip via a waist belt 100 (or equivalent waist-positioned connection members) and at the heel via a footwear connection element 130. As defined herein, the footwear connection element 130 includes any connection elements attached to an outside of worn footwear (e.g., FIGS. 21-22, 26A-26C), attached to a user's foot (e.g., FIGS. $26D_1$-$26D_5$, and/or disposed within worn footwear (e.g., FIGS. 26E-26F). The soft exosuit 100 structure, in this example, comprises a first connector element 104 having a length (path S1) between the waist belt 110 and the thigh brace 110, which itself is shown to have a length S2. A second connector element 107 having a length (path S3) is attached to the bottom of the thigh brace 110, runs along the lateral gastrocnemius, and is connected to the footwear connection element 130. The first connector element 104 (S1) will change in accord with changes in the hip angle during movement. The length of the thigh brace 110 (S2) is generally fixed, as it extends over a segment of the body that does not traverse any joint. The length of the second connector element 107 (S3) will change based on relative changes between the knee and ankle angles. As a whole, the distance between the two anchor points (the hip and the heel) is a combination of lengths Sl, S2, and S3 and the selective tensioning of the soft exosuit desirably takes into account the combined effects of multiple joints.

In accord with the invention, by understanding timing of the moments applied to that set joints, a soft exosuit can be configured to apply moments to some or all of the set of joints in timed and coordinated manner to supplement the moments created by natural muscle movements and enable the body to move at the same rate while expending less metabolic energy or restoring mobility for those with reduced muscle function. These moments can be created in a passive or an active manner. In a passive configuration, the natural motion can create tensions in the soft exosuit between the support features and the connected elements of the soft exosuit to create moments at specific joints at specific times during the motion cycle. In an active configuration, one or more actuator(s), however powered, can be employed to create tensions in the soft exosuit that generate moments at specific joints at specific times during the motion cycle. In accord with some embodiments of the invention, the soft exosuit can be configured to actively as well as passively generate forces on the body that supplement the forces generated by the musculature, to enable the body can to do less work and reduce the metabolic cost of a given motion as compared to the unassisted execution of that motion. This can be accomplished using a soft exosuit configuration that can passively create tensions using the natural body movement in combination with one or more actuators that actively applies tension to the soft exosuit in a coordinated manner.

In at least some aspects of the present concepts, the soft exosuit is configured to absorb energy from the user's motions, similar to the manner in which the user's muscles absorb energy from the user's motions. At various times in the walking cycle, for example, the muscles absorb power, such as to arrest the motion of the torso as it falls forward under the influence of gravity, or to slow down the leg in preparation for stance. To absorb power during these and other times, the muscles may contract eccentrically, extending under the applied external force while applying force. To reduce the amount of force the muscles must apply in these situations (or in a situation where power is absorbed by muscles/tendons when the muscles are isometrically contracting) and/or to reduce the probability of soft tissue damage, the soft exosuit can apply force parallel to active muscles at any time to absorbing power from the body that might otherwise prove potentially detrimental or minimally beneficial. This absorbed power could then be harvested via an energy storage device (e.g., a spring system, a resilient member, etc.), and returned to the body at some point later in time (e.g., at a subsequent point in the gait cycle). By way of example, the absorbed power could be harvested by compressing a spring, which then will then expand responsive to decreases in the applied compressive force. A compressed spring could optionally be temporarily held or locked using a latch or some other mechanism to retain the spring in the compressed state until a time which the energy is to be returned into the soft exosuit system. In another example, the absorbed power could be harvested by converting it to electrical energy and storing the energy in a battery. Potentially, energy could be stored through other means such as, but not limited to, hydraulic, pneumatic, or chemical energy storage appropriate to a given design envelope. Energy storage from power absorption could occur in both passive and active modes of the suit. In passive modes, energy storage could use passive mechanisms (e.g., a clutched spring, etc.), while in active mode the soft exosuit could either use these schemes or additionally use schemes which directly pull on an actuator to generate stored energy, for example back-driving the same electrical motor used to actuate the soft exosuit at other times.

Figure 25C:
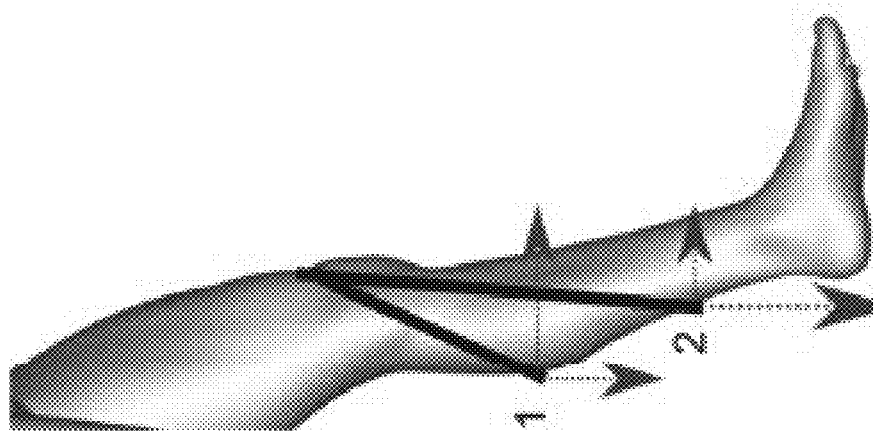
FIGS. 25A-25C show a representation of forces acting in the calf straps in the soft exosuit of FIG. 19.
Figure 25B:
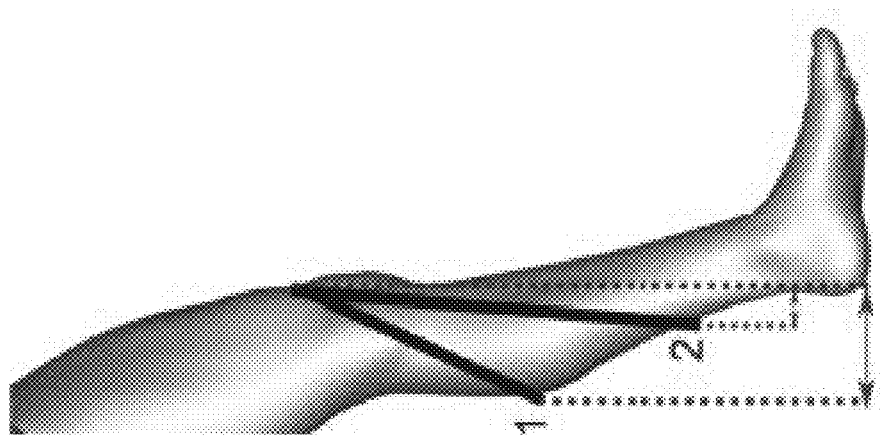
Figure 25A:
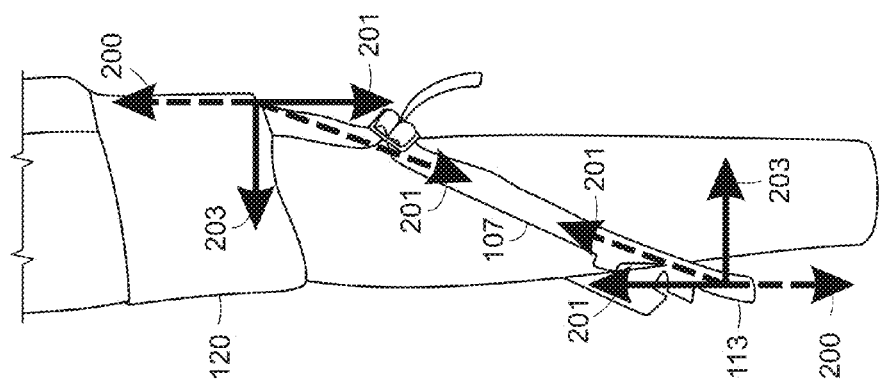

As shown in FIG. 10A and FIG. 25A, for example, the calf connection elements 107 apply a tension on a footwear connection element 130 that engages the foot. Depending on the position of the calf connection elements 107 with respect to the knee joint, tension in the calf connection elements 107 can apply a moment on the knee joint. By positioning the calf connection elements 107 forward of the axis of the knee joint, the tension in the calf connection elements 107 can encourage extension of the knee joint and by positioning the calf connection elements 107 behind the axis of the knee joint, the tension in the calf connection elements 107 can encourage flexion of the knee joint. Aligning the calf connection elements 107 through the axis of the knee joint can be used to transfer the tension without creating a moment (beneficial or harmful) on the knee joint.

In accord with a passive configuration embodiment of the invention, the calf connection elements 107 can be connected by an inelastic member (e.g., cable, strap, etc.) or elastic member to the heel connection element, such that during normal walking, the tensions created in the soft exosuit cause beneficial moments to applied on one or more of the leg joints (e.g., the hip, the knee and/or the ankle) of at the appropriate time to supplement the natural muscle movements. For example, a normal walking gait results in a backwardly extending leg at about half way (50%) through the gait cycle. As a result, a tension is created in the soft exosuit that extends from waist belt 110 down the connection elements 102-105 on the front of the thigh, along the calf connection elements 107, around the knee and down the back of the leg to the heel strap. The tension can create a beneficial moment in the hip joint causing assisting with hip extension and then subsequently assisting it to flex and propel the leg forward when the energy stored due to this tension is released potentially in addition to an active force from one or more actuators. The tension can also create a beneficial moment in the ankle joint where it assists with dorsiflexion and subsequently assists with plantar flexion of the ankle in addition to an active force applied by one or more actuators, causing the foot to push off in a forward direction.

In accord with an active configuration embodiment of the invention, a user's motion can be further assisted by adding one or more active components that actively pull on the heel connection element at the appropriate time to increase the push-off energy of the foot. In this embodiment, the heel connection element can be connected to an actuated cable or other actuation member that pulls on the heel connection element at a predetermined time to apply a beneficial moment about the heel. The actuated cable or other actuation member is connected, directly or through an intermediary power train, to a motor or other actuator controlled by a controller to apply the force to cause a specified moment at a predefined time. In one example, a cable (e.g., a Bowden cable comprising a substantially incompressible sheath) is provided to connect the calf connection elements 107 to one or more footwear connection elements 130 at the back of the leg. Such a force applied to assist with push off at the ankle can also assist with flexion at the hip.

In accord with some embodiments of the invention, the soft exosuit is configured to provide a plurality of anchor elements disposed at anchor points to permit engagement of the soft exosuit with natural features of the body that well serve as anchor points. However, in accord with other aspects of the present concepts, it may be desirable to establish anchor points or support point at a location where there is no such natural feature of the body, where application of a load would normally have undesirable consequences. In accord with these embodiments, one or more connection elements or struts can be used to transfer the forces from the support point disposed at a desired location to a different location on the body, such as one or more anchor points corresponding to natural features on the body (e.g., shoulders, iliac crest, etc.).

For example, in the Bowden cable embodiment noted above and shown in FIG. 10A, the Bowden cable sheath can extend from a point on a backpack of the user down along the side of the leg to a location behind the calf. Thus, the Bowden cable can be fastened to the calf connection elements 107 at the point where they meet below the calf in the back of the leg and the proximal end of the cable sheath is coupled to the housing of the actuator (e.g., a shoulder-borne backpack comprising a drive motor and pulley system) to help maintain tension in the exosuit. Similarly, as noted elsewhere herein, other cable types or actuation elements (e.g., ribbons, fabric, etc.) can be used and routed (e.g., though fabric of or channels in the soft exosuit) from the actuator(s) to specific locations at which a force is desired to be applied.

Forces then can be created between the point where the Bowden cable sheath 144 attaches to the soft exosuit and where the central cable 142 attaches to the soft exosuit 100. As a result, a tension can be created in the soft exosuit 100 between the waist belt 110 and the support point at the end of the Bowden cable sheath 144 that joins to the ankle connector element 113 at the back of the leg. This tension can be dynamic in the sense that, as the user walks the backpack moves, as does the lower leg, changing the distance between the proximal end of the Bowden cable sheath 144 and the distal end of the Bowden cable sheath that provides the connection point 113 for the lower connection members of the soft exosuit. In addition, the hip also moves, changing the distance between the anchor point on the hip and the anchor point at the lower leg which can affect the tension in the soft exosuit during use.

Thus, the beneficial moments of the soft exosuit can be enhanced by passive and/or active components that apply forces that can create beneficial moments to supplement muscle action. By analyzing the biomechanics of the natural motion to be assisted and the power expended by each joint in the execution of motion, supplemental moments can be identified to receive a desired level of assistance.

For example, during normal walking, power is expended by the body as it transitions support from one leg to the other in course of propelling the body forward. A significant portion of this power is provided by the hip and the ankle. FIG. 9A shows a graph of the joint moments for the ankle, knee and hip over a single step or one gait cycle. The graph shows that the ankle has a large positive moment at about 50% or midway through the gait cycle (see also FIG. 46). According to some embodiments of the invention, walking assistance can be provided by applying a positive moment to the ankle from approximately 35% to 60% of the gait cycle.

In accord with some embodiments of the invention, the soft exosuit 100 can be designed to take advantage of the natural motion of the various parts of the body, by identifying support points that are or become further apart at a time when a positive moment applied to one or more joints (e.g., the ankle) can be beneficial. The soft exosuit 100 can be configured with connection elements that extend around the joint to establish a tension using one or more nodes or anchor points to create a beneficial moment about the axis of the joint. In the example of FIG. 10A, for example, the soft exosuit 100 can be tensioned between the hip (via waist belt 110) and footwear connection element 130 to create a beneficial plantar flexion moment at the ankle at an appropriate time during the gait cycle. In addition, tension in the soft exosuit can be guided over the hip joint, applying a beneficial moment that encourages hip flexion and/or over the knee joint, applying a beneficial moment that encourage knee extension, each or both at point(s) in the gait cycle when the moments would be beneficial to the hip and/or knee motion.

Additional metabolic energy can be saved by providing one or more actuators that can create increased or additional tensions in the soft exosuit 100 to provide increased and/or additional beneficial moments. For example, in the soft exosuit 100 shown in FIG. 10A, an actuator cable 142 can be used to apply a positive moment on the ankle joint by pulling on the heel which is several centimeters displaced from the axis of the ankle joint. As noted above, in one embodiment of the present concepts, the cable is a Bowden cable comprising a substantially incompressible sheath. In another embodiment, the sheath itself is configured to provide dynamic properties, such as by having a resilient sheath that stores and releases energy, or by incorporating a spring element into the sheath.

As noted above, a distal end of the actuator cable 142 is attached, directly or indirectly (e.g., via a connection element) to an anchor element which, as shown in the example of FIG. 10A, extends from the heel under the foot and then wraps around the top of the foot. A drive motor and pulley system can be coupled to the proximal end of the actuator cable 142 and the drive motor controlled by an on-board controller (e.g., computer) to actuate the actuator cable during the desired time period (e.g., 35% to 60% of the gait cycle) to provide motion assistance. Sensors (e.g., foot strike sensors, joint angle sensors, etc.) are advantageously used to synchronize the actuator cable 142 cable actuation with the gait cycle of the user. As one example, tensile forces are sensed by force sensors in one or more connector elements, nodes or anchor elements and these forces are monitored and evaluated by the controller (e.g., could for several cycles of movement) to estimate the gait cycle, following which the controller progressively engages the actuator(s) over a few or more cycles of movement or after instruction by the user to enable actuation). Alternatively, the controller may infer the gait of the user by other feedback, such as manual inputs from the user or from tensile forces sensed by force sensors in the straps (e.g., the controller could monitor forces in the straps for several cycles of movement, following which actuation can progressively ramp up over a few more cycles of movement or after instruction by the user to enable actuation.

As previously noted, the soft exosuit concepts herein are deployable to reduce the metabolic cost of various activities, such as walking, by providing assistance at specific points of the activity and to reduce the loading on the soft tissue (muscles, tendons and ligaments) across the joint. Where a user expends less energy in the activity (e.g., walking), the user will be less fatigued than the user would be without assistance. Fatigue ultimately leads to a deterioration of performance (e.g., a breakdown of the gait), which can increase the risk of injury. Reduction in metabolic costs can decrease the risk of fatigue-related injury. In accord with at least some aspects of the present concepts, the soft exosuit system is able to decrease the user's metabolism below the level experienced by the user when conducting the activity (e.g., walking) without the soft exosuit. The soft exosuit can also reduce the stresses on the soft tissue by having some portion of the forces at each joint born by the soft exosuit.

The soft exosuit 100, shown in FIG. 10A, includes a plurality of connection elements comprising, by way of example, a cloth, textile, or webbing (e.g., synthetic and/or natural fibers, Kevlar, etc.), worn underneath or on top of the clothing. An actuator unit 200 can be worn on the back (e.g., in a shoulder-borne backpack, attached to a shoulder-borne frame, etc.), on the waist (e.g., attached to a waist belt, etc.), or in or on a device used by the user (e.g., a bike, a wheelchair, a kayak or canoe, a walker, etc.). In FIG. 10A, a Bowden cable unit 140 extends from the actuator unit 200 and connects the soft exosuit 100 to the footwear connection element 130. In a configuration where the actuator unit 200 is borne in or borne by a device used by the user, the Bowden cable sheath 144 may be advantageously attached to a fixed anchor point (e.g., on waist belt 110) and then the sheath and the Bowden cable 142 passed down for attachment to the footwear connection element 130. As noted, the soft exosuit 100 comprises one or more connecting elements (e.g., 102-105, 107), nodes (e.g., 113) and anchor points to control the transmission of forces along, to and from the user's body. The soft exosuit system 100 also optionally includes a foot sensor 150 or actuatable switch to sense the forces applied to the foot during walking or otherwise to actuate (switch on or off) at a point of substantially maximum force corresponding to a heel strike. Sensors able to be used to assist in the determination of gait, for example, include, but are not limited to foot switches, Inertial Measurement Units (IMUs), accelerometers, Electromyogram (EMG) sensors, strain sensors to detect strain in user's skin in selected locations, sensors built into the soft exosuit to detect tensile and/or shear forces in the suit, sensors in a motor or other actuator to detect the actuator position, sensors in series with a Bowden cable or part of the Bowden cable sheath to detect the force in the cable, or other sensors.

Figure 10B:
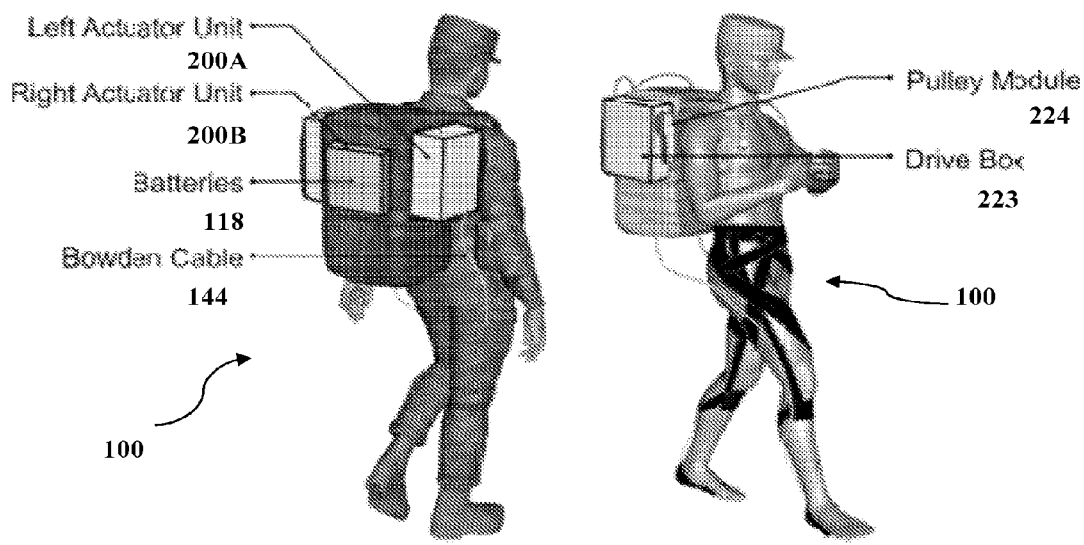

In accord with some embodiments of the invention, the soft exosuit 100 can include one or more actuator units 200 (see, e.g., FIGS. 10A-10B) that causes the distal end of the cable 142 of the Bowden cable unit 140 to retract into the sheath 144. The distal end of the cable 142 can be connected to the footwear connection element 130, and the distal end of the Bowden cable sheath 144 can be connected to the soft exosuit 100 at the back of the calf. When the cable 142 is retracted, the cable 142 pulls upwardly on the footwear connection element 130 and the sheath 144 pushes the soft exosuit 100 downward from the attachment point at the back of the calf. The soft exosuit 100 then transfers the forces through the connection elements (see, e.g., FIG. 7) up to the pelvis of the user via the waist belt 110. The user's bone structure then transfers the force back down to the ankle joint and to the ground through the foot.

The forces generated by the soft exosuit 100 are advantageously configured to complement the user's musculature by acting parallel to the user's musculature. This is accomplished by configuring the connecting elements (e.g., 102-105 in FIGS. 7-8) and nodes (e.g., node 1, FIG. 7) to extend along predefined locations along the body. So configured, the user's muscles can be activated less during certain portions of the gait cycle, because the soft exosuit provides the remaining forces necessary for locomotion. This reduction in muscle activation can be used to lower the user's metabolic rate and reduce the level of fatigue experienced over time.

In accord with some embodiments of the invention, metabolic reduction is achieved by applying power to the body at the same times that the muscles generate power and by absorbing power from the body during the times that the muscles absorb power. The ankle generates a large pulse of power between about 40-60% in the gait cycle, which extends from one heel-strike to the next. This power input at the ankle, occurring when the leg is pushing the body off the ground, is the largest power burst of any joint throughout the walking cycle. In accord with some embodiments of the invention, assistive forces or moments can be applied to the joint that experiences the largest power spikes at the point during the motion cycle that the musculature generates those power spikes to achieve metabolic reduction in an effective manner. For example, based on the evaluation of joint power, in accord with the invention, the soft exosuit 100 can be configured to apply assistive forces to the ankle joint during this point in time, between about 40-60% of the gait cycle.

In accord with some embodiments of the present concepts, the soft exosuit 100 can extend from the ankle up to the pelvis and can additionally, or alternatively, create moments at the knee and hip as well as the ankle. In a multi joint system, the forces applied can affect each of the joints beneficially, and thereby provide more effective assistance. In accord with these aspects, the soft exosuit 100 is able to create moments at the knee and/or at the hip at times during the gait cycle when such moments would beneficially affect these joints. Natural movements and/or actuators that generate tension or displacement of the soft exosuit at one location/joint can, accordingly, benefit more than one location/joint.

In accord with some embodiments of the invention, the soft exosuit 100 can provide a number of functions. The soft exosuit (e.g., 100) can create precisely-controlled beneficial moments through, for example, the hip and/or ankle joints. As previously noted, a moment is considered beneficial if it assists the natural musculature. The disclosed soft exosuit's architecture and the topology of the connection elements desirably are configured to mimic, as best possible, the force vectors approximating the forces provided by the user's muscles.

In accord with at some embodiments of the present concepts, the soft exosuit is optimized to maximize stiffness (e.g., strapping it securely to anchor elements at anchor parts of the body). For a low series spring stiffness in an ankle exoskeleton, required power increases as 1/k. It is accordingly desirable to make the soft exosuit as stiff as possible to provide for higher power efficiency when applying assistive forces to the wearer. Furthermore, high exosuit stiffness will reduce the displacement of the soft exosuit relative to the user's body during movement and/or during actuation, thus reducing the risk misalignment of nodes and connection elements and reducing chafing. It is contemplated, however, that various applications could favor a minimized stiffness and/or a variable stiffness (e.g., automatically varied by a controller or manually controlled) that enables the stiffness to vary based on the user's activity (e.g., to minimize stiffness and enhance transparency when assistance is not required and to maximize stiffness and when assistance is required).

Both the fit of the soft exosuit 100 and its stiffness can be influenced by the exosuit's tension and alignment. If the soft exosuit is improperly aligned, whether by initial set up or by movement of the soft exosuit 100 during use, the moments created will not be optimal and, more significantly, the moments may prove distracting or even deleterious over time, as they cease to occur where necessary. It is desirable that the soft exosuit 100 remain in the correct location on the body even as the user moves and as the soft exosuit is actuated, lest the soft exosuit functionality or efficiency be adversely affected. To facilitate retention of the soft exosuit 100 in the proper placement during use, it is advantageous to pre-tension the soft exosuit (e.g., actuator cable(s), connection elements, etc.) following donning of the soft exosuit. The initial tension in the soft exosuit can be adjusted manually (e.g., by adjusting strap, buckles, fittings, cables, controls that adjust a tension in a plurality of components at the same time, etc.) or automatically using one or more actuators (e.g. a motor-driven mechanism).

In the example of FIGS. 7-8 and 10, during donning of the soft exosuit 100 by the user, the user can tighten the connection elements to make the soft exosuit comfortably snug. The cable 142, attached to connector 113 (which in turn is attached to anchor member 130), is then retracted into the sheath 144, which pulls the soft exosuit 100 down and the anchor member 130 up, taking any slack out of the cable 142 and creating a small amount of tension in the system. In accord with some embodiments of the present concepts, the user can set the tension so to barely detect the exosuit's presence during movement (e.g., walking). Actuation can then be applied to the soft exosuit 100 from that point of system tension.

In accord with some embodiments of the present concepts, actuator actuation member(s), such as Bowden cables, are used to position the mass of the actuation system 200 (FIG. 10A) away from the foot and the ankle joint being actuated. Using such actuation member(s), the actuation system 200 can be attached to a user's waist or carried in a backpack. In accord with at least some aspects, an actuation system 200 utilizing Bowden cables permits routing of the cable sheath along a path that does not adversely impact the user's motion. There are many ways that the sheath 144 of the Bowden cable can be attached to the soft exosuit. By way of example, one attachment scheme for the sheath includes a male/female connector disposed on one or more points of the soft exosuit, with corresponding male/female connector(s) disposed along appropriate sections of the cable sheath. In another configuration, the cable sheath 144 can be fixedly attached to the soft exosuit (e.g., sewing, bonding agents, adhesives, etc.), routed through a formed channel in the soft exosuit, attached to the soft exosuit using VELCRO® attachment members, or attached to the soft exosuit using with one or more tying members.

Where the actuation system 200 utilizes Bowden cables, for example, a small, geared motor is provided to drive a pulley or, alternatively, a larger motor directly driving a pulley can be used to pull on the cable 142 to apply an assistive force on the heel, as shown in the example of FIG. 10A. Other drive mechanisms can be used, of course, such as, but not limited to, linear motors and hydraulic/pneumatic actuators. The manner of actuation system 200 utilized depends, in part, on the motion that is to be assisted and the specific weight and performance requirements for such assisted motion. In accord with some aspects directed to assistance with walking, the actuator system 200 utilizes a battery, or a plurality of batteries, configured to provide an average power output of less than 100 W, which minimizes the weight of the soft exosuit 100 actuation system 200, while retaining metabolic benefits. For example, additional mass carried by the user causes a corresponding and predictable increase in the user's metabolism (e.g., at the rate of about 0.9% per added kilogram on the back), so minimizing weight of the actuation system 200, when borne by the user, is generally beneficial.

Figure 11:
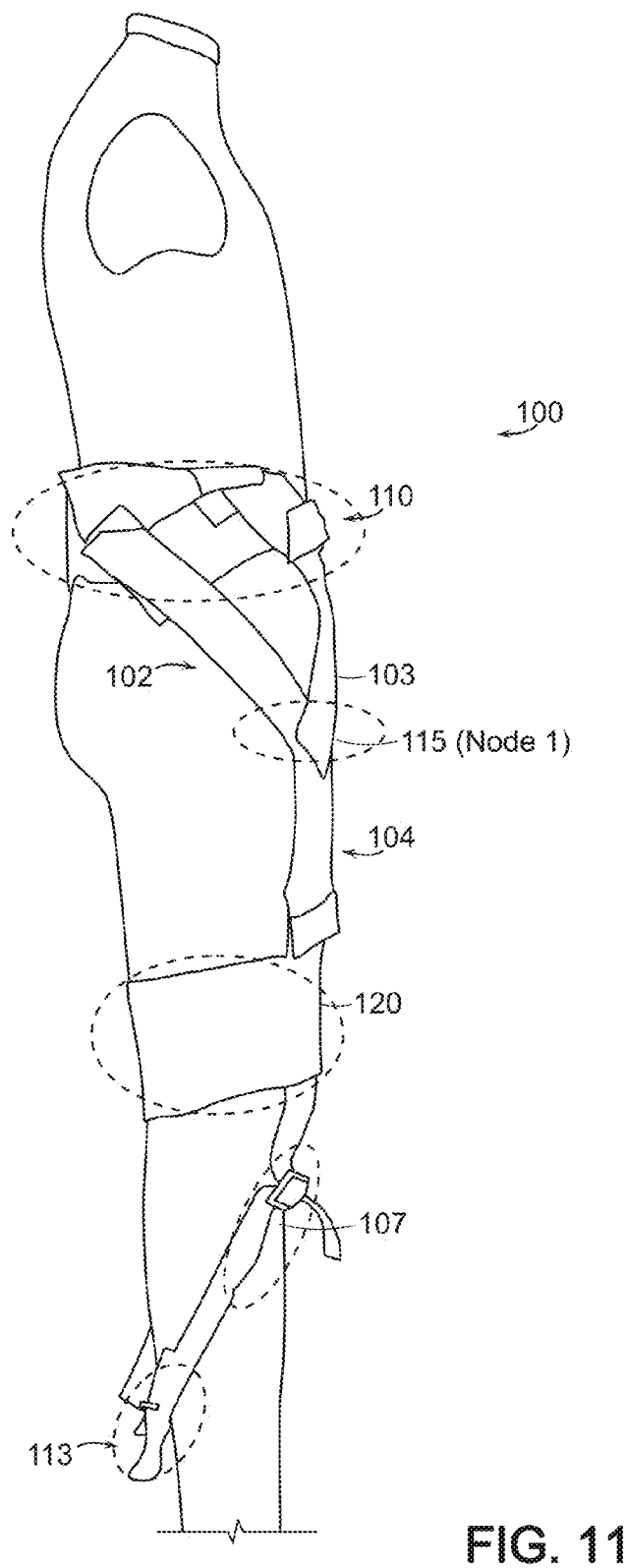
FIG. 11 shows a side view of a soft exosuit (V5), according to at least some aspects of the present concepts, depicting major components of the soft exosuit.

FIG. 11 shows an example of a soft exosuit 100 according to at least some aspects of the present concepts. The soft exosuit 100, as illustrated, includes a waist belt 110 connected by connection elements 102, 103 through a node 1 to connection elements 104, 105, which are in turn connected to thigh brace 120. The thigh brace 120 is connected to a T-connector 113 by calf straps 107. The soft exosuit 100 can be made adjustable to accommodate the natural motion of the user and to coordinate the forces generated by actuation system 200 and the cable 142 (see, e.g., FIG. 10A) with that of the forces of natural motion. As the user walks, the forces generated by the actuation system and transmitted to the cable are applied to heel of the user to reduce work the user's musculature while walking.

During walking and running, the muscles in the leg generate moments (moment forces) at the hip, knee and ankle joints during the gait cycle in order to propel the person's center of mass forward and resist gravity to maintain an upright posture. These moments change in magnitude and direction over time as they are generated by the muscles around these joints in order to guide the person from heel strike and weight acceptance through stance to push off and into swing. As noted, the soft exosuit system 100 in accord with aspects of the present concepts, desirably times forces generated by the actuation system 200 and the cable 142 to supplement the natural moments at the ankle joint, reducing the metabolic burden and improving mobility. In some aspects, the soft exosuit 100 structure extends as well around the hip joint and the knee joint to provide a beneficial moment at the hip and knee during gait cycle. When the actuation system 200 retracts the cable 142 and applies a force on the foot of the user, the sheath 144 also applies a downward force on the T-connector 113 and the soft exosuit 100, which can then apply beneficial moments to the hip or knee during the gait cycle.

In accord with some aspects, forces applied to the T-connector 113 of the soft exosuit 100 results in a tension in the soft exosuit between the T-connector 113 and the waist belt 110. Node 1 and the thigh brace 120 help to align the tension over the knee and hip to provide a beneficial moment at each joint. For a healthy adult, walking at a self-selected speed on level ground power is, for the most part, generated at the hip and ankle and dissipated at the knee. In turn, muscles consume metabolic energy to generate these moments. As noted, one of the benefits of aspects of the soft exosuit disclosed herein is to reduce the metabolic cost of walking by adding energy at the ankle to assist with plantar flexion during push-off and to assist with absorbing energy at the hip during late stance and add energy during an even later portion of stance. Adding energy at the ankle can reduce the muscle activation needed to generate the large ankle moment and power required at push-off and thereby reduce the necessary metabolic cost. To reduce the metabolic cost of walking, the soft exosuit disclosed herein advantageously permits natural gait dynamics. In some aspects of the soft exosuit, the energy applied at the ankle is provided by a cable, which pulls up on the heel and promotes and/or causes plantar extension. The force from the cable sheath 144 is distributed up through the connection elements of the soft exosuit 100 (see, e.g., FIG. 10A).

The soft exosuit 100 architecture as seen in FIG. 11 connects the waist belt 110 to a thigh brace 120 (secured to the user's lower thigh), which is connect to footwear (e.g., boot, shoe, etc.) connection elements 130. The waist belt 110 and thigh brace 120 are connected by connection elements 102, 103 that interact with node 1 on the front, middle part of the user's thigh. The thigh brace 120 and footwear connection elements 130 are connected by connection elements 107 and the cable 142, which applies the actuator force at the ankle The connection elements 102, 103 between the waist belt and node 1 and the connection elements 104, 105 between node 1 and the thigh brace 120 can be pre-tensioned, for example, by pulling the two sides together and connecting them with VELCRO® at desired position or by pulling on one side which passes through a slide or buckle on the other side, in order to remove any slack in the system that would inhibit efficient operation. Pre-tension in connection elements 104, 105 can be performed, for example, after node 1 has been secured in place and the thigh brace has been positioned and tightened about the user's thigh. Accordingly, the soft exosuit 100 is pre-tensioned between the thigh (thigh brace 120) and pelvis (waist belt 110) which are both conical in shape and thus provide resistance to the applied pre-tension.

When the force is applied at the ankle, such as by the soft exosuit 100 depicted in FIGS. 10-11, tension is also redirected across the knee and hip joints up the soft exosuit to the pelvis. As the connection elements are (further) tensioned, they create moments around the hip, knee and ankle as well as normal forces on the user at the various points of soft exosuit-to-user contact. In accord with some aspects, the soft exosuit 100 is advantageously fitted and aligned to the user to ensure that these moments and forces do not adversely affect the user's natural gait, which would cause the user to expend additional metabolic energy. The arrangement of and orientation of the connection elements, nodes and anchor points are selected to create beneficial moments around the joint or joints of interest (e.g., hip, knee and/or ankle) when tension is placed on various elements of the exosuit.

As a stiffness of the soft exosuit 100 increases, the soft exosuit is better able to transfer the actuation forces to the user in a manner that provides both the desired level of assistance and minimal dislocation of the constituent components of the soft exosuit (e.g., nodes, connection elements, etc.). As noted, the soft exosuit 100 is able to advantageously rely on one or more anchor points (e.g., pelvis, shoulders, etc.) to enhance exosuit stiffness, such as by permitting forces to be borne by the pelvis by placing the waist belt 110 on top of the iliac crest, which provides an anatomical ledge for distributing inferior and medial/lateral forces. As shown in the example of FIG. 7, the soft exosuit 100 transfers the forces generated in a leg to each side of the pelvis through connection elements 102, 103, which both originate from node 1. Providing connection elements 102, 103 to distribute forces from node 1 (e.g., of each leg) to both sides of the pelvis, the force from the actuation can be distributed over both sides of the pelvis, as opposed to the entire actuation force being anchored on the same side pelvis bone, reducing the peak point force on each respective iliac crest, enhancing comfort of the soft exosuit during use. Further, using a connecting element (e.g., 103 in FIG. 7) connecting node 1 to the opposite side hip, the soft exosuit can create horizontal forces as well as vertical forces on the opposite iliac crest due to the angle at which it attaches to the opposite side hip. This horizontal force helps to keep the waist belt 110 from slipping down as it helps bias the waist belt against the top of the iliac crest.

Figure 16:
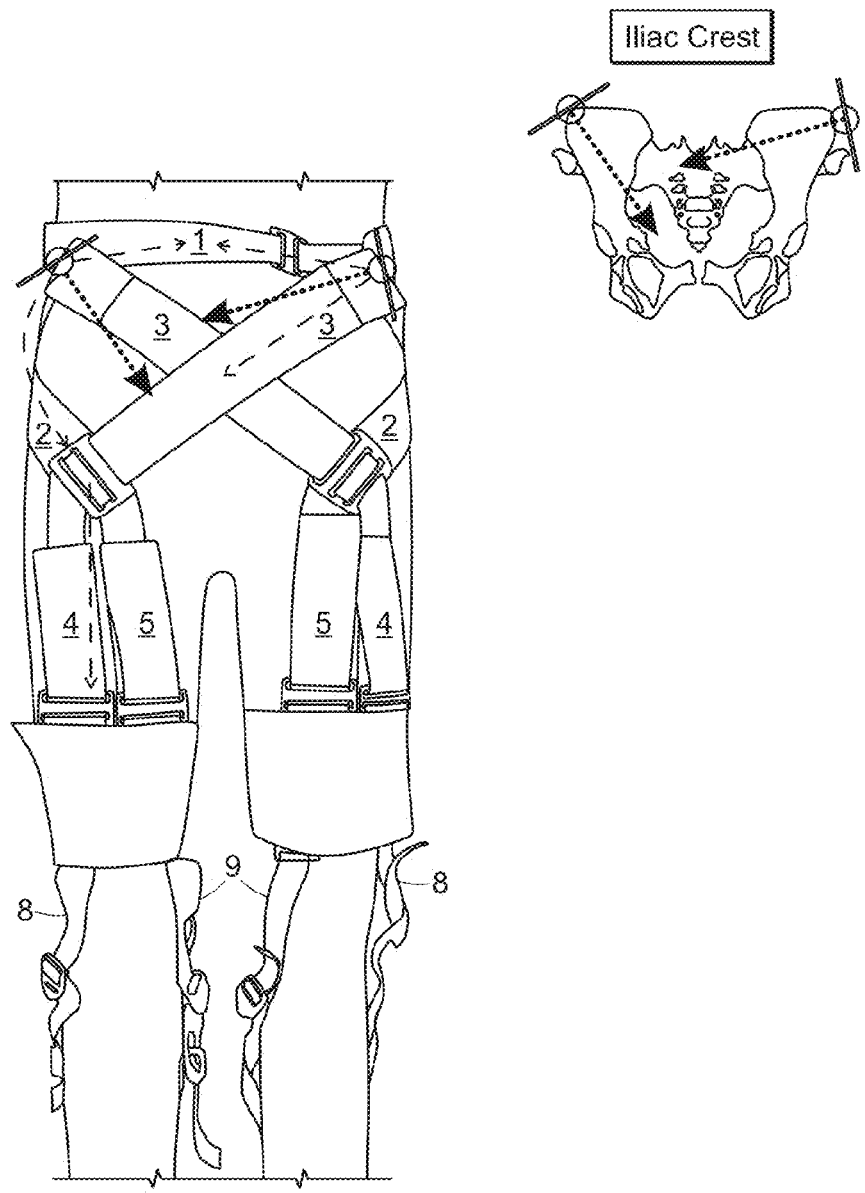
FIG. 16 shows a diagram of a soft exosuit (V5) according to the invention and the forces transmitted over the individual elements.

As shown in FIG. 16, the forces on the connection element 1 (waistband) go approximately horizontally around the body, while the forces on connection element 3 are angled downwardly. The resultant force vector from these two connection elements acting together lies between those two vectors and is approximately normal to the pelvis, which is rounded in this area as observed in the sagittal plane of the body. Pulling normally to the body enables the connection elements to remain in place while applying large loads, and avoids motion in the tangential direction which can cause discomfort.

The position of node 1 in FIG. 16 allows the forces coming up from the ankle to be routed into one point on each respective leg, which is then redirected to each side of the pelvis. In accord with some aspects of the present concepts, node 1 allows control over the moments that the soft exosuit 100 generates on the various joints by allowing adjustment of the connecting elements that connect node 1 to the waist belt 110 to adjust the direction of the forces to the waist belt.

The thigh brace 120 can be configured to maintain tension in the soft exosuit 100 by allowing the calf connecting elements 107 (see, e.g., FIG. 7) to be slightly angled in order to accommodate their position with respect to the knee's center of rotation. The calf connecting elements 107 can be connected to the footwear connection element 130 via the actuator cable 142. The footwear connection element 130 can comprise one or more elements (e.g., strap(s), etc.) which can act as a harness around the heel of the footwear (e.g., boot, shoe, etc.). The footwear connection element 130 can provide a stiff connection with the user's foot and distribute forces over the footwear. For example, when an actuator cable 142 exerts an upward force at the footwear connection element 130, the force is transferred through a system of connecting elements or materials to the bottom of the foot and the front of the foot, where an upward force is exerted at the back of the heel and a downward force is exerted on top of the forefoot.

The footwear connection element 130 provides an actuator cable 142 with a stiff attachment point at the heel to effectively apply force at the ankle. The footwear connection element 130 also assists the plantar flexion moment at push off by transferring the upward actuation force to back of the heel and also to the front of the foot where it applies a downward force on top of the foot, thus applying forces which assist plantar flexion on both sides of the ankle.

Figure 12:
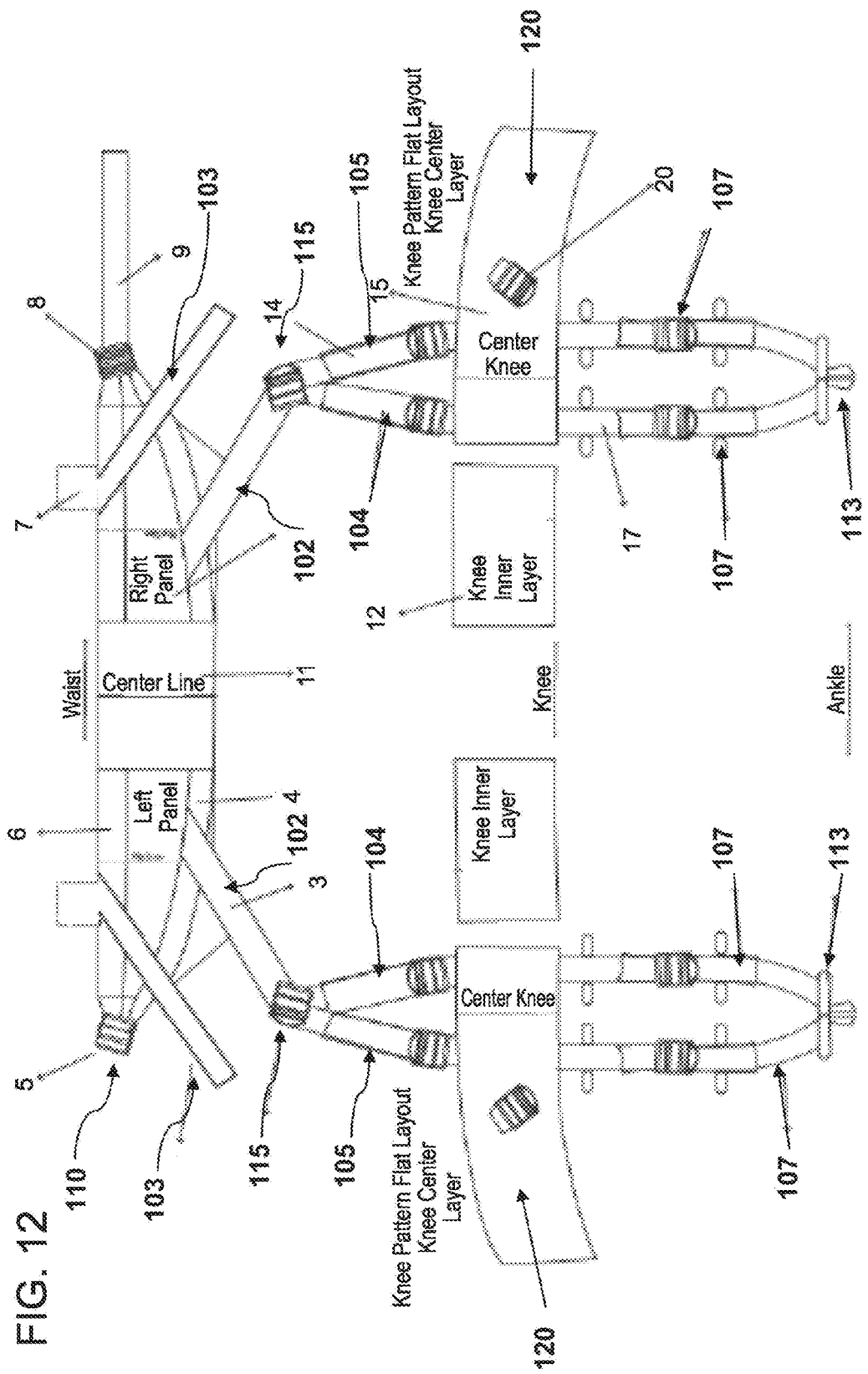
FIG. 12 shows an example of a flat pattern layout for a soft exosuit (V5) according to at least some aspects of the present concepts.

In at least some aspects, the soft exosuit 100 is constructed from flat materials (e.g., webbing, fabric, etc.) that are cut or otherwise formed to a predefined size and stitched together. FIG. 12 shows one example of a flat pattern layout for a soft exosuit according to at least some aspects of the present concepts. The waist belt 110 can be formed in sections, which can be overlapped and secured, as with conventional belt securement devices, to adjust the waist belt to people with various waist diameters. By way of example, the sections or panels shown in FIG. 12 can be constructed from one or more layers of rip-stop nylon and a fusible interfacing layer or from one or more layers of rip-stop nylon and a layer of foam padding (e.g., ⅟₁₆" to ½" thick polyurethane or ethylene-vinyl acetate (EVA)). The connection elements can be constructed from, for example, ½"-3" polyester webbing. In one aspect, the connection elements 102, 103 are formed from 2" wide polyester webbing, while the balance of the remaining connection elements are formed from 1" wide polyester webbing. Some connection elements (e.g., distal ends of calf connection elements 107) can be stitched to form loops to facilitate connection to other connection elements or structures. Buckles (e.g., plastic buckles) can be used to fasten and tighten the connection elements. The thigh braces 120 can comprise one piece or two pieces and is constructed, in at least some aspects, from a stretch twill material (e.g., a cotton-polyester blend) with hook and loop faster (e.g. Velcro®) stitched to one side.

Figure 13:
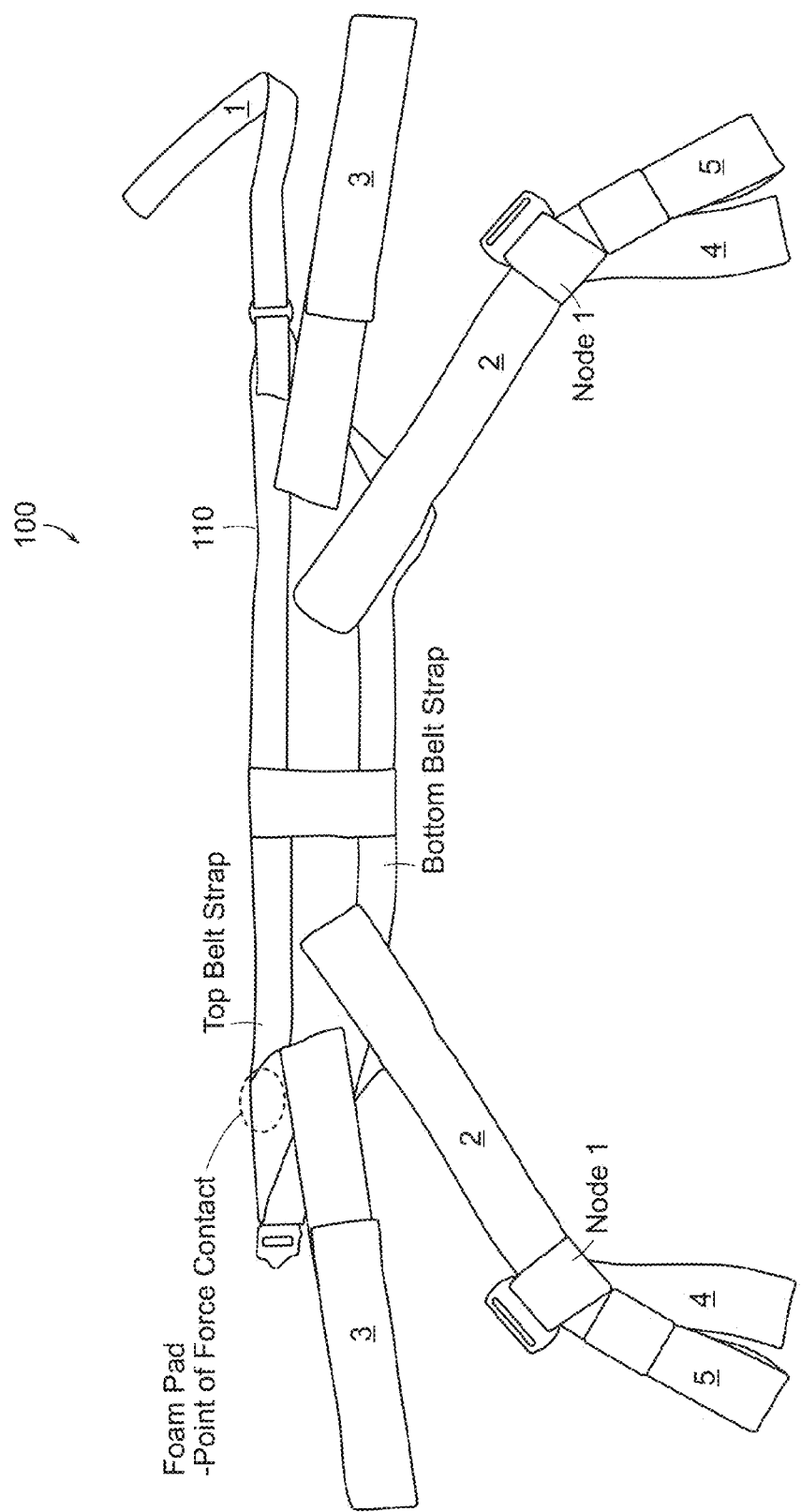
FIG. 13 shows a waist belt of a soft exosuit (V5) according to at least some aspects of the present concepts.

FIG. 13 provides an illustrative example of how the connection elements of a soft exosuit according to at least some embodiments of the present concepts can be arranged and configured. In FIG. 13, the different connection elements of the soft exosuit comprise straps and are numbered and named in Table 2, below.

TABLE 2

| Strap Number | Name/Description |
| --- | --- |
| 1 | Waist Belt Connection Element |
| 2 | Node 1 To Same Hip Connection Element |
| 3 | Node 1 To Opposite Hip Connection Element |
| 4 | Thigh Connection Element - Lateral |
| 5 | Thigh Connection Element - Medial |
| 6 | Thigh Connection Element To Calf Connection Element - Lateral |
| 7 | Thigh Connection Element To Calf Connection Element - Medial |
| 8 | Calf Connection Element - Lateral |
| 9 | Calf Connection Element - Medial |

Figure 14A:
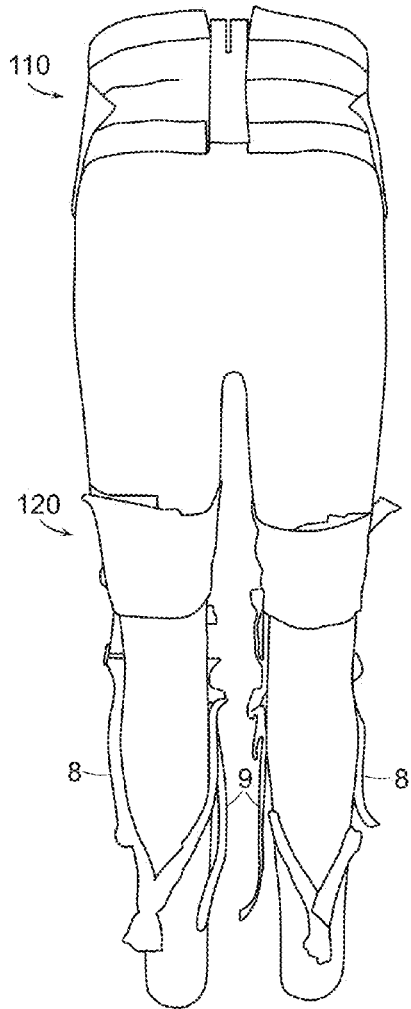
FIGS. 14A-14B show front and back views of a soft exosuit (V5) according to at least some aspects of the present concepts, an upper portion of which is shown in FIG. 13.
Figure 14B:
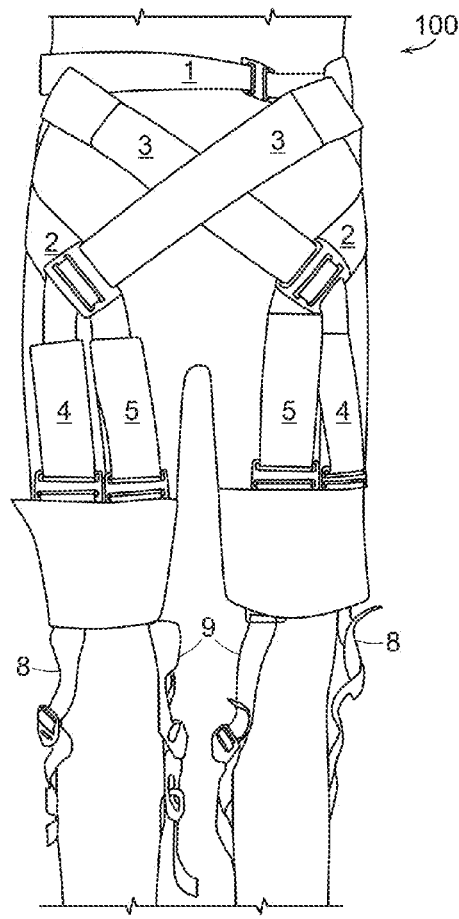
Figures 15A, 15B, 15C:
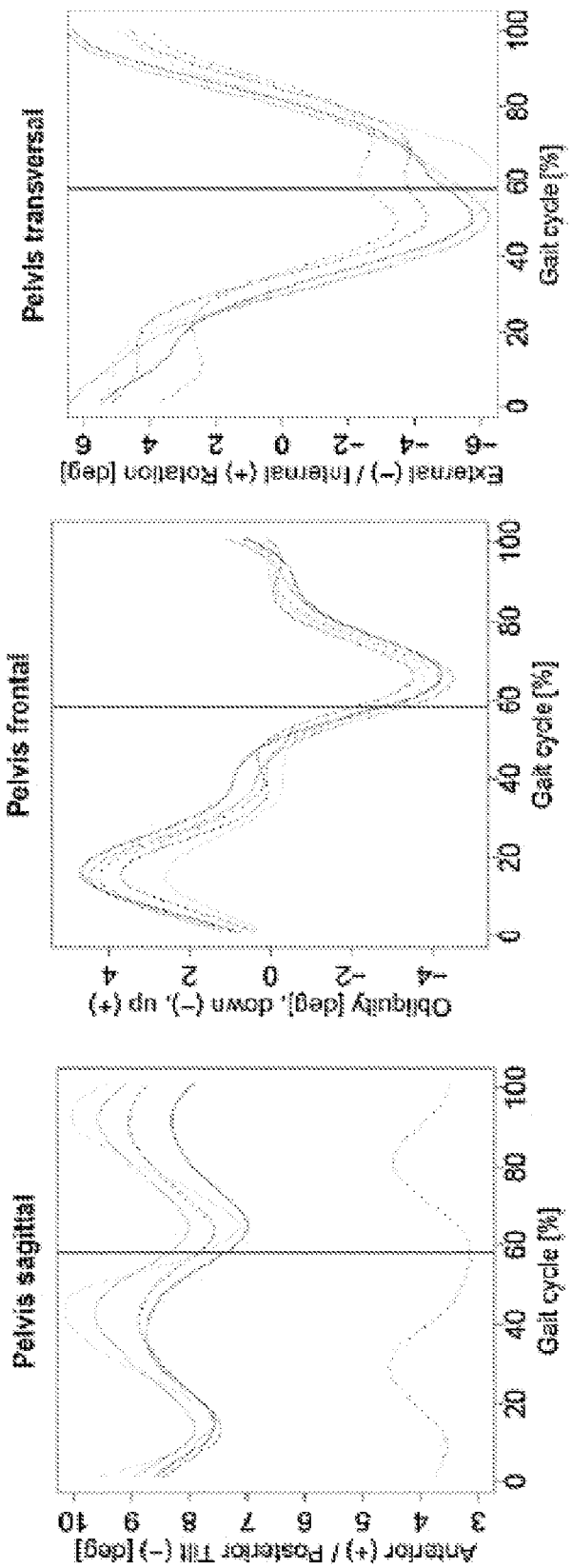
FIG. 15 shows graphs of the range of motion for pelvis.

In FIG. 13, the waist belt is displayed flattened out presenting the side facing away from the user. This view provides an overview of the waist belt and the connection elements attached directly to it. In accord with some embodiments of the invention, the waist belt includes a top belt connection element and a bottom belt connection element that can be joined at the ends to a connection element and buckle that enable the waist belt to be fastened around the waist of the user with foam or other padding arranged between the waist belt and any points of contact (e.g., iliac crest) on the body. Connection elements 2 and 3 of FIG. 13 depend from waist belt 110 and connect to a top of node 1, as shown in FIG. 13 and FIG. 14B. Connection elements 4 and 5 of FIG. 13 depend from a bottom portion of node 1 and connect to an upper portion of thigh brace 200. In FIGS. 14A-14B, the soft exosuit shown in part in FIG. 13 is shown on a mannequin for illustration.

The waist belt 110 keeps the soft exosuit from being pulled down under vertical force or slipping over the iliac crest due to horizontal force that is the result of the angle of the connection elements that attach the thigh braces to the pelvis portion of the exosuit. The belt is also prevented from slipping down due to the tension placed around the pelvis by tightening the waist belt connection element. It accomplishes this by creating tension around the pelvis where a portion of the belt passes on top of the iliac crest of the hip bones. The pelvis serves as a support or anchor point for the forces which are transmitted from the T-connector 113 at ankle up through the connection elements of the soft exosuit 100 to the waist belt 112.

In accord with some embodiments, the pelvis has a relatively small range of motion throughout the gait cycle compared to other bony landmarks, such as the knee and shoulder. The pelvis has its largest movement in the transverse plane where it rotates a total of approximately 12° throughout the gait cycle. In comparison, the knee moves approximately 50° in the sagittal plane and movement of the shoulders is highly dependent on the user's posture at any given time. Accordingly, in accord with the present concepts, use of the pelvis is favorable for embodiments of the soft exosuit 110 in accord with the present concepts that are directed primarily to gait assistance. The pelvis's range of motion and the cyclic nature of the positions of the various leg segments throughout the gait cycle make the distances between the pelvis and various leg segments highly predictable throughout the gait cycle, which help inform selection of appropriate anchor points capable of maintaining soft exosuit 100 tension at specific times during the gait cycle. Further, the pelvis structure defines a ledge to which the waist belt 110 can be effectively attached to anchor both vertical and horizontal forces.

The stiffness of the soft exosuit 100 is, in part, determined by the compliance of the user-soft exosuit interface. The lower the compliance of the interface between the user and the soft exosuit 100, the higher the stiffness of soft exosuit in operation. By anchoring to a stable and low compliance feature, the soft exosuit can transmit higher forces to the body of the user. In addition, the symmetry of the pelvis allows for the loads to be distributed evenly onto the body of the user. By distributing the actuation forces to each side of the body, the normal forces acting on the body from the soft exosuit at any one point can be reduced, helping to minimize the formation of pressure sores, friction and rubbing and thereby increasing the perceived comfort of the exosuit. As noted previously, in at least some aspects of the present concepts, the actuation forces may also be, or may alternatively be, distributed to one or more other locations on the body (e.g. torso, shoulders, etc.).

In at least one aspect, the waist belt 110 comprises a top belt connection element and a bottom belt connection element, with the top belt connection element being disposed over the top of the hip bone (optionally with foam padding provided on the top belt connection element at locations where it rests on top of the iliac crest), and the bottom belt connection element disposed to lie just below the iliac crest. These two connection elements provide, in combination, a stable attachment platform.

The pelvis, at the iliac crest, provides a suitable anchor point for minimizing the compliance of the soft exosuit. As noted, the soft exosuit advantageously leverages the geometry of the pelvis, which provides a ledge at the iliac crest on which the waist belt may rest. This makes it possible to anchor both vertical and horizontal forces. Horizontal forces can also be resisted by connection elements (e.g., bottom belt strap) which surround the side of the pelvis. Reducing compliance allows for a stiffer soft exosuit, which can be useful to effectively apply forces to it and thus the wearer. As the soft exosuit reaches a certain level of stiffness, it can be useful to protect the user from the forces being transferred to them via the soft exosuit. Padding, such as layered fabric or foam padding, can be used to spread these forces across a greater surface area on the user as well as providing a damping medium which reduces the impact of these forces. However, this padding can increase the compliance in the system and thus presents another variable to control to optimize compliance and stiffness to achieve a balance in efficiency and comfort.

In at least some aspects, node 1 (see, e.g., FIG. 7, FIG. 13, 14B) can be configured as the junction at which the forces resulting from the ankle actuation on each respective leg converge and then divide up to be distributed to each side of the user's pelvis. Adjusting the position of node 1 on the user's thigh can be useful to maintain force balance and soft exosuit 100 tension. The force may be distributed via one or more straps that attach the thigh braces 120 to the waist belt 110 of the soft exosuit.

As shown by way of example in FIG. 7 and FIG. 14B, 16, a node (e.g., Node 1 in FIG. 14B) is placed at the middle of the thigh in the frontal plane, in accord with at least some aspects of the present concepts, and can be adjusted by connection element 2 and connection element 3, as shown in FIG. 14A. The vertical placement of node 1 on the thigh can be adjusted according to the size of the user and the distance from the node to the top of the thigh, which varies from user to user, but is generally far enough down so that it does not interfere with hip flexion. Proper vertical placement can be verified by having the user wearing the soft exosuit flex their hip after the node position has been set to see whether it interferes with hip flexion. The placement of the node can be used to optimally align and adjust the force paths in the soft exosuit 100 which, in accord with some aspects of the present concepts, can prevent or reduce problems associated with the thigh brace 120 rotating due to force imbalances. Improperly aligned force paths can create unwanted moments at the hip and knee which can result in unnatural motion, muscle fatigue and soreness. Through the use of node 1 (see, e.g., FIG. 13,14B, 16), the forces resulting from the ankle actuation are transmitted in a controlled and linear path from the ankle to the front of the thigh, where it can be further distributed to either side of the pelvis. With the connection elements passing into one junction (node) in this way it allows for the tension paths around the hip and knee to be adjusted more coherently by tightening, loosening or repositioning the connection elements on the exosuit. This enables greater control and fine tuning of the moments that the soft exosuit generates at the hip and knee throughout the gait cycle.

In accord with some embodiments of the invention, the particular configuration of soft exosuit utilizing node 1 helps to achieve a much higher exosuit stiffness than would otherwise be achievable since it anchors the force path to each side of the pelvis, where it is possible to achieve a much higher exosuit stiffness. The use of node 1 enables the soft exosuit 100 to distribute the forces over the pelvis, where the stiffness of the waist belt was far greater, resulting in the soft exosuit being able to maintain higher forces while suffering very little displacement. The connection elements connecting node 1 to the waist belt 110 can be secured to the node's position as they are constrained in the medial, lateral and vertical directions.

Connection elements 4 and 5 (see, e.g., FIG. 16) can be tensioned to establish a pretension in the soft exosuit between the waist belt 110 and thigh brace 120 that increases the soft exosuit stiffness through pre-loading it downwardly against the pelvis and upwardly against the thigh. Correct pre-load resulting from tensioning connection elements 4 and 5 can be accomplished by creating, qualitatively, a snug tension across the front of the thigh that can be adjusted according to the user's comfort, which can vary from user to user.

In accord with at least some aspects of the present concepts, the waist belt 110 (see, e.g., FIG. 7) functions optimally when tension is maintained in the waist belt. If the waist belt 110 is not properly tensioned, the soft exosuit 100 will sag when actuation is applied.

Proper vertical placement of the waist belt 110 is desirable to maintain proper soft exosuit stiffness. In accord with some embodiments of the present concepts, the soft exosuit 100 utilizes the iliac crest on the pelvis as an anchor for the majority of the forces acting on the user. If the waist belt 110 is not supported by the iliac crest then the soft exosuit 100 may not be able to provide as much initial stiffness, unless it is supported by other features of the body. If the waist belt 110 position is set too low, or becomes too low during use, it could interfere with the hip motion of the user, causing discomfort (e.g., soreness of the hip flexors) and decreasing soft exosuit functionality.

During evaluation of aspects of the soft exosuit, it was found by the inventors that tension created across the hip during early to mid-stance could lead to muscle fatigue in the hip flexor and gluteus medius muscles. In early to mid-stance, the hip is flexed and, thus, to create a moment that will resist this flexion, tension is required to pass from behind the hip's center of rotation, below it, and to the front of the thigh. Thus, if connection element 2 in FIG. 13 or FIG. 14B passes below the hip's center of rotation, it could create such moments. There are two possible ways that could lead to connection element 2 creating these moments. The first is that node 1 is positioned too low on the thigh. The second is that connection element 2 attaches further behind the waist belt. Connection element 2 can be attached directly to the waist belt (e.g., via Velcro®) once node 1 (see FIG. 13 or FIG. 14B) is positioned correctly with respect to the center of the thigh. Once node 1 is correctly placed, it can be secured by attaching connection element 2 to the waist belt 110 by extending connection element 2 in a straight line from node 1 to the waist belt (i.e. making sure that the connection element remains smooth and flush with the wearer), ensuring that connection element 2 has a proper angle of attachment to the waist belt. Generally, node 1 can be laterally positioned in the center of the thigh, about 10 cm inward of the pelvis (e.g. iliac crest), directly above the patella and vertically positioned just below the crease between the thigh and torso. Connection elements 2 and 3 can each extend angled upwardly from this point to the side of the pelvis (side of the iliac crest), on the same side and opposite side of the body, respectively. Outer connection element 2 can be angled between about 40-65° with respect to the horizontal and connection element 3 can have a correspondingly smaller angle with the horizontal.

Figure 17A:
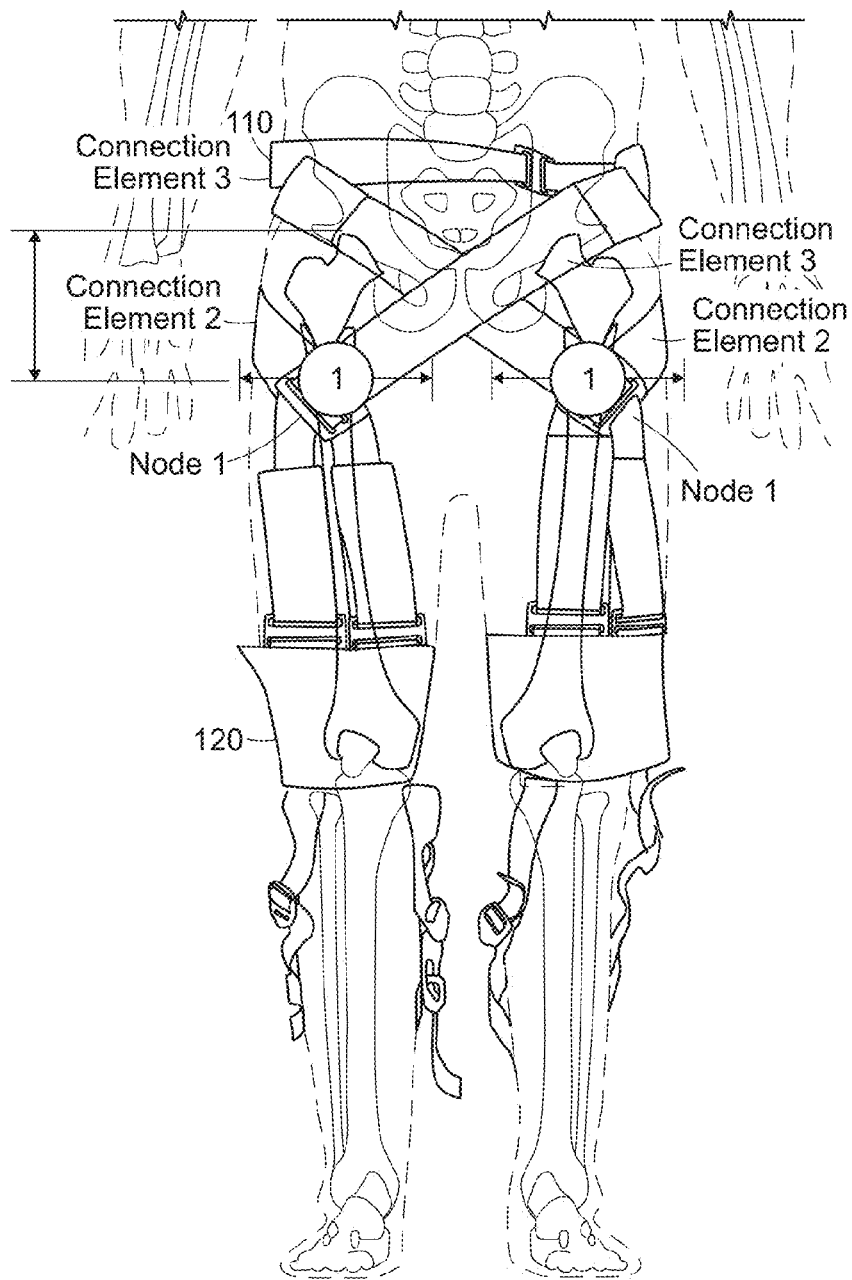
FIGS. 17A-17B show, respectively, the soft exosuit of FIG. 16 overlaid on a skeleton showing the positioning of the waist belt and Node 1 and an example of a horizontal misalignment of Node 1 resulting in rotational forces on the thigh brace.
Figure 17B:
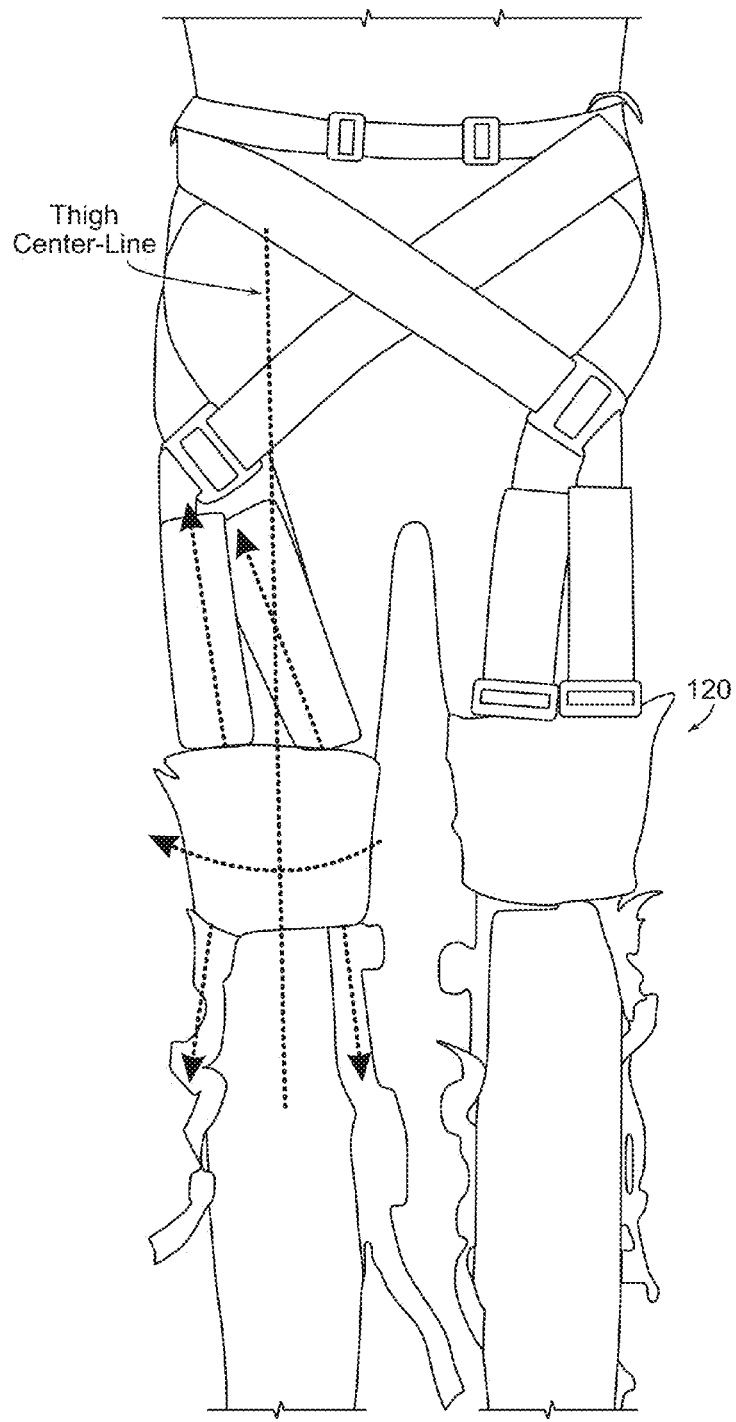

If node 1 is placed in an incorrect horizontal location, it will result in a disadvantageous rotation of the exosuit. As shown in FIG. 17B, if node 1 is placed either to the left or to the right of the middle of the thigh, tension in the soft exosuit will then be unbalanced with respect to the symmetry of the leg. In this case, node 1 is constrained by connection elements 2 and 3 and thus will be secured in its position. Connection elements 4 and 5 will begin to exert a rotational force on the thigh brace when the soft exosuit 100 is actuated because of the force path being directed to one side of the leg's line of symmetry or the other as opposed to being in-line with the leg's line of symmetry. The rotation is caused by the thigh brace 120 being pulled to whichever side the imbalance is on when the soft exosuit 100 is actuated. When the soft exosuit 100 tension releases after the actuation, the thigh brace 120 settles back down on the user, but does not go back to its original position as it has now translated slightly in a direction toward the imbalance. This will repeat for every actuation cycle until connection elements 4 and 5 have regained symmetry with node 1. At that point the thigh brace 120 will have rotated such that the calf connection elements 107 no longer align correctly with the knee's center of rotation, such that the soft exosuit now creates incorrect moments on the user.

In at least some aspects of the present concepts, node 1 is placed directly in the center of the thigh several centimeters below the flexion point of the thigh, as is shown by way of example in FIG. 17A. The approximate vertical position can be determined by having the wearer flex their hip once the node has been positioned to see if the node 1 interferes in any way with their hip flexion. Nominally, node 1 is placed close to the flexion point, but not so close that it interferes with hip flexion. Node 1 should be horizontally positioned in the center of the thigh, as horizontal misalignment could cause the soft exosuit to rotate undesirably. Once node 1 is positioned correctly with respect to the thigh, it is first secured by attaching connection member 2 to the waist belt by extending it in a straight line from node 1 to the waist belt, this ensures that connection member 2 has a proper angle of attachment to the waist belt, second connection member 3 is looped through node 1 buckle and attached, using care to ensure that, when securing connection member 3, the node center position does not shift. Vertical placement of node 1 is not as critical to the soft exosuit's function as the horizontal placement. If node 1 is positioned too high up on the thigh it will interfere with the user's hip flexion and will be apparent.

In accord with some embodiments of the present concepts, the thigh brace 120 can wrap around the lower thigh. In one aspect, the thigh brace 120 comprises two pieces that are joined together, the front piece which can have a hook and loop fastener (e.g., Velcro®) facing towards the user and a back piece which can have a hook and loop fastener (e.g., Velcro®) facing away from the user. The calf connection elements 107 can be sandwiched between the two layers and secured in place by the hook and loop fastener (e.g., Velcro®).

Figure 18:
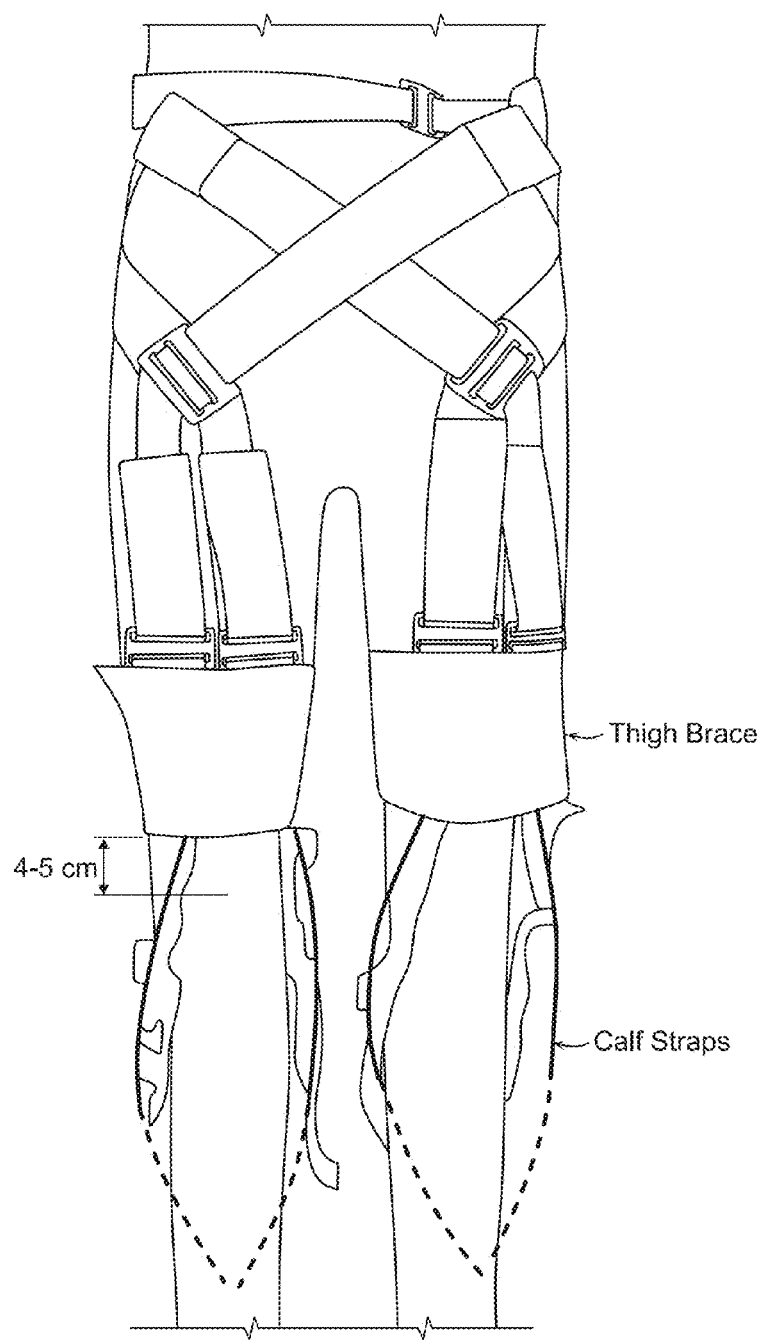
FIG. 18 shows the positioning of the thigh brace of a soft exosuit (V5) according to at least some aspects of the present concepts.

In accord with at least some embodiments of the present concepts, the bottom of the thigh brace 120 is placed between approximately 3-6 centimeters (and preferably between about 4-5 cm) above the top of the patella, as shown in FIG. 18, but this distance can vary depending on user's physiology. Preferably, the thigh brace 120 is positioned higher to allow for a greater range of adjustability for the calf connecting elements 107. For a skinny to medium sized user with low to moderate muscle mass, the thigh brace 120 can be positioned 4 centimeters above the patella. For users with larger thigh diameters, the thigh brace 120 can be positioned 5 or 6 centimeters above the patella to permit correct positioning of the calf connecting elements 107. Thus, the position of the thigh brace 120 above the knee can be selected to provide for proper placement of the calf connecting elements 107, which are attached to the thigh brace 120, and to ensure that the calf connection elements 107 do not interfere with the knee's range of motion. Furthermore, with the thigh typically having a larger diameter further up the leg, this allows the calf connecting elements to avoid contacting the knee area, thereby avoiding chafing in the knee area.

Figure 19:
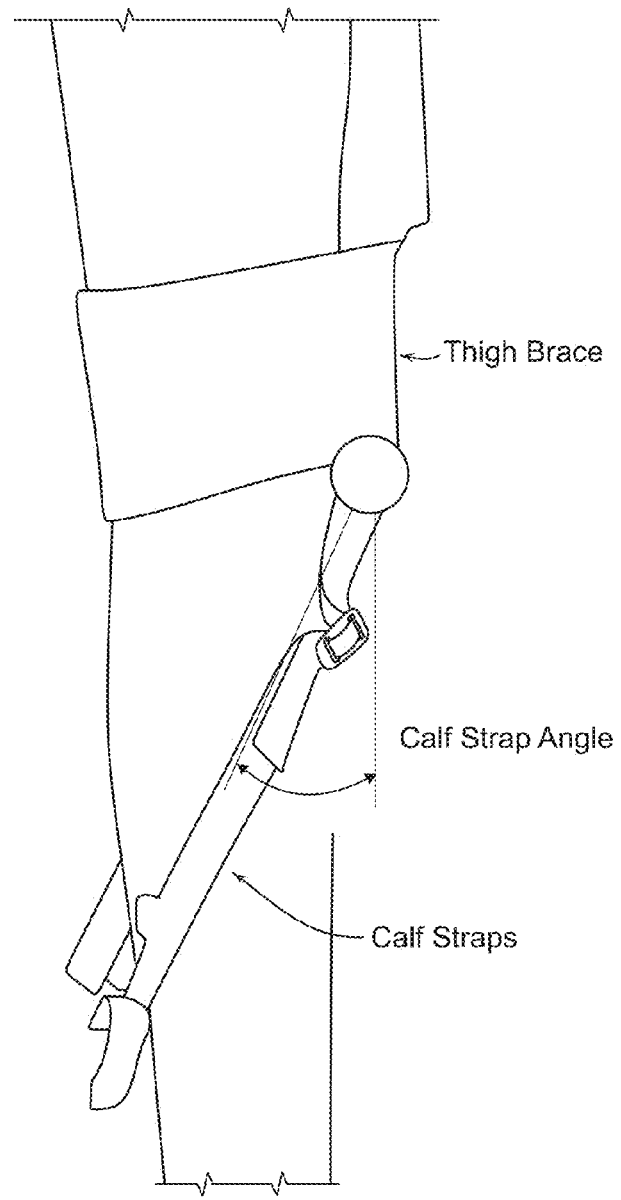
FIG. 19 shows the angle of the calf straps of a soft exosuit (V5) according to at least some aspects of the present concepts.

As shown in FIG. 19, the location and angle at which the calf connecting elements 107 exit the thigh brace 120 can be adjusted. This adjustability permits a user to adjust the soft exosuit to accommodate their particular physiology and musculature while positioning the calf connection element 107 appropriately relative to the knee's center of rotation. Adjustments to the placement of the calf connection elements 107 with respect to the knee's center of rotation are used to ensure the correct moments are produced at the knee.

In accord with some embodiments of the invention, the thigh brace 120 can contribute to exosuit stiffness by balancing the horizontal load when the soft exosuit is tensioned. This horizontal load can be a result of the loading path of the soft exosuit being angled slightly as it travels up from the ankle to the pelvis, such as is shown in FIGS. 19 and 20A-20B. A change in direction occurs at the thigh brace 120 to accommodate the correct placement of the calf connection elements 107 with respect to the knee's center of rotation. The correct placement of the calf connection elements 107 is desirable because a tension is created across the knee joint when the soft exosuit is actuated. Depending on where the calf connection elements 107 are positioned with respect to the knee's center of rotation, the moment generated responsive to this tension can either help or hinder the user. In order for the soft exosuit tension to not adversely affect the user's natural knee moments, the tension can be in line with or slightly in front of the knee's center of rotation at the time of actuation. The position of the calf connection elements 107 on the thigh brace 120 and the angle at which it exits the thigh brace 120 can be adjusted so that the tension is in-line with or in front of the knee's center of rotation.

FIG. 19 shows the tension in the lateral calf connection element 107 as a force is applied at the T-connector, the same is occurring to the medial calf connection element 107 on the other side of the leg (not shown). FIGS. 20A-20B show how the forces on the medial and lateral calf connection elements 107 converge at the thigh brace 120. The calf connection elements 107 are each coupled to the thigh brace 120 via a secure attachment (e.g., Velcro®). The direction of the force acting on the calf connection elements 107 acts to pull them apart from one other and puts tension on the fabric between the two calf connection element 107 attachment points to the thigh brace 120. The resulting tension profile is shown in FIG. 20A by horizontal vectors in FIG. 16A, with the highest tension (largest vector) in the thigh brace 120 being at the bottom of the thigh brace 120, with decreasing tension (smaller vectors) with increase in height from the bottom of the thigh brace. It is possible that, for some users, the horizontal force will reverse sign at the top of the thigh brace 120 as the force profile depends on both the direction of the force being applied and how the calf connection elements 107 are angled with respect to the thigh brace 120.

The calf connection elements 107 can attach to the thigh brace 120 and join together in the back of the shank below the bulk of the calf muscle. The junction where the two straps meet below the bulk of the calf muscle is a point at which the Bowden cable sheath 144 can be attached to the soft exosuit 100. As noted, in at least some aspects of the present concepts, the calf connection element 107 length, angle, and location of connection to the thigh brace 120 can all be adjusted to accommodate users of different physiologies. In some embodiments, there are four adjustment factors that provide for correct placement of the calf connection element 107, and an overarching objective for each of these variables is to position the calf connection elements 107 correctly with respect to the user's knee center of rotation. The first factor is the location at which the calf connection elements 107 exit the thigh brace 120 (FIG. 20B), the second is the angle at which the calf connection elements 107 exit the thigh brace 120 (FIG. 19), the third is the vertical position of the thigh brace above the patella (FIG. 18), and the fourth is the vertical location of the Bowden Cable T-attachment with respect to the shank (FIG. 21).

The factors noted above can be adjusted with respect to the thigh circumference and the thigh length of the user. Where embodiments of soft exosuits in accord with at least some aspects of the present concepts enable such variability in one or more of these factors (e.g., in a suit designed or fitted for a specific user, the soft exosuit may not need to provide for such subsequent adjustability), the optimal placement of the calf connection elements 107 is such that, when the calf connection elements 107 are tensioned, they do not cause moments at the knee that will negatively impact the user's natural gait cycle. One way to ensure the calf connection elements 107 do not cause moments at the knee that will negatively impact the user's natural gait cycle is to having the tension pass through the knee's center of rotation, thus ensuring that the soft exosuit creates no moments on the knee. However, since the knee flexes and extends through a wide range of motion throughout the gait cycle, with a constantly changing instantaneous center of rotation, this approach is difficult to realize. Another, more practical, way to achieve this end is to permit creation of moments that do not negatively impact the user's natural gait.

To further illustrate correct calf connection element 107 placement, an understanding of knee and ankle dynamics is helpful. In at least some aspects of the present concepts, a soft exosuit configured to assist walking movement is actuated during the terminal stance phase and pre-swing phases that occur from approximately 30% of the gait cycle to 62% of the gait cycle. At the beginning of terminal stance (30% gait cycle) the gastrocnemius (calf muscle) and soleus (inner calf muscle) gradually increase their contraction to counter the growing plantar forefoot flexor moment, as well as to store elastic energy in the muscle and tendon tissue to rebound during heel lift/push-off, that occurs as the body is falling forward. This action increases as the ankle begins to plantar flex as the heel comes up and the pivot point moves to the forefoot. Additionally as this is happening, the knee flexion reaches its lowest point (about 5° at 40%). This reduction in flexion occurs as the body's mass is now falling forward on the forefoot that places the force vector of the falling body in front of the knees center of rotation causing passive extension of the knee. However this extension is resisted by posterior muscle action, i.e. the gastrocnemius that is already tensing due to the action at the knee and ankle as well as the popliteus that lies across the knee joint. As the minimum flexion angle is reached (40% gait cycle) the knee immediately begins to flex as at that point the knee joint will have moved in front of the body vector due to the heel rising. At this point, the posterior muscles that were acting to resist knee extension are now promoting knee flexion as well as the body vector that is now posterior to the knee's center of rotation and thus passively promoting knee flexion. Terminal stance ends with initial contact of the contralateral limb (50% gait cycle). With the onset of pre-swing (50% gait cycle) the weight is shifting over to the other leg allowing the knee to flex freely that results from the elastic recoil of the Achilles tendon, the action of the posterior muscles and the passive action of the body vector being posterior to the knees center of rotation. However, if knee flexion occurs too rapidly then the rectus femoris comes on to decelerate the knee causing an extension moment at the knee, thus the extension moment during pre-swing is not always present and is dependent on how rapidly the leg goes into flexion.

From the above description, three points are to be made about the tension of the soft exosuit across the knee joint during the actuation phase. First, if such tension is present in front of the knee's center of rotation between 30 and 40% of the gait cycle, this will cause the posterior muscles (gastrocnemius and popliteus) to work even harder to reduce the decrease in flexion. This creates a feeling of "too much tension" from those wearing the exosuit, which can be remedied by moving the calf connection elements 107 to a more posterior position on the thigh brace 120. Second, if the tension is in front of the knee from 40 to 50% of the gait cycle, this will resist knee flexion that, at that point, is occurring passively due to the body vector being behind the center of rotation as well as actively due to the posterior muscles. At this point, it would be beneficial to dispose the calf connection elements 107 either in-line with or behind the knee's center of rotation as disposing them in front of the knee's center of rotation would likely overwork the posterior muscles. Third, if the tension is in front of the knee from 50 to 62% of the gait cycle, it will be resisting the knee's flexion motion that is occurring passively due to the recoil of the Achilles tendon, as well as the direct muscle action of the posterior muscles. Although the knee's flexion moment is sometimes resisted by the rectus femoris during pre-swing, this is not always the case and the extension moment that may be expected for this portion of the gait cycle may not necessarily occur.

By observing the moments and corresponding movements of the knee and analyzing results of extensive laboratory testing of different configurations of the soft exosuit, the present inventors developed configurations of the calf connection elements 107 that are, or can be, tensioned so as to create moments that do not impede the user's natural walking cycle for a wide range of user physiology. A first challenge to determining appropriate soft exosuit connection element positioning (e.g., to achieve an optimal balance of weight, power, metabolic effect, comfort, and variability of different physiology, to name a few) was simply large person-to-person dimensional variances. A second challenge was the rate at which the knee goes from being extended to flexing right around push off (50% gait cycle), which is close to the end of the actuation phase. If the strap migrates behind the knee's center of rotation too early, this would cause unwanted flexion moment that would impede the user's natural gait. At this point, it can be beneficial to have the calf connection elements 107 migrate to be either in-line with or behind the knee's center of rotation to avoid adversely affecting the user.

Figures 23A, 23B:
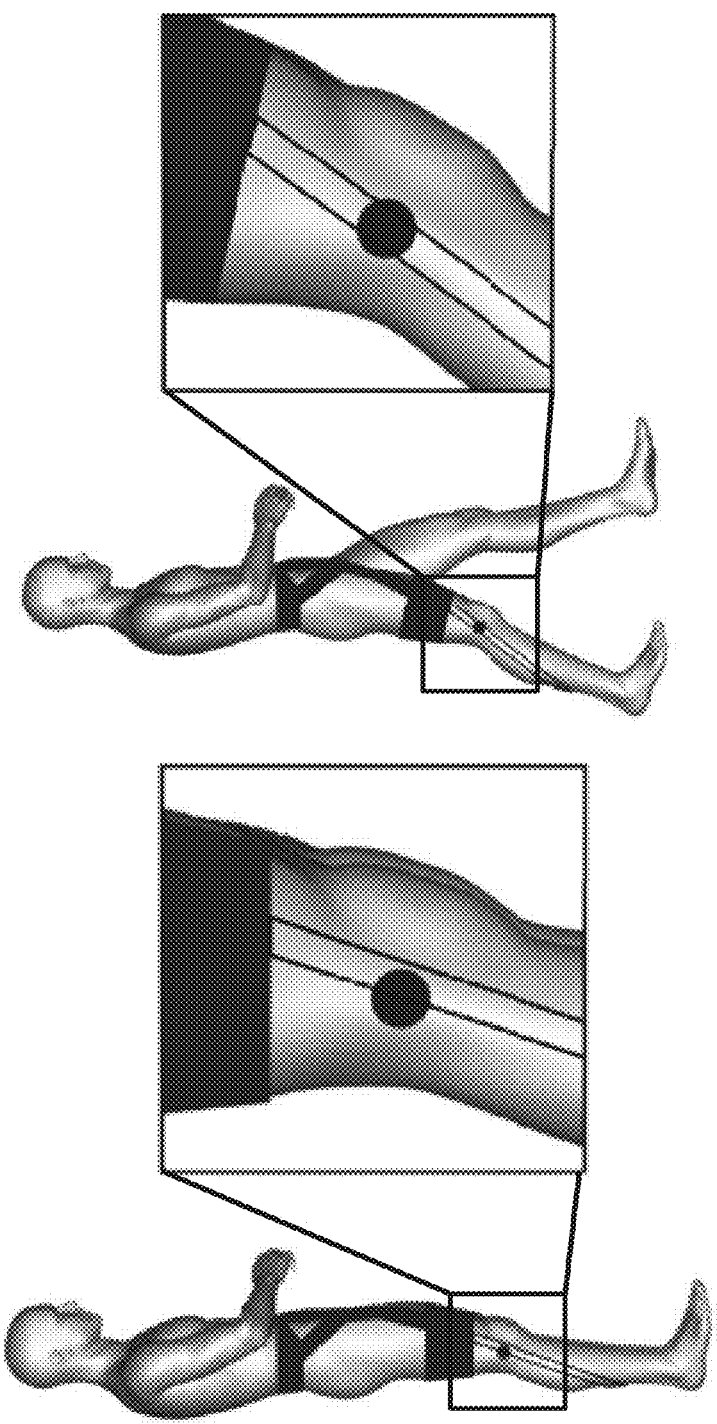
FIGS. 23A-23B show the alignment of the calf straps with the axis of the knee joint in a soft exosuit according to at least some aspects of the present concepts.

In accord with some embodiments, the desired placement of the calf connection elements 107 is shown in FIGS. 23A-23B, which avoids the problems noted above by having their line of action pass through the effective center of rotation of the knee when the wearer is in an upright standing position. This position can be determined by finding the junction between the femur and tibia on each side of the tibia and by observing the surface anatomy, with the appropriate position being identified by a bone protrusion on the femur and tibia respectively, between which is a "valley" or depression which runs in the anterior-posterior direction. If looking at the knee from the side, the location that the calf connection elements 107 will nominally pass through is approximately 30%-40% of the distance from the back side (posterior) of the knee. For some people, this is exactly the case. For others (e.g., large people, muscular people) the correct placement is determined on a case-by-case basis using an approximation and trial and error approach.

Figure 24A:
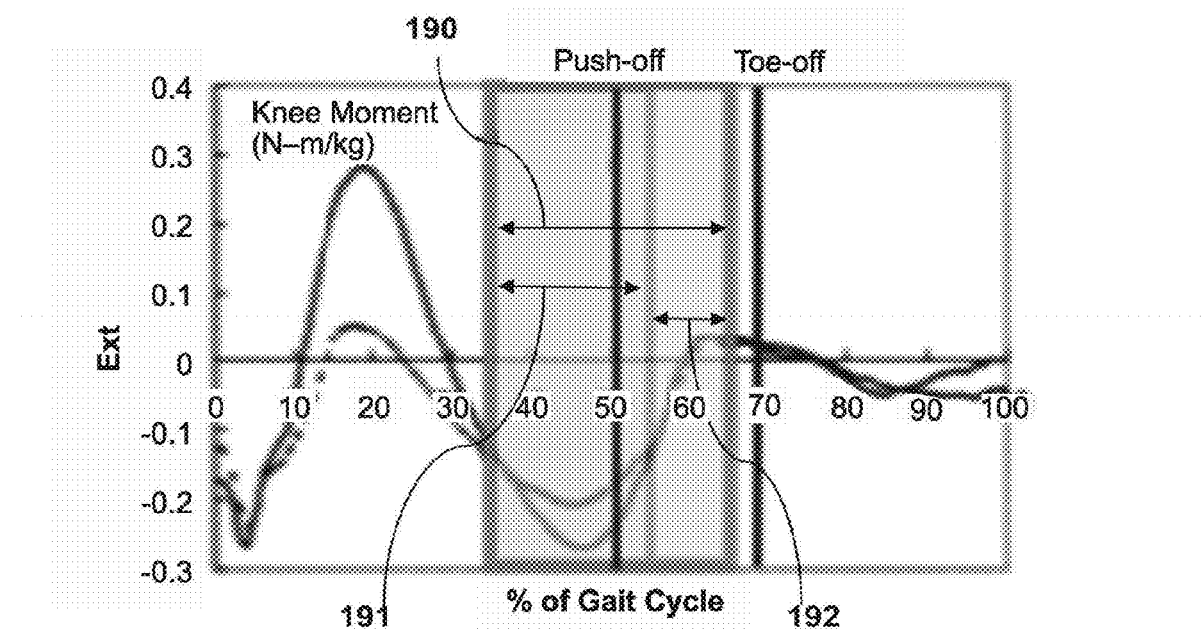
FIGS. 24A-24B shows the power requirements graph over a gait cycle in a soft exosuit according to at least some aspects of the present concepts.
Figure 24B:
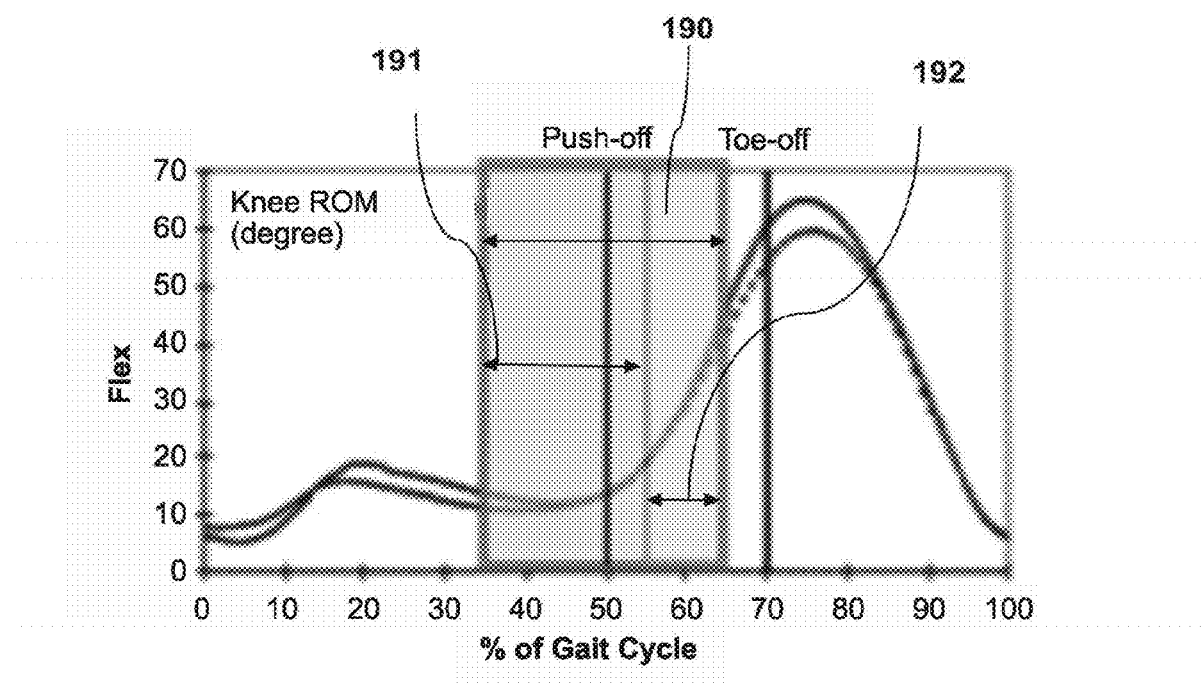

FIGS. 24A-24B show an actuation phase over one gait cycle for one embodiment of a soft exosuit 100 in accord with aspects of the present concepts. The actuation phase 190 is highlighted on both the knee moment (FIG. 24A) and range of motion (FIG. 24B) graphs. The left portion 191 represents when the soft exosuit 100 creates an extension moment around the knee and the right portion 192 shows when the knee creates a flexion movement around the knee. Desirably, the moments the soft exosuit places on the wearer mirror those naturally created by the wearer (i.e., moments about the joint(s) that equal as closely as possible the natural biological moments during motion). In situations where joint moments from the soft exosuit 100 may be reversed from a natural moment for the movement at a given time, the soft exosuit 100 desirably minimizes the moment arm about the joint (e.g., to make the knee moment as small as possible by putting the connection elements 107 through the knee center of rotation).

As shown in FIG. 25A, the calf connection elements 107 terminate at the T-connector 113 where the Bowden Cable sheath 144 (not shown) connects to the soft exosuit. In accord with some embodiments, the T-connector 113 is positioned below the bulk of the calf muscle. The calf muscle is compliant and protruding and, accordingly, if the T-connector 113 is placed on it at the time of actuation, it will dig into the muscle thereby increasing the compliance in the system and causing user irritation. The space below the calf muscle is much less compliant and also allows the calf connection element 107 to descend down the shank in a straighter path as opposed to being angled more deeply to accommodate the calf's bulk. If the calf connection element 107 descends the shank at a greater angle with respect to the vertical, this makes the soft exosuit's force path less efficient, as it now wants to straighten when it is tensioned.

FIG. 25A shows forces acting on the calf connection elements 107 from a side view according to some embodiments of the present concepts. The dotted-line vectors 200 (the upper and lower arrows) represent the actuation force path, the solid lines vectors 201 represent the reaction component forces at the bottom of the calf connection element 107 and the T-connector and at the top where they exit the thigh brace 120. The dotted line vectors 202 acting along the calf connection elements 107 represent the tension in the illustrated calf connection element 107 resulting from actuation. The horizontal component forces 203 that act on the user are also shown.

FIG. 25B shows the T-connector placement with respect to the calf of the wearer. FIG. 25C shows the difference in angles with respect to the vertical with respect to the vertical placements (1) and (2). The larger angle resulting from placement (1) will have the effect of creating a larger horizontal force component that will cause the T-connector to push into the wearer's calf. Correct positioning of the calf connection elements 107 contributes to the overall compliance in the system by circumventing the bulk of the calf muscle. The area below the calf muscle is mostly skin and bone and thus provides relatively low compliance. Circumventing the calf muscle also allows the calf connection elements 107 to descend the shank in a straighter line with respect to the vertical. If the calf connection elements 107 terminated on top of the calf, two adverse effects would follow. First, the calf connection elements 107 would descend the shank at a greater angle with respect to the vertical, making the soft exosuit's force path less efficient as it would want to straighten when tensioned. Second, due to the calf's compliance, the tendency for the calf strap to straighten with respect to the vertical will result in the T-connector 113 digging into the calf, which will reduce the stiffness in the soft exosuit as the actuator will need to compensate for this additional displacement. The T-connector 113 at the end of the calf connection elements 107 can be positioned correctly with respect to the horizontal by positioning the T-connector 113 directly in-line with the center line of the heel. In order to position the calf connection elements 107 correctly with respect to the vertical, the connection elements are adjusted such that the T-attachment gets positioned at the top of the footwear (if worn) or nominally so that the T-connector 113 is located below the bulk of the calf muscle, which allows the calf straps to successfully circumvent the mushy bulk of the calf. In accord with some embodiments, some of the more rigid components can be replaced with softer more compliant ones.

The footwear connection element 130 provides a stiff interface with the user's foot. It at least some aspects, the footwear connection element 130 takes the form of a harness disposed around a boot, as shown by way of example in FIGS. 26A-26C, which respectively depict side, rear and bottom views of such boot. FIG. 27 (side view) shows the three adjustment points provided on the exemplary footwear connection element 130 depicted, with the adjustment points 1-3 being circled with a white dashed line. Table 3 below shows the function of each adjustment point. The footwear connection element 130 relays the upward force due to the actuation at the heel to the front of the foot where it applies a downward force as seen in FIG. 28A. Transferring the upward horizontal force to the front of the foot in such a way helps to promote ankle plantar flexion by virtue of the complimentary moments that are generated. FIG. 28B shows the force path on the footwear connection element 130 on the bottom of the boot.

As to the positioning of the connection members, connection member 1 in FIGS. 26A-26C wraps around the middle of the footwear as shown. It should be placed in the groove between the heel and the fore-foot. The connection member 1 must be secured by an attachment mechanism (e.g., Velcro®) to prevent slippage. Connection member 2 comprises a wide section in the example shown and is connected to a central portion of connection member 1 on top of the foot. Connection member 3 wraps around the ankle, as shown, providing a constraint to keep the footwear connection element 130 from slipping off the heel and being tensioned upwardly to provide greater stiffness. Connection member 4 constrains the footwear connection element 130 from slipping medially and laterally. The bottom edge of connection member 4 may be advantageously placed about 0.5 cm about the edge of the boot at the back. This positioning of connection member 4 will result from correct positioning of node 2. Connection member 5 is the actuator cable attachment point and connection member 6 transmits the actuation force to the heel. Node 2 is desirably placed as close to the bottom of the heel as possible in the vertical direction and directly in the middle of the heel in the medial-lateral direction. Node 3 is placed slightly behind the middle of the foot-sole and its position is dictated by the placement of node 2.

In one example of a method of donning the boot attachments correctly, Node 2 is first placed on the heel, and then connection members 1 and 6, shown in FIGS. 26A-26C, are placed under the boot in their correct position as shown. At this point, it is likely effective for the wearer to stand up on the boot, securing connection members 1 and 6 in place. With these connection members held in their nominal positions, connection member 1 is adjusted as needed (e.g., tensioned/loosened), then connection member 3 is adjusted as needed (e.g., tensioned/loosened), and finally connection member 4 is adjusted as needed (e.g., tensioned/loosened), in that order.

TABLE 3

| Boot Strap | Function |
| --- | --- |
| 1 | Constrains the boot attachment to the front of the boot as well as transfers the forces from the actuation to the front of the foot where it pulls down on connection member 1. This downward force in the front of the foot also contributes to creating a moment about the ankle joint. This mechanism helps to increase the stiffness in the system that makes lifting the heel more effective. |
| 2 | Wide webbing to spread the forces acting on the top of the foot as connection member 1 tensions across the front of the foot |
| 3 | Provides constraint to keep attachment from slipping off the heel. By keeping connection member 3 tensioned ensures stiffness in the system by pre-tensioning the boot attachment in the vertical direction such that when the cable begins to pull there is little to no slack in the boot attachment. |
| 4 | Constrains the attachment from slipping medially and laterally. |
| 5 | Cable attachment |
| 6 | Transmits force from actuation to heel |
| Node 2 | Connects connection member 3, 4, 5 and 6. This point acts to equalize the forces on the boot attachment to avoid the footwear connection element 130 from slipping when the soft exosuit is actuated. |
| Node 3 | Connects connection member 1 and 6. As the force from the actuation tensions connection member 6 the tension gets relayed through Node 3 to connection member 1 where it travels up the sides of the boot and creates a downward force at the top of the foot. |

In another embodiment, the footwear connection element 130 can comprise a sock-like structure that can be donned, much like a sock (see, e.g., FIGS. $26D_1$-$26D_5$, 79). Optionally, the footwear connection element 130 comprises one or more fasteners that may be adjusted (e.g., by tightening or cinching, such as by using VELCRO®, etc.) to secure the footwear connection element around the wearer's foot. Alternatively still, the footwear connection element 130 can comprise a step-into structure that may then be folded over to envelop the foot, at which position one or more fasteners tightened or cinched (e.g., VELCRO®, etc.) to secure the footwear connection element 130 around the wearer's foot. An example of such a footwear connection element130 is shown in the panels of FIGS. $26D_1$-$26D_5$, which shows views of an in-boot attachment to the foot, shown with the foot at a neutral position (FIG. $26D_1$), foot in plantar flexion with the attachment taut against the foot (FIG. $26D_2$), and foot in dorsiflexion with the attachment slack (FIG. $26D_3$) and, at the bottom, views of foot attachment showing its construction (FIGS. $26D_4$-$26D_5$). The footwear connection element 130 of FIGS. $26D_1$-$26D_5$ is a simple textile-based structure, in which webbing extends under the wearer's heel and over the forefoot. As shown, the webbing attaches with VELCRO® over the forefoot, but this could be sewn to be a single piece. The footwear connection element 130 of FIGS. $26D_1$-$26D_5$ comprises a connection element configured to connect around the wearer's ankle that can be used to hold the footwear connection element in place.

Figure 26F:
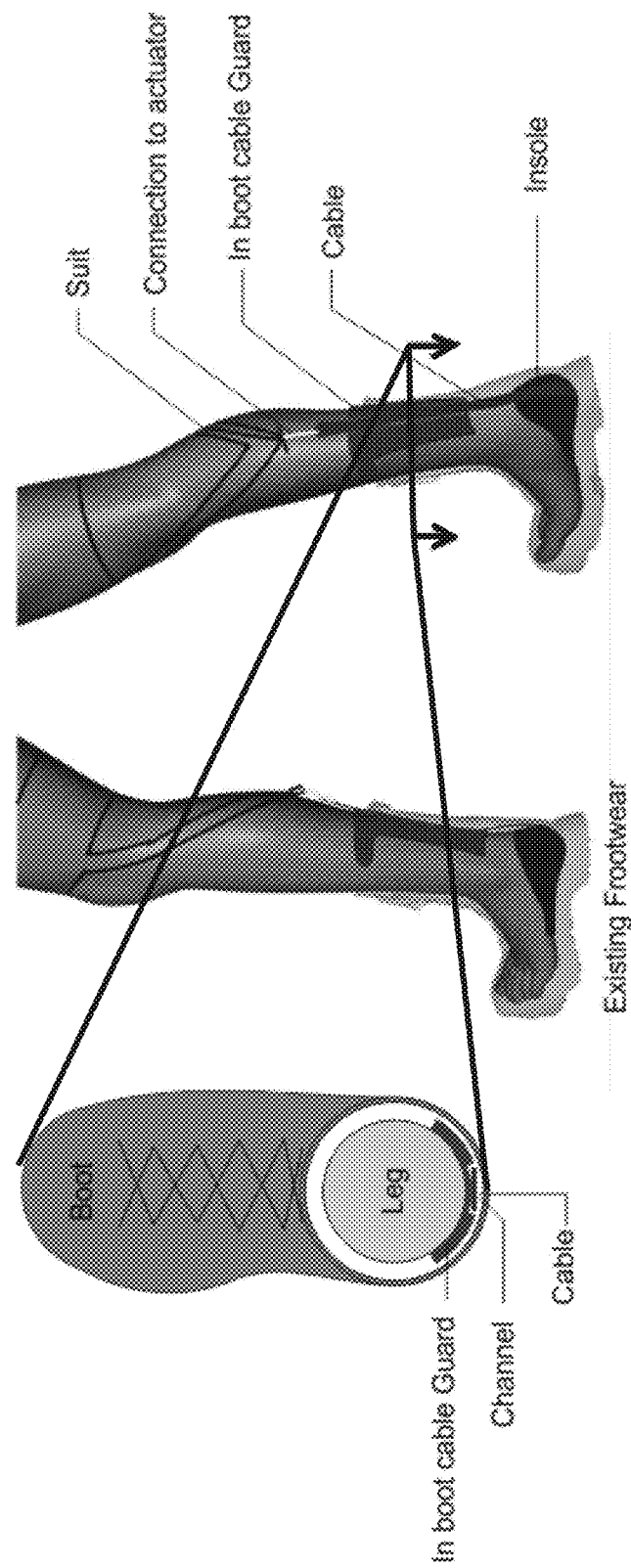

FIGS. 26E-$26G_2$ show aspects of another embodiment of soft exosuit footwear attachment 130 according to at least some aspects of the present concepts. The designs noted in FIGS. 26A-26C focused on a footwear connection element 130 in the form of a harness disposed over boots or shoes which provided a connection point to the Bowden cable 142 actuator. These solutions are "out of boot" solutions on which the cable 142 pulls to create a force on the boot heel upward with respect to the heel. For a footwear connection element 130 that utilizes an "inside the boot" force actuator (such as shown in FIGS. 26E-26G$_2$) to create moments about the ankle joint, two parts are utilized, a cable attached insole and a cable guard. In order to apply forces to the wearer, a cable must extend into the wearer's shoe or boot with one end fixed to the actuator external to the shoe (A) and the other affixed an object internal to the shoe under the wearer's foot (B) insole, such as is shown in FIG. 26E.

In another aspect, a plastic or foam element 131 is optionally inserted in between the webbing 133 over the forefoot and the wearer's foot to distribute the pressure over the top of the foot more evenly than if the webbing was used in isolation, such as is shown by way of example in FIG. 26G$_1$. In another aspect, a midsole 132 can be combined with webbing (and optionally foam or plastic as previously noted) over the top of the foot and/or ankle, to provide additional paths for torque to transfer to the foot, such as is shown in FIG. 26G$_2$.

Attaching a cable or webbing at the rear part of an insole element 130, such as shown in FIGS. 26E-26F, provides a method of fixing point B such that forces applied to a point on the cable or webbing are transferred to the wearer's heel proximal to the ankle joint in the sagittal plane, this creating torque around the joint. This insole can either be a partial or full insole. It may be desired that the insole have some stiffening elements such as carbon fiber to distribute load to the heel. If stiffening elements are used, the insole could advantageously be segmented to allow for maximum range of motion on the ball of the foot. A cable guard is provided (see, e.g., FIG. 26F) at a rear portion of the lower leg. For actuation, the cable needs to retract. In situations where the cable is compressed between the boot and wearer's leg abrasion could result as well as loss in efficiency due to friction between the cable wearer and boot. Thus, a system that provides an open channel for the cable to freely move is desirable.

Once secured to the wearer's foot, the sock-like footwear connection element 130 would then be connected to the soft exosuit 100 via a connection element (e.g., webbing) that attaches to the top of the sock-like structure and goes directly up to the bottom of the calf connection elements 107. In yet another embodiment, the footwear connection element 130 comprises a heel cup configured to wrap around the heel (e.g., the wearer's heel, a heel of the footwear). In still another embodiment, the footwear connection element 130 comprises an insole insert that goes into the footwear under a portion of the wearer's foot (e.g., the heel) or the entire foot, such insole insert, or the aforementioned heel cup, attaching at a rear portion and/or rear lateral portions to a connection member (e.g., webbing) that exits the footwear and attaches to the soft exosuit actuator cable. Desirably, any connection members disposed within the footwear comprises a low friction sheath, low friction coating, or low friction material so as to minimize friction against the wearer. In yet another aspect, the footwear connection element 130 comprises a sole insert that goes under a portion of the sole of the footwear (e.g., just the heel) or the entire sole of the footwear. A connection member (e.g., webbing, cable, etc.) is provided at a rear portion and/or rear lateral portions of the sole insert to connect to a connection member attaching to the soft exosuit actuator cable.

In accord with some embodiments of the invention, an actuator 200 can also be used to reduce the metabolic cost of walking (or other movements or activities) while wearing a soft exosuit 100 in accord with the present concepts. The actuator 200 is used to supplement forces of the desired moment, such as (for walking), supplementing forces about the ankle during the toe push-off portion of the gait cycle when the ankle muscles are generating the greatest power. To perform this action, by way of example, a motor can be used to create the necessary force/displacement on a Bowden cable 142 and sensors 150 can be used to sense joint position and determine actuation timing.

The actuator 200 generates a force that can be transmitted to the user's footwear (e.g., a boot) using a cable to change the distance between a point on the user's boot and the bottom of the soft exosuit (see, e.g., FIGS. 21-22). With a minimally extensible soft exosuit, this contracting distance generates a tensile force in the soft exosuit 100, footwear connection element (e.g., boot attachment), and cable 142. This tensile force can be applied at a position offset from the axis of the ankle joint and result in a moment about the joint.

As one example, flexible Bowden cables 142 can be used by the system 100 to transmit forces from actuator(s) in an actuator unit 200 to the soft exosuit 100. Rigid and/or heavier actuator(s) 200 can be mounted remotely or distally (e.g., on a backpack away from the lower body), such as is shown in FIG. 10A.

In at least some aspects of the present concepts, each limb (e.g., leg) can be driven by its own actuator unit 200, which may comprise one or more actuators. In yet other aspects of the present concepts, each joint can be driven separately by its own actuator unit 200, which may comprise one or more actuators. In still other aspects of the present concepts, a plurality of joints can be driven by an actuator unit 200, which may comprise one or more actuators.

In one embodiment in accord with the present concepts, each actuator unit 200 includes a drive motor 222 and a pulley module 224, such as is shown in FIG. 29. The actuator unit 200 is used to drive a Bowden cable 142 and to sense the user's gait by measuring heel strike contact (See foot switch, FIG. 30). The Bowden cable 142 is attached to a pulley wheel 225 in the pulley module 224 and is extended and retracted by rotation of the pulley wheel 125. In accord with some embodiments, the drive motor 222 includes gearing (e.g., a gear box as shown in FIG. 29) to increase the drive torque of an output shaft coupled to the pulley module 224 to drive the Bowden cable 142 that provides the assist to the user's motion. In other aspects, the motor 222 is connected directly to the pulley module 224 without intermediate gearing.

The drive motor 222 advantageously comprises an encoder (not shown) or other positional sensor configured to indicate the rotational position of the motor output shaft. The drive motor 222 (and encoder if provided) are connected to a motor controller 228 used to control the power, speed and direction of the drive motor 222. In accord with some aspects of the present concepts, a centralized motor controller is provided to control more than one motor. Alternatively, each actuator unit 200 includes its own resident system controller 226 configured to receive sensor inputs and to communicate with the motor controller 228 to control the operation of the drive motor 222 for that actuator unit. The system controller 226 (or optionally centralized motor controller) can include a computer or microprocessor-based system, such as, but not limited to, those based on the PC/104 standard. The drive motor 222 is coupled directly or indirectly (e.g., through a gear train) to the pulley module 224 comprising a pulley wheel 225 engaging the proximal end of the Bowden cable 142.

The pulley module 224 comprises a housing 230 adapted to engage the Bowden cable sheath 144 such that, when the pulley wheel 225 is rotated in a first direction, the Bowden cable 142 wraps around the pulley causing the distal end of the Bowden cable 142 to be retracted into the distal end of Bowden cable sheath 144 and, when the pulley is rotated in a second direction, the Bowden cable is unwound from the pulley, causing the distal end of the Bowden cable 142 to extend from the Bowden cable sheath 144. In at least some embodiments, the pulley 225 is enclosed in the housing 230 such that, when it is rotated in the second direction, the cable 142 is driven out and can apply an extension force.

As noted above, in at least some aspects of the present concepts, a single actuator unit 200 can be used to provide energy to one or more limbs and/or one or more joints. As one example, alternating power transmission to separate limbs may be accomplished via a clutch switching power transmission between the limbs, which takes advantage of the out-of-phase movement of opposing limbs (e.g., the legs are typically out of phase during walking).

The control system 226 is configured to sense or determine the gait of the user and actuate the drive motor 222 to pull on the Bowden cable during specific times of the gait cycle or to actuate another actuation system configured to introduce forces at specific times of the gait cycle (or other movement). Actuating the drive motor 222 at predefined points during the gait cycle can create a predefined tension in the soft exosuit 100 that applies a force about the ankle that aids in walking. One or more sensors worn by the user (e.g., one or more foot switches, one or more joint angle sensors, etc.) are provided to transmit signals to the control system 226 enable the control system 226 to synchronize the motor actuation with the user's gait cycle (or other movement). In accord with various embodiments of the invention, the sensor can take many forms, including sensors that sense the angular position of specific joints. See, for example, commonly owned WO 2013/044226 A2, which is hereby incorporated by reference in its entirety. In accord with some aspects, the sensors comprise a pressure sensor or a simple on/off switch that senses the pressure of the foot during the gait cycle, e.g., a heel-strike.

In accord with other aspects of the present concepts, one or more sensors can take the form of EMG sensors that sense muscle activation at specific locations. The pattern and scale of these activations can either determine gait cycle (pattern) or amount of assistance required (based on scale). Other sensors that detect joint position, relative or absolute, either with respect to ground or respect to a point on the wearer, may be used to determine gait pattern and, therefore, can be used to control actuator activation. Other sensors can include, but are not limited to, hyper elastic strain sensors, accelerometers, inertial measurement units, internal measurement Units (IMU) and/or Goniometer sensors. These sensors, or other sensors, singly or in combination, can detect motion indicative of body position. Depending on the sensor(s) used, heuristics specific to that system are able to be developed to determine when the muscles in the body are applying force to a joint (e.g., such as the ankle, knee, or hip) so that the soft exosuit 100 can, in turn, be configured to apply force at the appropriate time and in proportion to the estimated muscle force. For example, one possible scheme would be to estimate the dynamics of the user's body by estimating velocities of each of the joints and, using an approximate rigid body model of the wearer, estimating torques at each joint, from which appropriate tension to produce resultant, beneficial torques are determined.

An alternate scheme would involve recording EMG measurements and sensors simultaneously in a training phase. After this data is collected, machine learning algorithms are used to predict when the muscles are contracting, as a function of the sensor inputs. Then, in practice, the EMG sensors would not be used, and instead the trained algorithm would predict muscle activation based on the sensors, and apply tension to the soft exosuit when the appropriate muscles would be activated.

Another scheme would involve directly measuring the muscle activation using EMGs, sensors which detect the muscle diameter, or some other means. Then, the soft exosuit 100 could be tensioned in proportion to the activation of certain muscles or combinations of muscles.

In accord with some embodiments of the invention, one or more foot switches are positioned between the foot and sole of the boot to sense heel strikes to provide measurement of the rate of the user's gait cycle. The foot switch or sensor is used to detect the moment when the heel of each foot first hits the ground during the gait cycle, and the control system 226 uses the signal from the foot switch to calculate the gait period. The position of the ankle at any point during the gait cycle can be estimated based on a known ankle position vs. time curve (assuming level ground and a nominal gate). The estimated ankle position can be used to determine when to retract the Bowden cable 142 and tension the soft exosuit 100. The tensioned soft exosuit 100 can provide a moment about the ankle during the toe push-off portion of the gait cycle to supplement the muscle supplied forces and reduce the energy expended by the user.

In some aspects, Velcro® or some other attachment mechanism is used to connect one portion of the soft exosuit 100 to another after being manually pulled to a desired tension. For example, node 1 (see, e.g., FIG. 7) can be connected to the waist belt 110 and to the thigh brace 120 using connecting elements have Velcro® fasteners. For example, in FIG. 16, connecting elements 4 and 5 loop through buckles on the thigh brace 120 at the bottom and then can be pulled upwardly and fastened down upon themselves with Velcro® or other fastening component(s). Alternatively, connecting elements 2 and 3 can each be secured at the waist belt 110 with Velcro® directly, without looping through buckles, or by another fastening member or element. Another option is to use a piece of webbing passing through a feed-through buckle preventing it from backing out after it is tensioned, and manually pulling taut the protruding end of the webbing.

In accord with some aspects, a force sensor is used to continuously measure the tension in each Bowden cable 142. An idler pulley 232 (see, e.g., FIG. 29, 30, 34) is biased against the Bowden cable 142 and a load cell 234 (see, e.g., FIG. 29) can be used to sense the cable 142 tension. These measurements are logged and used to automatically tension the soft exosuit to an appropriate level. In accord with some aspects, the soft exosuit controller(s) (e.g., system controller 226) detects an increase in the tension of the soft exosuit due to natural body motion and applies actuation based on this signal. In one aspect, the soft exosuit controller(s) continuously monitor the force in the exosuit. When the soft exosuit is tensioned to some small amount because of geometric changes in the user's position, the controller(s) can sense that (small) force and actuate the soft exosuit to increase or decrease the tension, as appropriate. For walking, soft exosuit tensioning can be accomplished, for example, by applying a constant offset to the motor position signal from the control system 226 (e.g., PC/104).

In some aspects, the actuator unit 200 is configured to communicate with a local or remote external computer (e.g., a desktop or laptop computer, tablet or a smartphone) over a communication channel, such as Ethernet (e.g. wired or wireless—WiFi), Blue Tooth, I2C, or other open or proprietary communication channel. The external computer can be used, for example, to boot-up the actuator system control program upon first power up, adjust control parameters such as exosuit tension, execute diagnostic checks, transmit software, or even remotely control the actuator unit 200. In at least some aspects, the control system 226 automatically boots on power-up and receives control inputs from switches on the exterior of the actuator unit 200 or on a hand held wired or wireless remote control or electronic device (e.g., smart phone app). In other aspects, the control system operates autonomously based on preprogrammed algorithms that detects or anticipates the intent or actions of the user and applies appropriate assistance.

In at least some aspects, as shown in the example of FIGS. 29-30, the actuator unit 200 is controlled by a Diamond Systems Aurora single board computer 250 in a PC/104 form factor connected to a Diamond Systems MM-32DX-AT analog and digital I/O expansion board. The PC/104 computer 250 can be powered from a 4-cell (14.8-16.8V) Lithium Polymer battery via a Diamond Systems Jupiter power regulation board. Of course, it is expected to utilize improved processors (e.g., faster, smaller, etc.) as well as smaller and lighter batteries and/or batteries with higher power densities as technology improves. FIGS. 29-30 show an example of a pulley module 224 and drive box 223, in accord with one aspect of the present concepts. Tension in the Bowden cable 142 can be sensed with a 50 kg beam-style load cell 234 (Phidgets, product code 3135) mounted against an idler pulley 232 in the pulley module 224. A full bridge strain gauge on the load cell 234 is connected to a signal amplifier 242 (e.g., Futek CSG110) through an electrical interface (e.g., pogo pin). Each amplifier/load cell pair is calibrated by adjusting the output of the amplifier 242 while applying known loads to the load cell 234. The amplifier 242 outputs a DC voltage from 0-10V corresponding to the force on the load cell 234. This voltage is read by an analog input pin of the MM-32DX-AT. The amplifiers 242 can be powered by the PC/104's 14.8V battery via their own on-board power regulators.

In accord with some aspects of the present concepts, the heel strikes can be sensed with foot switches 150 (FIG. 30), such as foot switches from B&L Engineering (product code FSW). The foot switches 150 can be foot-sole-shaped force sensitive resistors. The terminals of the heel portion of each foot switch 150 are connected to ground and a digital input pin of the MM-32DX-AT respectively, as shown in FIG. 31. A 1 kΩ and a 10 kΩ resistor in parallel between each foot switch digital input and a +5V rail can pull the digital pin up. When a heel strike occurs, the resistance between the two terminals of the foot switch 150 drops, the voltage at the digital pin decreases to approximately zero, and the change in state can be read by the MM-32DX-AT I/O board. The foot switch 150 can be wired to a 3.5 mm audio jack, which plugs into a stereo cable and to a corresponding 3.5 mm audio jack in the pulley module 224. The electrical connection to the foot switch 150 can be passed through the pogo pin interface to the PC/104 computer 250. The audio jack permits easy disconnection of the foot switch from the rest of the exosuit, which facilitates donning and doffing of the soft exosuit 100.

FIG. 32 shows the connections to the PC/104 computer 250 and MM-32DX-AT I/O board according to some embodiments of the invention. The PC/104 computer 250 is connected to control switches on the outside of the drive box 223. Power switches are provided for each drive box to break the positive voltage lines of the PC/104 and motor controller batteries. Two momentary toggle switches and a rocker switch provide user input to the control algorithm running on the PC/104 computer 250. The rocker switch can be used to engage the walk mode of the control algorithm and the momentary toggle switches can be used to rotate the left or right motor to tension the soft exosuit prior to walking. These three user interface switches are connected to digital input pins on the MM-32DX-AT with 10 kΩ pull-up resistors and share a common ground with the PC/104. When each switch is activated, the digital input is connected to ground and the pin pulled low. In addition to, or in the alternative to, the box mounted switches, a small hand-held wired or wireless remote (not shown) can be provided. The remote's switches can be connected in parallel with the box's switches and provide duplicate functionality. In addition to, or instead of, the user input switches, other user interface systems can be integrated into the soft exosuit, including voice controls, a touch screen, wearable computer, or a heads-up-display (e.g., Google glasses or wearable display with retinal sensing or other input, such as a wirelessly connected track pad or softkeys).

In accord with some embodiments, the motor 246, motor encoder 248, and motor controller assembly is shown in FIG. 33. Each EC-4pole 30 Maxon motor 246 is connected to a Copley Controls Accelnet Panel ACP motor controller 260. A HEDL 5540 3-channel encoder 248 with 500 counts per turn with RS-422 digital signaling is used for feedback. Each motor controller 260 can be powered, by way of example, by two 4-cell (+14.8-16.8V) lithium polymer batteries in series for a total of +29.6-33.6V. The motor controller 260, in the example shown, supplies the motor with up to +24V. The Accelnet Panel motor controller 260 can accept a DC voltage between −10 and 10V to change the angular orientation of the pulley and tension or slacken the cable 142. A −10V signal can move the pulley one full rotation in the counter-clockwise direction from the starting point upon power up and a +10V signal can rotate the pulley clockwise one full rotation. In accord with some aspects, the negative voltages are not used, since in operation the motor controllers 260 are powered on only when the cables 142 are extended out as far as possible. In software, the control signal can be limited to being positive to prevent damaging the system by running the motors into the physical stops.

The control voltage can be generated from one of the analog out pins of the MM-32DX-AT. To ensure smooth motor operation, the voltage signal is sent through a low pass filter. This filter can include an RC single pole construction with R=68Ω and C=47 µF, and provide a cutoff frequency of 48.9 Hz. The signal can additionally be filtered by the motor controller, which implements a digital filter operating on the analog input.

In accord with some aspects of the present concepts, each pulley module 224 include one or more indicators, such as a blue, green and/or red LED which illuminate to indicate various states of the system status (e.g., green illumination when the pulley module is correctly connected to the drive box 223). The power and ground for the LED(s) can passed through the pogo pin interface from the PC/104's battery. A 1 kΩ resistor can be used to bring the voltage from the battery down to a suitable driving current.

In accord with some aspects of the present concepts, the Bowden cables 142 are grounded via the metal pulley box 224 and drive box 223 shell, which serves as the ground for the circuitry inside. Grounding the Bowden cable 142 advantageously prevents the Bowden cable from acting like an antenna and transmitting electrical noise to the load cells and other components of the system.

In accord with some aspects of the present concepts, the actuator unit 200 uses a 200 W brushless motor 222 (which operates at a reduced duty cycle) to move the pulley 225 and cable 142 through the assistance trajectory. The pulley 225 converts the motors torque and rotational speed to a force and displacement that can be applied through the cable to the ankle (FIG. 34).

The assistance provided by the actuator unit can be limited, for example, by motor supply power, which was 100 W in the soft exosuits under test, but is not a functional limitation. In the tested soft exosuits, the duty cycle of the motor 246 provided up to approximately 200 W for a portion of the cycle, then returning to a low power draw for the remainder of the cycle while maintaining an average power consumption at or below a working 100 W requirement selected for testing (FIG. 35).

In accord with some aspects of the present concepts, the EC-4pole 30 brushless motor 246 by Maxon Motors can be used because it is a high efficiency motor that provides high power to weight ratio and a compact size. Other motors can be used depending on the performance requirements of the system. While a rotary motor was used in various of the above examples, other actuators can also be used including, but not limited to, electro-mechanical actuators (e.g., motors, solenoids, etc.), pneumatic actuators (e.g., pneumatic cylinders, McKibben type actuators, etc.) and hydraulic actuators (e.g., hydraulic cylinders, etc.). In yet other aspects of the present concepts, different types of motors can be utilized (e.g., high torque and low speed) that require no gearhead and consequently provide reduced weight, reduced noise and improved efficiency.

Further, while preceding examples disclose the cable actuator 142 system as comprising a pulley system 224 controlling movement of a Bowden cable, other actuators may advantageously be used with the soft exosuit. By way of example, any actuator capable of shortening the length of a cable or cord connected between two points having a sheath (Bowden cable) or not (Free cable described above) can be used. These actuators could be placed anywhere on or off the person, depending on the movement to be assisted, the context of such motion, contraindications, and the availability of alternative actuation placements. The actuator(s) may be distally located (e.g., in a backpack borne by the user's shoulders) with a proximal end of the actuator power transmissions element (e.g., cable) attached to a suitable location of the soft exosuit system (e.g., footwear attachment element 130) as described above. Alternatively, one or more actuator(s) may be disposed in between anchor points, connection elements and/or nodes, or over a portion of the length between terminal ends of the cable. Examples of other types of actuators can include one or more pneumatic or hydraulic linear actuators, pneumatic of hydraulic rotary actuators, ball or lead screw actuators, belt or cable driven actuators.

In accord with other aspects of the present concepts, actuators which reduce the length between the terminal ends are used and include one or more semi-passive actuators, such as a magnetic or mechanical clutch. These actuators would engage at a point in the gait where the length between points is shorter then when assistance should be given (e.g., when the knee is bent). In conjunction with a retractable length of cable such that it has a minimum level of tension, the clutch would lock the length at shorter state such that when the leg naturally extended, force would be generated due to the stretch in the soft exosuit and cable. This would be classified as a semi-passive system and would be expected to require a lower energy level than active systems.

In accord with the other aspects of the present concepts, various mechanisms can be used to adjust the tension in the soft exosuit. In some embodiments, the same mechanism that actuates the soft exosuit can also be used to adjust the tension in the exosuit. In other embodiments, a separate mechanism can be used to tension the soft exosuit, singly or together with an actuator. The soft exosuit can be actively shortened using an actuator which reduces the length between two points on the suit. One mechanism that could accomplish this is a motor pulling on a Bowden cable, the sheath of which is connected to one point on the soft exosuit and the center of which is connected to a different point on the suit. This can be accomplished using, mechanical pneumatic, hydraulic, or other actuators.

Of course, as previously noted, the tension may be adjusted manually at one or more points by physical adjustments to the relative positions of the connection elements, anchor points, and nodes (e.g., adjusting straps using buckles and/or Velcro®, tensioning a drawstring, wire or cable and locking it in place, etc.). As another example, the wearer could pull on a webbing strap passing through a locking buckle, which secures the webbing strap after release. In another example, the wearer could pull on a piece of webbing (e.g., a connection element) and secure the webbing with Velcro® to a part of the suit.

The wearer could also pull on or otherwise tension a cable passing through a ratchet mechanism (e.g., a rotary ratchet mechanism, such as made by made by Boa Technology Inc., disposed on the waist belt 110) or lockable spool configured to secure the cable in place at a set tension. The ratchet mechanism or spool it attached to one end of a Bowden cable (e.g., at a top of the cable where the ratchet mechanism is hip mounted), the other end of which was connected to two locations on the soft exosuit to reduce the distance between them, with interacting elements (e.g., pawl element, ratchet element) providing releasable securement. The wearer could also advance a ratcheting mechanism by rotating a central hub around which a cable is wrapped, or could tension the soft exosuit with a screw mechanism that is then locked into the final position. Tension can be released by pushing a button to release the interacting elements of the ratchet mechanism (e.g., to move a lever away from ratchet gear teeth). The ratchet mechanism or spool can either be turned manually (to tension or de-tension) by the soft exosuit wearer or by an actuator, for example a geared motor. Even where a soft exosuit is not being actuated as an assistive system, the soft exosuit may still be worn in a tensioned mode. In various configurations, the ratchet mechanism can be located at the wearer's waist or hip (so as to facilitate adjustment while walking or running), near the ankle, or potentially elsewhere on or about the wearer's torso.

In accord with some embodiments, a mechanism to tension the soft exosuit can include a screw element. In one aspect, a carriage element is connected to an end of a Bowden cable and is configured to move up and down by means of a threaded portion in which a screw element is disposed. A support structure holds the carriage element in place relative to the cable sheath, and a top portion of the screw is exposed to the user to permit rotation of the screw. Rotation of the screw causes a linear movement of the carriage and the attached Bowden cable end, thereby increasing or decreasing, respectively, a tension in the soft exosuit. An optional locking element in provided to minimize the potential for loosening of the setting. In one aspect, the screw could be controlled by a small motor or other actuator to turn the thread, in which case no locking element would be needed.

As previously noted, the soft exosuit can optionally be actively tensioned (e.g., cable shortened or lengthened) is accord with a program as the user of the soft exosuit moves. Alternatively, in other aspects, the soft exosuit is automatically tensioned using one or more actuators, and maintained at one or more set tension(s) (e.g., a fixed value, a fixed range of values, different values or ranges of values for different portions of movement, a nominal average value, a nominal peak value, etc.), the set point(s) of which could be adjusted by the user. In this respect, the system is configured to sense the tension in the soft exosuit to provide appropriate inputs for the controller controlling the tension.

With all of these mechanisms, the soft exosuit can be made to be loose-fitting on the wearer by releasing these tensioning mechanisms, such as to facilitate doffing of the soft exosuit. Such tensioning (or detensioning) devices permit a user, for example, to retain a first level of tension between certain points on the soft exosuit and a second level of tension (higher or lower than the first tension). The soft exosuit advantageously comprises multiple tensioning mechanisms capable of operating simultaneously.

During the gait cycle, the motor(s) 246 can operate over a range of torques and speeds to achieve the desired cable 142 trajectory. Since higher motor efficiencies occur at high speeds and low torques, some embodiments of the invention can select a combination that includes a motor with a pulley and gearbox that keeps the motor operating as close to maximum efficiency as possible during the gait cycle.

In accord with some embodiments, the Maxon EC-4pole 30 has a nominal continuous speed of 15,900 RPM. However, for this embodiment, the motor is limited by the max speed of the encoder: 12,000 RPM. An alternative encoder (MR, Type ML, 500 CPT, 3 Channels, with Line Driver Maxon #225778) can be used in the actuator system would increase the maximum motor speed.

In accord with some embodiments of the present concepts, a better motor for this system would have a lower nominal continuous speed for higher torques. A lower operating speed would reduce the number of necessary stages in the gearbox and would result in a higher overall efficiency.

In accord with some embodiments of the present concepts, the pulley 225 and gearbox 244 convert the motor's fast rotation into cable 142 lengthening and shortening movements of the pulley wheel 225. The pulley wheel 225 and the gearbox 244 together determine the maximum cable travel and the maximum cable speed for given load states. The pulley wheel 225 diameter and the gear reduction can be determined by working backwards from the minimum cable travel needed and the maximum cable speed required to meet the biomechanics and exosuit stiffness needs. The total amount of assistance was driven by these two limits, as well as the power budget.

In accord with some embodiments of the present concepts, the pulley wheel 225 can be a single wrap design, while in other embodiments, the pulley can be a multiple wrap design. With a single wrap design, the pulley wheel 225 circumference cannot be less than the cable travel distance. In accord with some embodiments, the cable travel can be based on the soft exosuit 100 architecture and biomechanics of walking of the user. In accord with some embodiments, the cable travel can include three lengths: cable pull length, exosuit tension length, and a margin of safety to prevent bottoming out. In accord with some embodiments, the cable travel was given a significant safety length due to uncertainty in design parameters and user variability. The cable pull length and the cable tension length were measured from the soft exosuit and previous actuator system with participants ranging in height from 5'8" to 6'5". The three lengths and calculated pulley diameter can be seen in Table 4.

TABLE 4

| | | |
|---|---|---|
| Cable pull length (Lp) | 8 cm | Length needed to assist foot given the lever arm to the back of the boot + the soft exosuit stiffness |
| Cable tension length (Lt) | 5 cm | Length needed to tension the soft exosuit prior to walking. Takes up slack in the system due to wearer differences |
| Cable safety length (Ls) | 7 cm | Length needed at the end of travel to prevent bottoming and to accommodate various sized people or added pull length |
| Total Length (Lcirc) | 20 cm | |
| Pulley diameter | 70 mm | Distance over circumference multiplied by working revolutions |

In accord with some embodiments of the present concepts, the use of a single wrap pulley resulted in a usable angle of 340° (0.94 revs). The selected pulley diameter of approximately 70 mm provided appropriate cable length. In general, a larger pulley and a larger bend radius provide less wear and reduced cable stress.

In accord with some embodiments of the present concepts, the gearbox 244 is chosen to meet the maximum speed required during cable pull and release when assisting the ankle. As seen in FIG. 36, the cable displacement for maximum assisting case can be treated as a triangle operating over the active portion of the cycle. The leading line is the commanded motor position signal in units of centimeters and the following line is the resultant motor position as measured by the CME-2 motor controller software scope. A positive displacement corresponds to a retraction of the cable and the delay between signal command and motor movement stems from acceleration limit of the motor controller.

As seen in Table 5, which shows gear reduction calculations in accord with at least some aspects of the present concepts, the maximum cable speed was found to be 37 cm/sec for the given pulley diameter (70 mm) and maximum motor speed. From the maximum cable speed, the necessary gear reduction was found to be 107:1 and a gearbox with a reduction of 111:1 was selected.

TABLE 5

| Variable | Value |
|---|---|
| Gait Cycle (T) | 1 sec |
| Duty cycle ($p_1$-$p_2$) | 40% to 83% |
| Length of pull and release over duty cycle (Lp) | 8 cm |
| Maximum cable speed ($V_{cable}$) | $1Lp/T(p_2 - p_1) = 37$ cm/s |
| Pulley diameter (D) | 7 cm |
| Max motor speed limit | 12000 RPM |
| Gear reduction (R:1) | $R = (M_{speed}/60)/(V_{cable}/L_{circ}) = 107$ |
| Selected gearbox reduction | Closest gear reduction is 111:1 |

It is desirable for the motor to operate within its speed-torque curve and that forces applied during high speed pulls do not exceed the motor's limits to preserve the life of the motor.

In accord with some embodiments of the present concepts, a Bowden cable is utilized that includes an inextensible cable translating inside an inextensible sheath. The Bowden cable 142 transmits forces from the actuator unit 200 to the ankle (via forces transmitted to a footwear connection element 130). The Bowden cable sheath 144 is attached to the soft exosuit and actuator unit 200 and the cable 142 is anchored to the footwear connection element 130 (FIGS. 21-22). In other embodiments, webbing or cables can be routed through guides in the fabric.

In accord with some embodiments of the present concepts, many types of Bowden Cables can be used in the system. In addition to standard Bowden cables, non-standard and similar operating cables, such as Nokon® brand cables can be used.

The Nokon® cables can provide increased efficiency over traditional Bowden cables. The more efficient cables enable more power to be delivered to the ankle per a given input power. This can provide an advantage for a system with a limited power budget. The wound wire cable in the Nokon® system is 1.5 mm in diameter and has a maximum tensile strength of 2200 N.

FIG. 37 shows the end fittings on the Bowden cable 144. These ferrule end fittings 146 can integrate with both the actuator unit 200 and the soft exosuit. A T-connector can be created which interfaces with the soft exosuit through sewn in loops at the calf straps and the boot attachment. In other embodiments, an alternative to the T-connector can be a VELCRO® attachment, a buckle. In some embodiments, the T-connector can be removed and a continuous webbing with adjustable slider used in its place. Ferrules on the ends of the cable can both engage the pulley and secure the cable to the lower T-connector. These ferrules can also act as mechanical fuses, coming off the cable when a predefined force (e.g., 600-650 N) is applied to the T-connector—thus providing a safety feature that limits the force that the system can apply to the user. At the proximal end, the Nokon® cable can include an extended aluminum housing which can be fitted into a hole on the pulley module and can be secured by a set screw. Other end fittings for the Bowden cable can include, for example, a button tab. In some embodiments, a rivet or grommet can be provided in the webbing, which allows the cable to pass thru while restraining the outer sheath. In some embodiments, a compression fitting clamps the outer sheath to webbing.

In accord with some embodiments of the present concepts, the current system tension in the cable can be input to the control system for data logging and pre-tensioning the soft exosuit prior to walking. Sensing tension in the cable can also be used in a gait control algorithm. The pulley module's load cell can be mounted to a small idler wheel which deflects the cable by a small angle as it passes from outside the box to the pulley. In general, the force required to deflect the cable for an 8° cable angle increases linearly with the tension in the cable, as shown by reference numeral 167 in FIG. 38. The general range of system tension in the current embodiments of the pulley system 224 are represented by the operational envelope 166, showing a load cell force of approximately 150 N and a cable tension of about 500 N. A 50 kg beam load cell can be used along with an 8° bend angle to measure the full range to cable tensions possible with the system. Reference numeral 168 represents the cable breaking strength.

In accord with alternative embodiments of the present concepts, FIGS. 39-40 show the differences between a series mounted and parallel mounted force sensor and a hybrid combination. The deflecting idler wheel 232 geometry can be used instead of an inline force sensor setup (see series force sensor 275 in FIG. 39 and FIG. 40) because the idler wheel does not limit the cable travel. However, the inline-series sensor 275 can provide direct measurement of force and can be placed at or near the ankle, which would remove measurement error due to friction in the Bowden cables 142. Another embodiment is to have a force sensor (e.g., 275) located at the distal end of the Bowden cable sheath 144 attached to the Bowden cable sheath and the connection element. This would allow for unlimited cable travel and a superior measurement due to the distal location of the sensor.

In accord with some embodiments of the present concepts, a B&L Engineering foot switch can be mounted in the boot and provides the right sensitivity for an average adult person (foot switches may optionally be optimized for a user's weight or operational weight ranges). When not compressed, the foot switch has a nominal resistance of a few hundred mega-ohms, creating an effective closed circuit. The resistance drops down to 14Ω during heel strike (around 300 lbs. of force), a value much less than the 909Ω pull-up resistance (1 kΩ in parallel with 10 kΩ), which pulls the PC/104 digital pin low. The 1 kΩ resistor was added in parallel with the 10 kΩ resistor to minimize on/off toggling during transitional motions, such as when the heel strikes and when the heel is lifted up.

As configured in the tested configurations of soft exosuits, a Diamond Systems Aurora PC/104 computer 250 having a 1.6 GHz Intel Atom CPU, 2 GB of RAM was used and booted MS-DOS with a real-time kernel from a 4 GB SSD disk. The MS-DOS installation can be configured to launch an xPC Target binary executable on startup. The xPC Target application waits for a connection from the host computer, receives a compiled program from MATLAB/Simulink on the host computer, and executes the program. The Aurora PC/104 can be paired with a Diamond Systems MM-32DX-AT I/O expansion board to provide 32 analog inputs, 4 analog outputs, and 24 digital pins assignable as inputs or outputs. In accord with some embodiments of the present concepts, the PC/104 xPC Target combination provided a useful amount of processing power and flexibility. The PC/104 has a desktop CPU capable of 48.2 FLOPS and 2 GB of RAM, and control algorithms can be developed for use in the invention without worrying about speed or memory. The small size and low power consumption make the PC/104 suitable for use in a portable system. In accord with some embodiments of the present concepts, the Copley Controls Accelnet Panel ACP motor controller is a high performance controller capable of velocity control and position control. It has numerous command inputs (RS232 serial, CAN, PWM, analog voltage). The Copley Controls software allows basic auto-tuning and calculations of controller gains.

In accord with some embodiments of the present concepts, a Futek CSG110 was used as a general purpose amplifier for the full bridge strain gauges. The Futek CSG110 has DIP switches for setting excitation voltage and the mV/V sensor range as well as rotary potentiometers for calibrating the zero point and span of the DC voltage output to each particular load cell. The Futek CSG110 amplifier allows the load cells to be interfaced with the PC/104.

In accord with some embodiments of the present concepts five batteries are used to power this system. Four Gens Ace 14.8V 4S1P 5000 mAh 40C lithium polymer batteries are used to power the motor controllers and motors, two per drive box (one drive box per limb). Each pair of batteries is wired in series in order to supply the motor controller with 29.6V DC. The fifth battery is a lithium polymer Gens Ace 14.8V 2S1P 4000 mAh 25C that is used to power the PC/104 computer, both Futek amplifiers, pulley module LED's, and a cooling fan in each drive box. The PC/104 battery can share a common ground with the motor controller battery pairs and every component in the system. Batteries in accord with some embodiments of the invention could be an attachment to the system. These batteries could be contained in a housing with a terminal connector contacting at least 2 electrical connector blades capable of carrying greater than 200 W. These blades could interface with mating connector inside the motor hosing to form a power connection capable of powering the motors. The battery housing and motor housing could have mating retaining features such as latches to secure the housings making a quick release interchangeable system.

Lithium polymer batteries were selected because they provide acceptable performance in this application. Lithium polymer chemical construction provides one of the highest energy storage to weight ratios and is more robust and safer than lithium ion. In other embodiments of the invention, the soft exosuit may include energy harvest elements (e.g. from sun, wind, natural body motion, body heat, vibration, inductive coupling with a charging station, corded Li battery charging port, etc.) to reduce the overall battery size required to power the suit.

In accord with some embodiments of the present concepts, the pulley module shown in FIG. 29 can be made of the five parts. The pulley housing 230 can provide the mechanical structure to support the pulley module 224 and comprises a pulley housing (e.g., aluminum) having an inner shell (e.g., Delrin) and an outer shell (e.g., Delrin). The pulley housing 230 resists loads created by the pulley on the Bowden cable, provides additional support to the motor shaft, aligns and attaches the pulley system to the drive box, optionally includes a window that allows visual inspection and movement of the pulley system, optionally includes a guide slot or channel that retains cable in an enclosure to allow push and pull cable actuation, optionally provides a stop to prevent over-rotation or backwards rotation of the pulley, optionally attaches to the drive box by two screws that allows for "quick release" removal of the pulley module sub system, and provides secondary bearing surface for the pulley when pulley module is detached from drive box. The primary bearing surface is provided by the motor shaft, and when the pulley module is detached from the drive box, the pulley flanges can be supported by mating housing surfaces. In another example, a bearing can be centrally located under the pulley cable groove to reduce moment forces perpendicular to the axis of rotation. This centrally located bearing would be fixed to the pulley housing via a cantilevered surface. This configuration allows for minimal side force to act on the motor bearings. Additionally, the pulley module could use latches to secure it to the motor housing and provide a quick release mechanism.

The pulley wheel 225 guides the cable 142 and can include some or all of the following additional features: 1) number/color markings to give absolution position in the view window for trouble-shooting purposes, 2) weight reducing webbing to provide a light weight design to reduce pulley inertia, 3) ferrule capture screws to keep the cable in place during push and pull actuation, 4) a stop pin to interact with the pulley housing to limit pulley travel.

In accord with some embodiments of the present concepts, the motor mount, while considered part of the pulley module, can be located in the drive box and provide locating and fastening points for the pulley module to be secured to the motor in place on the drive box.

In accord with some embodiments of the present concepts, the control scheme can include the process of deciding how to move the motors based on the input from the sensors. The control scheme can be implemented in the code that runs on the PC/104 embedded computer. In accord with some embodiments, the control scheme can be written in Simulink blocks and MATLAB code. Simulink blocks for the MM-32DX-AT analog expansion board can handle input and output (e.g., I/O). One Simulink block can be used to read values for all the sensors and another Simulink block can be used to send the position values to the motor controllers. Additional Simulink blocks can be used to capture data and save it to the PC/104's disk or send it to a host computer for saving or debugging. The bulk of the processing can be accomplished by a MATLAB script embedded in a Simulink block. This MATLAB script can use the foot switch states, user interface buttons, and the current time step to calculate the desired motor positions. In accord with some embodiments of the invention, the Simulink block diagram can run at a fixed time step of 0.001 seconds (1 millisecond) on the PC/104.

In accord with some embodiments of the present concepts, the motor 246 outputs for each leg can be calculated from a trapezoidal trajectory, generated prior to runtime. This trajectory has a unit width and a variable peak height corresponding to the level of actuation desired (e.g., a pulse with a 4 cm amplitude, a pulse with a 6 cm amplitude). The cadence of the user's gait can be calculated from the timing between multiple heel strikes. In particular, the gait period can be recorded for a predefined number of steps, for example, the previous 20 steps, and the average taken. A twenty step moving average proved sufficient for a low pass filter. This average gait period can be used to scale the trapezoidal trajectory across one full gait cycle for each leg. Each leg can be treated independently and the waveform for each leg can be calculated independently. In some embodiments, both legs can be treated the same and the same calculated waveform can be used for each leg.

Upon heel strike, the control scheme can use a look-up table to generate the required motor pull. The flat trajectory from 0-40% of the Gait Cycle (GC) acts as a delay, keeping the soft exosuit slack as the foot is planted on the ground and the user's hip pivots into position above the foot. Starting at 40%, the motor pulls the cable in and tensions the soft exosuit to the maximum level at 62.5% GC when toe off occurs. After a period of holding, the motor then unwinds the cable back down to zero at 83% GC and resets for a new cycle.

The trajectory can be limited by the physical performance of the motor 246, gearbox 244, and Bowden cable 142. The downward slope of the trajectory can be bound by the maximum slew rate of the motor. Additionally, the motor controller can limit the maximum acceleration of the motor to 2500 rotations/sec2 and the maximum velocity of the motor to 11500 rpm, effectively rounding the sharp corners of the trapezoidal trajectory and shifting it slightly (~3%) to the right. Finally, this trajectory can be generated based on ankle position vs. time charts that begin when the heel first touches the ground. The foot switches used in this system require a significant amount of pressure to trigger and thus a heel strike is not sensed until the heel is on the ground and the user's weight has begun to load the foot. This occurs at somewhere between 2-6% in the nominal gait cycle, most likely 2-3%.

In accord with some embodiments of the present concepts, the user interface switches are provided on the outside of the drive box 223, on a handheld remote, or via a wireless device, to modify the way the control scheme functions. When the walk switch is disengaged, the control scheme can optionally continue to run, but does not output pulse signals after heel strikes. Each tension toggles adds or subtracts an offset to the motor positions looked up from the trapezoidal trajectory. The offset grows in magnitude depending on how long a tension toggle is held down.

In accord with some embodiments of the present concepts, the value of the force sensors can be data logged and used to adjust the magnitude of the trapezoidal trajectory, but not used to calculate the desired motor positions. In accord with some embodiments of the invention, the force sensors can be incorporated in a feedback loop to follow a desired force trajectory throughout the gait cycle instead of desired motor position.

In accord with some aspects of the present concepts, a direct line cable can be used instead of a Bowden cable. A direct line cable can include a free cable from the actuator to the point of action. This will create a force in line with the cable between the two end points. In accord with other aspects of the present concepts, a multi-point cable system is used. For example, a multi-point cable system can include a free cable from the actuator 120 that passes through angle transition points along the path to the distal end and transfers forces and displacements along its length through some or all of the transition points including the end. Moments about each joint between the ends of the cable depends on their location with respect to the transition points of the free cable. The cable or webbing can be configured to slide with respect to the transition points and the wearer, unlike the Bowden cables where the cable is shielded until exiting the end. A multi-point cable and/or direct cable can include one or more of a wire or filament rope, webbing, such as the soft exosuit material, an elastic element (e.g., rubber) or any other flexible force transmission element.

In accord with some embodiments of the present concepts, the Bowden cable 142 system can be replaced by a solenoid or other type of actuator disposed remotely (e.g., in a user-borne backpack) or locally (e.g., on an assisted limb, such as a thigh-based actuator used to add energy to the knee or ankle or a gastrocnemius-based actuator to add energy to the ankle, etc.). In accord with some embodiments, a hydraulic piston transducer can be used. In this embodiment, a linear piston could replace the lower portion of the Bowden cable and can be connected via hydraulic tubing to a source of hydraulic pressure and flow. The transducer would include a cylinder and a piston that would reduce its length to actuate the exosuit. In an alternative embodiment, a pneumatic transducer, such as a McKibbon actuator, could be replace the lower portion of the Bowden cable and be connected via pneumatic tubing to a source of air pressure and flow. The transducer could include a cylinder and piston or an inflatable bladder which would reduce its length when inflated.

The cable actuator described includes a motor driven a pulley system which connects to a Bowden cable. Other actuators could be used in place of the motor. Alternative actuators can include actuators or motors which can be used to shorten the length of a cable or cord connected between two points having a sheath (Bowden cable) or not having a sheath (e.g., free cable). These actuators could be placed at the proximal end as described or in some cases over a portion of the length between the terminal ends of the cable. These actuators can include one or more pneumatic or hydraulic linear actuators, pneumatic of hydraulic rotary actuators, ball or lead screw actuators, and belt or cable driven actuators.

In accord with some embodiments of the present concepts, Textile based force sensors can be used to measure linear displacement of woven fabric webbing between two points A and B. This linear displacement measurement can be combined with the properties (e.g., elastic properties) of the woven substrate to a calculated force measurement. The force can be measured along the collinear line formed by points A and B and terminating at the end points of that line where fabric meets other connectors. Woven webbing generally provides a strong durable fabric typically made in ribbon form (e.g., length, width, and thickness). Applying force linearly along the length of the fabric causes a stretch (strain) in the fabric. This stretch has been measured and is relatively consistent such that a force applied to the fabric will result in a specific strain measurement. Using this property the textile based force sensor can calculate the force based on the measured strain. In order for this to work properly the sensor must be able to measure strains in about the 0.05-5% range as well as have a very low stiffness. The need for the 0.05-5% range is based on material properties of webbing. The need for the low stiffness is so that the force sensor will not contribute significantly to the webbing stiffness.

In accord with some embodiments of the present concepts, the textile based force sensor can be used to aid in control of one or more exosuit actuators. The force measurement combined with actuator position measurements and force displacement profiles can be used by the control system to detect motion and provide feedback. It also aids in determine correct position of suit elements (via a stiffness measurement)

In accord with some embodiments of the invention, textile based force sensor can be used for recoding of forces in the soft exosuit elements during any activities, to aid in development by measuring forces in specific areas of the soft exosuit, to detect injury by measuring joint angles, and to detect joint angles either for control or data analysis.

In accord with some embodiments of the present concepts, the sensors can be placed at various locations on the soft exosuit. In one aspect, a surface based sensor is adhered to or attached to a connection element (e.g., woven webbing fabric) or other element at two points along a length of the connection element or other element. In another aspect, a full surface sensor is adhered to or attached to a connection element (e.g., woven webbing fabric) or other element at two points over an area of the connection element or other element. In another aspect, a pocket is formed in or woven in (for a woven material) a connection element or other element and a sensor is placed in the pocket (the material properties of the pocket would need to be used when calculating force). In yet other aspects, a sensor is constructed into the webbing directly. In still other aspects, the connection element or other element bearing one or more sensor elements (of any type) is a layered material or a composite material and the sensor(s) are disposed internally between layers of the layered or composite material.

In accord with some embodiments of the present concepts, sensors which measure linear displacement can be used in the system. Preferably, the sensor can be capable of measuring strains in the range of about 0.05-5% for current webbing. Traditional strain sensors with a medium strain range generally include those with a strain range 0%-10%. Other sensors include hyper elastic sensors with a large strain range (e.g., liquid metal such as disclosed in WO 2013/044226 A2, which is hereby incorporated by reference in its entirety). Alternatively, traditional strain sensors with low strain range can be used by making the area where strain sensor is attached very stiff to lower the webbing strain.

FIGS. 41A-41B shows alternative embodiments of the present concepts wherein actuators 200 apply forces to both sides of the hip joint (FIG. 41A) or to the ankle (FIG. 41B). The actuators could be any device that causes the two ends of the blocks, shown at the front and rear of the thigh in FIG. 41A, to move together. The actuators could include, for example, a Bowden cable connected across the space, a pneumatic actuator controlled by a hose, or by an electromagnetic actuator having a displaceable plunger.

In accord with some embodiments of the present concepts, actuation can be provided at the hip joint to assist with motion and, in particular, walking, running and jumping. Also, as the hip joint is close to the torso, force can be transferred directly from a torso-mounted actuator to the hip joint itself. This can be accomplished by pulling on the hip with a tensile element such as a cable, piece of webbing, ribbon, etc. With no sheath required for this tensile element, the friction will be very low and thus the efficiency of the system high. One benefit of the hip joint being located close to the torso is that donning and doffing the soft exosuit is readily accomplished. The actuator, located on a backpack or fanny pack structure on top of the user's clothing, and the tensile elements can remain outside the body and secured to the thigh with a brace that is also outside the clothing and thus provide for a low-profile device that is easy to attach to and remove from the thigh.

The soft exosuit 100, in accord with at least some of the present concepts, comprises an actuator unit with a length of webbing, strapping, cable, or another other means of applying tensile forces (called the "ribbon" henceforth) extending from it and attaching to the hip. In operation, the actuator unit 120 can retract the ribbon to create forces causing the hip to extend, and extend the ribbon causing the ribbon to slacken.

As discussed herein, the actuator unit 120 can be attached to a person such as by a waist belt or a backpack. Other components could be used to secure the actuator relative to the user (e.g., on the posterior side, anterior side, or distributed about both the posterior and anterior sides). In accord with some embodiments of the invention, the actuator can be attachment by two screws which can be found on both sides of the device and which gives the option to attach the unit facing in either direction—the ribbon can either extend from the device close to the person or with some offset from the person. The device could also be mounted further up on the user's back, with the ribbon running parallel to the back for some distance. In some aspects, the ribbon extending from the actuator unit 120 can wrap or extend around the user's gluteal region to cross the hip. The lower end of the ribbon can attach to a brace around the thigh, which could potentially extend around the knee and all the way down to the ankle for increased support in some embodiments.

When the actuator unit 120 retracts the ribbon, the ribbon will tend to push into the gluteal region if the hip is flexed due to the change in angle of the ribbon. To prevent discomfort from this configuration, several solutions are possible. One is to have the ribbon offset from the body to some extent at the actuator end, such as is shown in the left, center of the above figure.

This will increase the hip angle that can be reached before the ribbon pushes into the gluteus. Another option is to have a wide ribbon (e.g., 2"), to minimize pressures on the wearer. A low-friction material also may be worn on the gluteal region to reduce friction and increase comfort of the ribbon moving against the body. A sheath may also be used over a large length of the ribbon, i.e. a Bowden cable could be used, to protect the body from motion of the ribbon. An alternate means of reducing pressures on the body is to offset the distal end of the ribbon at the thigh attachment. This could be accomplished with rigid or semi-rigid components attached to the thigh brace, which may extend backward as a "spur" to provide an offset for the ribbon connection point from the thigh. For example, in one embodiment of a hip attachment system, a piece of fabric can be secured around the thigh with VELCRO® in the front. The actuator can attach to this thigh brace with a 2" wide ribbon, and the top of this ribbon can be pulled upward. The thigh brace is restricted from moving up the user's leg due to the conical shape of the thigh. Also due to the conical shape, there is little to prevent the thigh brace from moving downward, and so it can have a tendency to slip down the leg if there is no tension on the ribbon pulling it upward. The thigh brace can be held upward by other elements connected it to a waist belt, or by other means.

In some aspects, an actuator unit 120 ribbon (webbing, cable, etc.) extends down over the gluteal region of the user and connects directly or indirectly to a soft element that engages the thigh (e.g., thigh brace). In one aspect, a rigid or semi-rigid spur can be used to create an offset from the back of the thigh. In one example, a semi-rigid element is connected at the back of the thigh and, as force is applied via the ribbon to the bottom of the semi-rigid element, it bends outwardly from the thigh, thus increasing the offset (and moment) from the thigh. This could be useful for creating a low-profile suit that collapses against the body when not in use, and creating a larger moment arm when large forces are needed. At intermediate forces, the moment arm could be in an intermediate position. Many other configurations of elements, each having different amounts of stiffness can be used in a single system, including various arrangements of soft, flexible, rigid, and semi-rigid elements. Springs and other elastic elements can also be included as elements of the system for regenerative purposes.

In accord with one or more embodiments of the present concepts, the actuator unit 120 comprises a motor driven drive pulley adapted to engage and wind the ribbon in response to control signals from a control system. The drive motor can be connected to the drive pulley using a transmission. The transmission can include a timing belt and timing gears or a set of gears that transfer power from the drive motor to the drive pulley. In alternative embodiments, a drive shaft and one or more gears or timing pulleys can also be used to connect the drive motor to the drive pulley to wind and unwind the ribbon at a predefined rate to provide motion assistance. The actuator can also include an idler pulley that engages the ribbon and measures the force applied on the idler. The force signal, for example, provided by one or more strain gauges, can be transmitted to an actuator controller to control actuation of the ribbon. Additional sensors can be provided on the hip or other joints of the user to detect motion and control the actuator to provide assistance. For example, flexion of hip can be an indication that the user is starting to move.

In accord with some embodiments of the present concepts, a control system can be provided for one or both legs to control the actuator and receive signals from sensor to detect motion and adjust the actuator forces to coordinate them to the motion, as described above.

Figure 42A:
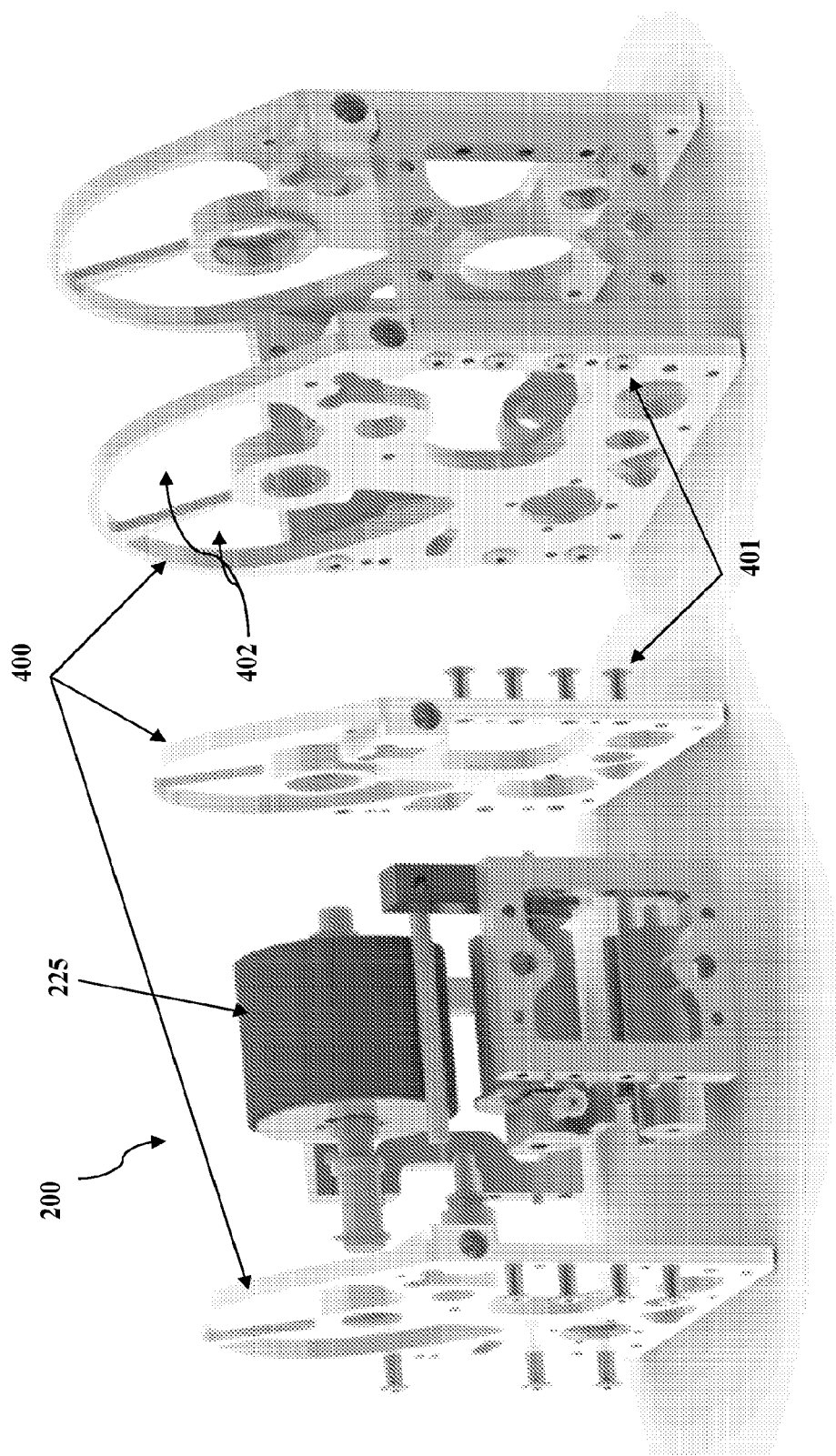
Figure 42B:
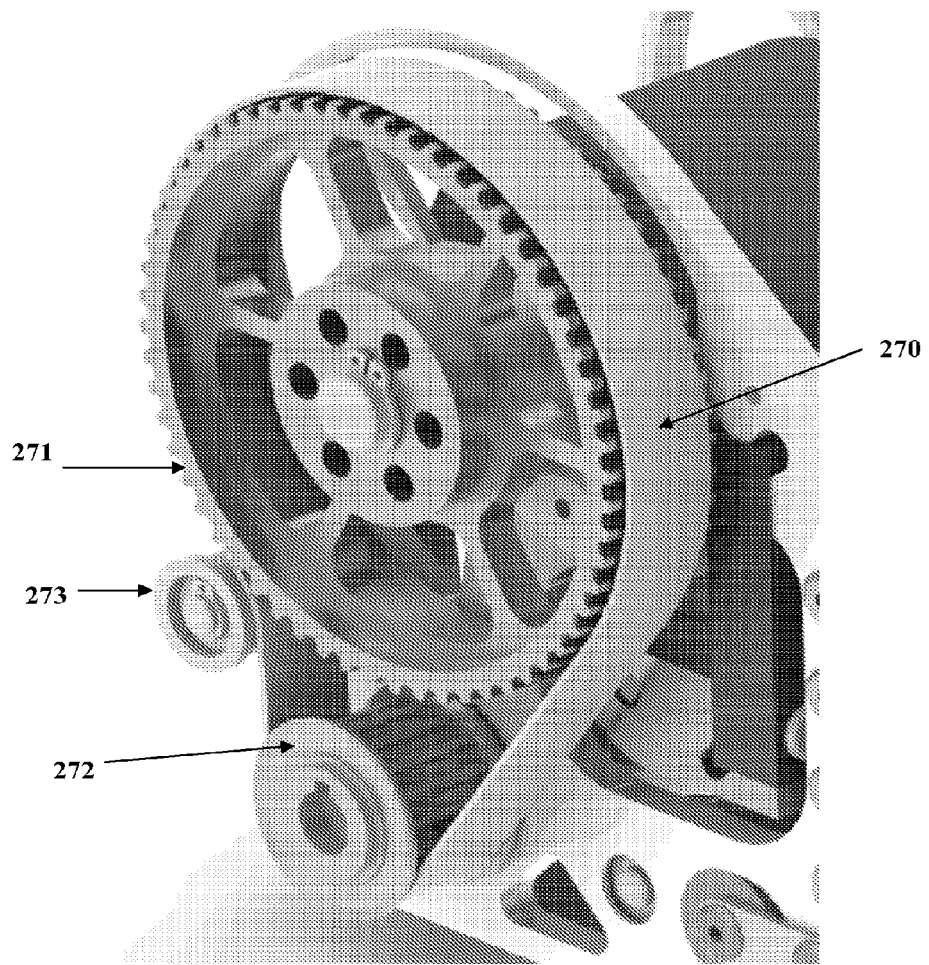
Figure 42C:
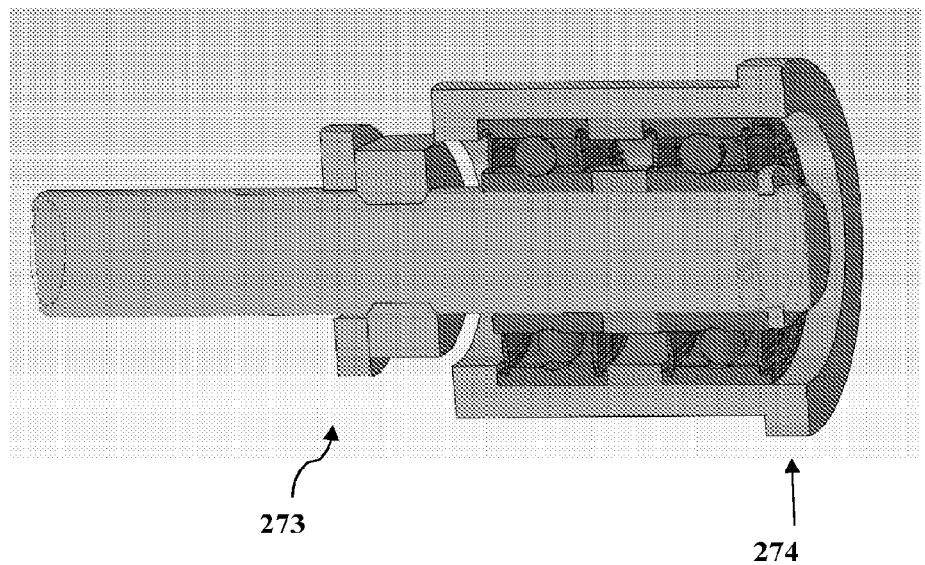
Figure 42D:
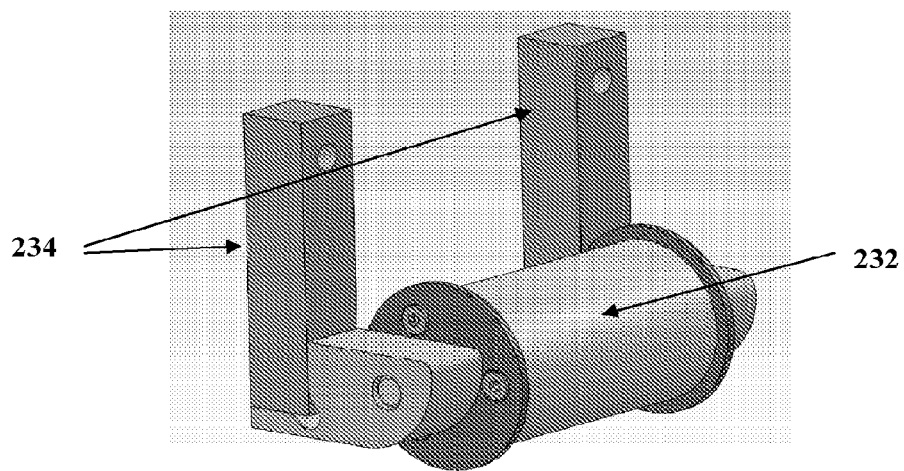

In accord with one embodiment of the present concepts, constructed as a lightweight, small and quickly-built prototype, shown in FIG. 42A, all system components are mounted between and/or on two aluminum side plates 400, the alignment of which is realized by dowel pins. The side plates 400 comprise cutouts 402 to lighten the entire system and/or provide access to specific parts of the system. In the example shown, an actuator 200 uses a pulley 235 adapted to drive a 2" webbing to transmit force to the back of a user's thigh to apply a moment about a person's hip; other similarly configured examples could utilize webbing of different width if desired. The use of a wide ribbon instead of a Bowden cable, shown in prior embodiments and examples, allows the material to contact the user's body without cutting or incising. However, narrower webbing sizes or cables could be advantageously used in combination with reinforced fabric, elements (e.g., padding, Delrin, etc.) or guides to similarly reduce the ability of the webbing to chafe, cut or incise.

The hip system will tend to touch the gluteal region especially when a person does motions like squatting or climbing stairs. The ribbon travel is about 200 mm (8"), which facilitates activities such as squatting. By using wide webbing and a spool the ribbon can be wound up for multiple turns of the spool without the need for additional guiding features. For winding up a round cable the spool needs to have additional grooves and probably some kind of feeder to locate the cable within the grooves. Furthermore, Bowden cable losses are higher compared to the losses experienced when using a ribbon. The main disadvantage of having wide webbing is that it may fold back on itself since the hip has three degrees of freedom. To prevent folding, flanges can be attached to the pulley which guides the ribbon.

Initial measurements of the hip speed revealed that linear speeds of about 0.325 m/s are needed to actuate the hip at its maximum speed during walking, jogging, jumping, and squatting. This linear speed is due to the angular velocity of the hip joint in combination with the offset of the tensile element around the gluteus muscles, a distance of around 8 cm. The system uses a motor gear box with a 23:1 gear ratio and a timing belt with a 3.333:1 transmission ratio. So, the overall gear ratio is about 77:1. The spool diameter also has a significant influence on the ribbon speed and therefore enables the system to be used flexible concerning ribbon speeds.

One challenge in designing a compact system is to find the best position of motor 246, gearbox 244 and encoder 248 that will not unduly restrict movements of the wearer. The assembly of these parts has a length about 150 mm. In some aspects, spur gears or bevel gears can be used to attach the drive unit in a 90° angle. The timing belt 270 (see FIGS. 42B, 43A) provides a high flexibility with respect to positioning of the drive unit 223 (FIG. 30). The timing belt 270 allows a flexible adaption of the system transmission by changing the diameter of the timing pulleys without changing the position of the drive unit 223. Using spur gears or bevel gears would set the unit on a fixed position which cannot be easily changed. In at least some aspects, the timing belt 270 design comprises two timing pulleys 271, 272 and an idler 273 which applies pre-tension to the system. The maximum belt force is about 300N, which is consistent with the allowed force on the gearbox shaft.

Figure 42E:
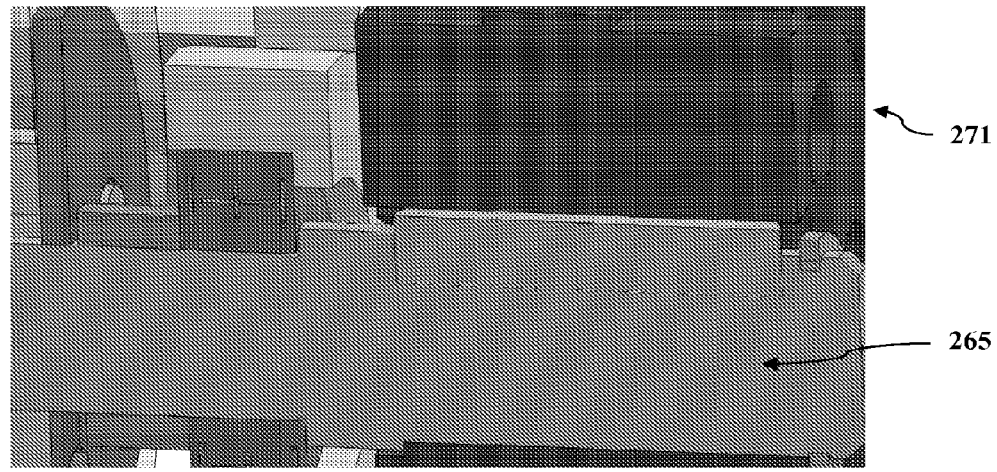
Figure 42F:
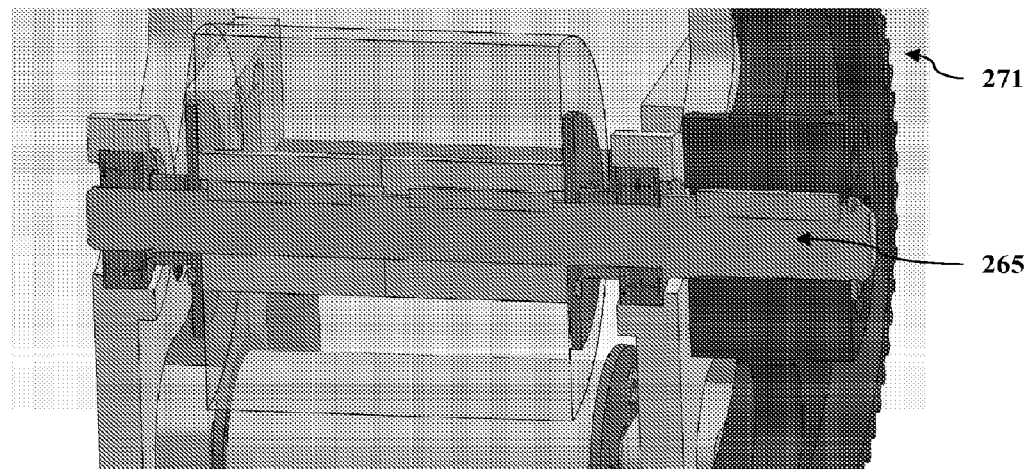
Figure 42G:
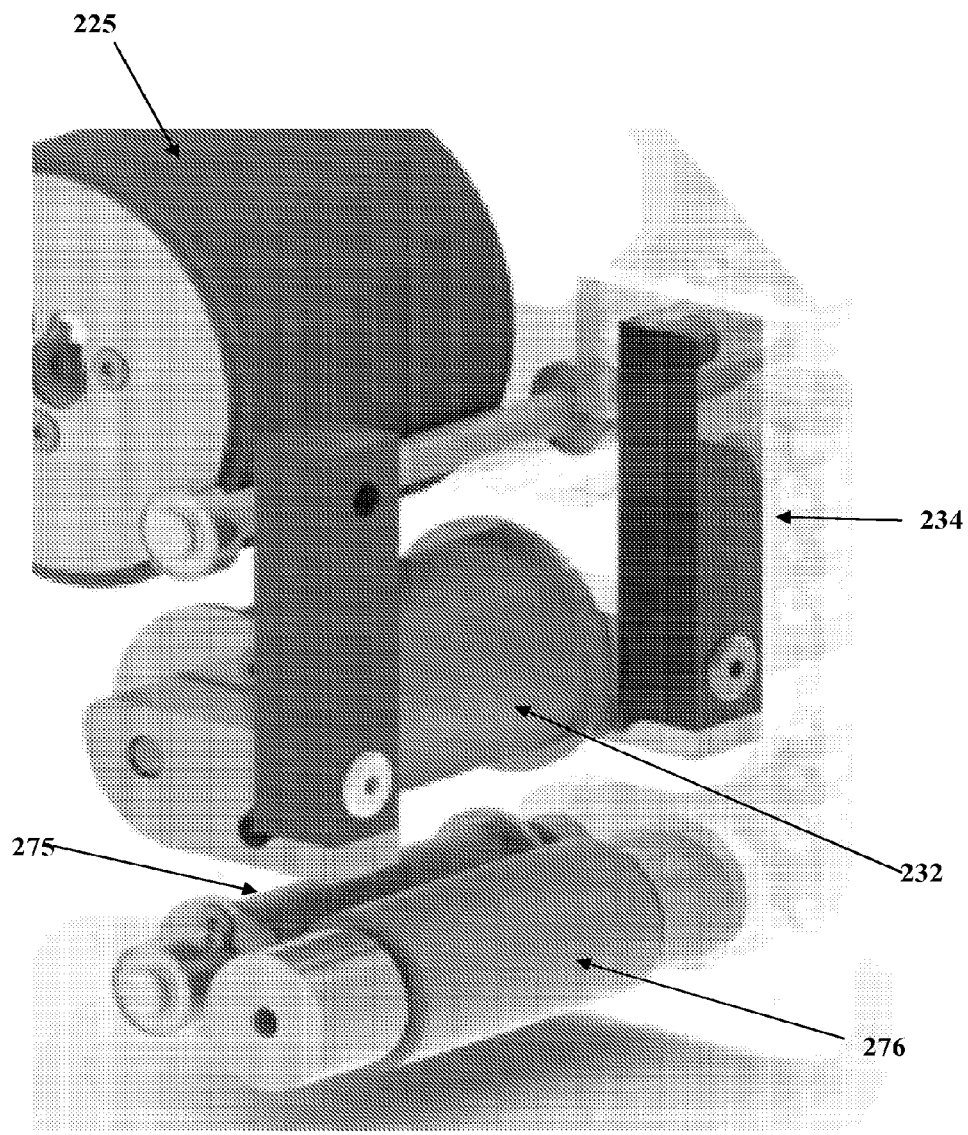

As shown in FIG. 42F, the drive shaft 265, an off-the-shelf Misumi part, has a 12 mm diameter on the shorter end (left) and a 10 mm diameter on the longer end (right), selected to fit the 12 mm minimal inner diameter for the selected timing pulley 271. In addition, the flange 274 of the pre-tensioning idler 273, shown in FIGS. 42B-42C, should prevent the belt 270 from slipping down. The large timing pulley 271 comprises an optional skeletonized structure to advantageously reduce the weight of the part. As shown in FIG. 42E, the pre-tensioner consists of a shaft and two bearing that are secured by a retaining ring.

As shown in the example of FIG. 43B, several idlers 232 and 275-276 are used to guide the wide webbing used in some aspects of the present concepts. To measure forces within the system two load cells 234 are used. When force is applied to the ribbon the two load cells 234 are pulled in a direction which causes a capacity change in the load cells proportional to the applied forces. In order to assure that the ribbon always has the same angle along the force measuring idler 232 one or more additional idlers (e.g., 275-276) are used. In some aspects, the angle to measure forces is about 13°. As depicted in FIG. 43B, the mechanism controls movement of the ribbon (not shown) and also keeps the angle to the force sensor constant.

The actuator described here could be implemented a number of different ways. It could include a ratcheting spool and clutch, to permit the spool to retract freely but resist extension except when unlocked by the clutch. This could provide a very low-power solution, in which the actuator merely resists further extension and any forces applied to the body are those stored from previous motion of the body. This mechanism could also include a spring in series with the ribbon to permit energy storage and energy return.

Alternately, the actuator could include a mechanism powered by a tensioning spring that acts to continuously retract the webbing with a light force. In conjunction with a back-drivable actuator or ratcheting mechanism, this could permit the ribbon to track the motion of the hip continuously without needing to use the actuator. Then, the actuator could apply forces to the ribbon when needed.

A ratcheting mechanism could be used to connect the spool to the motor because the motor only applies forces that pull in one direction on the ribbon. This could be used in combination with a light tensioning spring that was winding up the spool. If the motor turned in one direction, it could engage the ratchet mechanism and transfer torques to the spool. If the hip was moved in extension so fast that the actuator could not keep up with the motion, the ratchet mechanism would permit the spool to move faster than the motor and continue winding up the ribbon. If the hip was flexed, then the motor could rotate a small distance to disengage the ratchet, at which point the hip would be free to move without the motor resisting its motion. Alternately, a small clutch mechanism could be used to engage or disengage the motor from the spool.

FIGS. 44A-44C show, respectively, front, back and side views of a soft exosuit (V3.2) in accord with at least some aspects of the present concepts. Connection element 1 connects the two sides of the waist belt together, which secures the anchor points and keeps the soft exosuit from sagging when downward forces are applied to it. Connection element 2 maintains tension between the waist belt and thigh brace. Its location at the side of the thigh allows it to maintain a constant tension throughout the stance phase. Connection element 3 constrains node 1 in the downward and medial direction. Connection element 4 acts to balance the forces at the thigh brace by counteracting tension from Connection element 7 and, further, allows the suit to be pre-tensioned by putting a vertical force on the thigh brace. Connection element 5 also constrains node 1 in the downward vertical and lateral directions. Connection element 6 was added to increase the tension across the front of the thigh. Connection element 7 applies an upward force on the inside of the thigh brace in order to even out the upward forces applied to the thigh brace. Calf connection elements 8-9 are attached in front of the knee so that the tension created during actuation creates beneficial moments around the knee.

FIGS. 45A-45D show, respectively, front, back and side views of a soft exosuit (V4) in accord with at least some aspects of the present concepts. In relation to FIGS. 44A-44C, connection elements 4 and 6 were added to constrain node 2 in the downward vertical and lateral directions, connection elements 8-9 were added to replace the connection elements on the front of the thigh (to allow for better force distribution that reduced the amount of rotation of the thigh brace), and connection element 10 was added to increase the adjustability of the calf strap placement. Connection element 12 is attached to the bottom of connection element 10 at a slight angle. Connection element 10 is then aligned and fastened between the thigh brace layers so that connection element 12 is placed correctly with respect to the center of rotation of the knee. The geometry of connection elements 4 and 6 were found to create a very high stiffness path between node 2 and the pelvis, resulting in node 2 deflecting very little under high loads. Connection elements 8-9 were also found to distribute the load effectively and evenly between node 2 and the thigh brace, eliminating thigh brace rotation.

FIGS. 46A-46B shows front view and rear view pictures, respectively, of an example of a soft exosuit worn by a user in accord with at least some aspects of the present concepts.

FIG. 47 presents a comparison of statistics showing evolution of initial embodiments of soft exosuits in accord with at least some aspects of the present concepts. In the first version (V1) of the soft exosuit 100, the maximum walking speed was 1.25 m/s (2.8 mph), with a total power draw of 59.2 W, a battery duration of 4.1 hours (2.5 kg of batteries), a maximum output force of 150 N, and a stiffness at 100 N of 3500 N/m.

In the second version (V2) of the soft exosuit, the maximum walking speed was 1.5 m/s (3.4 mph), with a total power draw of 59.2W, a battery duration of 4.1 hours (2.5 kg of batteries), a maximum output force of 200 N, and a stiffness at 100N of 4000 N/m. In the third version (V3) of the soft exosuit, the maximum walking speed was 2.0 m/s (4.5 mph), with a total power draw of 50 W, a battery duration of 5.5 hours (2.5 kg of batteries), a maximum output force of 270 N, and a stiffness at 100 N of 5000 N/m. These improvements in performance were also accompanied by a decrease in the overall weight of the soft exosuit 100 (exosuit, actuators, electronics, batteries, etc.), as is shown in FIGS. 48A-48B, which show a bar chart depicting a decrease in weight of soft exosuits from soft exosuit V1 (12.2 kg), to soft exosuit V2 (10.00 kg), and to soft exosuit V3 (6.53 kg).

FIGS. 49A-49E show kinematic results for the soft exosuit 100 shown in FIGS. 46A-46B. FIG. 49A shows right ankle angle as a function of percentage of gait cycle (upper left), FIG. 49B shows right knee angle as a function of percentage of gait cycle (upper right), and FIG. 49C shows right hip angle as a function of percentage of gait cycle (lower left). In each of these graphs, a first plot 301 shows the respective kinematic angles when the soft exosuit 100 is in a "slack" non-actuated condition during movement and a second plot 302 shows the respective kinematic angles when the soft exosuit 100 is actuated during movement at a level of a 150 N assisting force applied to a footwear connection element 130. Significantly, the close correspondence in the kinematic angles for each of the joints as between the slack condition and the actuated condition demonstrates that the operation of the soft exosuit 100 does not markedly or negatively impact gait. Likewise, FIG. 50 shows a force versus time curve for ankle actuation performance for the soft exosuit 100 shown in FIGS. 46A-46B. The data was recorded while the subject was walking at 1.25 m/s, with a local peak force of up to 300 N represented in graph 302 (actuated), as compared to the forces when the soft exosuit 100 is in a "slack" non-actuated condition during movement (graph 301). Again, graphs 301, 302 in FIG. 50 show a close correspondence as between the slack condition and the actuated condition of the soft exosuit 100.

FIG. 51 shows metabolic results for different subjects, under similar test conditions, utilizing the soft exosuit 100 shown in FIGS. 46A-46B and represented in FIGS. 49-50. For subject 1, subject 1 expended 710 W of energy during movement while wearing the soft exosuit 100 in a "slack" non-actuated condition, but expended only 611 W of energy during similar movement while wearing the soft exosuit 100 and wherein the ankle was activated during movement, for a reduction of expended energy of 99 W (a 14% reduction in expended energy). Subject 2 expended 530 W of energy during movement while wearing the soft exosuit 100 in a "slack" non-actuated condition, but expended only 460 W of energy during similar movement while wearing the soft exosuit 100 and wherein the ankle was activated during movement, for a reduction of expended energy of 70 W (a 13% reduction in expended energy). Similar, but lesser, benefits were realized by subjects 3-5. Based on this sample, the average reduction of expended energy was 53 W, a 9% reduction in expended energy.

FIG. 52A shows a biological metabolic power pie chart indicating that, a total joint active power at a walking speed of 1.25 m/s comprises a 46% contribution from the ankle, a 40% contribution from the hip, and a 14% contribution from the knee. The soft exosuit 100 metabolic benefit, in testing thus far, has shown a metabolic benefit (reduction in expended energy) of up to 12% at the hip and 14% at the ankle, as shown in FIG. 52B.

FIG. 53 shows evolution of soft exosuit 100 stiffness between different versions of soft exosuits (v3-v7) in accord with various aspects of the present concepts. The subject wore a number of different versions of soft exosuit 100 including V3, V3.1, V3.2 (see FIGS. 44A-44C), V5 (see, e.g., FIGS. 14A-14B, FIGS. 46A-46B) and V7 (see FIGS. 54A-54E$_3$). Through the evolution of the disclosed soft exosuit 100 from V3 to V7, the resultant stiffness of the soft exosuit 100 increased markedly and nonlinearly.

FIG. 54A-54E$_3$ shows aspects of a soft exosuit (V7) in accord with at least some aspects of the present concepts. In each of FIG. 54A-54$_3$, the following reference numbers are used: (1) connection elements, such as webbing or strapping material; (2) an inextensible fabric; (3) 1" webbing connected to top of waist portion of the suit for securing around the wearer's waist; (4) routing pockets for cable and calf strap webbing; (5) cable (e.g., Bowden cable); (6) spandex base material; and (7) slideable part of Bowden cable connection to the soft exosuit. Overall, the soft exosuit 100 of FIGS. 54A-54E$_3$ comprises two legging portions 400 and a waist attachment 3 that encircles the waist. The waist attachment 3 is similar to the waist belts 110 described previously (see, e.g., FIG. 13) in that it is adjustable (e.g., at the back, side or front) and has webbing strengthening the fabric in higher stress areas.

In one aspect, a first piece of webbing for the waist attachment extends from the top of the iliac crest on each side of the leg and crosses over to the opposite leg and a second piece of webbing extends around the hip on the same side. A 1" belt is provided in or the waist attachment 3 (optionally secured by sewing, straps, loops, snaps or other means of securement), allowing the suit to be secured around the waist (e.g., loosely secured while the rest of the soft exosuit is tightened, snugly secured during use, etc.). In one embodiment, a fly-type opening is provided on the front of the suit (e.g., in the center or offset from the center), where the two sides can be readily, but securely connected (e.g., via Velcro®, zipper, buttons, etc.) or separated. A Velcro®-based fly-type opening permits the soft exosuit 100 to be better adapted to fit a variety of physiologies. The entire waist portion is constructed of a largely inextensible fabric, strengthened with Velcro®. Foam inserts are desirably positioned over the iliac crest regions of the pelvis to provide additional padding for comfort.

The waist attachment 3 connects to the legging portions 400 through a large patch of VELCRO®, as shown in FIG. 54C$_4$, which can be compared to FIG. 54C$_4$, wherein the same section of the left leg 2 is connected by the large patch 2 of VELCRO®. This patch of VELCRO® is on top of a large patch of inextensible fabric 2 on the front of the thigh. The rest of the legging portions are constructed of a stretchy spandex material 6. This construction prevents the front of the thigh from stretching when loads are applied to the suit. The wide fabric area distributes loads across the thigh, minimizing displacement and pressure. This wide fabric area is held closely against the thigh with the spandex around the back of the suit. The spandex should be stretched and pull the inextensible fabric tightly against the thigh to prevent it moving during soft exosuit operation.

Also attached to the VELCRO® on the front of the thigh are two connection elements (e.g., straps) that extend from the front of the thigh through the knee and to the back of the calf (similar to connection elements 107 shown in FIGS. 14A-14B). A bottom portion of these connection elements are shown as reference numeral 1 FIGS. 54E$_1$-54E$_3$. These connection elements pass through spandex pockets on the sides of the soft exosuit, which extend from just above the knee to the base of the calf. The spandex at the base of the pocket between the connection elements and the skin helps prevent chafing and rubbing from the connection elements on the skin. The spandex on the top of the pocket enclosing the connection elements is to keep the connection elements lying flat against the leg, which can increase stiffness, and prevent the connection elements from being a snag hazard. The VEL-CRO® attachment at the front of the thigh permits the effective length of the connection element to be changed so the suit is adjustable for different heights of wearer, as well as tensioning the suit to the appropriate level. This adjustment could be accomplished by strapping and buckles, lacing, or any other means.

In another configuration, instead of having the connection elements 1 of FIGS. 54A-54E$_3$ slide within a pocket, they could be sewn into the garment to make inextensible portions of the fabric. Thus in general, the soft exosuit 100 would comprise a spandex under-layer with regions of inextensible fabric sewn in to create paths where the soft exosuit would not stretch and would transfer force. Alternatively, the soft exosuit could comprise a spandex fabric with regions reinforced with inextensible fibers woven into the fabric.

In general, the leggings 400 could be combined into a single pant structure, which would consist of the two leggings sewn together into a traditional pants shape by adding spandex at the top, which would cover the wearer's posterior and groin region. This pant structure would go under the waist attachment structure.

On top of or adjacent to the pocket that contains the connection elements 1 going to the back of the calf, a second pocket is sewn which contains the Bowden cable going down to the back of the calf, as shown in FIGS. 54E$_1$-54E$_3$.

A connection element utilized in the spandex pocket may comprise, for example, a webbing strap that is 2" wide at the top and bottom, in order to provide a large surface area against the calf and to minimize strain, and 1" wide in a mid-section, which corresponds to a location of the knee. This configuration is presently accomplished by sewing together different widths of webbing, but such structure could alternatively be achieved by creating a custom-woven piece of webbing. The webbing tapers to 1" wide around the knee to prevent the webbing from bulging outward a large amount when the knee is bent, such as occurs during the swing phase of walking. If the strap were 2" wide all the way down, the webbing would bulge out more than 1 cm at times which can rub against the opposite leg during walking.

As shown in FIGS. 54E$_1$-54E$_3$, the Bowden cable 5 attaches to the connection elements 1 extending down the side of the leg through a sliding attachment. The connection elements loop through a metal slide (webbing buckle) after going down one side of the leg and before extending back up the leg. This permits the length of the connection elements on the right side and left side to equalize when forces are applied to the cable. With this sliding mechanism, the Bowden cable 5 will move along the connection elements 1 until it reaches the position of least energy, which will tend to be in the center of the calf, since the end of the inner cable 5 is secured at the back of the heel.

FIGS. 55A-55B show aspects of a soft exosuit 100 in accord with at least some aspects of the present concepts. The soft exosuit 100 of FIGS. 55A-55B provides appropriate assistance to hip flexion and extension by using Bowden cable actuation to create a parallel force to accompany hip flexion and extension and is similar in concept to the embodiment shown in FIG. 41A. In this aspect of the present concepts, the soft exosuit comprises a waist belt (1), thigh braces (2) which hold the distal end of anchor points for Bowden cable, and connection elements (e.g., webbing straps) (3), which form the proximal end of anchor points for Bowden cable, and two stretchable side connection elements (e.g., webbing straps) (4) on the side of the legs for holding the positions of thigh braces from dropping. The anchor points on the front side of the leg for hip flexion are labeled as points 5 and 7 in FIGS. 55A-55B and the anchor points for hip extension are labeled as points 6 and 8 on the back side of the leg. The proximal anchor points 5, 6, for hip flexion and extension, respectively, are right above the hip joint, while the distal anchor points 7, 8 are on the top side of the thigh braces 2, which are also in the same sagittal plane with 5 and 6, respectively.

Each of FIG. 55A and FIG. 55B also show, adjacent thereto, detail figures showing the Bowden cable 142 and load cell 425 attachments. The Bowden cable sheath 144 is connected to the proximal end anchor points 5, 6, and the inner cable 142 with the load cell 425 in between is attached to the distal end anchor points 7, 8 on the thigh brace 120. To assist the hip joint, the soft exosuit 100 creates a contracting force by actuating the Bowden cable 142 to bring those anchor points 5-8 closer to each other, thus creating an upward parallel force with the hip flexor and extensors, respectively. Because the anchor points are several centimeters away from the hip rotation center, the contraction of the Bowden cable 142 creates hip flexion and extension torques. By implementing the actuation of the Bowden cable 142 at the right timing, torque created by the soft exosuit synchronize with the hip muscles to help with wearer's propulsion and swing during walking (or running), thus decreasing the wearer's energy expenditure and improving metabolic power.

The thigh brace 2 shown in FIGS. 55A-55B comprises, in at least some aspects, a low-stretch cotton or other low-stretch material that wraps around the thigh and is secured with Velcro®. Four low-stretch polyester webbings are warped outside the low-stretch cotton to form the two distal anchor points for the Bowden cable 142 and distribute the tension force around the thigh brace 2 when the suit is actuated. Sewn into, or otherwise integrated with, the low-stretch cotton are four straps of 2" polyester webbing. When assisting with hip extension, these two straps originate in the top of the posterior of the thigh strap, wrap diagonally around to the anterior where the two cross, and then wrap back to the posterior where they are secured on top of one another using Velcro®. Stretchable side webbing straps 4 are 1" wide, 18" long stretchable cotton with Velcro® on both ends and connect the waist belt 1 and the thigh brace 2 in order to keep the thigh brace in position when the suit is not actuated.

FIGS. 56A-56B show aspects of a waist belt 110 for a soft exosuit in accord with at least some aspects of the present concepts. The waist belt 110 comprises, in the example shown, a back pad 9, two side pads 10, and two diagonal connection elements (e.g., straps, webbing) 11. The waist belt 110 was designed to distribute the force from the Bowden Cables 142 (not shown in FIGS. 56A-56B) through the diagonal straps, to the iliac crests, and around the waist. When the Bowden cable 142 is actuated, the downward force on the waist belt 110 starts at the diagonal connection elements 11 right above the hip joint. Owing to this configuration, the normal force created by the tension on the Bowden cable 142 will not add up extra torque to affect the desired flexion or extension assistance and the downward forces are distributed around the 4" inch wide waist belt 110.

FIG. 57 shows aspects of another waist belt 110 (V5) for a soft exosuit in accord with at least some aspects of the present concepts. In FIG. 57, labels show components that transfer force from the right leg to the pelvis. In this version, for each leg, one connection element 5 (e.g., webbing strap) crosses the front of the pelvis to attach to the opposite side of the pelvis, and one connection element 2 (e.g., webbing strap) wraps around the side of the pelvis on the same side as the leg. Connection element 5 terminates on the top of the iliac crest of the pelvis. Connection element 2 wraps around the hip below the iliac crest. Both connection elements 2, 5 then connect to a wide waist belt 110 which goes behind the person and sits on the small of their back and pelvis in the back (see also reference numerals 9,10,11 in FIG. 58C, which has a similar construction in the back). This configuration permits high forces to be transferred to the waist because the top of the pelvis (where the cross-strap terminates) acts as a ledge which resists downward and sideways forces (see inset photo). On the same-side, the hip is stiff which resists the inward forces caused by the strap wrapping around the side of the hip. The downward force of the strap is resisted by the small of the back and back of pelvis.

In yet other aspects, another system of connection elements that will displace less under the same force can be achieved by the topology shown in FIGS. 58A-58F, which has the same component numbering as FIG. 57. FIGS. 58A-58F shows aspects of yet another waist belt (V5) for a soft exosuit and shows a waist belt attachment to apply forces to the right leg, with FIGS. 58A-58C showing components of the waist belt and FIGS. 58D-58F showing how the waist belt is positioned relative to the iliac crest of the pelvis, which is shown by the arcs drawn on the photos. In FIGS. 58A-58B, in addition to connection elements (e.g., webbing straps) 2 and 5, connection element 1 and 4, which form a V-shape, are added, as is connection element 6 which connects connection element 1 and 4 to connection element 2 and 5. Connection element 1 goes above the iliac crest on the same side of the pelvis as that which the load is applied (the right side, as shown). Connection element 4 goes above the iliac crest on the opposite side of the pelvis. The junction of connection element 1 and connection element 4 then is connected to the junction of connection elements 2 and 5 via connection element 6. In this configuration, connection elements 1 and 4 support some load, but connection element 1 will slip over the side of the iliac crest under high forces. However, in conjunction with connection elements 2 and 5, this can be used to increase the maximum force able to be applied to the pelvis, or can increase the stiffness of the attachment to the body (measured by pulling down on the bottom of connection element 6 and recording the applied force vs. resulting displacement of that point).

To achieve ideal load-sharing between these connection elements, the tension should be set in connection elements 1, 2, 4, 5 and 6 so they are all approximately equal. Alternatively, because connection elements 2 and 5 take more force than connection elements 1 and 4, the tension in connection elements 2 and 5 can have higher tension than 1 and 4, or connection element 6 can be made to have lower tension such that connection elements 2 and 5 need to displace slightly to draw taut.

Also in FIG. 58A, the gap between connection elements 1 and 2 is labeled as reference numeral "3". The bulk of the iliac crest protrudes in this gap. It is covered by a Spandex stretch material which connects connection elements 1 and 2, although this can be left uncovered with no fabric as well. The material is resilient (e.g., permitting connection elements 1 and 2 to move relative to each other in the vertical direction) so that downward motion of connection element 2 does not pull connection element 1 over the edge of the iliac crest. FIG. 58B also shows a waist belt 7 connected in the front by a buckle 8. The waist belt 7 is useful for pulling the connection elements snugly against the iliac crest, and holding the entire structure up while the connection elements are tightened.

In general, fabric that stretches less than about 20%, ideally with stretch less than about 5%, can be used in place of any of the connection elements in these and other figures.

FIGS. 59A-59D shows aspects of yet another waist belt 110 (V7.1) for a soft exosuit in accord with at least some aspects of the present concepts. FIG. 59 shows a waist belt attachment utilizing fabric as a compliant element to balance forces within the waist belt, with the top row showing components of the waist belt and the bottom row showing how the waist belt is positioned relative to the iliac crest of the pelvis, which is shown by the arcs drawn on the photos. In the example of FIGS. 59A-59D, the reference numerals used refer broadly to the same components as in FIGS. 57-58F. Here, connection elements 2 and 5 are similar to the connection elements in the FIGS. 57-58F, connecting above the iliac crest on the opposite side of the body and below the iliac crest on the same side of the body as that which forces are applied downward to the waist belt. Now, connection elements 1, 4, and 6 have been replaced by a fabric, which covers the front of the pelvis with more surface area than the webbing did in FIGS. 58A-58B. Also, the fabric is more extensible than the connection element material.

In this example of FIGS. 59A-59D, the fabric stretched 5% under a load of 300 N when loaded parallel to the fibers, and the connection element material (2" wide seatbelt webbing) stretched 0.2% under a load of 300 N. So, when loads are applied downward to the bottom of element 6, the connection elements 2 and 5 will displace less for a given load than the fabric 1 and 4. This means that the force supported by elements 1 and 4 will be less than the force supported by the connection elements 2 and 5, due to their relative higher compliance. This permits the suit to be adjusted easily, so it lies flat on the wearer's front when they are standing vertically, and the forces will be distributed between the two sections automatically. In general, the construction of the waist belt could be comprised entirely of the same type of fabric, at the cost of being harder to adjust properly for a snug fit.

Element 3 of FIG. 59A comprises a spandex fabric. There is no waist belt in this embodiment because the fabric adequately covers the top part of the abdomen and secures the waist belt to the pelvis. A waist belt could optionally be added. In general, additional elements could be used, in addition to the elements (connection elements and fabric) shown in FIGS. 59A-59D. It would be possible to place connection elements or fabric to connect to below the iliac crest on the opposite side of the pelvis. For example, after connection element 5 crosses the midline of the person, it could split like a "Y" into two segments, one of which goes over the iliac crest and one of which goes below it.

In the example of FIGS. 59A-59D, the waist belt is constructed so that the waist belt principles can be maintained for each leg separately. This permits high stiffness, since fasteners connecting two pieces of fabric will likely introduce compliance or hysteresis. It is to be noted that, in any of the aspects of the soft exosuit disclosed herein, the soft exosuit may be advantageously configured to have hysteresis. This may be useful, for example, because the actuator 200 can move to apply forces when pulling on the suit (e.g. during 40-50% of the gait cycle), which may require fast motions, and then can move more slowly to go back to the original position later (e.g. during 60-80% of the gait cycle).

As to donning of the waist belt of FIGS. 59A-59D, FIGS. 61A-61D is illustrative. The left two images in FIG. 61 are the part of the soft exosuit that sits over the right thigh, and the right two images are the part of the soft exosuit that sits over the left thigh. In each case the images show the side of the suit that faces away from the person when they are wearing it. To don the soft exosuit, first the part of the suit which supports downward forces over the right thigh is connected. A connection element 2 is placed through a slide (webbing buckle) at the end of connection element 4, which extends from the left side of the body over the left iliac crest. Connection element 2 is then secured back on itself with VELCRO®. Next, the part of the soft exosuit which supports forces on the left leg is connected. Connection element 3 is placed through the slide on the end of connection element 1, which extends from the right side of the body over the right iliac crest. Connection element 3 is then doubled back on itself and secured with VELCRO®. In this manner, the waist belt structures which support the right leg are underneath the waist belt structures which support the left leg, and they are not connected to each other in the middle (although they could be to further secure the waist attachment). Following the attachment of the device around the waist, it is further tensioned using connection element 7 and VELCRO® 8 on the left side of the body, and a similar strap and VELCRO® attachment on the right side of the body. Connection element 7 in FIGS. 61A-61D corresponds to connection element 2 in FIGS. 59A-59D.

FIG. 60 shows aspects of the waist belt (V7.1) of FIGS. 59A-59D and shows the grain directions of the fabric. The directions shown by the double-headed arrows are the directions in which those pieces of fabric are relatively inextensible. Seams connect these pieces of fabric to provide force transfer through the desired path. This alignment of grain directions has been determined to provide the highest stiffness. In general, woven fabrics have warp and weft directions, which are the principal axes when the fabric is mounted on the loom. Woven fabrics tend to be relatively inextensible along these axes, and relatively extensible along a set of axes rotated 45° from the warp and weft axes. As such, to create high stiffness in the waist belt fabric, the fabric is sewn as shown, wherein three pieces of fabric are oriented in different directions so their axes of lowest stretch (indicated by the arrows) are oriented in line with the force paths the fabric pieces will sustain. Seams can optionally be taped to provide additional lines of low-stretch material.

FIG. 62 depicts aspects of a soft exosuit in accord with at least some aspects of the present concepts configured for actuation of multiple joints. In the left image, an actuator 200 is shown having a pulley 224 configured to actuate multiple sets of Bowden cables 142 to separate provide assistive forces to different joints (e.g., ankle, hip). In the right image, the soft exosuit is shown to integrate sensors 350 for measuring joint kinematics. Exemplary sensors are disclosed in WO 2013/044226 A2, WO 2012/103073 A2, WO 2012/050938 A2, and U.S. Pat. No. 8,316,719 B2, each of which is hereby incorporated by reference in their entirety. Further, any of the aspects of the present concepts may further integrate other actively controlled materials such as, but not limited to, those disclosed in WO 2011/008934 A2 or WO 2013/033669 A2, each of which is hereby incorporated by reference in their entirety. By way of example, soft exosuits in accord with any of the disclosed aspects may comprise hyperelastic strain sensors located, by way of example, at any one or more of the ankle, knee and hip (i.e., attached to both sides of each respective joint), to measure human biological joint rotations in the saggital plane. The resulting soft exosuit is very lightweight, cost-effective and easy to don and doff.

FIGS. 63A-63B show examples of a soft exosuit in accord with at least some aspects of the present concepts configured for actuation of multiple joints. This soft exosuit is formed from a combination of elastic and inextensible fabrics or material capable of applying forces across joints in the lower limbs. Forces in the illustrated example are created by contracting a cable with a first end fixed to the suit above the joint and a second end fixed below the joint. As described herein, the contracting cable (e.g., a Bowden cable) would transmit forces through the soft exosuit's inextensible members to the various anchor points to carry the loading. So configured, the soft exosuit allows for multiple joints to be acted upon simultaneously in a beneficial way using a multi-pulley and a drive box, described below. Advantageously, the soft exosuit comprises a sensor system which can measure joint angle of the one or more joints and, desirably, three joints (hip, knee, ankle). The sensors can include, but are not limited to, the sensors noted above in relation to FIG. 62 and include any sensor(s) or the same type, or of different types, that can measure joint angle.

Although the examples of FIGS. 62 and 63A-63B relates to the legs, wherein the activity of interest is walking or running, the present concepts include motions other than walking or running, and limbs other than the legs (e.g., the arms). Correspondingly, a multi-pulley and a drive box could also (i.e., in addition to the above), or alternatively (separately from the above), provide assistance for arm movements.

FIG. 64A-64B show an example of a multi-pulley for a soft exosuit 100 configured for actuation of multiple joints in accord with at least some aspects of the present concepts. Continuing with the example of FIGS. 62 and 63A-63B, a multi joint actuation capability is provided by a single drive unit configured to activate 1-N pulleys (where N is an integer). The drive unit comprises a single input (e.g., shaft) adapted to drive, directly or indirectly (e.g., through one or more gears), a plurality of pulleys. For joints such as hip flexion and ankle flexion, which operate in tandem, the two pulleys could be active at the same time. Activating two or more pulleys could be done via a permanent connection between the pulleys or a selector which would engage one or more pulleys simultaneously. Pulleys for each actuation point can have different diameters. The ratio of the pulley diameters will allow a single input to drive actuators at each joint which may have different force and velocity requirements.

FIG. 65 shows a rear view of a thigh brace for a soft exosuit in accord with at least some aspects of the present concepts. The depicted thigh brace, shown in an optional single-piece construction, is configured to not only accommodate varying thigh sizes and provide adjustment points above the knee to allow for a tight fit, but is also configured to allow adjustment for optimal conical form match. Lateral cutouts and a minimized height at the back of the thigh facilitate movement and comfort, while providing ample securement through Velcro® provided at the tapered ends. Circumferential adjustment is a simple matter of releasing the Velcro® attachment, tensioning the thigh brace as desired while holding one end of the thigh brace stationary, and securing the Velcro® attachment.

FIG. 66 shows Bowden cable termination points for a soft exosuit 100 in accord with at least some aspects of the present concepts. As previously noted, Bowden cable actuators act by reducing the distance between two fixed points. The fixed points operated on herein are points are attachments to the suit and through the suit forces are grounded to the body above and below the joint(s) acted upon. These grounded forces create moments about the joints. A hip flexion moment is created by grounding the sleeve upper portion of the Bowden cable (1) to the suit above the iliac crest anterior to the frontal plane and the cable (2) below the iliac crest. The soft exosuit grounds the force created when contraction of this cable occurs through inextensible fabric around the conical section of the thigh and the waist belt. A hip extension moment is created by grounding the sleeve upper portion of the Bowden cable (3) to the soft exosuit above the iliac crest posterior to the frontal plane and the cable (4) below the iliac crest. The soft exosuit grounds the force created when contraction of this cable occurs through inextensible fabric around the conical section of the thigh and the waist belt. An ankle extension moment is created by grounding the sleeve upper portion of the Bowden cable (5) to a point on the calf above the wearers boot and the cable (6) below the wearer's heel. The soft exosuit grounds the force created when contraction of this cable occurs through inextensible fabric at waist belt.

FIGS. 67A-67D show aspects of an actuator 200 for a soft exosuit in accord with at least some aspects of the present concepts. As shown by way of example, such as in FIGS. 46A-46B and FIG. 62, backpack born actuators are one advantageous implementation of a soft exosuit actuation system. However, due to the size and weight current actuation systems, it could be awkward to doff were the wearer to need to quickly drop the backpack and move away from it. Where the Bowden cables are fixed to the power and drive unit, as well as electrical connections, this can present an impediment to such maneuvers. Accordingly, in at least some aspects of the present concepts, the actuator 200 may comprise a quick release feature to permit rapid removal of a portion of the system that tethers the actuation system to the soft exosuit. By way of example, as shown in FIGS. 67A-67D, a quick release is configured to permit rapid detachment of a small pulley cassette 510 from the primary drive 500 (and power boxes). The pulley cassette 510 consists of a pulley with Bowden cable mating features as well as a soft exosuit electrical connection. Accordingly, when the wearer wishes to eject from the backpack, he or she simply pulls a cord or pin/skewer attached to the two securing latches and the latches open, allowing the cassette to eject of the drive spline. Other conventional quick release mechanisms (QRMs) could also be employed to releasably connect the pulley cassette 510 from the primary drive 500.

In accord with the example of FIGS. 67A-67D, the ready detachability of the disclosed cassette pulley 510 is facilitated by utilization of a spline drive on the motor unit 500 which mates with the corresponding, mating features on the cassette pulley. Large, slim bearing(s) further facilitate utilization of a central spline engagement between the motor of the drive box 500 and cassette pulley 510. Clips retaining the cassette pulley 510 to the motor of the drive box 500 may comprise any conventional clip that, when opened, allow the unit to be freed. Spring clips are presently preferred, but are not required. In addition, keying pins or features and/or alignment features which resist motor torque allow motor power to be transferred to the pulley when the units are connected.

Use of contact spring pins (e.g., POGO pins) allow establishment of a stable electrical connection between the cassette pulley 510 and the drive box 500 that permits two-way signal and/or two-way power transmission (e.g., regenerative power transmission) between the soft exosuit 100 and the drive box 500 without a permanent connection. When the cassette pulley 510 is ejected, the electrical connections are temporarily severed. A similar system of quick connects can be implemented for any soft exosuit that utilizes fluidic or air connections for any on-board soft exosuit system (e.g., actuation, etc.). Once the cassette pulley 510 is ejected, nothing connects the wearer of the soft exosuit to the backpack (or fannypack) bearing the actuator 200 and/or associated systems, and the backpack may be quickly removed without impediment. The cassette pulley 510 may be held in hand, dropped to hang free, or may be quickly inserted into a pouch or pocket in the wearer's clothing (e.g., if the soft exosuit is worn under clothing) or a pouch or pocket of the soft exosuit, if provided and accessible.

Figure 67A:
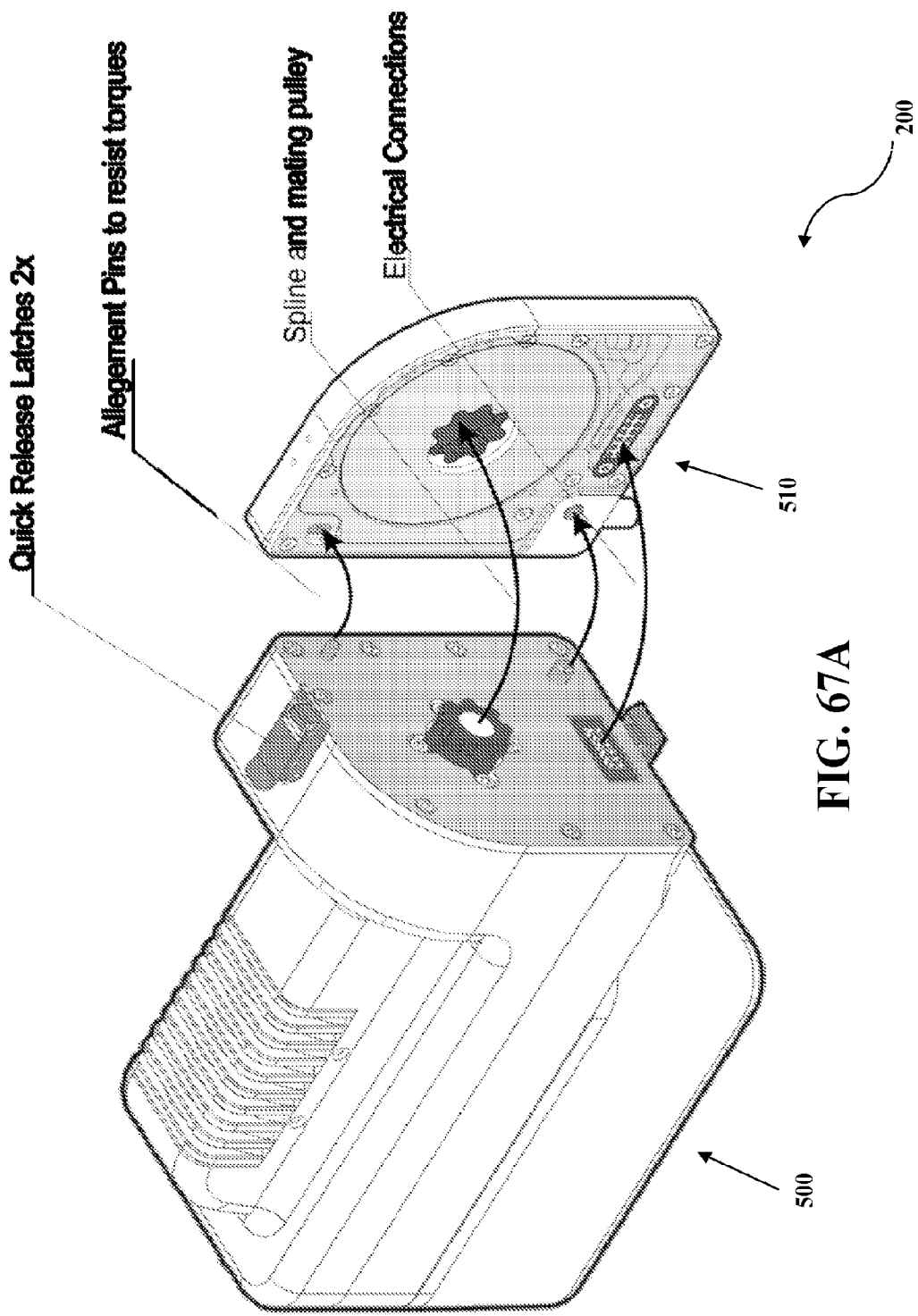
Figure 67B:
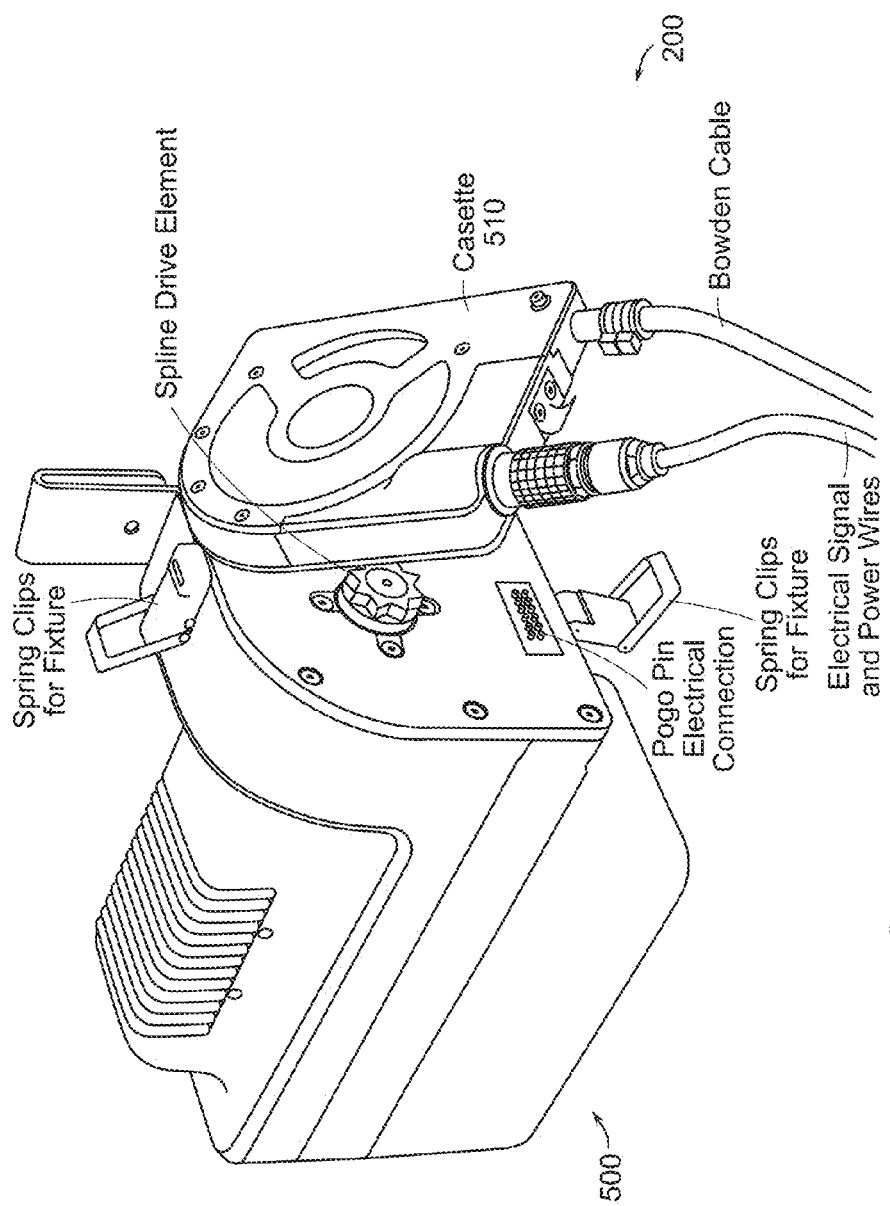
Figure 67C:
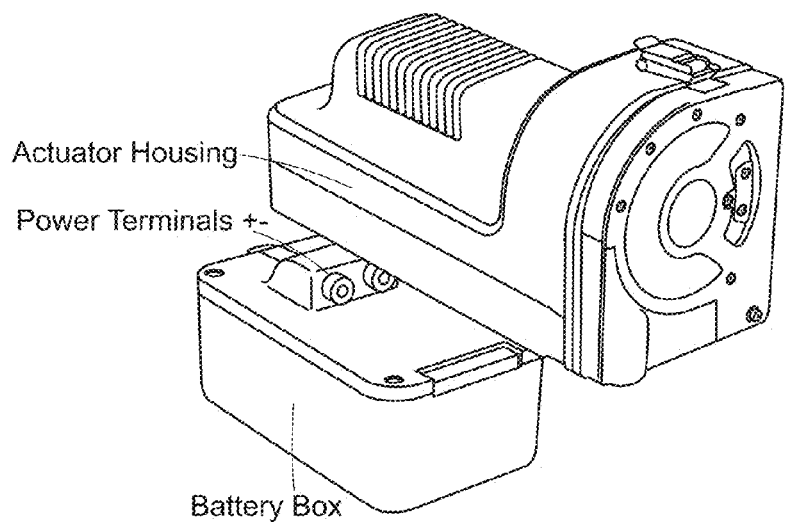
Figure 67D:
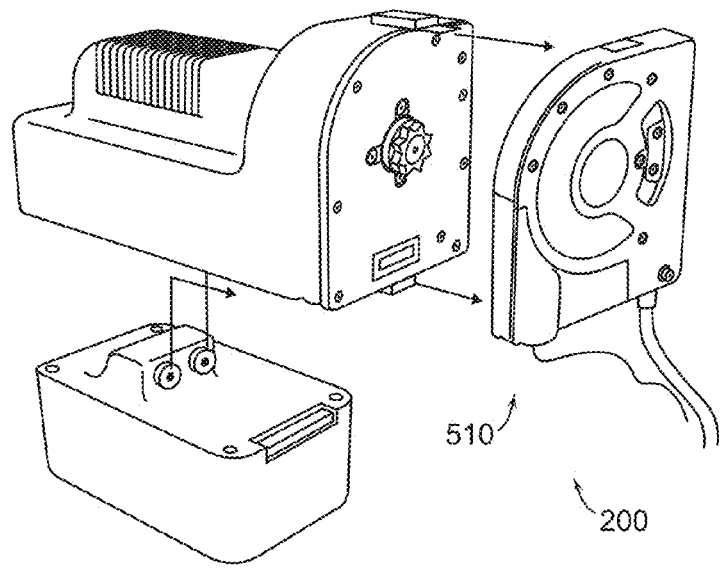

Another optional, but advantageous, feature of the actuator 200 of FIGS. 67A-67B comprises an integrated fast-swappable battery system. This permits rapid removal of a depleted or insufficiently charged battery and replacement of a new battery and/or replacement of an existing battery for a larger or smaller battery to change the operational envelope of the soft exosuit (e.g., to increase a battery duration, to decrease a system weight where a lower capacity and lighter battery satisfied mission specific or task specific goals, etc.). FIGS. 67C-67D show the battery box removed from and beneath the drive box 500 and further show the cassette pulley 510 ejected from the drive box.

As shown, the drive box 500 comprises a passive cooling system (i.e., air cooled). Although, in some aspects, cooling fans are suitably used to maintain the motor within an appropriate temperature operating range, some tasks and operational conditions benefit from an air cooled cooling system. In such aspects, the motors are cooled by a radiant fin system (e.g., a machined aluminum block comprising a conductive base having a plurality of fins projecting outwardly therefrom) placed over a surface of the motor (e.g., a top half of the motor) to permit conductive heat transfer from the motor to the conductive base and fins of the radiant fin system, which the convectively transfers heat from the fins to the atmosphere). This fins system has the benefit of silent cooling and allows for a sealed device. The air cooled system advantageously is silent, reduces the overall power requirement of the actuator system, and avoids openings in the actuator system from which waste heat would otherwise be discharged by the (omitted) cooling fan.

FIGS. 68-70 show various aspects of control schemes that may be implemented for a soft exosuit in accord with at least some aspects of the present concepts. Such control schemes are flexible and can be adapted as desired for a particular suit and application. By way of example, the soft exosuit 100 of FIG. 68 comprises a plurality of hyperelastic strain-sensors (such as disclosed in WO 2013/044226 A2) to measure suit stiffness and pressure. By way of example, such hyperelastic strain-sensors may comprise a stretchable silicone rubber (e.g., EcoFlex 0030, SmoothOn; PDMS, Dow Corning) sheet embedded with conductive liquid microchannels of non-toxic eutectic gallium-indium (eGaIn), wherein deformation of the channels causes a change in electrical resistance corresponding to the change in length (which in turn can be related to the rotation of the joint). As shown, hyperelastic strain-sensors are disposed across the ankle, knee and hip to measure changes in angle of the monitored joints. The hyperelastic strain sensors can be disposed in parallel with the force-path of the active suit in order to measure real-time suit deformations, such as shown in FIG. 68.

The control system is able to relate, via a human motion pattern detection algorithm or look-up table, the sensed movements of the joints (e.g., looking only at absolute changes in angle, looking at changes in angle in relation to time, velocity and/or acceleration, etc.) to one of a plurality of predicated activities such as walking on a level surface, walking on an incline, walking on a decline, running on a level surface, running on an incline, running on a decline, walking up stairs, walking down stairs, crouching, crawling, jumping, limping, favoring one limb over the other, etcetera. Based on this motion data, the control system may (1) store the data on a local physical storage media, (2) wirelessly transmit the data to another local or remote device via an on-board communication system, (3) transmit the data, through a wired connection (e.g., communication cable), to another local or remote device, device via an on-board communication system and/or (4) use the data to provide real-time force assistance control to adapt the suit seamlessly to the wearer's state of activity and environment. For example, if the soft exosuit measured joint deformations are above a threshold defined based on comfort (e.g., user preference) and/or suit mechanical capabilities considerations, the control system may be configured to automatically decrease assistance level until these deformations are again within a desired operational region. Additionally, the soft exosuit may be used in combination with an active, wearable exoskeleton. In such implementations, the measurement data can be transmitted wirelessly or through a wired connection to a controller of the exoskeleton to thereby cause the exoskeleton to adapt the level of assistance. Moreover, the soft, hyperelastic sensors can be used to measure pressure in relation to any point of interface between the wearer and the soft exosuit, which can be used for online adaptation of the assistance level based on comfort considerations.

Additional control schemes can be used with the soft exosuit if a force sensor is used to measure tension in the cable (e.g., an in-line sensor). The soft exosuit creates tension passively due to the biomechanics of walking. For a given leg, this tension occurs starting around 15-35% of the gait cycle, depending on how the soft exosuit is adjusted, and rises as the leg pushes off from the ground. This rising force can be used as an input to the control system, giving information about when and/or how (e.g., force profile, force timing, etc.) the soft exosuit should be actuated.

One control scheme from this information involves, first, tensioning the suit to the point where, during level-ground walking, the peak forces are at a certain threshold magnitude (e.g., $F_{peak}$). Once the suit is pre-tensioned in this manner, the force on the cable is monitored and can be used to predict where in a gait cycle the user is, or is about to be, since the force on the cable predictably crosses the threshold at the same point of the gait cycle. With respect thereto, FIG. 77 shows a graph depicting the timing of actuation of the soft exosuit 100 during a gait cycle and the corresponding suit force under two conditions: when the suit is tensioned 800 and when the suit is actuated 810. The tensioned graph 800 means that the suit has been set to a certain length, and then the length is held fixed throughout the gait cycle. The actuated graph 810 means that the tension in the suit is changed by pulling it together with a Bowden cable, or the like, at the ankle. In graph 800, the tension in the suit changes throughout the gait cycle due to the different motions of the joints (as in FIG. 9D). FIG. 78 shows, for the actuated case 810, the relative timing of the cable position and the suit force and more particularly a graph depicting the timing of actuation of the soft exosuit during a gait cycle (as a percentage of gait cycle) and the corresponding suit force (graph 830) in relation to cable position (graph 820).

In the graph of FIG. 77, the tensioned force crosses 50 N at 40% in the walking cycle, which is repeatable across many steps. This force occurs before actuation begins each cycle, and thus this information can be gained regardless of if the cable is actuated or not. Thus, for the example of FIG. 77, where the control system measures a force in the actuating cable that approaches (or optionally equals or exceeds) a threshold force $F_{thresh}$, the control system is able to utilize this information of the wearer's position in the gait cycle to take one or more actions (e.g., actuate immediately or after a delay). For example, the controller can get an estimate of the person's gait period by looking at the elapsed time between when the force crosses the threshold on two successive steps, or on several successive steps and then taking an average.

Further, from this information on the threshold cable force magnitude and/or flag indicative of crossing a threshold force magnitude, the controller also knows where the person is in their gait at that time. For example, the controller could be set to start a position-controlled pull on the cable at 40% in the gait cycle. In this case, whenever the controller detected that the force crossed the threshold that corresponded to 40% in the gait cycle, the controller could initiate the pull immediately. Or, if the controller was supposed to start a position-controlled pull at 43% in the gait cycle, then the controller would use the gait period to compute the delay between 40% in the gait cycle and 43% in the gait cycle and predictively initiate the pull only after lapse of that computer delay.

Further, to get a more accurate assessment of where the person is in their gait cycle, the controller could also monitor the tension force over time and look at several points where it crosses different force thresholds. In general, the pattern of force versus time will change depending on the person's walking speed. The slope of the force-versus-time curve can also be used to estimate the person's walking speed (or gait period). The slope should also be used in predicting where the person is in the gait cycle since the peak tension force is also a function of the person's walking speed, where the tension decreases as walking speed increases. In summary, a controller can be configured to made that estimates $$(\text{Current \% InGait}, \text{GaitPeriod}) = f(\text{CableForce}(t), \text{CableForce}(t-1), \ldots, \text{CableForce}(t-N))$$

where f( ) is a function and N is the number of samples used to track the cable force over time. N can be as small as 1 (using two samples to estimate the slope) or as large as 100-1000, depending on the sample rate of the force sensor. To get a good estimate of the slope, forces should be examined for the period of around 5-10% of the gait period. That is, if our gait period is 1 second, then to estimate the slope, the controller should use samples from the current time back to 0.05 or 0.1 seconds prior to the current time.

Yet further, instead of having the cable (e.g., Bowden cable 142) or cables (e.g., for a multi-joint activated soft exosuit) pull in (and release) with a position profile (% of gait), there are other control options. The motor could pull in with some specified velocity until a certain peak force is reached. The motor could also pull such that the force at the ankle follows some prescribed force trajectory. The motor could also pull in with some specified velocity until it detects force decreasing due to the biomechanics of walking. Similarly to how the tension increases in the soft exosuit and cable at 15-35% in the gait cycle due to the biomechanics of walking and the soft exosuit changing length, the tension in the soft exosuit and cable will also decrease at around 60-65% in the gait cycle due to the configuration of the body causing the soft exosuit to slacken. In particular, the ankle lifting up at around 60-65% of the gait cycle and the knee bending cause the soft exosuit to become slack even if the cable is held at a fixed length or is being pulled by the motor (and decreasing in length) at moderate or slow rates. This decrease in force due to the biomechanics can be used as a trigger for when the cable should be released and fed out again. At that point, the cable should be released at some specified velocity or following a certain force trajectory back to the nominal tensioned point.

In general, the process of tensioning and releasing the cable(s) can be done following a force trajectory, position trajectory, velocity trajectory, some combination of these, or some other scheme.

As noted above, real-time measurements of human biological joint angles using wearable strain sensors (e.g., hyperelastic strain sensors comprising liquid metal conductors, conductive fibers integrated with nonconductive stretchable fabric, etc.) or other type(s) of sensors (e.g., inertial systems, angular velocities measured from a plurality of gyroscopes/accelerometers attached on different limb portions, etc.) can be used to inform the control system of the soft exosuit and/or of assistive exoskeletons when performing daily-life or field tasks, such as represented in FIG. 69. The information provided by these strain sensors (or other sensors providing positional data or derivatives thereof) can be used to classify different human motions such as walking, going up or down the stairs, incline walking, crouching, crawling, stopping, jumping, etcetera, once suitable baselines are established either for the wearer or for a population similar to the wearer (e.g., anatomically similar). Real-time analysis of human motion is of vital importance when a person is wearing a wearable exoskeleton or assistive devices in real-world applications (i.e., out-of-lab). The assistance required to perform these various activities totally differs and a strategy that works well for walking won't benefit the user or may even destabilize the user's motion when the user performs variations of the same task (incline walking) or performs other movements. In accord with at least some aspects of the present concepts, sensors integrated into the soft exosuit (e.g., strain sensors, pressure sensors, gyroscopic sensors, accelerometers, etc.) are used to measure one or more joint rotations or limb motions (e.g., rotation of the hip, knee and/or ankle), or are used to permit determination of one or more joint rotations or limb motions, and this information is compared to reference data for the wearer of the soft exosuit (e.g., wearer baseline data) or for a population having similar characteristics (e.g., look-up tables, algorithms, etc.) to determine kinematics and/or other characteristics of motion. The determined motion(s) can then be used by the soft exosuit control system to affect on-board systems (e.g., actuation times and/or magnitudes for a single joint type, actuation times and/or magnitudes for a plurality of joint types, etc.) or to communicate with and/or effect local or remote external systems (e.g., worn exoskeleton). Thus, the obtained classification of human motion(s) can be used to define a state-machine that updates in real-time to inform the control system as to what motion(s) the wearer is performing.

Further, where a plurality of soft exosuits are deployed amongst a plurality of users (e.g., a squad of soldiers), motion data from the plurality of soft exosuits are communicated, in real-time, to one or more local or remote external systems and the motion data analyzed (either singly or in combination with other measured data, such as position data for each wearer, respiration, heartrate, etc.), in the aggregate to determine the motions of the group and characteristics of such motion, infer causes for deviations from expected values, and initiate corrective actions or engage other local or remote systems deemed appropriate responsive to such characteristics of motion. By way of example, if a squad of soldiers is expected to be walking along a road, and GPS data for the soldiers shows the soldiers moving to opposing sides of the road, GPS data alone doesn't indicate whether the soldiers are taking cover in ditches or simply allowing a vehicle to pass. However, if the same GPS data is combined with information that showed rapid movement of each of the soldiers combined with an assumed prone or semi-prone position, such information transmitted in real-time to a remote control system could automatically initiate an alert that the squad has possibly been engaged by hostiles and data on nearby assets could automatically be routed to appropriate decision makers remotely or in the field. Thus, the soft exosuit sensor data is not only utilizable by a soft exosuit control system for an individual user, but can be used by external (command and) control systems, which may utilize as control inputs data from a single channel (e.g., one soft exosuit) or multiple channels (e.g., a plurality of soft exosuits).

In accord with the aforementioned use of sensor data, such sensor data can also be used to provide to the soft exosuit control system information about the user's gait, such as gait phase, speed and amplitude. These parameters will allow the force profiles delivered to the user biological joints during walking by actuator(s) 200 to be adapted in real-time, resulting in an increased efficiency of the assistance. By way of example, such utilization of sensor data can permit elimination of other sensors, such as the aforementioned foot switch sensors, which would be rendered unnecessary.

FIG. 70 shows an example of one exemplary advanced control architecture adapted to change soft exosuit assistance based on detected soft exosuit wearer motions. Since the assistive forces required by each joint while performing different motions are completely different, a control system should be configured to provide adequate assistive forces to the user during the different considered activities. In FIG. 70, a human motion pattern recognition algorithm output, such as was generally described above in relation to FIGS. 68-69, informs the control system to determine the reference trajectory forces to be delivered to the user. Humans adapt the biological impedance of their limbs when performing different motions, such as walking in an inclined terrain, running, etcetera. Implementing a position-based admittance control with force as an input ($F_{Ref}$) allows defining the virtual impedance (inertia, damping and stiffness) felt by the user during actuation ($F_{Suit}$), provided that the inner position control loop compensates the dynamic and friction components. The use of on-board soft exosuit sensors thus permits utilization of sensed motions in combination with an admittance control architecture to adapt the soft exosuit to work with the user based on the movements of the user, as shown in FIG. 70, providing more natural and efficient actuation. The human motion pattern recognition would be used to change the assistance force of an active exoskeleton and to change the virtual impedance delivered to the user.

FIG. 71A-71H show aspects of an soft exosuit 100 in accord with at least some aspects of the present concepts. In relation to the actuator system 200 described above in FIGS. 29-43B, the actuator system 200 shown in 71A-71H show a number of beneficial improvements thereto (e.g. further reduction in weight, increased reliability, etc.). By way of example, the higher stiffness of the four-plate frame 500 makes it possible to reduce wall thicknesses and to cut off more material, which results itself in a weight of 1.5 kg. The actuator 200 shown in FIGS. 71A-71H also comprises a different design for the lower pulleys 510. Where the prior design of the lower pulleys did not absolutely prevent cable jam, the design shown in FIGS. 71A-71H makes cable jams impossible. Flange radii have increased and an additional part 520, a guide structure, is added on each side, such as by mounting to the side plates directly between the rotating pulleys, with only small tolerances to prevent the webbing from being lodged between adjacent rotating parts. As another enhancement, the load cell design is changed as well to permit use of high quality (e.g., low noise), market-based load cells. Instead of beam load cells, as described above, the design of FIG. 71C uses button load cells 530. FIGS. 71A-71H also variously show, for reference, the timing pulley 271, pulley wheel 225, and cutouts 402 shown above with respect to FIGS. 29-43B.

Figure 71A:
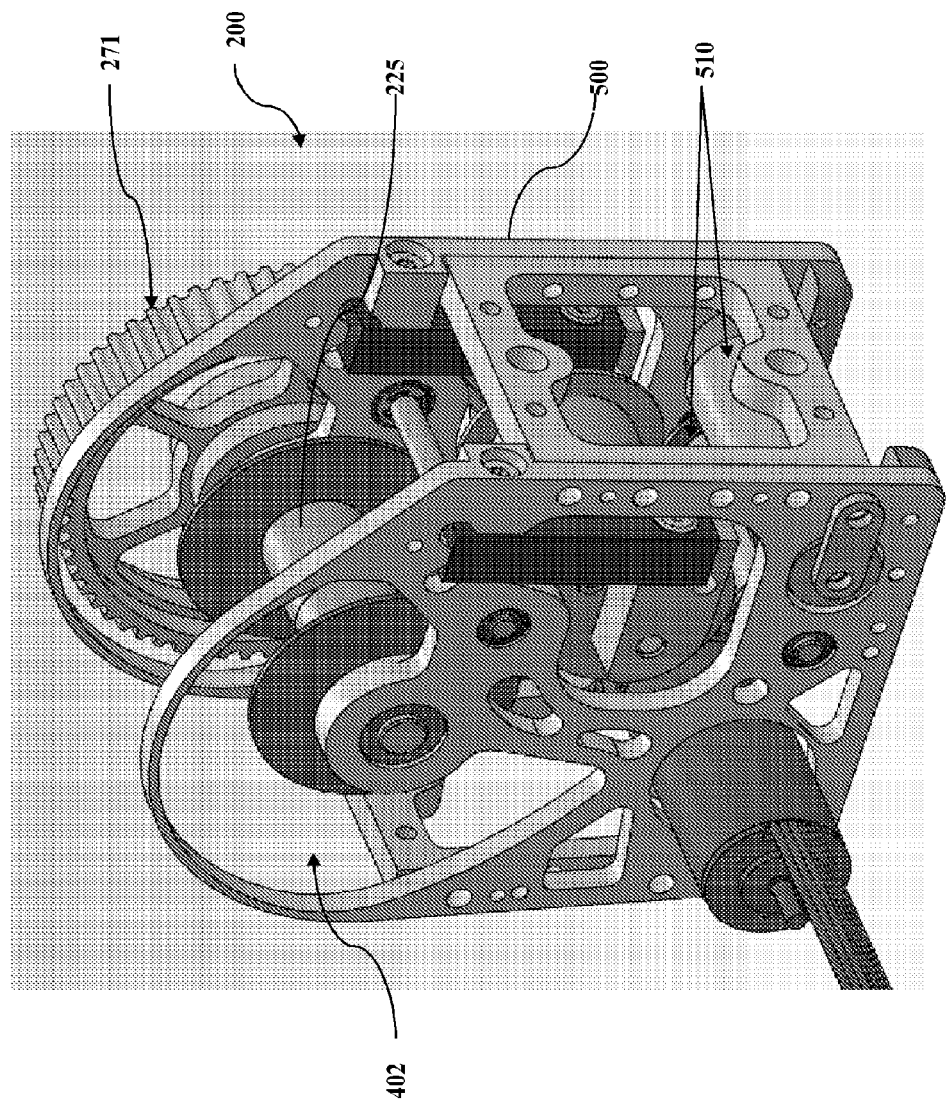
Figure 71B:
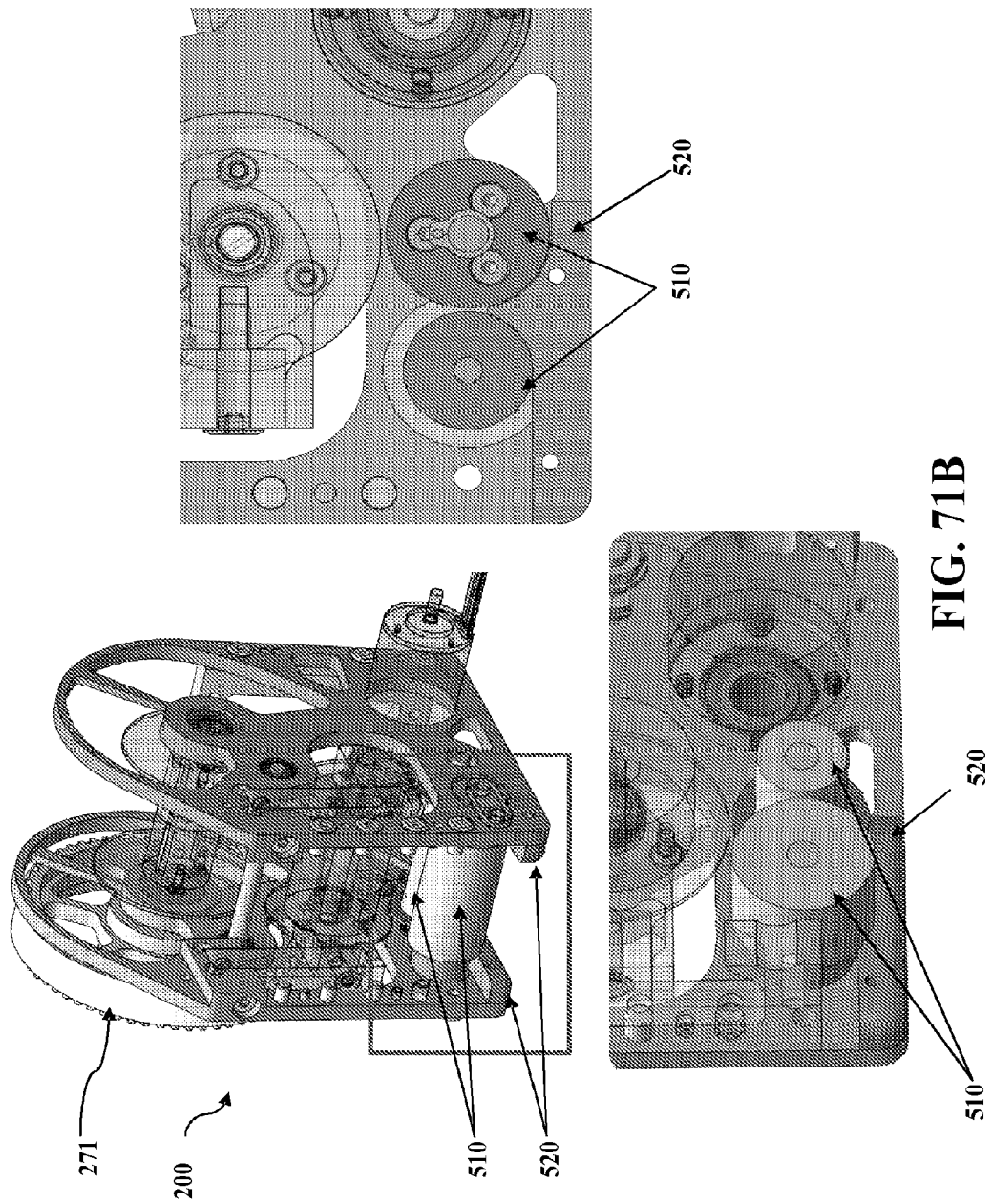
Figure 71C:
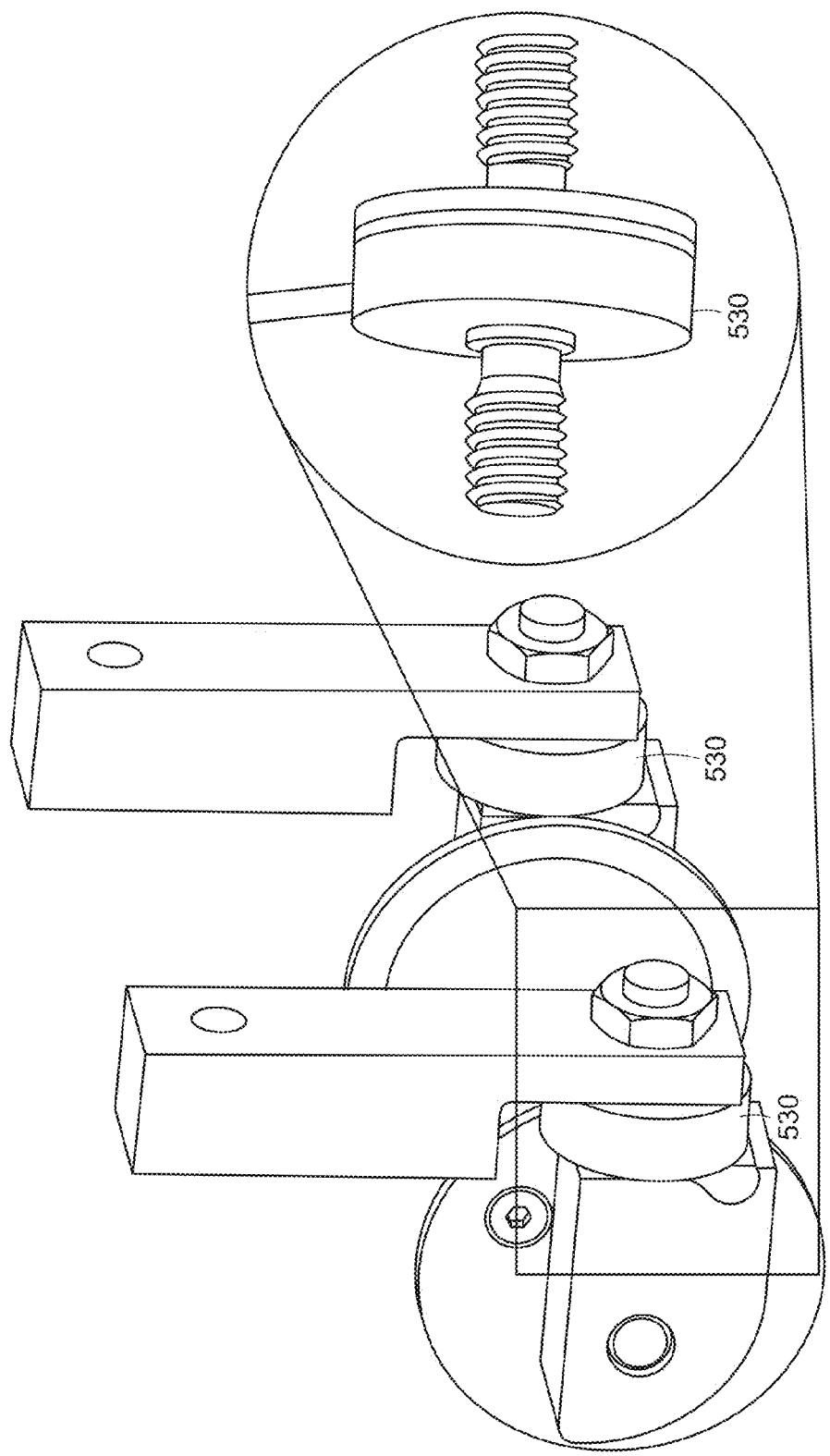
Figure 71D:
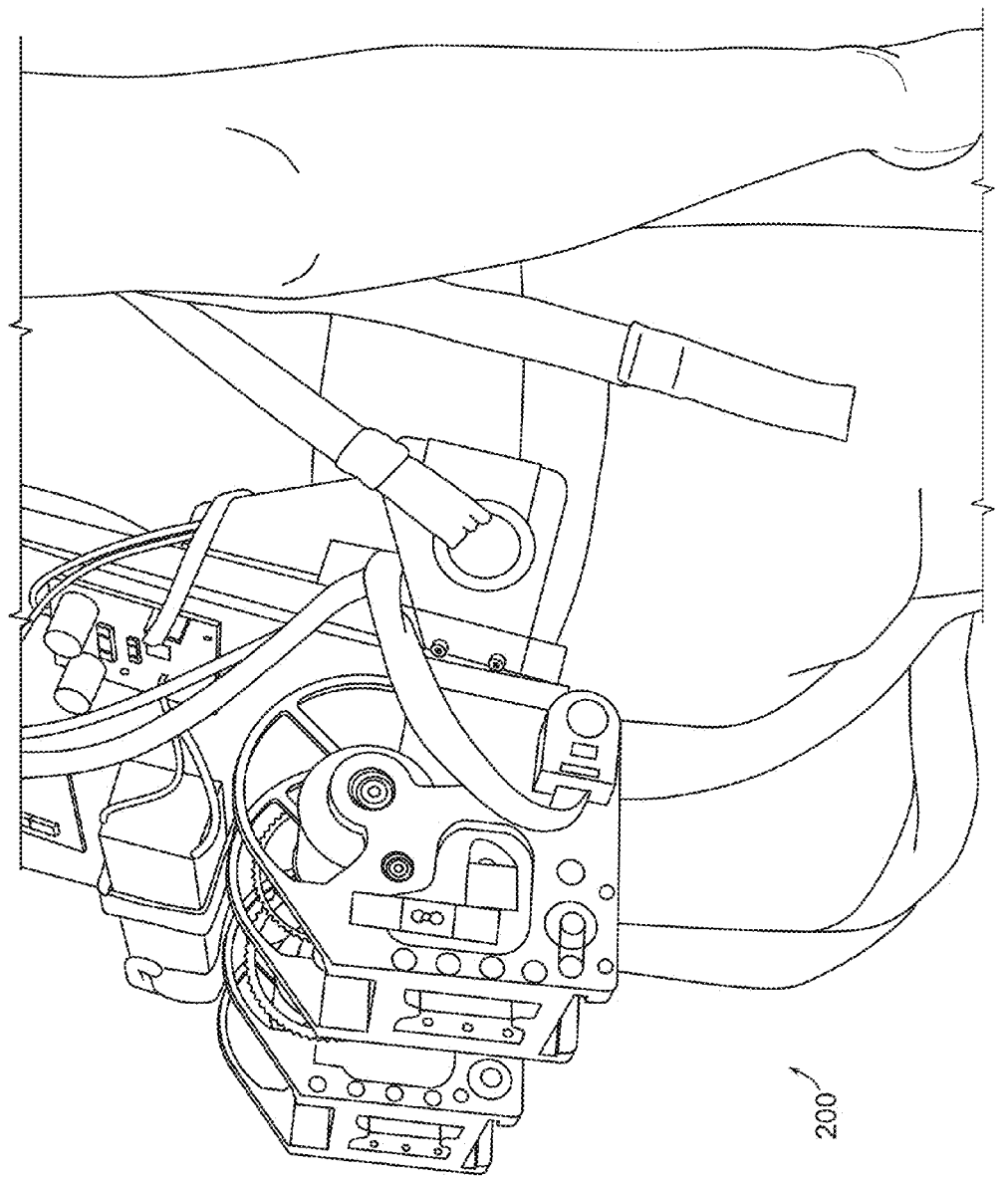
Figure 71E:
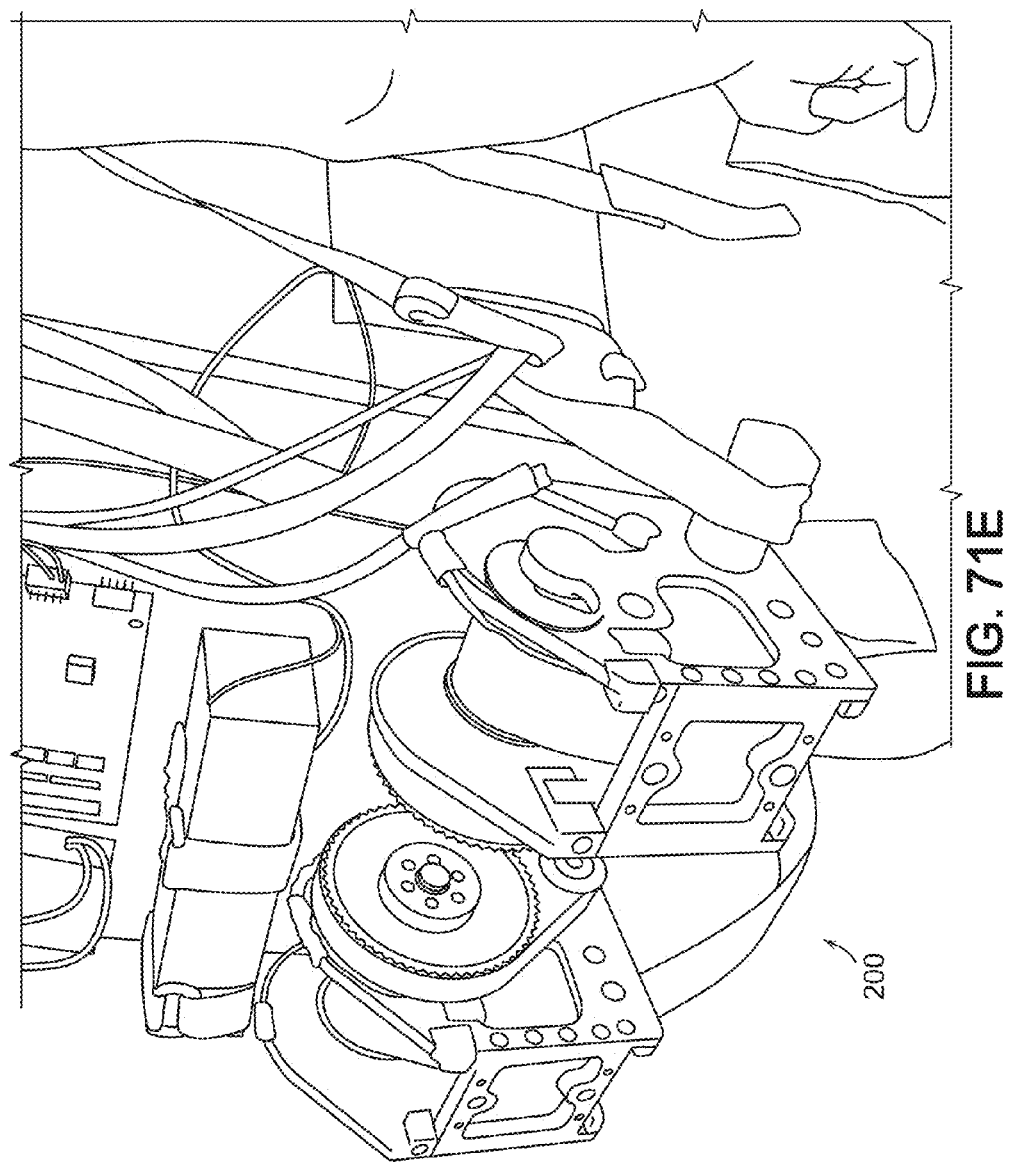
Figure 71F:
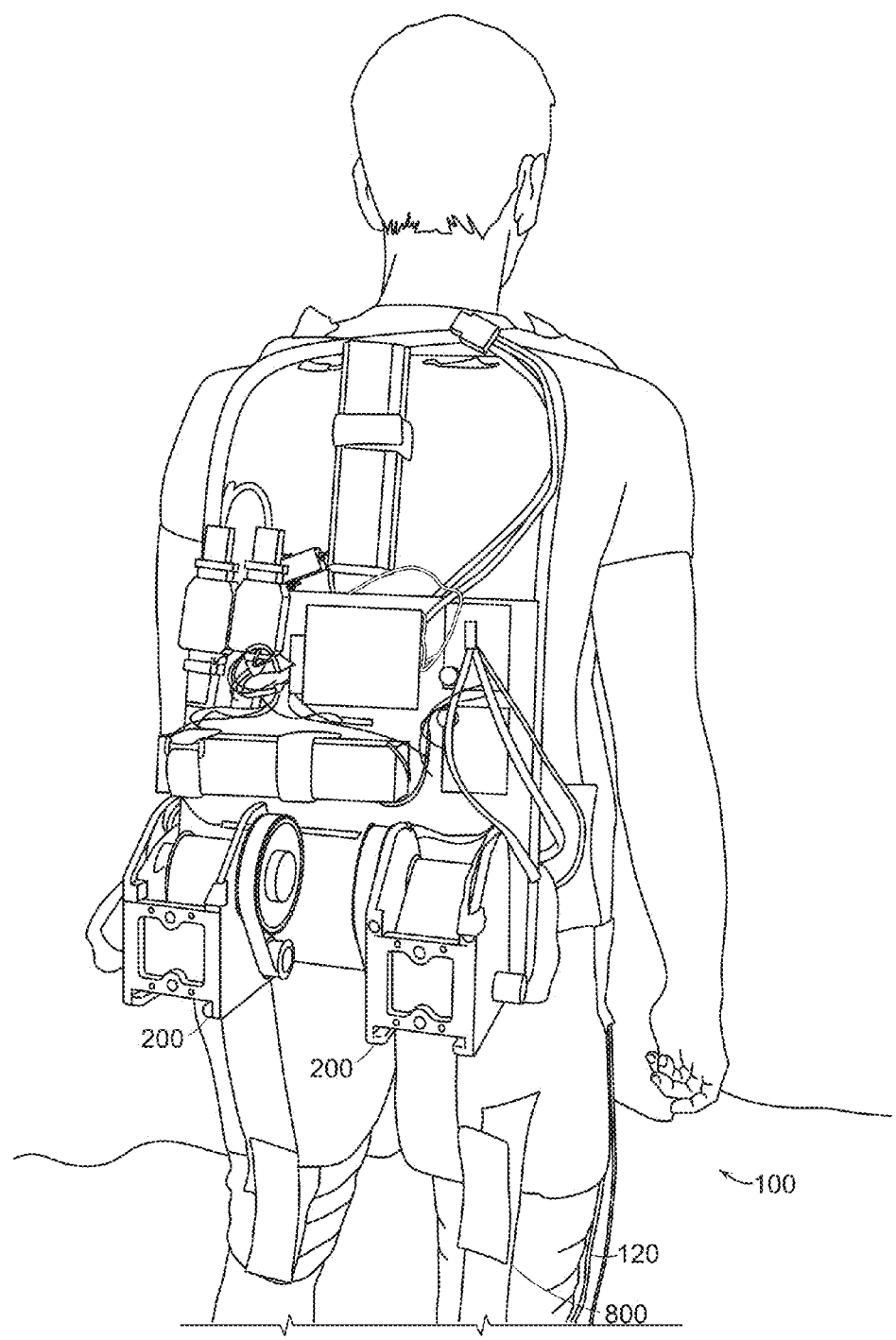
Figure 71G:
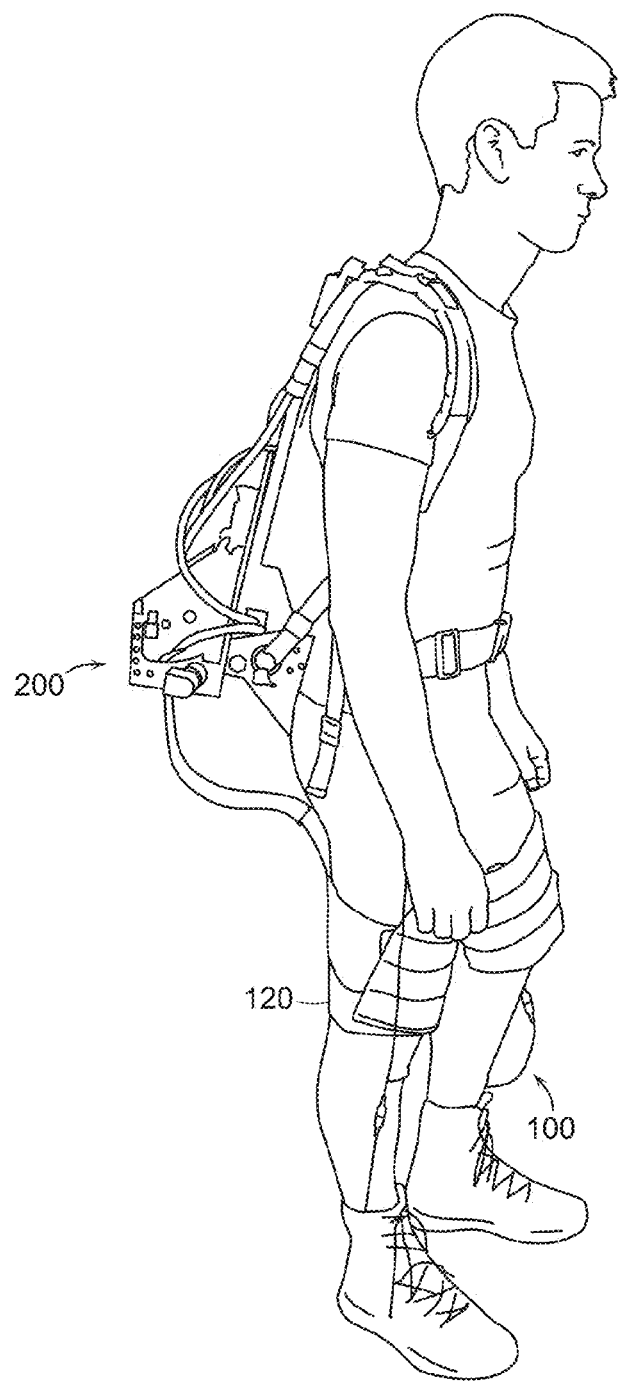
Figure 71H:
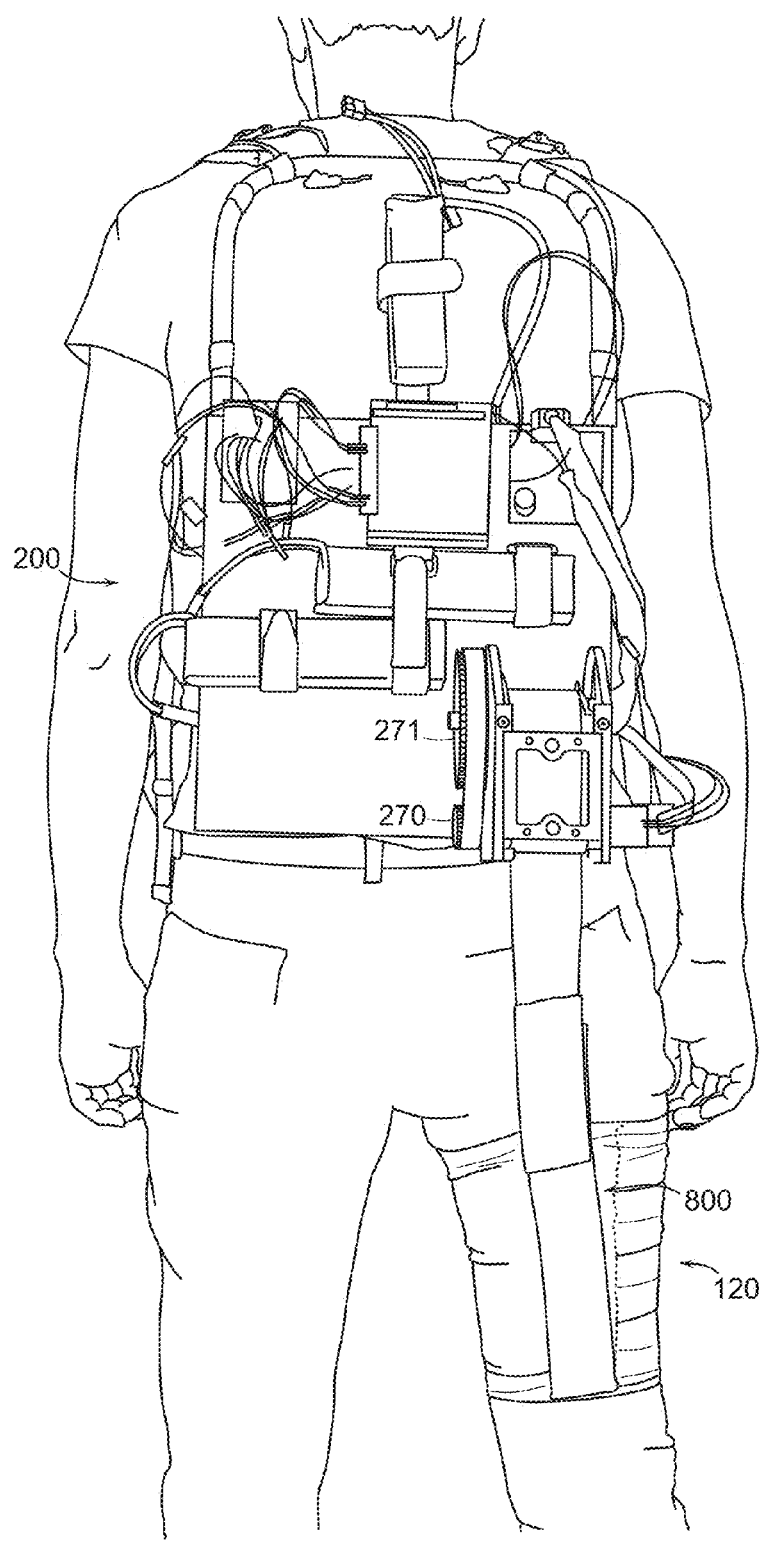

FIGS. 71D-71H show images of a soft exosuit 100 having an actuator 200, as described above, configured to provide hip actuation using thigh brace 120 and connection elements 800. As shown, the actuator 200 comprises two actuators, each configured to actuate a specific side of the body (left/right). In FIG. 71H, the left channel of the actuator 200 has been removed.

FIGS. 72-74 show several possible implementations of a soft suit 600 comprising a passive systems configured to support hip flexion and/or hip extension. The soft suit 600 and disclosed passive systems can be used in combination with the soft exosuit 100 described herein, or could be used entirely separately therefrom as a stand-alone system. Moreover, the soft suit 600 may advantageously integrate sensors such as, but not limited to, a plurality of hyperelastic strain-sensors (such as disclosed in WO 2013/044226 A2) to measure changes in angle of monitored joints (e.g., hip) or changes in soft suit deformation. This data and/or other sensor data from other sensors, may be output to a local storage device (e.g., solid state memory device) and/or wirelessly transmitted to a local device (e.g., via Bluetooth, etc.) or a remote device for storage and/or processing.

Turning to FIG. 72(a), the passive soft suit 600 is a garment based on a spandex short with added material to make certain paths inextensible in the garment. In FIG. 72(a), label 1 is inextensible fabric providing forces on the right leg, and label 2 is inextensible fabric providing forces on the left leg. Element 3 is a stretchy spandex material, connected to (e.g., sewn) the inextensible fabrics along their edges or provided as a base layer underneath all of the other elements. Element 4, which is optional, is an elastic region to permit the soft suit 600 to fit closely around the waist, while elements 5, which are optional, are elastic regions to permit the soft suit to fit closely around the thighs. Both of optional element 4 and optional elements 5 can comprise spandex or can comprise a different material with a different stiffness and/or hysteresis than the spandex. If elements 4 and 5 of FIG. 72(a) are not included, the inextensible fabric 1 and 2 should connect together in these regions. Elements 4, 5 could alternatively comprise snaps, hooks, VELCRO®, a zipper, a lacing system based on shoelace or string, or a tensioning system based on straps, or a variety of other closure devices. The important aspect is that these regions permit the soft suit 600 to attach closely around the waist and leg. Instead of or in addition to elements 4, 5 being located at the back of the thigh and waist, they could be located at a variety of other locations on the soft suit, for example on the sides of the waist (to replace element 4), in the front of the abdomen on the angled straps (to replace element 4), in the front of the thigh where the inextensible fabric makes an "X", or on the sides of the thigh (to replace elements 5), among other locations. An additional waist belt 600 is optionally added around the top of the soft suit 600. This waist belt 600 could also secure in the center with elastic, VELCRO®, lacing, or any of a variety of other conventional securement methods.

Similarly, inextensible fabric elements 1, 2 can comprise a variety of materials, including fabric which is stiffer than spandex but still stretchy. In this case, elements 4, 5 would not be necessary because the entire soft suit 600 would expand and contract to fit the wearer snugly. The particular paths that elements 1, 2 take can follow any of the paths that transmit force, as described previously. For example, elements 1, 2 should ideally extend over the top of the iliac crest of the pelvis on the opposite side of the body, while on the same side of the body they can wrap around the body below the iliac crest, or could have one branch go below the iliac crest and one branch go above the iliac crest. This soft suit 600 functions by pulling forward on the thigh when it is extended backwards, thereby creating a torque around the hip which can aid the return of the leg to the neutral position, which is influenced by soft suit 600 position when the soft suit is donned or movement of the soft suit subsequent thereto.

FIG. 72(b) shows the soft suit 600 in FIG. 72(a) with an additional element 6 positioned over the crease between the wearer's thigh and abdomen. This element 6 can comprise an elastic material to provide a given stiffness in conjunction with elements 1, 2, which would be largely inextensible in this case. Adding the elastic element 6 would decrease the stiffness of the soft suit 600, and thereby provide a smaller torque around the hip for a given angular displacement of the hip. However, adding an elastic element (which could comprise rubber, silicone, a different type of spandex, several layers of spandex, elastic strapping, or other materials) could reduce the hysteresis of the overall system, thereby returning more energy to the wearer's leg if the leg is deflected in flexion and then moves forward again.

FIG. 73(a) shows a soft suit 600 similar to that in 72(b), except that the configuration depicted in FIG. 73(a) is designed to assist with hip extension. In this case, if the wearer moves their knee forward, the soft suit 600 will pull on the front of the thigh to try to return the thigh to a vertical orientation. This could be useful in several instances, such as when walking downhill, where the hip takes an increased amount of torque. The soft suit 600 could, in this case, provide some of that force so the muscles do less work. Another possible use for the soft suit 600 would be if someone was walking uphill while carrying a heavy backpack. In this case, there is a large moment about the hip at the beginning of the gait cycle as the person lifts their entire body mass and backpack mass up with one leg. If the user were wearing the soft suit 600 adapted to assist with hip extension, they would still have to expend additional energy lifting the leg before planting it on the ground, but this additional energy would go into stretching the suit (for example, stretching element 6 which is at the crease of the posterior and thigh). Once the wearer had planted their foot on the ground, the soft suit 600 could then apply a force in parallel with their gluteus muscles, permitting them to do less work during the part of the gait when they lift up their mass and their backpack's mass. Finally, FIG. 73(b) shows a soft suit 600 system adapted to assist with both hip flexion and hip extension, by combining the systems of FIGS. 72(a) and 73(a).

FIG. 74 shows another possible implementation where the soft suit 600 of FIGS. 72-73 comprises an elastic element 6 at the front of the thigh and further depicts a method of adjusting the length of the suit in the front of the thigh. In this case, the wearer could tighten or loosen the soft suit 600 (e.g., by securing Velcro® at the top edge of element 6 higher or lower on the front of the soft suit) to fit their preference. In this case, element 6 would be separated from the underlying spandex so it could move up or down to be secured higher or lower on the front of the soft suit 600. The inextensible fabric at the top edge of element 6 would have the complementary means of securing down element 6. For example, element 6 could have hook Velcro® facing downward on the top edge. The inextensible fabric underneath could have loop Velcro® facing upward some distance above and below the nominal position of element 6. Elements 4 and 5 in FIGS. 72 and 73 could also have this construction.

As to the soft exosuit 600 embodiment shown in FIG. 72A, during normal walking, around 30-70% of the gait cycle, the hip extends. Initially, the hip absorbs power from 30-50% in the gait cycle, and then generates power from 50-70%. When wearing the FIG. 72A-72B embodiment of the soft exosuit 600, the soft exosuit will take over some of the function of the muscles in absorbing and generating power during this time period. The embodiment of the soft exosuit 600 in FIG. 73A, may be particularly beneficial in movement over diverse terrain (e.g., rugged territory, mountain climbing, etc.), either going uphill or downhill. During both uphill and downhill walking, the hip supports an increased torque in the extension direction. For downhill walking, the soft exosuit 600 in FIG. 73A will passively provide support to the hip to reduce the muscular activity required. For uphill walking, the soft exosuit 600 in FIG. 73A must be pre-stretched by lifting the knee when the foot is being placed on the ground. Then, the suit will act in parallel with the muscles to reduce the extension torques required by the body.

Although primary functional elements of the soft exosuit 600 in FIGS. 72-73 are shown, additional elements may be included. For example, functional fabric (e.g., inextensible fabric, stretchable fabric, etc.) may also be incorporated in regions other than shown, such as extending to the sides of the leg.

Turning again to the aforementioned embodiments of the soft exosuit 100, such embodiments can be advantageously used for a variety of different applications including, but not limited to medical applications, sporting or recreational applications, and/or control system inputs. As to medical applications, the soft suit 100 provides a cost-effective, easy to use (e.g., easy to don and doff), comfortable sensing suit to permit improved evaluation of patient outcome (e.g., range of motion) both during and after a rehabilitation therapy (e.g., post-stroke rehabilitation, physical rehabilitation, etc.) and may be used in the clinic, and/or at a patient's home. The sensed data (e.g., joint angles, performance of recommended repetitions of physical therapy, etc.) may be used not only to track progress to use as inputs for changes to a therapy regimen, but may also be used (or may be required to be used) to ensure compliance, such an by a health insurance company seeking to ensure that the patient is doing their part to ensure their own well-being.

In accord with least some aspects of the soft suit 100, the sensed data may be advantageously saved locally to a physical memory device (e.g., solid state memory) that can then be inserted into a user's home computer, wireless device, or home health care monitoring device (e.g., datalogger and/or wireless communication device) for recordation and/or transmission. In some aspects, the soft suit 100 sensors are advantageously networked (e.g., via Bluetooth or other frequency-hopping spread spectrum (FHSS) system) with a user's device, such as a smart watch, smart phone, or heads-up display device.

Returning to the soft exosuit 100, and particularly to a system built to assist hip extension both during normal and walking uphill/downhill (see, e.g., soft exosuit of FIGS. 71A-71H), FIG. 75 shows hip joint torque during level walking where the soft exosuit is actuating between about 0% to about 25% of the gait cycle, not actuating between about 25% to about 75% of the gait cycle, and again actuating between about 75% to about 100% of the gait cycle. The positive torque corresponds to hip extension (portion of curve associated with actuation) whereas the negative torque corresponds to hip flexion (portion of curve associated with no actuation).

Two control schemes are useful in providing such assistance, position-based control and force based and admittance control.

As to position-based control, during normal gait, hip extension starts before heel strike occurs. A position-based control scheme needs to take such characteristic into consideration. In order to get information about the step frequency during normal gait, foot switches are used to detect the heel strikes. The time for one step is measured by subtracting the time for the last heel strike from the time of the previous one. This information is then stored in a buffer which consequently comprises the step frequency. By averaging the step data saved in the buffer, or data derived therefrom, the next heel strike can be predicted by adding that specific time to the last heel strike event. In that context, position control means that a fixed trajectory is replayed if the system time reaches the predicted time for the next heel strike. In order to adapt the position controller to different speeds, the fixed trajectory is time scaled, meaning that the peak of the trajectory never changes but the time the motor reaches that maximum can change depending on the measured step frequency.

FIG. 76 shows an extract of recorded data during ground level walking depicting curves for force profile, motor position and footswitch signal. It can be seen from curve 705 that the motor starts spinning before heel strike occurs, shown by curve 710. By playing back the scaled motor trajectory, a corresponding force is generated, as shown by curve 715. It is to be noted that the force is the force in the cable and not the actual hip moment. The main disadvantage of such position-based control is that the system needs to be at least slightly pretensioned to permit the trajectory to be played back to apply the desired forces. Otherwise, the system would mainly wind up slack cable, resulting in low applied forces.

As to force based and admittance control, force based control can advantageously be used to track hip motion. By always having a slight (<5N) tension in the cable, the controller is able to follow the hip motion, which eliminates the main disadvantage of the position based controller. Since the position based control showed good results for the applied moment and for assisting the user, admittance control is chosen as an advanced controller for the system. The motor is still position controlled, which shapes the inner control loop. By developing an efficient position controller, the physical system properties like inertia and friction can be neglected. By adding an outer admittance control loop, the system behavior can be simulated and shaped to the physical system accordingly. The controller set point, the desired value, and the error are now forces in that specific case.

In order to follow the correct torque profile for hip extension (see FIG. 75), foot switches are used to synchronize the controller in the first place. The exact same principle is used as for the position controller. Tracking the hip motion by using the admittance controller enables the system to work without foot switches as well. Foot switches can only provide the time a heel strike occurs. Similar information can be obtained by reading the motor encoder and marking the point where extension changes into flexion. By knowing that specific point, the same principle can be applied as for using footswitches. As mentioned, the motor encoder signal is used to estimate the hip angle. Although, it is not necessary to know the exact angle since the only information needed to synchronize the controller with gait is the change between extension and flexion.

Although the above concepts regarding the soft exosuit 100 and the soft suit 600 have been generally described in terms of land-based applications adapted generally for activities such as walking, running, or rehabilitation, both the soft exosuit and the soft suit are adaptable for utilization in wet or potentially wet environments (e.g., cross-country skiing, scuba diving, etc.) using suitable materials, enclosures, and connections appropriate to the activity. By way of example, the soft exosuit 100 and the soft suit 600 could be integrated into a wet suit, or a dry suit, with the actuation system 200 enclosed in a neutral buoyancy dry bag that the diver can attach to the air tank(s).

In applications where it is desirable for the soft exosuit 100 or the soft suit 600 to wirelessly communicate with a remote computer or remote control system (and/or command and control system), a wearable antenna may be advantageously integrated into the soft exosuit 100 the soft suit 600, such as, but not limited to the Pharad (Hanover, Md.) wearable antenna products (frequency and application selected, as appropriate, for the activity) or Patric (Helsinki, Finland) washable-wearable antenna.

Other embodiments are within the scope and spirit of the invention. For example, due to the nature of software, functions described above can be implemented using software, hardware, firmware, hardwiring, or combinations of any of these. Features implementing functions may also be physically located at various positions, including being distributed such that portions of functions are implemented at different physical locations.

In accord with at least some aspects of the present concepts, the soft exosuit disclosed herein is, advantageously, sufficiently flexible and light-weight to permit the soft exosuit to be worn under clothing. In at least some aspects, the soft exosuit connection elements, nodes and optionally anchor elements are integrated into a wearable undergarment.

Still further, the soft exosuit 100 in accord with any of the disclosed aspects of the present concepts may be further configured with to interact wirelessly with a variety of other user devices and/or interacting through wired connections with a variety of other user devices. By way of example, the soft exosuit 100 may comprise ports and connectors adapted to enable utilization of the power supply from the soft exosuit to power one or more other external devices (e.g., a communication device, night vision goggles, GPS equipment, etc.) as the need may arise (e.g., operation in a Tier-1 environment), should there be sufficient power in the soft exosuit to spare. Similarly, ports and connectors may be provided to enable recharging of the soft exosuit battery system from an external source (e.g., vehicle battery, stationary battery, portable solar cells, wearable solar cells, AC power outlet in combination with an adapter suitable for the power grid voltage/frequency, etc.).

FIG. 79 shows an example of a soft exosuit component (here a footwear attachment element) made of a soft material (e.g., neoprene) comprising a haptic actuator (e.g., piezoelectric actuators, Piezo Fibers, Bimorph Piezo, Non-Rigid Piezo, Electroactive Polymers, etc.) to provide inputs to the wearer according to at least some aspects of the present concepts. It at least one aspect, small haptic actuators are advantageously integrated into one or more areas of the soft exosuit 100 (e.g., anywhere covered by fabric in FIG. 54A, under connecting elements, under thigh brace 120, etc.). These haptic actuators could be sub-threshold (so person doesn't feel vibration) for a stochastic resonance (SR) effect or supra-threshold (so person does feel vibration) and provide a user-machine interface capable of informing the user as to whether the wearer is doing something correctly or incorrectly (e.g., performing a movement correctly, performing a movement incorrectly, approaching a preset limit, exceeding a preset limit, performing a minimum required motion of a joint, etc.). In the example of FIG. 79, piezoelectric actuators having an insulated coating are embedded within a fabric pocket on an inside of an ankle brace. An insulated cable connects an enclosed electronics box to the piezoelectric actuators.

Such haptic actuators can acts as a feedback control system for human balance. In this feedback loop, an external stimulus triggers receptors in the body, mechanoreceptors, to send information about the stimulus to the central nervous system, which then signals the muscles. The mechanoreceptors for balance are found in the skin, muscle, tendon, and other soft tissues of the lower limbs. For the sensory neurons to send a signal, the stimulus must exceed the minimum sensory threshold, which can increase with fatigue or injury. The presence of a particular sub-threshold level of noise effectively lowers this sensory threshold and can be used to enhance signal recognition and detection (SR). Thus, haptic devices, whether sub-threshold or supra-threshold may enhance performance of static and dynamic balance activities for the wearer of the soft exosuit 100.

In at least some aspects of the present concepts, one or more of the soft exosuit components may comprise an interior lining (and/or optionally exterior lining) comprising a reversible adhesive (e.g. a "gecko style" adhesive comprising nanoscale surface features such as, but not limited to, nano polymer pillar arrays). Such a reversible adhesive can facilitate retention of the soft exosuit is a fixed location relative to the body. Alternatively, other surface treatments may be selectively applied to enhance surface properties of the interior or exterior of the soft exosuit.

FIGS. 80A-8B show an example of soft exosuit components according to at least some aspects of the present concepts. The soft exosuit 100 shown is configured to provide an extension torque around the knee, as well as plantar flexion torque around the ankle and extension torque to the hip. During squatting or downhill walking, the ankle, knee, and hip have these torques from 15-40% or 15-60% of the gait cycle depending on the steepness of the slope and the person's gait. In FIG. 80(*a*), the soft exosuit 100 is shown to include a waist belt 1 comprising a flap that extends over the gluteal region to the top of the thigh and fabric regions 2, 3 over the front of the thigh and front of the shin, respectively. The soft exosuit 100 is also shown to include an element 4 surrounding the foot as an attachment, which has the same functionality as element 130 in FIGS. 26A-26F, except it contacts more of the foot area to distribute the forces more uniformly. Fabric regions 2, 3 are bordered by a stretch of Bowden cable sheath on their sides, drawn as thick lines and labeled as elements 5, 6 for the outside of the leg (lateral aspects). The inside of the leg (medial aspects) has similar sheaths on the edges of elements 2, 3, although those are not shown in FIGS. 80A-8B.

A cable 7 connects the waist belt 1 and foot attachment 4, passing through these cable sheaths 5, 6 on the inside and outside of the legs. A second cable (not shown) passes from the waist belt 1 to the heel on the inside of the leg. The positioning of the cable 7 ends and the sheaths 5, 6 at the edges of fabric regions 2, 3 cause the cable to extend at the back of the hip joint, in front of the knee joint (labeled 8 in FIG. 80A), and behind the ankle joint. As such, if there is tension in the cable 7, then the appropriate torques are created about these joints. The cable 7 could comprise a spring or other resilient or stretchy material to permit additional energy storage or absorption. In FIG. 80(*a*), the system shown is a passive system in which the cable 7 can be tensioned (e.g. manually, etc.) to an appropriate level before downhill walking is begun. The cable 7 can then be loosened for uphill or level walking or other activities.

FIG. 80(*b*) shows the same suit as in FIG. 80(*a*) except with the addition of another segment of Bowden cable sheath 9 and an actuator, clutch, or damper unit 10. An actuator could create tension in the cable 7 at the appropriate points in the gait cycle (e.g. between about 15-40% for a walking gait cycle) so as to increase the moment that the soft exosuit creates around these joints, or just increase the tension to a base level once it is detected that the wearer is walking downhill (e.g., through one or more sensors providing data to controller indicative of walking downhill including but not limited to accelerometer data, GPS data, heel strike force, etc.). Alternatively, a clutch unit (e.g., 10) could reel in the cable 7 (e.g., with a low force over a portion of, or most of, the gait cycle) and hold the cable in place to create forces in the suit during appropriate points in the gait cycle. In other aspects, such a clutch unit (e.g., 10) could be configured to continuously reel in the cable with a light spring and then, if the cable 7 is pulled out due to the biomechanics of walking, the clutch unit would apply a damping force to the cable, causing a transient force in the suit which could benefit the user.

Further, while the description above refers to the invention, the description may include more than one invention. Each of these embodiments and obvious variations thereof is contemplated as falling within the spirit and scope of the claimed invention, at least some aspects of which are set forth in the following claims.

What is claimed is:

1. A wearable soft exosuit comprising:
   a first anchor element configured for positioning at or near a first body part of a person wearing the wearable soft exosuit;
   a second anchor element configured for positioning at or near a second body part of the person wearing the wearable soft exosuit;
   an actuation member coupled to the second anchor element configured to be behind an ankle joint of the person;
   a plurality of connection elements extending between and connected directly or indirectly to the first anchor element and the actuation member, and at least one of the plurality of connection elements spanning at least one joint disposed between the first anchor element and the second anchor element;
   at least one actuator; and
   at least one controller configured to actuate the at least one actuator at a predetermined time during movement of the at least one joint to generate a beneficial moment about the at least one joint,
   wherein each of the plurality of connection elements comprise webbing, a strap, a cord, a functional textile, fabric, a wire, a cable, or a composite material,
   wherein the at least one actuator comprises at least one motor driven actuator, at least one pneumatic actuator, or at least one hydraulic actuator,
   wherein the second anchor element comprises a footwear anchor element,
   wherein the first anchor element comprises a waist belt anchor element,
   wherein the at least one actuator is configured to apply a tensile force to the second anchor element via the actuation member,
   wherein the plurality of connection elements comprise a first connection element on a first side of the waist belt anchor element configured to extend from the waist belt to a position adjacent a center of the wearer's first thigh, a second connection element on the first side of the waist belt anchor element configured to extend from the waist belt to a position adjacent a center of the wearer's second thigh, a third connection element on a second side of the waist belt anchor element configured to extend from the waist belt to a position adjacent a center of the wearer's second thigh, and a fourth connection element on the second side of the waist belt anchor element configured to extend from the waist belt to a position adjacent a center of the wearer's first thigh,
   wherein the first connection element and the fourth connection element are connected to form a first node at the position adjacent the center of the wearer's first thigh, and
   wherein the second connection element and the third connection element are connected to form a second node at the position adjacent the center of the wearer's second thigh.

2. The wearable soft exosuit according to claim 1, further comprising:
   a first thigh brace for the wearer's first thigh;
   a second thigh brace for the wearer's second thigh;
   one or more connection elements connecting the first node to the first thigh brace; and
   one or more connection elements connecting the second node to the second thigh brace.

3. The wearable soft exosuit according to claim 2, further comprising:
   a first lateral calf connection element connected to the first thigh brace;
   a first medial calf connection element connected to the first thigh brace;
   a second lateral calf connection element connected to the second thigh brace; and
   a second medial calf connection element connected to the second thigh brace.

4. The wearable soft exosuit according to claim 3,
   wherein the at least one actuator comprises a motor driven actuator configured to drive a first cable attached to a first footwear anchor element on a wearer's first foot and to drive a second cable attached to a second footwear anchor element on a wearer's second foot.

5. The wearable soft exosuit according to claim 4,
   wherein the first footwear anchor element and the second footwear anchor element comprise a footwear insole insert defining a cable channel,
   wherein a distal end of the first cable is fixed to the first footwear anchor element at a position proximal to the ankle joint to create a torque around the first ankle when the first cable is actuated, and
   wherein a distal end of the second cable is fixed to the second footwear anchor element at a position proximal to the ankle joint to create a torque around the second ankle the second cable is actuated.

6. The wearable soft exosuit according to claim 1, wherein the actuation member includes a flexible ribbon or a flexible cable.

7. The wearable soft exosuit according to claim 1, wherein the plurality of connection elements are non-extensible.

8. The wearable soft exosuit according to claim 1, wherein the plurality of connection elements are semi-extensible.

9. The wearable soft exosuit according to claim 1, wherein the beneficial moment assists or promotes normal plantarflexion motion of the ankle joint.

10. The wearable soft exosuit according to claim 1, wherein the beneficial moment assists or promotes normal flexion motion of a hip joint of the person.

11. The wearable soft exosuit according to claim 1, wherein the beneficial moments assist or promote normal plantarflexion motion of the ankle joint and normal flexion motion of a hip joint.

12. A wearable soft exosuit comprising:
a first anchor element configured for positioning at or near a first body part of a person wearing the wearable soft exosuit;
a second anchor element configured for positioning at or near a second body part of the person wearing the wearable soft exosuit;
an actuation member coupled to the second anchor element configured to be behind an ankle joint of the person;
a plurality of connection elements extending between and connected directly or indirectly to the first anchor element and the actuation member, and at least one of the plurality of connection elements spanning at least one joint disposed between the first anchor element and the second anchor element;
at least one actuator; and
at least one controller configured to actuate the at least one actuator at a predetermined time during movement of the at least one joint to generate a beneficial moment about the at least one joint,
wherein at least some of the plurality of connection elements are connected to form at least one node,
wherein each of the plurality of connection elements comprise webbing, a strap, a cord, a functional textile, fabric, a wire, a cable, or a composite material,
wherein the at least one actuator comprises at least one motor driven actuator, at least one pneumatic actuator, or at least one hydraulic actuator,
wherein the second anchor element comprises a footwear anchor element,
wherein the first anchor element comprises a waist belt anchor element,
wherein the at least one actuator is configured to apply a tensile force to the second anchor element via the actuation member,
wherein the plurality of connection elements comprise a first connection element on a first side of the waist belt anchor element configured to extend from the waist belt to a position adjacent a center of the wearer's first thigh, a second connection element on the first side of the waist belt anchor element configured to extend from the waist belt to a position adjacent a center of the wearer's second thigh, a third connection element on a second side of the waist belt anchor element configured to extend from the waist belt to a position adjacent a center of the wearer's second thigh, and a fourth connection element on the second side of the waist belt anchor element configured to extend from the waist belt to a position adjacent a center of the wearer's first thigh,
wherein the first connection element and the fourth connection element are connected to form a first node at the position adjacent the center of the wearer's first thigh, and
wherein the second connection element and the third connection element are connected to form a second node at the position adjacent the center of the wearer's second thigh.

13. The wearable soft exosuit according to claim 12, further comprising:
a first thigh brace for the wearer's first thigh;
a second thigh brace for the wearer's second thigh;
one or more connection elements connecting the first node to the first thigh brace; and
one or more connection elements connecting the second node to the second thigh brace.

14. The wearable soft exosuit according to claim 13, further comprising:
a first lateral calf connection element connected to the first thigh brace;
a first medial calf connection element connected to the first thigh brace;
a second lateral calf connection element connected to the second thigh brace; and
a second medial calf connection element connected to the second thigh brace.

15. The wearable soft exosuit according to claim 14, wherein the at least one actuator comprises a motor driven actuator configured to drive a first cable attached to a first footwear anchor element on a wearer's first foot and to drive a second cable attached to a second footwear anchor element on a wearer's second foot.

16. The wearable soft exosuit according to claim 15, wherein the first footwear anchor element and the second footwear anchor element comprise a footwear insole insert defining a cable channel,
wherein a distal end of the first cable is fixed to the first footwear anchor element at a position proximal to the ankle joint to create a torque around the first ankle when the first cable is actuated, and
wherein a distal end of the second cable is fixed to the second footwear anchor element at a position proximal to the ankle joint to create a torque around the second ankle the second cable is actuated.

17. The wearable soft exosuit according to claim 12, wherein the actuation member includes a flexible ribbon or a flexible cable.

18. The wearable soft exosuit according to claim 12, wherein the plurality of connection elements are non-extensible.

19. The wearable soft exosuit according to claim 12, wherein the plurality of connection elements are semi-extensible.

20. The wearable soft exosuit according to claim 12, wherein the beneficial moment assists or promotes normal plantarflexion motion of the ankle joint.

21. The wearable soft exosuit according to claim 12, wherein the beneficial moment assists or promotes normal flexion motion of a hip joint of the person.

22. The wearable soft exosuit according to claim 12, wherein the beneficial moments assist or promote normal plantarflexion motion of the ankle joint and normal flexion motion of a hip joint.

23. A wearable soft exosuit comprising:
a first anchor element configured for positioning at or near a first body part of a person wearing the wearable soft exosuit;
a second anchor element configured for positioning at or near a second body part of the person wearing the wearable soft exosuit;
an actuation member coupled to the second anchor element configured to be behind an ankle joint of the person;
a plurality of connection elements extending between and connected directly or indirectly to the first anchor element and the actuation member, and at least one of the plurality of connection elements spanning at least one joint disposed between the first anchor element and the second anchor element;
at least one actuator; and
at least one controller configured to actuate the at least one actuator at a predetermined time during movement of the at least one joint to generate a beneficial moment about the at least one joint, wherein at least some of the plurality of connection elements are connected to form at least one node, wherein each of the first anchor elements and second anchor element comprise at least one footwear anchor element, waist belt anchor element, shoulder strap anchor element, or node, wherein each of the plurality of connection elements comprise webbing, a strap, a cord, a functional textile, fabric, a wire, a cable, or a composite material, wherein the at least one actuator comprises at least one motor driven actuator, at least one pneumatic actuator, or at least one hydraulic actuator, wherein the second anchor element comprises a footwear anchor element, wherein the first anchor element comprises a waist belt anchor element, wherein the at least one actuator is configured to apply a tensile force to the second anchor element via the actuation member, wherein the plurality of connection elements comprise a first connection element on a first side of the waist belt anchor element configured to extend from the waist belt to a position adjacent a center of the wearer's first thigh, a second connection element on the first side of the waist belt anchor element configured to extend from the waist belt to a position adjacent a center of the wearer's second thigh, a third connection element on a second side of the waist belt anchor element configured to extend from the waist belt to a position adjacent a center of the wearer's second thigh, and a fourth connection element on the second side of the waist belt anchor element configured to extend from the waist belt to a position adjacent a center of the wearer's first thigh, wherein the first connection element and the fourth connection element are connected to form a first node at the position adjacent the center of the wearer's first thigh, and wherein the second connection element and the third connection element are connected to form a second node at the position adjacent the center of the wearer's second thigh.

24. The wearable soft exosuit according to claim 23, further comprising:
a first thigh brace for the wearer's first thigh;
a second thigh brace for the wearer's second thigh;
one or more connection elements connecting the first node to the first thigh brace; and
one or more connection elements connecting the second node to the second thigh brace.

25. The wearable soft exosuit according to claim 24, further comprising:
a first lateral calf connection element connected to the first thigh brace;
a first medial calf connection element connected to the first thigh brace;
a second lateral calf connection element connected to the second thigh brace; and
a second medial calf connection element connected to the second thigh brace.

26. The wearable soft exosuit according to claim 25, wherein the at least one actuator comprises a motor driven actuator configured to drive a first cable attached to a first footwear anchor element on a wearer's first foot and to drive a second cable attached to a second footwear anchor element on a wearer's second foot.

27. The wearable soft exosuit according to claim 26, wherein the first footwear anchor element and the second footwear anchor element comprise a footwear insole insert defining a cable channel,
wherein a distal end of the first cable is fixed to the first footwear anchor element at a position proximal to the ankle joint to create a torque around the first ankle when the first cable is actuated, and
wherein a distal end of the second cable is fixed to the second footwear anchor element at a position proximal to the ankle joint to create a torque around the second ankle the second cable is actuated.

28. The wearable soft exosuit according to claim 23, wherein the actuation member includes a flexible ribbon or a flexible cable.

29. The wearable soft exosuit according to claim 23, wherein the plurality of connection elements are non-extensible.

30. The wearable soft exosuit according to claim 23, wherein the plurality of connection elements are semi-extensible.

31. The wearable soft exosuit according to claim 23, wherein the beneficial moment assists or promotes normal plantarflexion motion of the ankle joint.

32. The wearable soft exosuit according to claim 23, wherein the beneficial moment assists or promotes normal flexion motion of a hip joint of the person.

33. The wearable soft exosuit according to claim 23, wherein the beneficial moments assist or promote normal plantarflexion motion of the ankle joint and normal flexion motion of a hip joint.

34. A wearable soft exosuit comprising:
a first anchor element configured for positioning at or near a first body part of a person wearing the wearable soft exosuit;
a second anchor element configured for positioning at or near a second body part of the person wearing the wearable soft exosuit;
an actuation member coupled to the second anchor element configured to be behind an ankle joint of the person;
a plurality of connection elements extending between and connected directly or indirectly to the first anchor element and the actuation member, and at least one of the plurality of connection elements spanning at least one joint disposed between the first anchor element and the second anchor element;
at least one actuator; and
at least one controller configured to actuate the at least one actuator at a predetermined time during movement of the at least one joint to generate a beneficial moment about the at least one joint,
wherein at least some of the plurality of connection elements are connected to form at least one node,
wherein each of the first anchor elements and second anchor element are formed from at least one of webbing, a strap, a cord, a functional textile, fabric, a wire, a cable, or a composite material,
wherein each of the plurality of connection elements comprise webbing, a strap, a cord, a functional textile, fabric, a wire, a cable, or a composite material,
wherein the at least one actuator comprises at least one motor driven actuator, at least one pneumatic actuator, or at least one hydraulic actuator,
wherein the second anchor element comprises a footwear anchor element,
wherein the first anchor element comprises a waist belt anchor element, wherein the at least one actuator is configured to apply a tensile force to the second anchor element via the actuation member, wherein the plurality of connection elements comprise a first connection element on a first side of the waist belt anchor element configured to extend from the waist belt to a position adjacent a center of the wearer's first thigh, a second connection element on the first side of the waist belt anchor element configured to extend from the waist belt to a position adjacent a center of the wearer's second thigh, a third connection element on a second side of the waist belt anchor element configured to extend from the waist belt to a position adjacent a center of the wearer's second thigh, and a fourth connection element on the second side of the waist belt anchor element configured to extend from the waist belt to a position adjacent a center of the wearer's first thigh, wherein the first connection element and the fourth connection element are connected to form a first node at the position adjacent the center of the wearer's first thigh, and wherein the second connection element and the third connection element are connected to form a second node at the position adjacent the center of the wearer's second thigh.

35. The wearable soft exosuit according to claim 34, further comprising:
a first thigh brace for the wearer's first thigh;
a second thigh brace for the wearer's second thigh;
one or more connection elements connecting the first node to the first thigh brace; and
one or more connection elements connecting the second node to the second thigh brace.

36. The wearable soft exosuit according to claim 35, further comprising:
a first lateral calf connection element connected to the first thigh brace;
a first medial calf connection element connected to the first thigh brace;
a second lateral calf connection element connected to the second thigh brace; and
a second medial calf connection element connected to the second thigh brace.

37. The wearable soft exosuit according to claim 36,
wherein the at least one actuator comprises a motor driven actuator configured to drive a first cable attached to a first footwear anchor element on a wearer's first foot and to drive a second cable attached to a second footwear anchor element on a wearer's second foot.

38. The wearable soft exosuit according to claim 37,
wherein the first footwear anchor element and the second footwear anchor element comprise a footwear insole insert defining a cable channel,
wherein a distal end of the first cable is fixed to the first footwear anchor element at a position proximal to the ankle joint to create a torque around the first ankle when the first cable is actuated, and
wherein a distal end of the second cable is fixed to the second footwear anchor element at a position proximal to the ankle joint to create a torque around the second ankle the second cable is actuated.

39. The wearable soft exosuit according to claim 34, wherein the actuation member includes a flexible ribbon or a flexible cable.

40. The wearable soft exosuit according to claim 34, wherein the plurality of connection elements are non-extensible.

41. The wearable soft exosuit according to claim 34, wherein the plurality of connection elements are semi-extensible.

42. The wearable soft exosuit according to claim 34, wherein the beneficial moment assists or promotes normal plantarflexion motion of the ankle joint.

43. The wearable soft exosuit according to claim 34, wherein the beneficial moment assists or promotes normal flexion motion of a hip joint of the person.

44. The wearable soft exosuit according to claim 34, wherein the beneficial moments assist or promote normal plantarflexion motion of the ankle joint and normal flexion motion of a hip joint.

* * * * *